United States Patent
Li et al.

(10) Patent No.: US 9,224,963 B2
(45) Date of Patent: Dec. 29, 2015

(54) STABLE EMITTERS

(71) Applicants: Jian Li, Tempe, AZ (US); Guijie Li, Tempe, AZ (US)

(72) Inventors: Jian Li, Tempe, AZ (US); Guijie Li, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 14/562,195

(22) Filed: Dec. 5, 2014

(65) Prior Publication Data

US 2015/0162552 A1 Jun. 11, 2015

Related U.S. Application Data

(60) Provisional application No. 61/913,552, filed on Dec. 9, 2013, provisional application No. 61/969,729, filed on Mar. 24, 2014, provisional application No. 62/021,488, filed on Jul. 7, 2014.

(51) Int. Cl.
   C07F 15/00 (2006.01)
   H01L 51/50 (2006.01)
   H01L 51/00 (2006.01)

(52) U.S. Cl.
   CPC ........ *H01L 51/0087* (2013.01); *C07F 15/0086* (2013.01); *H01L 51/0081* (2013.01); *H01L 51/5016* (2013.01); *H01L 2251/308* (2013.01)

(58) Field of Classification Search
   USPC ........................ 546/2, 10; 313/504; 428/690
   See application file for complete search history.

(56) References Cited

U.S. PATENT DOCUMENTS

| | | | |
|---|---|---|---|
| 4,769,292 A | 9/1988 | Tang et al. | |
| 5,707,745 A | 1/1998 | Forrest et al. | |
| 5,844,363 A | 12/1998 | Gu et al. | |
| 6,303,238 B1 | 10/2001 | Thompson et al. | |
| 6,780,528 B2 | 8/2004 | Tsuboyama et al. | |
| 7,002,013 B1 | 2/2006 | Chi et al. | |
| 7,279,704 B2 | 10/2007 | Walters et al. | |
| 7,442,797 B2 | 10/2008 | Itoh et al. | |
| 7,501,190 B2 | 3/2009 | Ise | |
| 7,655,322 B2 | 2/2010 | Forrest et al. | |
| 7,947,383 B2 | 5/2011 | Ise et al. | |
| 8,816,080 B2 | 8/2014 | Li et al. | |
| 8,927,713 B2 | 1/2015 | Li et al. | |
| 8,946,417 B2 | 2/2015 | Li et al. | |
| 9,059,412 B2 | 6/2015 | Zeng et al. | |
| 2002/0068190 A1 | 6/2002 | Tsuboyama et al. | |
| 2005/0170207 A1 | 8/2005 | Ma et al. | |
| 2005/0260446 A1 | 11/2005 | Mackenzie et al. | |
| 2006/0202197 A1 | 9/2006 | Nakayama et al. | |
| 2006/0210831 A1 | 9/2006 | Sano et al. | |
| 2006/0263635 A1 | 11/2006 | Ise | |
| 2006/0286406 A1 | 12/2006 | Igarashi et al. | |
| 2007/0057630 A1 | 3/2007 | Nishita et al. | |
| 2007/0059551 A1 | 3/2007 | Yamazaki | |
| 2007/0082284 A1 | 4/2007 | Stoessel et al. | |
| 2008/0001530 A1 | 1/2008 | Ise et al. | |
| 2008/0036373 A1 | 2/2008 | Itoh et al. | |
| 2008/0054799 A1 | 3/2008 | Satou | |
| 2008/0079358 A1 | 4/2008 | Satou | |
| 2008/0241518 A1 | 10/2008 | Satou et al. | |
| 2008/0241589 A1 | 10/2008 | Fukunaga et al. | |
| 2009/0026936 A1 | 1/2009 | Satou et al. | |
| 2009/0026939 A1 | 1/2009 | Kinoshita et al. | |
| 2009/0032989 A1 | 2/2009 | Karim et al. | |
| 2009/0039768 A1 | 2/2009 | Igarashi et al. | |
| 2009/0128008 A1 | 5/2009 | Ise et al. | |
| 2009/0218561 A1 | 9/2009 | Kitamura et al. | |
| 2009/0261721 A1 | 10/2009 | Murakami et al. | |
| 2009/0267500 A1 | 10/2009 | Kinoshita et al. | |
| 2010/0000606 A1 | 1/2010 | Thompson et al. | |
| 2010/0013386 A1 | 1/2010 | Thompson et al. | |
| 2010/0171111 A1 | 7/2010 | Takada et al. | |
| 2012/0095232 A1 | 4/2012 | Li et al. | |
| 2012/0181528 A1 | 7/2012 | Takada et al. | |
| 2012/0215001 A1 | 8/2012 | Li et al. | |
| 2012/0302753 A1 | 11/2012 | Li | |
| 2013/0048963 A1 | 2/2013 | Beers et al. | |
| 2013/0168656 A1 | 7/2013 | Tsai et al. | |

(Continued)

FOREIGN PATENT DOCUMENTS

| | | |
|---|---|---|
| CN | 1777663 | 5/2006 |
| CN | 1894269 | 1/2007 |

(Continued)

OTHER PUBLICATIONS

Brien, B.O. et al.: White organic light emitting diodes using Pt-based red, green and blue phosphorescent dopants. Proc. SPIE, vol. 8829, pp. 1-6, Aug. 25, 2013 ).*
Wong; Challenges in organometallic research—Great opportunity for solar cells and OLEDs, Journal of Organometallic Chemistry, 2009, 694, 2644-2647.
JP2009267244, English Translation from EPO, Nov. 2009, 80 pages.
JP2010135689, English translation from EPO, Jun. 2010, 95 pages.
Chi et al.; Transition-metal phosphors with cyclometalating ligands: fundamentals and applications, Chemical Society Reviews, vol. 39, No. 2, Feb. 2010, pp. 638-655.
Satake et al., "Interconvertible Cationic and Neutral Pyridinylimidazole η3-Allylpalladium Complexes. Structural Assignment by 1H, 13C, and 15N NMR and X-ray Diffraction", Organometallics, vol. 18, No. 24, 1999, pp. 5108-5111.

(Continued)

*Primary Examiner* — Charanjit Aulakh
(74) *Attorney, Agent, or Firm* — Fish & Richardson P.C.

(57) ABSTRACT

Stable and efficient organic light-emitting diodes were prepared using tetradentate platinum-based blue and red emitters. In one example, a series of stable and efficient red phosphorescent OLEDs was fabricated employing a phenylpyridyl-carbazole based tetradentate cyclometalated Pt(II) complex as an emitting dopant and utilizing a commercially available host, transporting, and blocking materials. By implementing this platinum complex in electrochemically stable device architectures, long operational lifetimes were achieved with an estimated $LT_{97}$ of over 600 hrs at luminance of 1000 cd/m².

12 Claims, 52 Drawing Sheets

(56) References Cited

U.S. PATENT DOCUMENTS

| | | |
|---|---|---|
| 2013/0203996 A1 | 8/2013 | Li et al. |
| 2013/0237706 A1 | 9/2013 | Li |
| 2013/0341600 A1 | 12/2013 | Lin et al. |
| 2014/0014922 A1 | 1/2014 | Lin et al. |
| 2014/0027733 A1 | 1/2014 | Zeng et al. |
| 2014/0084261 A1 | 3/2014 | Brooks et al. |
| 2014/0114072 A1 | 4/2014 | Li et al. |
| 2014/0330019 A1 | 11/2014 | Li et al. |
| 2014/0364605 A1 | 12/2014 | Li et al. |
| 2015/0008419 A1 | 1/2015 | Li |
| 2015/0069334 A1 | 3/2015 | Xia et al. |
| 2015/0105556 A1 | 4/2015 | Li et al. |
| 2015/0194616 A1 | 7/2015 | Li et al. |
| 2015/0228914 A1 | 8/2015 | Li et al. |
| 2015/0287938 A1 | 10/2015 | Li et al. |

FOREIGN PATENT DOCUMENTS

| | | |
|---|---|---|
| CN | 101142223 A | 3/2008 |
| CN | 101667626 A | 3/2010 |
| CN | 102449108 A | 5/2012 |
| CN | 102892860 A | 1/2013 |
| CN | 102971396 A | 3/2013 |
| CN | 104232076 A | 12/2014 |
| CN | 104693243 A | 6/2015 |
| EP | 1808052 | 7/2007 |
| EP | 1874893 | 1/2008 |
| EP | 1874894 | 1/2008 |
| EP | 1919928 | 5/2008 |
| EP | 2036907 | 3/2009 |
| EP | 2096690 A2 | 9/2009 |
| EP | 2417217 | 2/2012 |
| EP | 2112213 | 7/2012 |
| EP | 2711999 | 3/2014 |
| JP | 2005267557 A | 9/2005 |
| JP | 2005310733 A | 11/2005 |
| JP | 2006047240 A | 2/2006 |
| JP | 2006232784 A | 9/2006 |
| JP | 2006242080 A | 9/2006 |
| JP | 2006242081 A | 9/2006 |
| JP | 2006256999 A | 9/2006 |
| JP | 2006257238 A | 9/2006 |
| JP | 2006261623 A | 9/2006 |
| JP | 2006290988 | 10/2006 |
| JP | 2006313796 A | 11/2006 |
| JP | 2006332622 A | 12/2006 |
| JP | 2006351638 A | 12/2006 |
| JP | 2007019462 A | 1/2007 |
| JP | 2007042875 A | 2/2007 |
| JP | 2007053132 | 3/2007 |
| JP | 2007066581 A | 3/2007 |
| JP | 2007073620 A | 3/2007 |
| JP | 2007073845 A | 3/2007 |
| JP | 2007073900 A | 3/2007 |
| JP | 2007080593 A | 3/2007 |
| JP | 2007080677 A | 3/2007 |
| JP | 2007088105 A | 4/2007 |
| JP | 2007088164 | 4/2007 |
| JP | 2007096259 A | 4/2007 |
| JP | 2007110067 A | 4/2007 |
| JP | 2007110102 A | 4/2007 |
| JP | 2007258550 A | 10/2007 |
| JP | 2007324309 A | 12/2007 |
| JP | 2008010353 A | 1/2008 |
| JP | 2008091860 A | 4/2008 |
| JP | 2008103535 A | 5/2008 |
| JP | 2008108617 A | 5/2008 |
| JP | 2008109085 A | 5/2008 |
| JP | 2008109103 A | 5/2008 |
| JP | 2008160087 A | 7/2008 |
| JP | 2008198801 A | 8/2008 |
| JP | 2008270729 A | 11/2008 |
| JP | 2008270736 A | 11/2008 |
| JP | 2009016184 A | 1/2009 |
| JP | 2009016579 A | 1/2009 |
| JP | 2009032977 A | 2/2009 |
| JP | 2009032988 A | 2/2009 |
| JP | 2009267171 | 11/2009 |
| JP | 2009267244 | 11/2009 |
| JP | 2009272339 A | 11/2009 |
| JP | 2009283891 | 12/2009 |
| JP | 2010135689 | 6/2010 |
| JP | 2012222255 A | 11/2012 |
| JP | 2013525436 | 6/2013 |
| JP | 5604505 | 10/2014 |
| JP | 2014221807 | 11/2014 |
| JP | 2015081257 | 4/2015 |
| KR | 102006011537 | 11/2006 |
| KR | 82007061830 | 6/2007 |
| KR | 2007112465 | 11/2007 |
| KR | 1020130043460 | 4/2013 |
| TW | 200701835 | 1/2007 |
| TW | 201307365 | 2/2013 |
| WO | WO0070655 | 11/2000 |
| WO | WO2004108857 | 12/2004 |
| WO | WO2005042444 | 5/2005 |
| WO | WO2005042550 | 5/2005 |
| WO | WO2006033440 | 3/2006 |
| WO | WO2006098505 | 9/2006 |
| WO | WO2006115299 | 11/2006 |
| WO | WO2006115301 | 11/2006 |
| WO | WO2007034985 A1 | 3/2007 |
| WO | WO2007069498 | 6/2007 |
| WO | WO2008066192 | 6/2008 |
| WO | WO2008066195 | 6/2008 |
| WO | WO2008066196 | 6/2008 |
| WO | WO2008117889 | 10/2008 |
| WO | WO2008123540 A2 | 10/2008 |
| WO | WO2009017211 | 2/2009 |
| WO | WO2010118026 | 10/2010 |
| WO | WO2011137429 | 11/2011 |
| WO | WO2011137431 | 11/2011 |
| WO | WO2012112853 | 8/2012 |
| WO | WO2012142387 | 10/2012 |
| WO | WO2012162488 | 11/2012 |
| WO | WO2012163471 | 12/2012 |
| WO | WO2013130483 | 9/2013 |
| WO | WO2014031977 | 2/2014 |
| WO | WO2014047616 | 3/2014 |
| WO | WO2014109814 | 7/2014 |
| WO | WO2015027060 | 2/2015 |
| WO | WO2015131158 A1 | 9/2015 |

OTHER PUBLICATIONS

Baldo et al., "Highly Efficient Phosphorescent Emission from Organic Electroluminescent Devices," Nature, vol. 395, Sep. 10, 1998, pp. 151-154.

Baldo et al., "Very high-efficiency green organic light-emitting devices based on electrophosphorescence," Applied Physics Letters, vol. 75, No. 1, Jul. 5, 1999, pp. 4-6.

Xiao-Chu Hang et al., "Highly Efficient Blue-Emitting Cyclometalated Platinum(II) Complexes by Judicious Molecular Design," Angewandte Chemie, International Edition, vol. 52, Issue 26, Jun. 24, 2013, pp. 6753-6756.

Ying Yang et al., "Induction of Circularly Polarized Electroluminescence from an Achiral Light-Emitting Polymer via a Chiral Small-Molecule Dopant," Advanced Materials, vol. 25, Issue 18, May 14, 2013, pp. 2624-2628.

Ayan Maity et al., "Room-temperature synthesis of cyclometalated iridium(III) complexes; kinetic isomers and reactive functionalities" Chem. Sci., vol. 4, pp. 1175-1181 (2013).

Shiro Koseki et al., "Spin-orbit coupling analyses of the geometrical effects on phosphorescence in Ir(ppy)3 and its derivatives", J. Phys. Chem. C, vol. 117, pp. 5314-5327 (2013).

Ji Hyun Seo et al., "Efficient blue-green organic light-emitting diodes based on heteroleptic tris-cyclometalated iridium (III) complexes". Thin Solid Films, vol. 517, pp. 1807-1810 (2009).

Vanessa Wood et al., "Colloidal quantum dot light-emitting devices," Nano Reviews, vol. 1, 2010, 8 pages.

Glauco Ponterini et al., "Comparison of Radiationless Decay Processes in Osmium and Platinum Porphyrins," J. Am. Chem. Soc., vol. 105, No. 14, 1983, pp. 4639-4645.

(56) References Cited

OTHER PUBLICATIONS

Shizuo Tokito et al., "Confinement of triplet energy on phosphorescent molecules for highly-efficient organic blue-light-emitting devices," Applied Physics Letters, vol. 83, No. 3, Jul. 21, 2003, pp. 569-571.
Brian W. D'Andrade et al., "Controlling Exciton Diffusion in Multilayer White Phosphorescent Organic Light Emitting Devices," Adv. Mater., vol. 14, No. 2, Jan. 16, 2002, pp. 147-151.
Dileep A. K. Vezzu et al., "Highly Luminescent Tetradentate Bis-Cyclometalated Platinum Complexes: Design, Synthesis, Structure, Photophysics, and Electroluminescence Application," Inorg. Chem., vol. 49, 2010, pp. 5107-5119.
Evan L. Williams et al., "Excimer-Based White Phosphorescent Organic Light Emitting Diodes with Nearly 100% Internal Quantum Efficiency," Adv. Mater., vol. 19, 2007, pp. 197-202.
Shih-Chun Lo et al., "High-Triplet-Energy Dendrons: Enhancing the Luminescence of Deep Blue Phosphorescent Iridium(III) Complexes," J. Am. Chem. Soc., vol. 131, 2009, pp. 16681-16688.
Jan Kalinowski et al., "Light-emitting devices based on organometallic platinum complexes as emitters," Coordination Chemistry Reviews, vol. 255, 2011, pp. 2401-2425.
Ke Feng et al., "Norbornene-Based Copolymers Containing Platinum Complexes and Bis(carbazolyl)benzene Groups in Their Side-Chains," Macromolecules, vol. 42, 2009, pp. 6855-6864.
Chi-Ming Che et al., "Photophysical Properties and OLED Applications of Phosphorescent Platinum(II) Schiff Base Complexes," Chem. Eur. J., vol. 16, 2010, pp. 233-247.
Stephen R. Forrest, "The path to ubiquitous and low-cost organic electronic appliances on plastic," Nature, vol. 428, Apr. 29, 2004, pp. 911-918.
Nicholas R. Evans et al., "Triplet Energy Back Transfer in Conjugated Polymers with Pendant Phosphorescent Iridium Complexes," J. Am. Chem. Soc., vol. 128, 2006, pp. 6647-6656.
Xiaofan Ren et al., "Ultrahigh Energy Gap Hosts in Deep Blue Organic Electrophosphorescent Devices," Chem. Mater., vol. 16, 2004, pp. 4743-4747.
Jeonghun Kwak et al., "Bright and Efficient Full-Color Colloidal Quantum Dot Light-Emitting Diodes Using an Inverted Device Structure," Nano Lett., 2012, Vo. 12, pp. 2362-2366.
Hirohiko Fukagawa et al., "Highly Efficient and Stable Red Phosphorescent Organic Light-Emitting Diodes Using Platinum Complexes," Adv. Mater., 2012, vol. 24, pp. 5099-5103.
Eric Turner et al., "Cyclometalated Platinum Complexes with Luminescent Quantum Yields Approaching 100%," Inorg. Chem., 2013, vol. 52, pp. 7344-7351.
Steven C. F. Kui et al., "Robust Phosphorescent Platinum(II) Complexes Containing Tetradentate $O^\wedge N^\wedge C^\wedge N$ Ligands: Excimeric Excited State and Application in Organic White-Light-Emitting Diodes," Chem. Eur. J., 2013, vol. 19, pp. 69-73.
Steven C. F. Kui et al., "Robust phosphorescent platinum(II) complexes with tetradentate $O^\wedge N^\wedge C^\wedge N$ ligands: high efficiency OLEDs with excellent efficiency stability," Chem. Commun., 2013, vol. 49, pp. 1497-1499.
Guijie Li et al., "Efficient and stable red organic light emitting devices from a tetradentate cyclometalated platinum complex," Organic Electronics, 2014, vol. 15 pp. 1862-1867.
Guijie Li et al., Efficient and Stable White Organic Light-Emitting Diodes Employing a Single Emitter, Adv. Mater., 2014, vol. 26, pp. 2931-2936.
Barry O'Brien et al., "High efficiency white organic light emitting diodes employing blue and red platinum emitters," Journal of Photonics for Energy, vol. 4, 2014, pp. 043597-1-043597-8.
Kai Li et al., "Light-emitting platinum(II) complexes supported by tetradentate dianionic bis(N-heterocyclic carbene) ligands: towards robust blue electrophosphors," Chem. Sci., 2013, vol. 4, pp. 2630-2644.
Tyler Fleetham et al., "Efficient "pure" blue OLEDs employing tetradentate Pt complexes with a narrow spectral bandwidth," Advanced Materials (Weinheim, Germany), Vo. 26, No. 41, 2014, pp. 7116-7121.
Murakami; JP 2007258550, English machine translation from EPO, Oct. 4, 2007. 80 pages.
Murakami; JP 2007324309, English machine translation from EPO, Dec. 13, 2007, 89 pages.
Dorwald; "Side Reactions in Organic Synthesis: A Guide to Successful Synthesis Design," Chapter 1, 2005 Wiley-VCH Verlag GmbH & Co. KGaA, Wienheim, 32 pages.

* cited by examiner

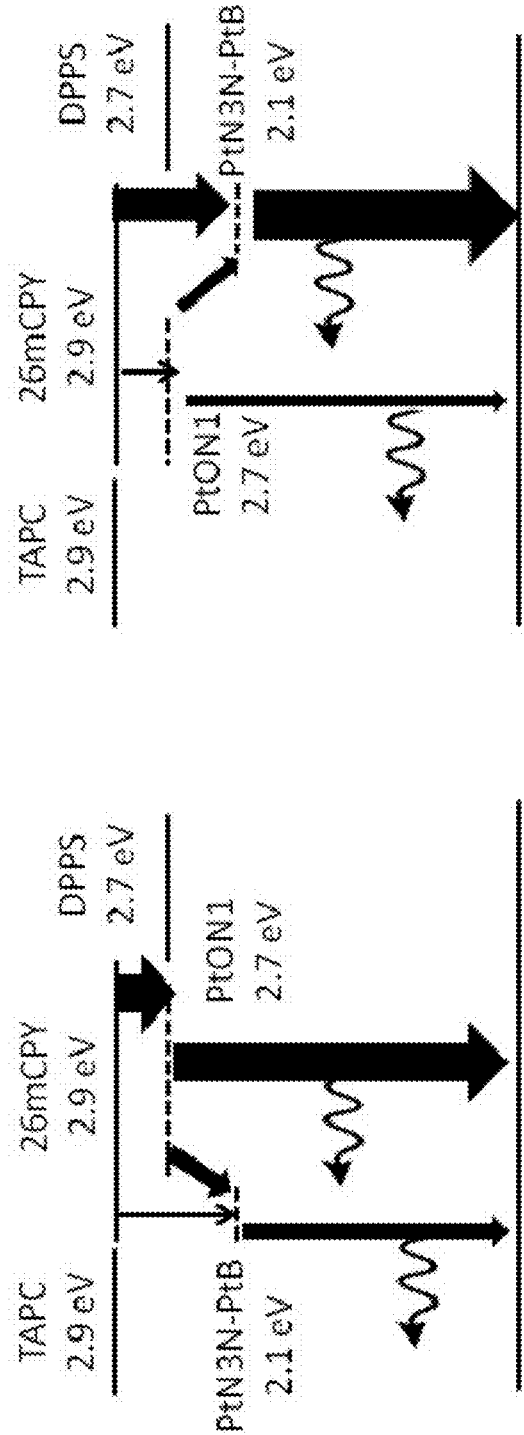

STABLE EMITTERS

CROSS-REFERENCE TO RELATED APPLICATIONS

This application claims priority from U.S. 61/913,552 entitled "Stable Emitters" and filed on Dec. 9, 2013; U.S. 61/969,729 entitled "Efficient Pure Blue OLEDs Employing Tetradentate Pt Complexes with Narrow Spectral Bandwidth" and filed on Mar. 24, 2014; and U.S. 62/021,488 entitled "Stable and Efficient Platinum Complexes as Red Phosphorescent Emitters" and filed on Jul. 7, 2014, all of which are incorporated herein by reference in their entirety.

TECHNICAL FIELD

This disclosure is related to emitters, light-emitting diodes and luminescent displays including the same, and methods of synthesizing the emitters.

BACKGROUND

Rising worldwide energy demand and limited supply of traditional energy sources have spurred research in alternative energy generation methods and improving energy efficiency for existing applications. Lighting, which by some estimates accounts for 20% of electrical energy consumption, is one major field targeted for improved energy efficiency. Current lighting sources primarily employ either short lasting, inefficient incandescent bulbs or fluorescent lighting which contain hazardous materials such as mercury. Solid-state approaches using inorganic or organic materials are becoming increasingly studied due to their potential to produce light much more efficient, with longer operational lifetime, while using environmentally benign materials. However, the cost of these sources remain high, and fabrication complexities may prohibit production on a large enough scale to replace all the current incandescent and fluorescent bulbs. Organic lighting sources have been proposed as an alternative solid state lighting sources due to potentially low cost fabrication processes, the ability to be deposited on a wide array of cheap substrates in a large number of unique form factors, and the ability to be easily color tuned. Furthermore, white organic light emitting diodes (WOLEDs) have demonstrated efficiencies approaching or exceeding fluorescent light. Nevertheless, in order to compete with the efficiency and stability of inorganic solid state lighting or the cost effectiveness of fluorescent lighting, more work is needed to meet commercial needs.

SUMMARY

Stable and efficient organic light-emitting diodes were prepared using tetradentate platinum-based blue and red emitters. In one example, a series of stable and efficient red phosphorescent OLEDs was fabricated employing a phenyl-pyridyl-carbazole based tetradentate cyclometalated Pt(II) complex as an emitting dopant and utilizing a commercially available host, transporting, and blocking materials. By implementing this platinum complex in electrochemically stable device architectures, long operational lifetimes were achieved with an estimated $LT_{97}$ of over 600 hrs at luminance of 1000 cd/m².

Examples of tetradentate platinum-based emitters include compounds represented by the following chemical structures:

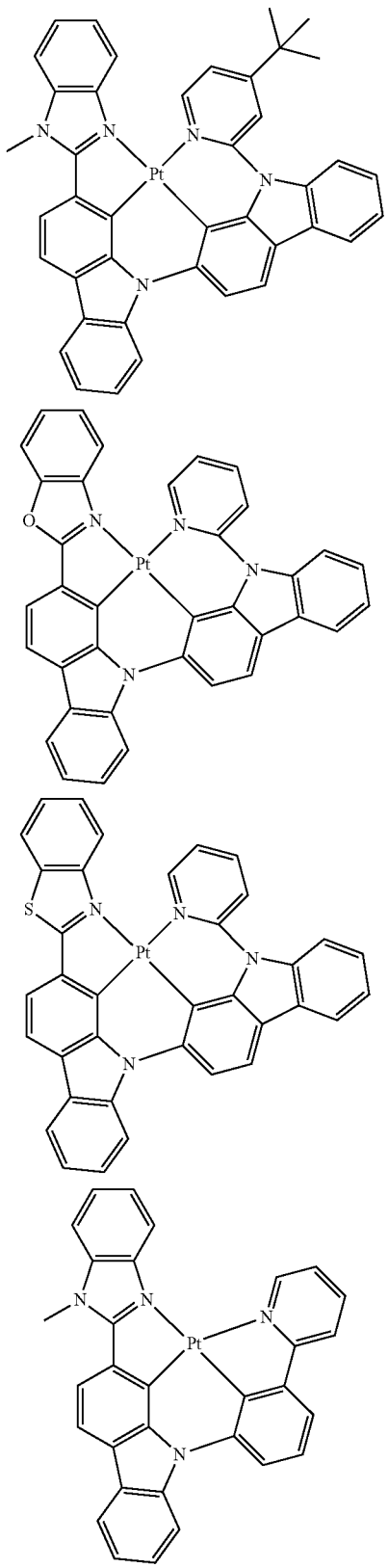

-continued

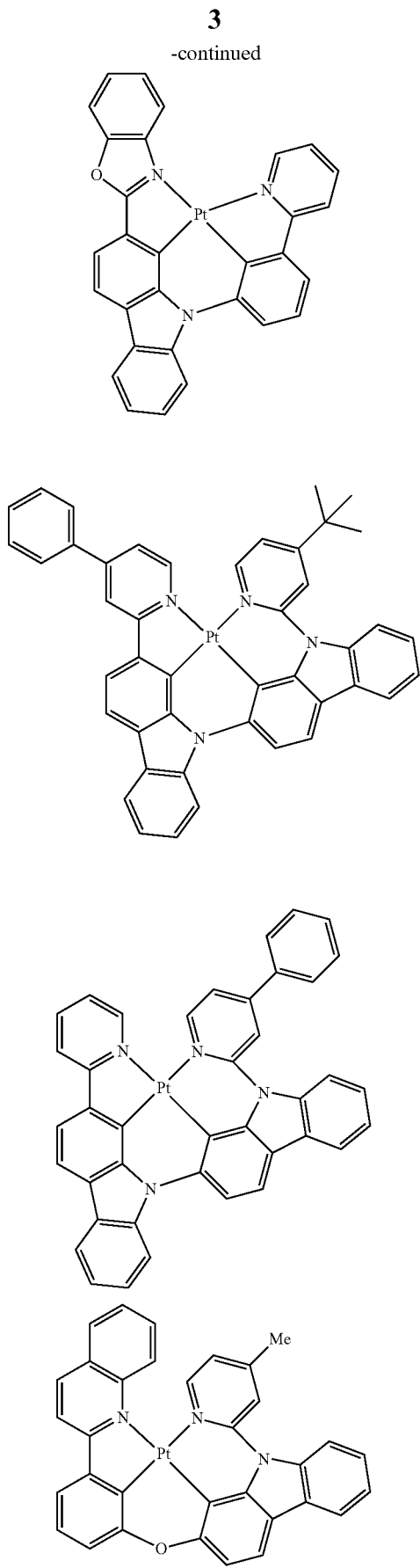

-continued

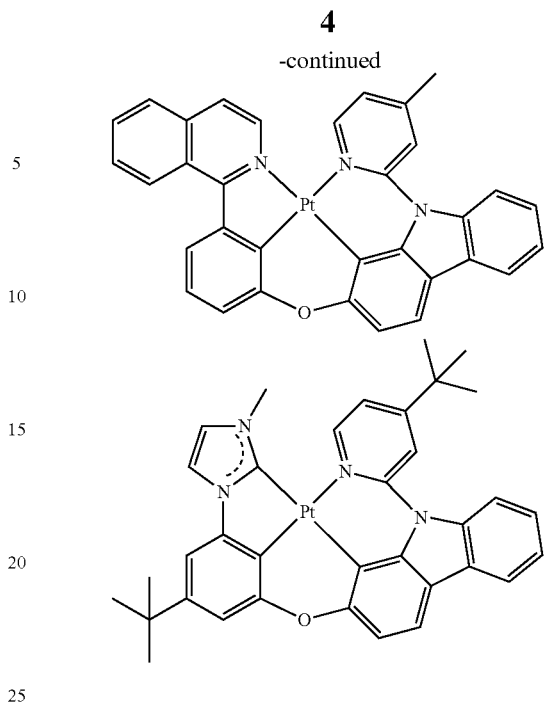

Other examples are shown in FIGS. 29A-29M. Light-emitting devices such as organic light-emitting devices including one or more of these tetradentate platinum complexes as emitters were fabricated. A luminescent display device may include one or more of these tetradentate platinum complexes.

BRIEF DESCRIPTION OF THE DRAWINGS

FIG. 27A is a diagram of various energy transfer processes in a device with R/B structure. FIG. 27B is a diagram of various energy transfer processes in a device with B/R structure.

WHITE ORGANIC LIGHT-EMITTING DIODES le;.5qWhile a large number of efficient red, green, and blue OLEDs have been reported based on phosphorescent complexes due to their ability to harvest 100% of electrogenerated excitons, the development of stable and efficient white devices remains a challenge. Tetradentate platinum complexes with tunable emission spectra described herein can be used as luminescent labels, emitters for organic light emitting diodes, and lighting applications, including full color displays.

Synthesis of PtN3N-ptb

Figure 1:
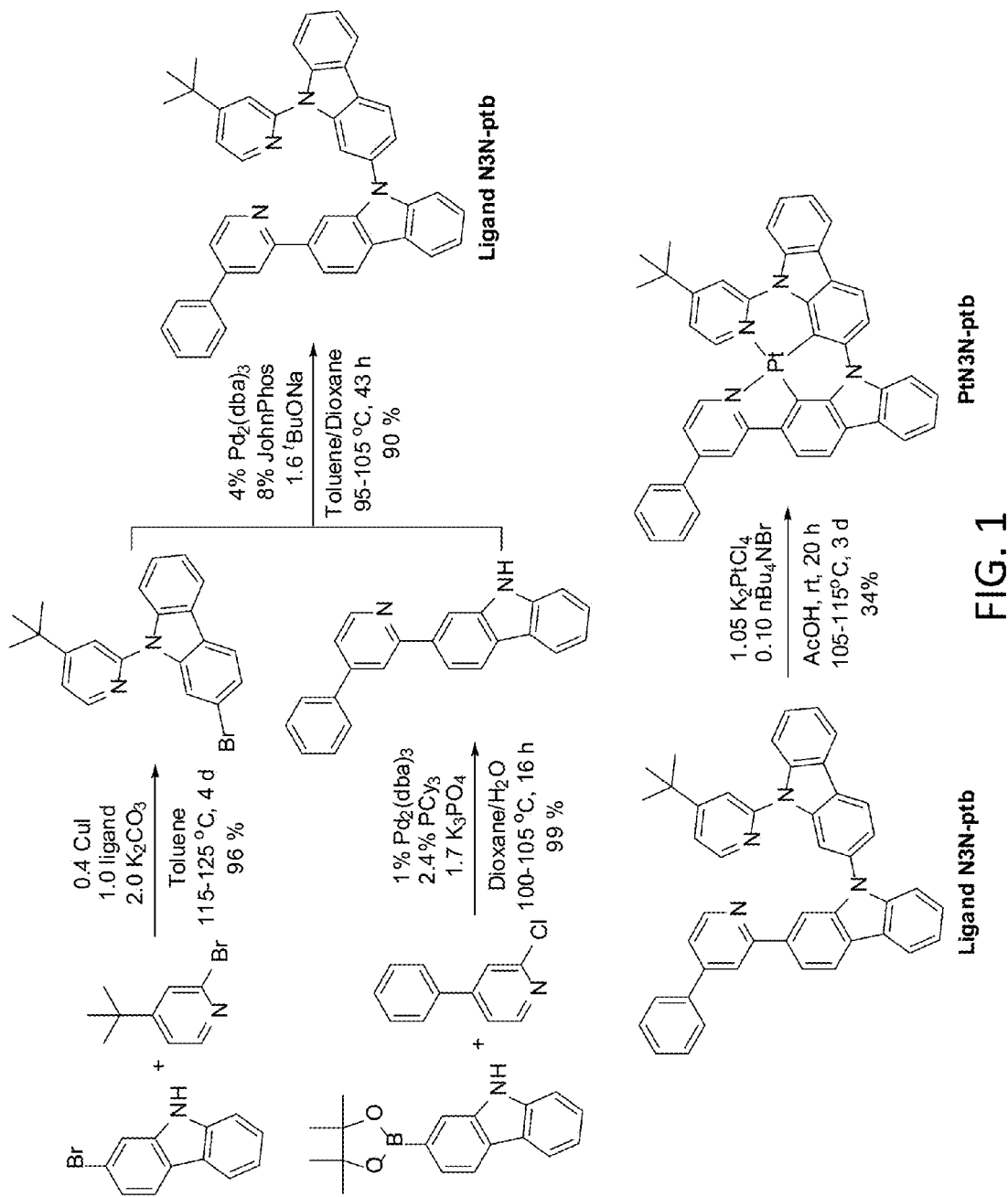
FIG. 1 depicts a method of synthesizing PtN3N-ptb.

PtN3N-ptb was synthesized as shown in FIG. 1.

Synthesis of 2-bromo-9-(4-tert-butylpyridin-2-yl)-9H-carbazole

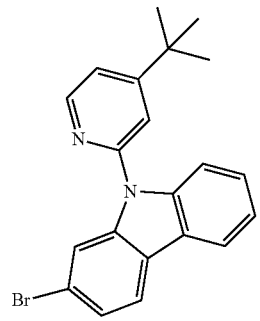 [SMILES: CC(C)(C)c1ccnc(-n2c3ccccc3c3ccc(Br)cc32)c1]

To a pressure vessel equipped with a magnetic stir bar was added 2-bromo-9H-carbazole (2461 mg, 10.0 mmol, 1.0 eq), CuI (762 mg, 4.0 mmol, 0.4 eq), and $K_2CO_3$ (2764 mg, 20.0 mmol, 2.0 eq). Then the vessel was evacuated and back-filled with nitrogen, and the evacuation and back-fill procedure was repeated twice. Then solvent toluene (60 mL), 1-methyl-1H-imidazole (792 uL, 10.0 mmol, 1.0 eq) and 2-bromo-4-tert-butylpyridine (5353 mg, 25.0 mmol, 2.5 eq) were added under the protection of nitrogen. The mixture was stirred in an oil bath at a temperature of 115-125° C. for 4 days. Then the mixture was cooled to ambient temperature. The solvent was removed under reduced pressure and the residue was purified through column chromatography on silica gel using dichloromethane as an eluent to obtain the desired product, 2-bromo-9-(4-tert-butylpyridin-2-yl)-9H-carbazole, as a colorless sticky liquid (3635 mg in 96% yield). $^1$H NMR (DMSO-$d_6$, 400 MHz): δ 1.39 (s, 9H), 7.36 (t, J=8.0 Hz, 1H), 7.48-7.55 (m, 3H), 7.71-7.73 (m, 2H), 7.94 (d, J=2.0 Hz, 1H), 8.23 (d, J=8.0 Hz, 1H), 8.28 (d, J=8.0 Hz, 1H), 8.66 (d, J=5.5 Hz, 1H).

Synthesis of 2-(4-phenylpyridin-2-yl)-9H-carbazole

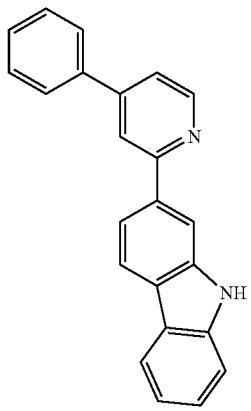 [SMILES: c1ccc(-c2ccnc(-c3ccc4c(c3)[nH]c3ccccc34)c2)cc1]

To a three-necked flask equipped with a magnetic stir bar was added 2-(4,4,5,5-tetramethyl-1,3,2-dioxaborolan-2-yl)-9H-carbazole (682 mg, 2.32 mmol, 1.1 eq), 2-chloro-4-phenylpyridine (400 mg, 2.11 mmol, 1.0 eq), $Pd_2(dba)_3$ (21 mg, 0.023 mmol, 0.01 eq), $PCy_3$ (14 mg, 0.051 mmol, 0.024 eq) and $K_3PO_4$ (761 mg, 3.59 mmol, 1.7 eq). Then the flask was evacuated and back-filled with nitrogen, and the evacuation and back-fill procedure was repeated twice. Then solvent dioxane (8 mL) and water (3.8 mL) were added under the protection of nitrogen. The mixture was stirred in an oil bath at a temperature of 100-105° C. for 16 hours. Then the mixture was cooled to ambient temperature and diluted with ethyl acetate. The organic layer was separated and dried over sodium sulfate, and filtered, the filtrate was concentrated under reduced pressure and the residue was purified through column chromatography on silica gel using hexane and ethyl acetate (5:1-3:1-2:1) as an eluent to obtain the desired product, 2-(4-phenylpyridin-2-yl)-9H-carbazole, as a brown solid (675 mg in 99% yield). $^1$H NMR (DMSO-$d_6$, 400 MHz): δ 7.20 (t, J=7.6 Hz, 1H), 7.41-7.45 (m, 1H), 7.51-7.61 (m, 4H), 7.68 (dd, J=4.8, 1.2 Hz, 1H), 7.96-7.98 (m, 2H), 8.05 (dd, J=7.6, 1.6 Hz, 1H), 8.18 (d, J=7.6 Hz, 1H), 8.24 (d, J=8.0 Hz, 1H), 8.31 (s, 1H), 8.35 (d, J=0.4 Hz, 1H), 8.77 (d, J=5.2 Hz, 1H), 11.37 (s, 1H).

Synthesis of 9-(4-tert-butylpyridin-2-yl)-2'-(4-phenylpyridin-2-yl)-9H-2,9'-bicarbazole Ligand N3NPh-ptb

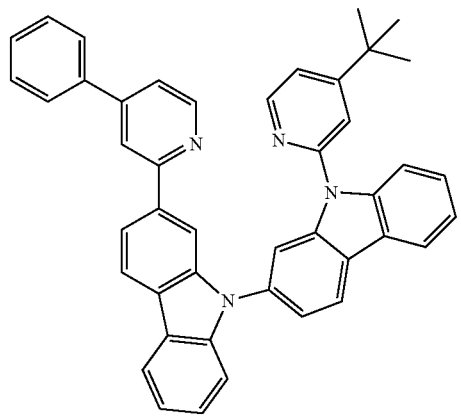

Ligand N3N-ptb

To a dry pressure Schlenk tube equipped with a magnetic stir bar was added 2-(4-phenylpyridin-2-yl)-9H-carbazole (676 mg, 2.11 mmol, 1.0 eq), 2-bromo-9-(4-tert-butylpyridin-2-yl)-9H-carbazole (958 mg, 2.53 mmol, 1.2 eq), $Pd_2(dba)_3$ (77 mg, 0.084 mmol, 0.04 eq), JohnPhos (50 mg, 0.169 mmol, 0.08 eq) and $^t$BuONa (324 mg, 3.38 mmol, 1.6 eq). Then the tube was evacuated and back-filled with nitrogen, and the evacuation and back-fill procedure was repeated twice. Then dry solvent toluene (10 mL), dioxane (10 mL) were added under the protection of nitrogen. The tube was sealed and the mixture was stirred in an oil bath at a temperature of 95-105° C. for 43 hours. Then the mixture was cooled to ambient temperature. The solvent was removed under reduced pressure and the residue was purified through column chromatography on silica gel using hexane and ethyl acetate (10:1-8:1-5:1) as an eluent to obtain the desired product, 9-(4-tert-butylpyridin-2-yl)-2'-(4-phenylpyridin-2-yl)-9H-2,9'-bicarbazole Ligand N3NPh-ptb, as a brown solid (1175 mg in 90% yield). $^1$H NMR (DMSO-$d_6$, 400 MHz): δ 1.15 (s, 9H), 7.25 (t, J=8.0 Hz, 1H), 7.31 (dd, J=5.2, 1.6 Hz, 1H), 7.34-7.57 (m, 9H), 7.74 (s, 1H), 7.78-7.82 (m, 3H), 7.91 (d, J=1.6 Hz, 1H), 8.11 (d, J=8.4 Hz, 1H), 8.21 (s, 1H), 8.24 (d, J=8.0 Hz, 1H), 8.29 (s, 1H), 8.31 (d, J=8.4 Hz, 2H), 8.45 (d, J=6.0 Hz, 1H), 8.51 (d, J=8.0 Hz, 1H), 8.57 (d, J=4.2 Hz, 1H). $^{13}$C NMR (DMSO-$d_6$, 100 MHz): δ 29.96, 34.72, 108.01, 109.82, 109.85, 111.36, 115.97, 117.92, 119.14, 119.31, 119.80, 119.92, 120.23, 120.72, 120.84, 121.29, 122.00, 122.39, 122.94, 123.02, 123.45, 126.63, 126.84, 127.05, 129.06, 129.16, 134.83, 136.92, 137.49, 139.73, 139.78, 141.13, 141.47, 148.33, 149.39, 149.97, 150.55, 157.15, 163.08.

Synthesis of 9-(4-tert-butylpyridin-2-yl)-2'-(4-phenylpyridin-2-yl)-9H-2,9'-bicarbazole platinum complex PtN3N-ptb

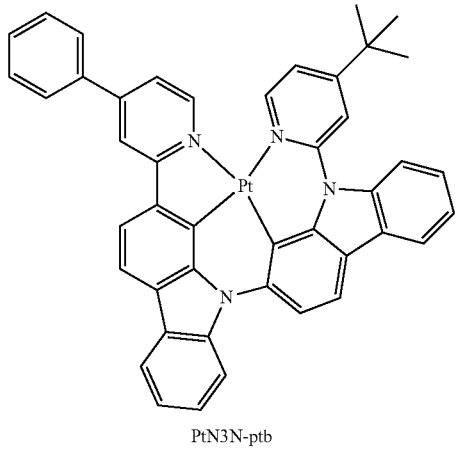

PtN3N-ptb

To a dry pressure tube equipped with a magnetic stir bar was added 9-(4-tert-butylpyridin-2-yl)-2'-(4-phenylpyridin-2-yl)-9H-2,9'-bicarbazole (536 mg, 0.87 mmol, 1.0 eq), $K_2PtCl_4$ (378 mg, 0.91 mmol, 1.05 eq) and $^nBu_4NBr$ (28 mg, 0.087 mmol, 0.1 eq). Then solvent acetic acid (52 mL) was added under nitrogen atmosphere. The mixture was bubbled with nitrogen for 30 minutes and then the tube was sealed. The mixture was stirred at room temperature for 20 hours and then at 105-115° C. in an oil bath for another three days, cooled to ambient temperature, and water (104 mL) was added slowly. After stirring at room temperature for 10 minutes, the precipitate was filtered off and washed with water three times. Then the solid was dried in air under reduced pressure. The collected solid was purified through column chromatography on silica gel using dichloromethane/hexane (2:1) as an eluent to obtain the desired product, PtN3N-ptb, as a red solid (240 mg in 34% yield). The product (335 mg) was further purified by sublimation in a sublimator with four zone controllers at 290° C., 285° C., 190° C., 150° C., 4.1×10$^{-6}$ Torr to obtain red needle crystals (140 mg in 42% yield). $^{1}$H NMR (DMSO-d$_6$, 400 MHz): δ 1.27 (s, 9H), 7.19 (t, J=7.6 Hz, 1H), 7.32 (t, J=7.6 Hz, 1H), 7.39-7.54 (m, 6H), 7.69 (dd, J=6.0, 1.6 Hz, 1H), 7.83 (d, J=7.6 Hz, 1H), 7.88 (d, J=8.0 Hz, 1H), 7.93 (d, J=8.0 Hz, 1H), 7.95-8.00 (m, 5H), 8.10-8.14 (m, 3H), 8.37 (d, J=1.2 Hz, 1H), 8.55 (d, J=6.0 Hz, 1H), 8.88 (d, J=6.4 Hz, 1H). $^{13}$C NMR (DMSO-d$_6$, 100 MHz): δ 29.73, 35.51, 111.17, 112.45, 112.87, 113.79, 114.23, 114.98, 115.24, 116.65, 116.97, 117.96, 118.74, 120.40, 120.44, 120.46, 121.56, 121.70, 122.92, 125.30, 126.06, 126.54, 127.27, 127.73, 128.45, 129.36, 130.19, 136.31, 138.03, 138.12, 138.50, 139.65, 143.17, 144.18, 147.72, 149.32, 149.90, 150.51, 163.62, 165.92. MS (MALDI) for $C_{44}H_{32}N_4Pt$ [M]$^+$: calcd 811.2. found 811.2.

Synthesis of PtN3NPh

Figure 2:
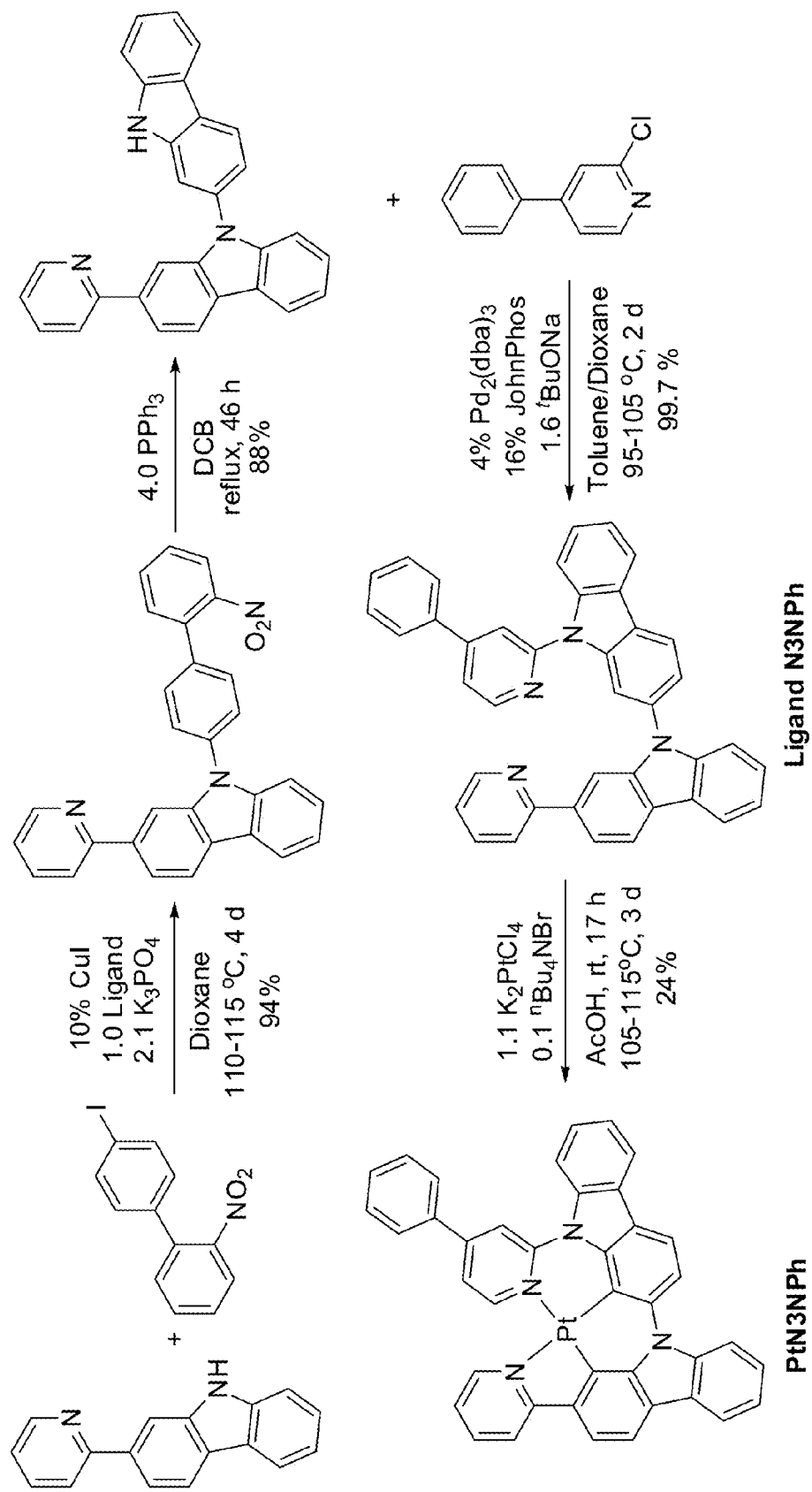
FIG. 2 depicts a method of synthesizing PtN3NPh.

PtN3NPh was synthesized as shown in FIG. 2.

Synthesis of 9-(2'-nitrobiphenyl-4-yl)-2-(pyridin-2-yl)-9H-carbazole

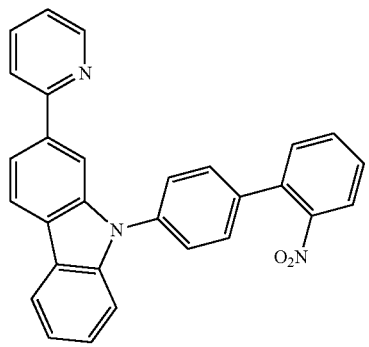 [SMILES: O=[N+]([O-])c1ccccc1-c1ccc(-n2c3ccccc3c3ccc(-c4ccccn4)cc32)cc1]

2-(Pyridin-2-yl)-9H-carbazole (611 mg, 2.5 mmol, 1.0 eq), 4'-iodo-2-nitrobiphenyl (975 mg, 3.0 mmol, 1.2 eq), CuI (48 mg, 0.25 mmol, 0.1 eq), trans-cyclohexane-1,2-diamine (250 uL, 2.5 mmol, 1.0 eq) and K$_3$PO$_4$ (1114 mg, 5.25 mmol, 2.1 eq) were added to a dry pressure vessel equipped with a magnetic stir bar. The vessel was evacuated and back-filled with nitrogen. The evacuation and back-fill procedure was repeated twice. Then solvent dioxane (10 mL) was added under nitrogen. After bubbling with nitrogen for 30 minutes, the mixture was stirred at 110-115° C. in an oil bath for 4 days. Then the mixture was cooled to ambient temperature. The solvent was removed under reduced pressure and the residue was purified through column chromatography on silica gel using hexane/ethyl acetate (10:1-3:1) then dichloromethane/methanol (20:1) as an eluent to obtain the desired product as a solid (1.04 g in 94% yield). $^{1}$H NMR (DMSO-d$_6$, 400 MHz): δ 7.36 (t, J=6.0 Hz, 2H), 7.45 (d, J=8.0 Hz, 1H), 7.51 (d, J=8.4 Hz, 1H), 7.70-7.92 (m, 8H), 8.05 (t, J=8.4 Hz, 2H), 8.10 (d, J=8.4 Hz, 1H), 8.22 (s, 1H), 8.33 (d, J=7.2 Hz, 1H), 8.39 (d, J=8.0 Hz, 1H), 8.67 (d, J=4.8 Hz, 1H).

Synthesis of 2'-(pyridin-2-yl)-9H-2,9'-bicarbazole

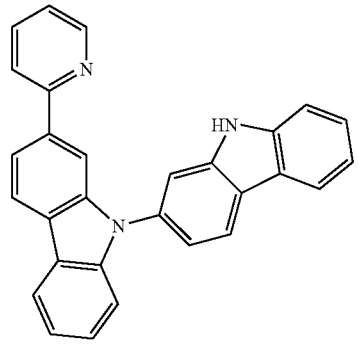 [SMILES: c1ccc(-c2ccc3c4ccccc4n(-c4ccc5c(c4)[nH]c4ccccc45)c3c2)nc1]

A solution of 9-(2'-nitrobiphenyl-4-yl)-2-(pyridin-2-yl)-9H-carbazole (1.00 g, 2.27 mmol, 1.0 eq) and PPh$_3$ (2.38 g, 9.06 mmol, 4.0 eq) in 1,2-dichlorobenzene (15 mL) was stirred at refluxed temperature of 175-185° C. in an oil bath and for 46 hours under nitrogen, and cooled. The solvent was removed by distillation under high vacuum. The residue was purified through column chromatography on silica gel using hexane/ethyl acetate (10:1-5:1-3:1) as an eluent to obtain the desired product, 2'-(pyridin-2-yl)-9H-2,9'-bicarbazole, as a brown solid (814 g in 88% yield). $^{1}$H NMR (DMSO-d$_6$, 400 MHz): δ 7.27 (t, J=8.0 Hz, 1H), 7.30-7.36 (m, 2H), 7.42 (dd, J=8.8, 1.2 Hz, 1H), 7.45-7.51 (m, 3H), 7.59 (d, J=8.8 Hz, 1H), 7.75 (d, J=1.6 Hz, 1H), 7.84-7.88 (m, 1H), 8.04 (d, J=8.4 Hz, 2H), 8.21 (s, 1H), 8.27 (d, J=8.0 Hz, 1H), 8.33 (d, J=7.2 Hz, 1H), 8.39 (d, J=7.6 Hz, 1H), 8.44 (d, J=8.8 Hz, 1H), 8.61 (d, J=4.8 Hz, 1H), 11.53 (s, 1H).

Synthesis of 9-(4-phenylpyridin-2-yl)-2'-(pyridin-2-yl)-9H-2,9'-bicarbazole Ligand N3NPh

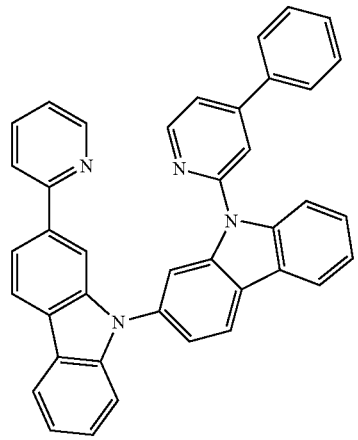

Ligand N3NPh

To a dry pressure Schlenk tube equipped with a magnetic stir bar was added 2'-(pyridin-2-yl)-9H-2,9'-bicarbazole (409 mg, 1.0 mmol, 1.0 eq), 2-chloro-4-phenylpyridine (228 mg, 1.2 mmol, 1.2 eq), Pd$_2$(dba)$_3$ (36 mg, 0.04 mmol, 0.04 eq), JohnPhos (48 mg, 0.16 mmol, 0.16 eq) and ⁱBuONa (154 mg, 1.6 mmol, 1.6 eq). Then the tube was evacuated and back-filled with nitrogen, the evacuation and back-fill procedure was repeated twice. Then dry solvent toluene (4 mL) and dioxane (4 mL) were added under the protection of nitrogen. The tube was sealed and the mixture was stirred in an oil bath at a temperature of 95-105° C. for 2 days. Then the mixture was cooled to ambient temperature. The solvent was removed under reduced pressure and the residue was purified through column chromatography on silica gel using hexane and ethyl acetate (10:1-5:1-3:1) as an eluent to obtain the desired product, 9-(4-phenylpyridin-2-yl)-2'-(pyridin-2-yl)-9H-2,9'-bicarbazole Ligand N3NPh, as a brown solid (561 mg in 99.7% yield). $^1$H NMR (DMSO-$d_6$, 400 MHz): δ 7.29-7.34 (m, 2H), 7.41-7.48 (m, 5H), 7.53-7.60 (m, 2H), 7.64 (dd, J=8.0, 1.2 Hz, 1H), 7.76 (d, J=4.8 Hz, 1H), 7.82-7.88 (m, 3H), 7.97 (d, J=8.0 Hz, 1H), 8.05 (d, J=8.4 Hz, 1H), 8.10 (s, 1H), 8.19 (s, 1H), 8.26 (s, 1H), 8.30 (d, J=7.6 Hz, 1H), 8.36 (d, J=8.4 Hz, 1H), 8.42 (d, J=8.0 Hz, 1H), 8.59-8.61 (m, 2H), 8.70 (d, J=5.6 Hz, 1H). $^{13}$C NMR (DMSO-$d_6$, 100 MHz): δ 107.61, 109.87, 110.25, 111.57, 116.34, 118.65, 119.76, 119.97, 120.25, 120.35, 120.77, 120.81, 120.88, 121.48, 122.05, 122.39, 122.42, 123.07, 123.13, 123.38, 126.70, 126.98, 127.09, 129.16, 129.66, 134.83, 136.48, 136.74, 137.22, 139.79, 139.80, 141.25, 141.50, 149.46, 150.17, 150.40, 151.30, 156.16.

Synthesis of 9-(4-phenylpyridin-2-yl)-2'-(pyridin-2-yl)-9H-2,9'-bicarbazole platinum complex PtN3NPh

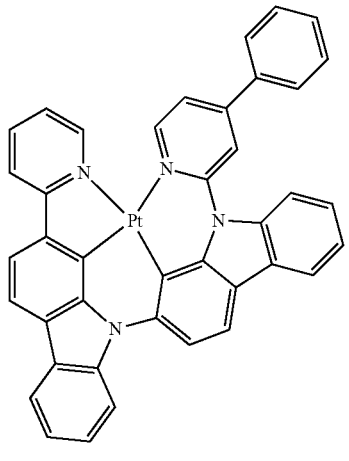

PtN3NPh 9-(4-phenylpyridin-2-yl)-2'-(pyridin-2-yl)-9H-2,9'-bicarbazole Ligand N3NPh (540 mg, 0.96 mmol, 1.0 eq), K$_2$PtCl$_4$ (438 mg, 1.06 mmol, 1.1 eq), ⁿBu$_4$NBr (31 mg, 0.096 mmol, 0.1 eq) and solvent acetic acid (58 mL) were added to a dry pressure tube equipped with a magnetic stir bar in nitrogen atmosphere. After bubbling with nitrogen for 30 minutes, the mixture was stirred at room temperature for 17 hours, followed at 105-115° C. for three days, cooled to ambient temperature and water (58 mL) was added slowly. After stirring at room temperature for 10 minutes, the precipitate was filtered off and washed with water three times, and dried in air. The collected solid was purified through column chromatography on silica gel using dichloromethane/hexane (2:1-3:1) as an eluent to afford the desired product platinum complex, PtN3NPh, as a red solid (175 mg in 24% yield). The product (165 mg) was further purified by sublimation in a sublimator with four zone controllers at 290° C., 280° C., 210° C., 170° C., 3.2×10$^{-6}$ Torr to obtain a red solid (52 mg in 30% yield). $^1$H NMR (DMSO-$d_6$, 500 MHz): δ 7.30 (t, J=7.5 Hz, 1H), 7.44 (t, J=8.5 Hz, 1H), 7.49-7.61 (m, 6H), 7.78 (dd, J=6.5, 2.0 Hz, 1H), 7.82 (d, J=8.0 Hz, 1H), 7.93-7.94 (m, 3H), 8.00 (d, J=8.5 Hz, 1H), 8.09-8.12 (m, 2H), 8.21-8.25 (m, 5H), 8.36 (d, J=1.0 Hz, 1H), 8.73 (d, J=5.5 Hz, 1H), 9.08 (d, J=6.0 Hz, 1H). $^{13}$C NMR (DMSO-$d_6$, 100 MHz): δ 110.89, 122.76, 122.87, 113.78, 114.44, 115.01, 115.21, 117.00, 117.42, 118.43, 119.56, 120.35, 121.49, 121.60, 122.94, 123.10, 125.38, 126.05, 126.45, 126.99, 127.74, 128.19, 129.47, 130.17, 136.10, 137.91, 138.06, 138.47, 139.32, 139.60, 143.10, 144.18, 148.05, 149.00, 150.13, 151.26, 165.26.

Synthesis of PtON11Me

Figure 3:
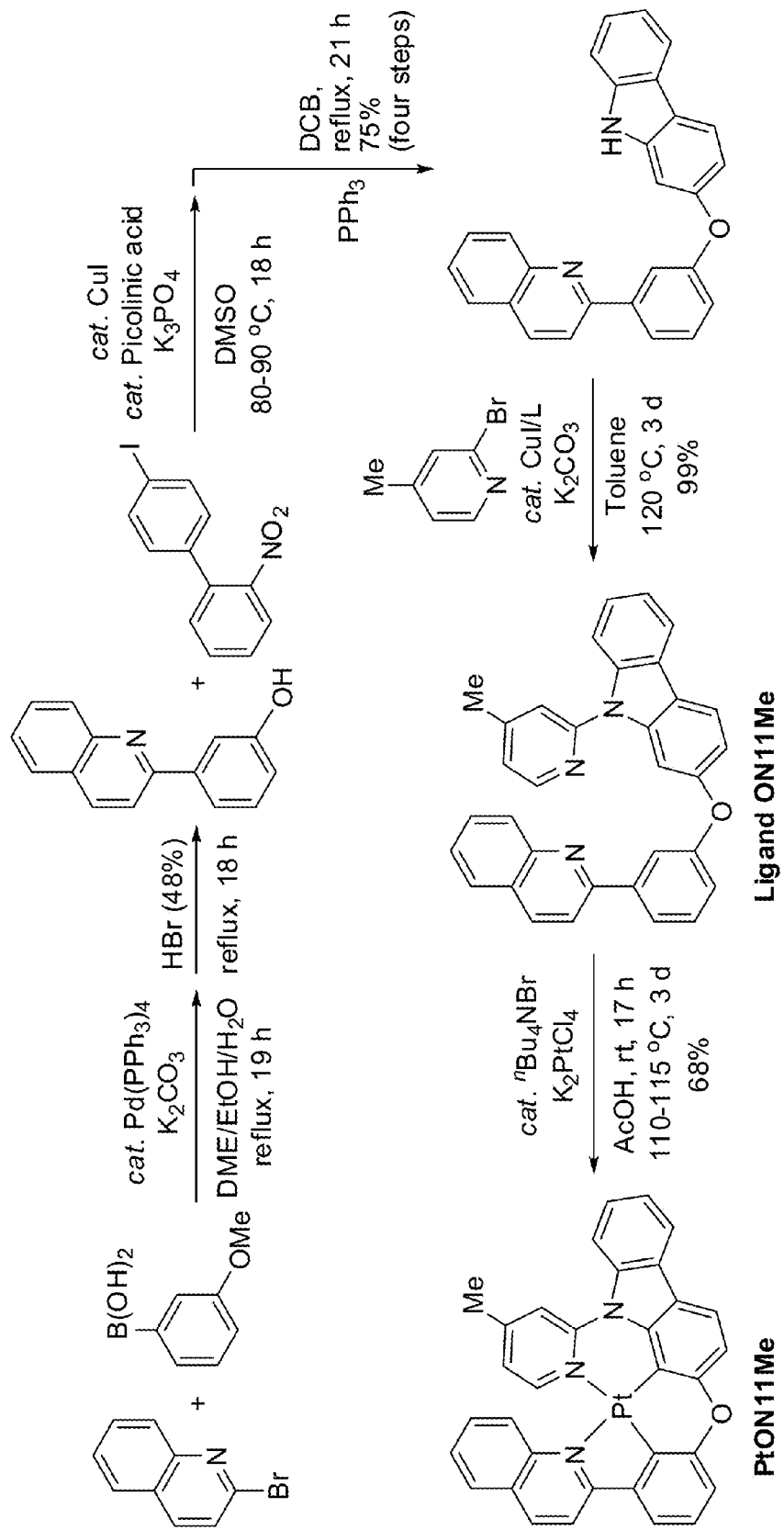
FIG. 3 depicts a method of synthesizing PtON11Me.

PtON11Me was synthesized as shown in FIG. 3.

Synthesis of 3-(quinolin-2-yl)phenol

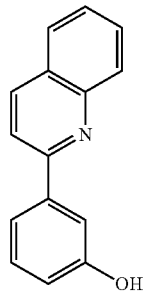 [SMILES: Oc1cccc(-c2ccc3ccccc3n2)c1]

2-Bromoquinoline (3.19 g, 15.3 mmol, 1.0 eq), 3-methoxyphenyl boronic acid (2.79 g, 18.4 mmol, 1.2 eq) and K$_2$CO$_3$ (4.65 g, 33.7 mmol, 2.2 eq) were added to a dry 100 mL three-necked flask equipped with a magnetic stir bar and a condenser. Then the flask was evacuated and back-filled with nitrogen. The evacuation and back-fill procedure was repeated twice. Then solvent DME (38 mL), EtOH (12 mL) and H$_2$O (17 mL) were added under nitrogen. The mixture was bubbled with nitrogen for 20 minutes and then Pd(PPh$_3$)$_4$ (0.53 g, 0.46 mmol, 0.03 eq) was added. The flask was then placed into an oil bath and heated to reflux (90-95° C.). The reaction was monitored by TLC, and about 19 hours later the starting material 2-bromoquinoline was consumed completely. Then the mixture was cooled to ambient temperature. The organic layer was separated and the aqueous layer was extracted with ethyl acetate. The combined organic layer was washed with water and then dried over sodium sulfate, and filtered and washed with ethyl acetate. The filtrate was concentrated and the residue was purified through column chromatography on silica gel using hexane and ethyl acetate (10:1) as an eluent to obtain the desired product 2-(3-methoxyphenyl)quinoline as a yellow liquid (3.76 g), which was used directly for the next step. A solution of the yellow liquid (3.75 g) in hydrogen bromide acid (25 mL, 48%) refluxed (110-120° C.) for 18 hours in an atmosphere of nitrogen. Then the mixture was cooled to ambient temperature and neutralized with a solution of K$_2$CO$_3$ in water until there was no gas to generate. Then the precipitate was filtered off and washed with water several times. The brown solid was dried in air under reduced pressure and product 3-(quinolin-2-yl)phenol 3.68 g was obtained. $^1$H NMR (DMSO-$d_6$, 400

MHz): δ 6.74 (dd, J=8.0, 2.4 Hz, 1H), 7.18 (t, J=8.0 Hz, 1H), 7.43-7.48 (m, 3H), 7.65 (t, J=7.6 Hz, 1H), 7.86 (d, J=7.6 Hz, 1H), 7.92 (t, J=8.0 Hz, 2H), 8.37 (d, J=8.4 Hz, 1H), 9.52 (bs, 1H).

Synthesis of
2-(3-(quinolin-2-yl)phenoxy)-9H-carbazole

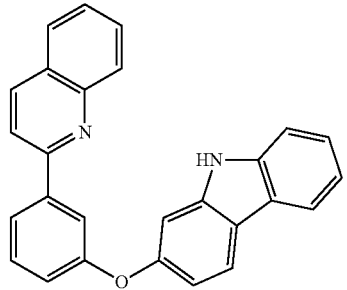 [SMILES: c1cc(Oc2ccc3c(c2)[nH]c2ccccc23)cc(-c2ccc3ccccc3n2)c1]

3-(quinolin-2-yl)phenol (3.68 g, 15.30 mmol, 1.0 eq), 4'-iodo-2-nitrobiphenyl (5.97 g, 18.36 mmol, 1.2 eq), CuI (0.15 g, 0.77 mmol, 0.05 eq), picolinic acid (0.19 g, 1.53 mmol, 0.1 eq) and $K_3PO_4$ (6.50 g, 30.60 mmol, 2.0 eq) were added to a dry pressure vessel equipped with a magnetic stir bar. The vessel was evacuated and back-filled with nitrogen. The evacuation and back-fill procedure was repeated twice. Then solvent DMSO (32 mL) was added under nitrogen. After bubbling with nitrogen for 20 minutes, the mixture was heated to 80-90° C. in an oil bath. The reaction was monitored by TLC and about 22 hours later the starting material 3-(quinolin-2-yl)phenol was consumed completely. Then the mixture was cooled to ambient temperature and diluted with water, extracted with ethyl acetate three times. The combined organic layer was washed with water three times and dried over sodium sulfate, and filtered and washed with ethyl acetate. The filtrate was concentrated and the residue was purified through column chromatography on silica gel using hexane and ethyl acetate (10:1-5:1-3:1) as an eluent to obtain the desired product as a sticky brown liquid (5.98 g), which was used directly for the next step. A solution of $PPh_3$ (11.19 g, 42.6 mmol) and the sticky brown liquid (5.95 g) obtained in the last step in 1,2-dichlorobenzene (28.4 mL) was stirred at a temperature of 175-185° C. in oil bath and for 21 hours under nitrogen, cooled and the solvent was removed by distillation under high vacuum. The residue was purified through column chromatography on silica gel using hexane and ethyl acetate (10:1-5:1-3:1) as an eluent to obtain the desired product 2-(3-(quinolin-2-yl)phenoxy)-9H-carbazole, which was further purified through recrystallization in ethyl acetate and hexane to get pure product as a white solid (4.45 g) in 75% total yield for the four steps. $^1$H NMR (DMSO-$d_6$, 400 MHz): δ 6.96 (dd, J=8.4, 2.4 Hz, 1H), 7.13 (d, J=2.4 Hz, 1H), 7.16 (d, J=7.6 Hz, 1H), 7.21 (dd, J=8.4, 2.4 Hz, 1H), 7.35 (d, J=8.0 Hz, 1H), 7.46 (d, J=8.0 Hz, 1H), 7.57-7.61 (m, 2H), 7.74-7.77 (m, 1H), 7.99-8.03 (m, 3H), 8.05-8.09 (m, 2H), 8.14 (d, J=5.6 Hz, 1H), 8.16 (d, J=5.2 Hz, 1H), 8.46 (d, J=9.2 Hz, 1H), 11.23 (s, 1H).

Synthesis of 9-(4-methylpyridin-2-yl)-2-(3-(quinolin-2-yl)phenoxy)-9H-carbazole Ligand ON11Me

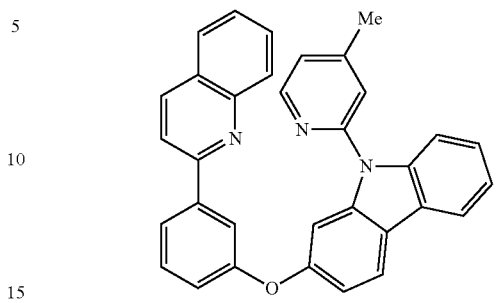

To a dry pressure vessel equipped with a magnetic stir bar was added 2-(3-(quinolin-2-yl)phenoxy)-9H-carbazole (773 mg, 2.0 mmol, 1.0 eq), CuI (76 mg, 0.4 mmol, 0.2 eq), and $K_2CO_3$ (553 mg, 4.0 mmol, 2.0 eq). The vessel was evacuated and back-filled with nitrogen. The evacuation and back-fill procedure was repeated twice. Then 2-bromo-4-methylpyridine (1032 mg, 6.0 mmol, 3.0 eq), 1-methyl-1H-imidazole (158 uL, 2.0 mmol, 1.0 eq) and solvent toluene (32 mL) were added under nitrogen. After bubbling with nitrogen for 25 minutes, the mixture was stirred in an oil bath at a temperature of 120° C. for three days, and cooled to ambient temperature. The solid was filtered off and washed with ethyl acetate. The filtrate was concentrated and the residue was purified through column chromatography on silica gel using hexane and ethyl acetate (10:1-5:1-3:1) as an eluent to afford the desired product Ligand ON11Me as a sticky liquid (955 mg) in 99%. $^1$H NMR (DMSO-$d_6$, 400 MHz): δ 2.38 (s, 3H), 7.09 (dd, J=8.4, 2.4 Hz, 1H), 7.18 (dd, J=8.4, 2.4 Hz, 1H), 7.25 (d, J=5.2 Hz, 1H), 7.32 (t, J=7.6 Hz, 1H), 7.43 (t, J=7.6 Hz, 1H), 7.50 (d, J=2.0 Hz, 1H), 7.54-7.60 (m, 3H), 7.72-7.77 (m, 2H), 7.97-8.04 (m, 4H), 8.13 (d, J=9.2 Hz, 1H), 8.21 (d, J=7.6 Hz, 1H), 8.27 (d, J=8.0 Hz, 1H), 8.44 (d, J=8.8 Hz, 1H), 8.49 (d, J=4.8 Hz, 1H).

Synthesis of 9-(4-methylpyridin-2-yl)-2-(3-(quinolin-2-yl)phenoxy)-9H-carbazole platinum complex PtON11Me

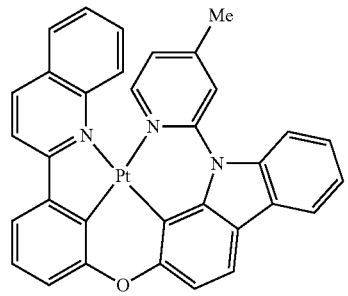

9-(4-Methylpyridin-2-yl)-2-(3-(quinolin-2-yl)phenoxy)-9H-carbazole Ligand ON11Me (955 mg, 2.0 mmol, 1.0 eq), $K_2PtCl_4$ (872 mg, 2.1 mmol, 1.05 eq), $^nBu_4NBr$ (65 mg, 0.2 mmol, 0.1 eq) and solvent acetic acid (120 mL) were added to a dry pressure tube equipped with a magnetic stir bar in nitrogen atmosphere. After bubbling with nitrogen for 30 minutes, the mixture was stirred at room temperature for 17 hours, followed at 110-115° C. for three days, cooled to ambient temperature and water (120 mL) was added slowly. After stirring at room temperature for 10 minutes, the precipitate was filtered off and washed with water three times, and dried in air. The collected solid was purified through column chromatography on silica gel using dichloromethane as an eluent to afford the desired product platinum complex PtON11Me as a red solid (907 mg in 68% yield). The product was further purified by sublimation in a sublimator with four zone controllers under high vacuum (270° C., 270° C., 200° C., 170° C., 2.9×10$^{-6}$ Pa) in 76% yield. $^1$H NMR (DMSO-d$_6$, 400 MHz): δ 2.37 (s, 3H), 6.88 (d, J=6.8 Hz, 1H), 7.19 (d, J=8.0 Hz, 1H), 7.26 (d, J=8.0 Hz, 1H), 7.35 (t, J=7.6 Hz, 1H), 7.44 (t, J=7.6 Hz, 1H), 7.54 (t, J=8.0 Hz, 1H), 7.64-7.69 (m, 2H), 7.96 (d, J=8.8 Hz, 1H), 7.98 (d, J=8.8 Hz, 1H), 7.99 (s, 1H), 8.18-8.22 (m, 3H), 8.34-8.36 (m, 2H), 8.51 (d, J=9.2 Hz, 1H), 8.76 (d, J=8.8 Hz, 1H). $^{13}$C NMR (DMSO-d$_6$, 100 MHz): 620.92, 98.59, 112.23, 115.01, 115.46, 115.74, 115.81, 117.84, 118.20, 119.88, 120.56, 121.04, 122.74, 124.35, 124.49, 125.65, 126.41, 126.81, 127.71, 128.64, 128.89, 130.40, 137.87, 139.41, 142.18, 145.43, 147.57, 147.97, 150.64, 151.45, 151.76, 152.16, 165.17. MS (MALDI) for C$_{33}$H$_{21}$N$_3$OPt [M]$^+$: calcd 670.1. found 670.6.

Synthesis of PtN13N

Figure 4:
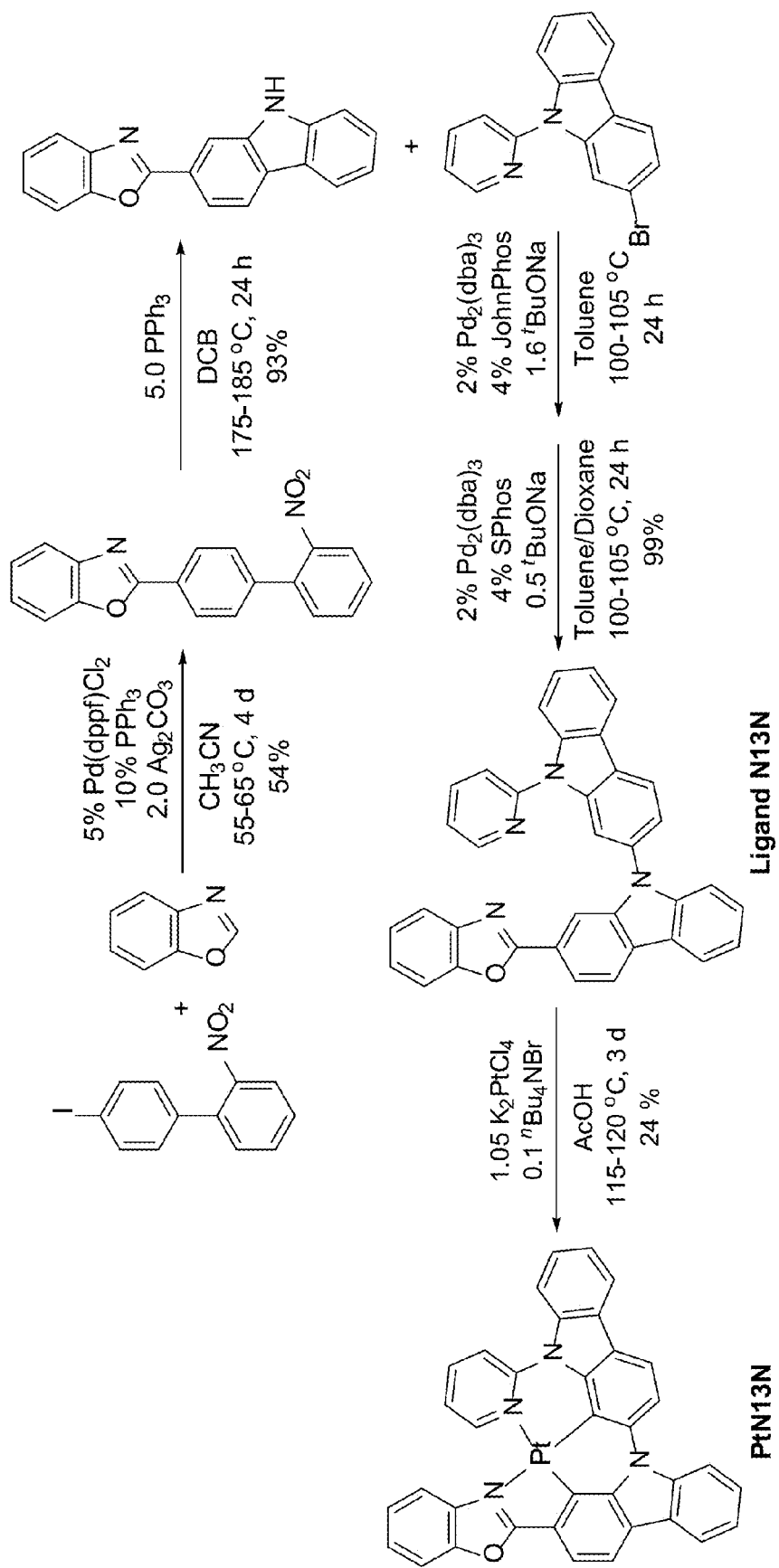
FIG. 4 depicts a method of synthesizing PtN13N.

PtN13N was synthesized as shown in FIG. 4.

Synthesis of 2-(2'-nitrobiphenyl-4-yl)benzo[d]oxazole

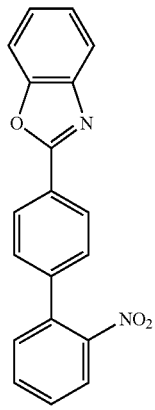 [SMILES: O=[N+]([O-])c1ccccc1-c1ccc(-c2nc3ccccc3o2)cc1]

To a three-necked flask equipped with a magnetic stir bar was added 4'-iodo-2-nitrobiphenyl (1.63 g, 5.0 mmol, 1.0 equiv), benzo[d]oxazole (0.72 g, 6.0 mmol, 1.2 equiv), Ag$_2$CO$_3$ (2.76 g, 10.0 mmol, 2.0 eq), Pd(dppf)Cl$_2$.CH$_2$Cl$_2$ (0.20 g, 0.25 mmol, 0.05 eq) and PPh$_3$ (0.13 g, 0.5 mmol, 0.1 eq). The tube was evacuated and back-filled with nitrogen and this evacuation/back-fill procedure was repeated twice. Then solvent CH$_3$CN (25 mL) was added under the protection of nitrogen. The mixture was stirred in an oil bath at a temperature of 55-65° C. for 4 days and then cooled. The solid was filtered off through a pad of celite and washed with ethyl acetate. The filtrate was concentrated under reduced pressure and the residue was purified through column chromatography on silica gel using hexane and ethyl acetate (10:1-5:1) as an eluent to afford the desired product 2-(2'-nitrobiphenyl-4-yl)benzo[d]oxazole (0.85 g in 54% yield). $^1$H NMR (DMSO-d$_6$, 400 MHz): δ 7.43-7.49 (m, 2H), 7.61-7.63 (m, 2H), 7.66 (d, J=7.6 Hz, 1H), 7.69-7.73 (m, 1H), 7.83-7.87 (m, 3H), 8.08 (d, J=8.8 Hz, 1H), 8.30 (dd, J=8.0, 1.2 Hz, 2H).

Synthesis of 2-(9H-carbazol-2-yl)benzo[d]oxazole

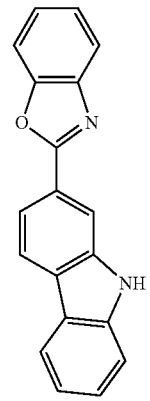 [SMILES: c1ccc2oc(-c3ccc4c(c3)[nH]c3ccccc34)nc2c1]

To a three-necked flask equipped with a magnetic stir bar and a condenser was added 2-(2'-nitrobiphenyl-4-yl)benzo[d]oxazole (1.08 g, 3.41 mmol, 1.0 eq) and PPh$_3$ (4.48 g, 17.07 mmol, 5.0 eq). The flask was evacuated and back-filled with nitrogen. The evacuation and back-fill procedure was repeated twice. Then 1,2-dichlorobenzene (20 mL) was added under the protection of nitrogen. The mixture was stirred in an oil bath at a temperature of 175-185° C. for 24 hours, and cooled. The solvent was removed by distillation under high vacuum. Some ethyl acetate and dichloromethane was added to the residue and stirred at room temperature overnight. The residue was filtered and washed with dichloromethane. The collected solid was dried in air to get the desired product as an off-white solid 809 mg. The filtrate was concentrated and the residue was purified through column chromatography on silica gel using hexane and ethyl acetate (10:1-5:1-3:1) as an eluent to obtain the desired product (117 mg in 96% total yield). $^1$H NMR (DMSO-d$_6$, 400 MHz): δ 7.25 (t, J=7.6 Hz, 1H), 7.41-7.52 (m, 3H), 7.60 (d, J=8.4 Hz, 1H), 7.82-7.86 (m, 2H), 8.05 (dd, J=8.4, 1.2 Hz, 1H), 8.24 (d, J=7.2 Hz, 1H), 8.34-8.37 (m, 2H), 11.63 (s, 1H).

Synthesis of 2-(9-(pyridin-2-yl)-9H-2,9'-bicarbazol-2'-yl)benzo[d]oxazole Ligand N13N

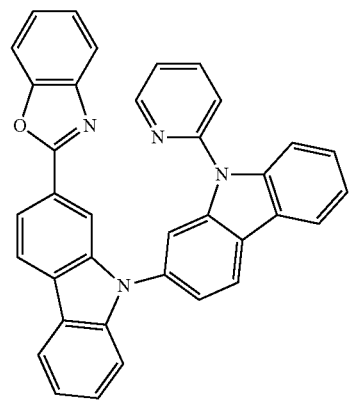

Ligand N13N

To a dry Schlenk tube equipped with a magnetic stir bar was added 2-(9H-carbazol-2-yl)benzo[d]oxazole (569 mg, 2.0 mmol, 1.0 eq), 2-bromo-9-(pyridin-2-yl)-9H-carbazole (711 mg, 2.2 mmol, 1.1 eq), Pd$_2$(dba)$_3$ (37 mg, 0.04 mmol, 0.02 eq), JohnPhos (24 mg, 0.04 mmol, 0.04 eq) and $^t$BuONa (308 mg, 3.2 mmol, 1.6 eq). The tube was evacuated and back-filled with nitrogen, and this evacuation/back-fill procedure was repeated twice. Then dry toluene (16 mL) was added under the atmosphere of nitrogen, the tube was then sealed quickly. The mixture was stirred in an oil bath at a temperature of 100-105° C. The reaction was monitored by TLC. 24 hours later, some starting material was not consumed. So more Pd$_2$(dba)$_3$ (37 mg, 0.04 mmol, 0.02 eq), SPhos (33 mg, 0.08 mmol, 0.04 eq) and $^t$BuONa (96 mg, 1.0 mmol, 0.5 eq) and dioxane (3 mL) were added. The mixture was stirred in an oil bath at a temperature of 105-105° C. for another 24 hours and cooled to ambient temperature. The mixture was concentrated and the residue was purified through column chromatography on silica gel using dichloromethane/methanol (10:1) as an eluent to obtain the desired product, 2-(9-(pyridin-2-yl)-9H-2,9'-bicarbazol-2'-yl)benzo[d]oxazole Ligand N13N, as a brown solid (1056 mg in 99% yield). $^1$H NMR (DMSO-d$_6$, 400 MHz): δ 7.37-7.50 (m, 6H), 7.52-7.61 (m, 2H), 7.66 (dd, J=8.0, 1.6 Hz, 1H), 7.75-7.78 (m, 2H), 7.91 (d, J=8.4 Hz, 2H), 8.06-8.11 (m, 2H), 8.17-8.19 (m, 2H), 8.40 (d, J=7.6 Hz, 1H), 8.45 (d, J=7.6 Hz, 1H), 8.52 (d, J=7.2 Hz, 1H), 8.64 (d, J=8.4 Hz, 1H), 8.67-8.68 (m, 1H).

Synthesis of 2-(9-(pyridin-2-yl)-9H-2,9'-bicarbazol-2'-yl)benzo[d]oxazole platinum complex PtN13N

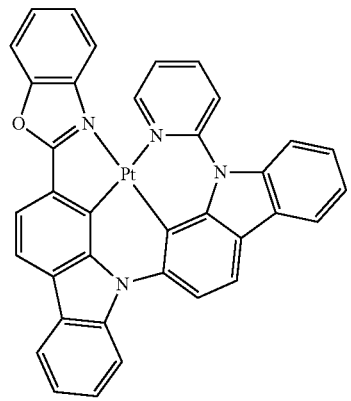

To a dry pressure tube equipped with a magnetic stir bar was added 2-(9-(pyridin-2-yl)-9H-2,9'-bicarbazol-2'-yl)benzo[d]oxazole Ligand N13N (620 mg, 1.17 mmol, 1.0 eq), K$_2$PtCl$_4$ (511 mg, 1.23 mmol, 1.05 eq) and $^n$Bu$_4$NBr (33 mg, 0.177 mmol, 0.1 eq). Then solvent acetic acid (70 mL) was added. The mixture was bubbled with nitrogen for 30 minutes and then the tube was sealed. The mixture was stirred in an oil bath at a temperature of 115-120° C. for three days. Then the mixture was cooled to ambient temperature and water (140 mL) was added slowly. The precipitate was filtered off and washed with water three times. Then the solid was dried in air under reduced pressure. The collected solid was purified through column chromatography on silica gel using dichloromethane/hexane (1:1) as an eluent to obtain the desired product, PtN13N, as an orange-red solid (205 mg in 24% yield). The product (250 mg) was further purified by sublimation in a sublimator with four zone controllers at 280° C., 280° C., 220° C., 180° C., 3.4×10$^{-6}$ Torr to obtain orange-red solid (210 mg in 84% yield). $^1$H NMR (DMSO-d$_6$, 400 MHz): δ 7.34 (t, J=7.6 Hz, 1H), 7.40-7.47 (m, 2H), 7.52-7.61 (m, 5H), 7.72 (d, J=8.4 Hz, 1H), 7.99-8.09 (m, 4H), 8.12 (d, J=8.0 Hz, 1H), 8.24 (d, J=7.6 Hz, 1H), 8.26-8.31 (m, 4H), 8.37 (d, J=6.0 Hz, 1H). $^{13}$C NMR (DMSO-d$_6$, 100 MHz): δ 107.15, 112.23, 113.00, 113.89, 114.60, 115.44, 115.48, 116.59, 116.61, 117.58, 118.48, 119.55, 120.32, 120.65, 122.09, 122.99, 123.85, 125.03, 125.31, 125.65, 126.24, 127.44, 127.48, 127.55, 129.35, 137.27, 137.54, 137.67, 138.24, 139.90, 140.79, 143.14, 147.60, 150.65, 152.42, 176.81.

Synthesis of PtN8N-tBu

Figure 5:
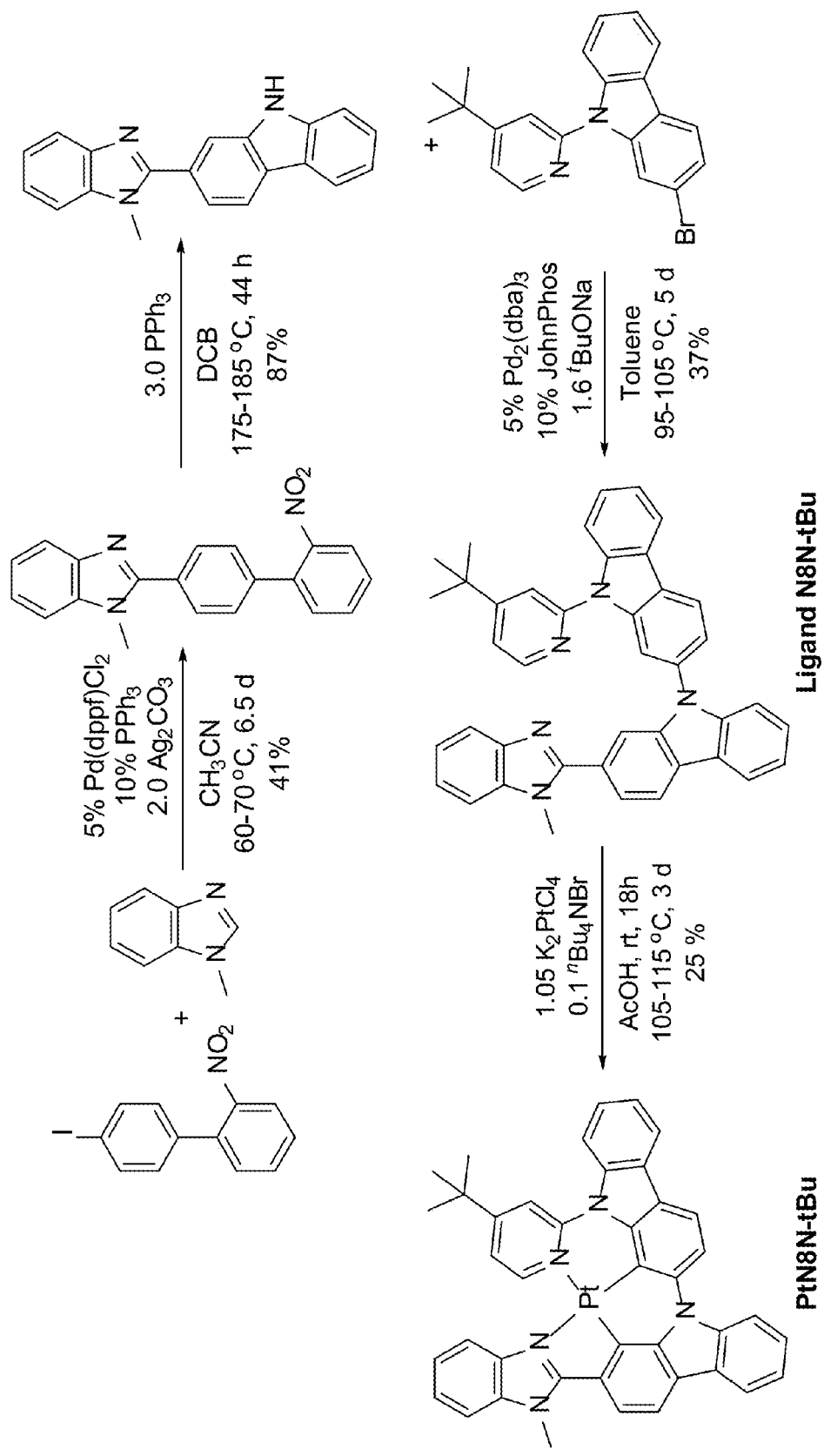
FIG. 5 depicts a method of synthesizing PtN8N-tBu.

PtN8N-tBu was synthesized as shown in FIG. 5.

Synthesis of 1-methyl-2-(2'-nitrobiphenyl-4-yl)-1H-benzo[d]imidazole

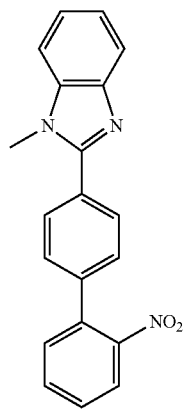 [SMILES: Cn1c(-c2ccc(-c3ccccc3[N+](=O)[O-])cc2)nc2ccccc21]

To a three-necked flask equipped with a magnetic stir bar was added 4'-iodo-2-nitrobiphenyl (3.90 g, 12.0 mmol, 1.2 equiv), 1-methyl-1H-benzo[d]imidazole (1.32 g, 10.0 mmol, 1.0 equiv), Ag$_2$CO$_3$ (5.52 g, 20.0 mmol, 2.0 eq), Pd(dppf)Cl$_2$.CH$_2$Cl$_2$ (0.41 g, 0.5 mmol, 0.05 eq) and PPh$_3$ (0.26 g, 1.0 mmol, 0.1 eq). The tube was evacuated and back-filled with nitrogen, and this evacuation/back-fill procedure was repeated twice. Then solvent CH$_3$CN (60 mL) was added under the protection of nitrogen. The mixture was stirred in an oil bath at a temperature of 60-70° C. for 6.5 days and then cooled. The solid was filtered off through a pad of celite, and washed with ethyl acetate. The filtrate was concentrated under reduced pressure and the residue was purified through column chromatography on silica gel using hexane and ethyl acetate (10:1-5:1-3:1-2:1) as an eluent to afford the desired product, 1-methyl-2-(2'-nitrobiphenyl-4-yl)-1H-benzo[d]imidazole, as a white solid (1.36 g in 41% yield). $^1$H NMR (DMSO-d$_6$, 400 MHz): δ 3.95 (s, 3H), 7.25-7.29 (m, 1H), 7.31-7035 (m, 1H), 7.57 (d, J=8.0 Hz, 2H), 7.65-7.72 (m, 4H), 7.84 (td, J=7.6, 1.2 Hz, 1H), 7.98 (d, J=7.6 Hz, 2H), 8.06-8.08 (m, 1H).

Synthesis of 1-methyl-2-(9H-carbazol-2-yl))-1H-benzo[d]imidazole

To a three-necked flask equipped with a magnetic stir bar and a condenser was added 1-methyl-2-(2'-nitrobiphenyl-4-yl)-1H-benzo[d]imidazole (1.30 g, 3.95 mmol, 1.0 eq) and PPh₃ (3.11 g, 11.84 mmol, 3.0 eq). The flask was evacuated and back-filled with nitrogen. The evacuation and back-fill procedure was repeated twice. Then 1,2-dichlorobenzene (20 mL) was added under the protection of nitrogen. The mixture was stirred in an oil bath at a temperature of 175-185° C. for 44 hours and cooled. The solvent was removed by distillation under high vacuum. The residue was purified through column chromatography on silica gel using hexane and ethyl acetate (10:1-5:1-3:1-2:1) as an eluent to obtain the desired product as a white solid (1.024 g, in 87% yield). ¹H NMR (DMSO-d₆, 400 MHz): δ 3.94 (s, 3H), 7.18-7.31 (m, 3H), 7.44 (td, J=7.6, 1.6 Hz, 1H), 7.55 (d, J=8.0 Hz, 1H), 7.60-7.64 (m, 2H), 7.69 (dd, J=6.4, 1.2 Hz, 1H), 7.94 (d, J=0.8 Hz, 1H), 8.19 (d, J=7.6 Hz, 1H), 8.28 (d, J=7.6 Hz, 1H), 11.49 (s, 1H).

Synthesis of 9-(4-tert-butylpyridin-2-yl)-2'-(1-methyl-1H-benzo[d]imidazol-2-yl)-9H-2,9'-bicarbazole Ligand N8N-tBu

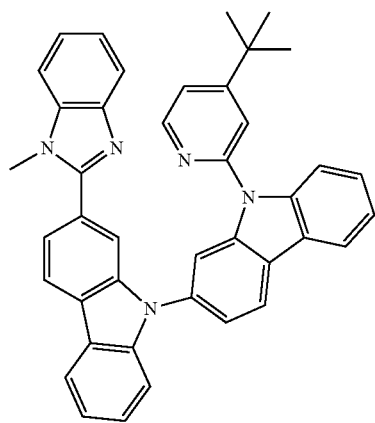 [SMILES: Cn1c(-c2ccc3c4ccccc4n(-c4ccc5c6ccccc6n(-c6cc(C(C)(C)C)ccn6)c5c4)c3c2)nc2ccccc21]

To a dry Schlenk tube equipped with a magnetic stir bar was added 1-methyl-2-(9H-carbazol-2-yl))-1H-benzo[d]imidazole (183 mg, 0.62 mmol, 1.0 eq), 9-(4-tert-butylpyridin-2-yl)-2-bromo-9H-carbazole (355 mg, 0.93 mmol, 1.5 eq), Pd₂(dba)₃ (28 mg, 0.031 mmol, 0.05 eq), JohnPhos (19 mg, 0.062 mmol, 0.10 eq) and ᵗBuONa (95 mg, 0.99 mmol, 1.6 eq). The tube was evacuated and back-filled with nitrogen, and this evacuation/back-fill procedure was repeated twice. Then dry toluene (7 mL) and dioxane (7 mL) were added under the atmosphere of nitrogen, and the tube was then sealed quickly. The mixture was then stirred in an oil bath at a temperature of 95-105° C. for 5 days and cooled to ambient temperature. The mixture was concentrated and the residue was purified through column chromatography on silica gel using dichloromethane/methanol (5:1-3:1) as an eluent to obtain the desired product, 9-(4-tert-butylpyridin-2-yl)-2'-(1-methyl-1H-benzo[d]imidazol-2-yl)-9H-2,9'-bicarbazole Ligand N8N-tBu, as a gray solid (135 mg in 37% yield). ¹H NMR (DMSO-d₆, 400 MHz): δ 1.27 (s, 9H), 3.91 (s, 3H), 7.22 (t, J=8.0 Hz, 1H), 7.29 (t, J=8.4 Hz, 1H), 7.38 (t, J=8.0 Hz, 1H), 7.42-7.47 (m, 2H), 7.52 (d, J=8.0 Hz, 1H), 7.55-7.67 (m, 5H), 7.80-7.85 (m, 3H), 7.92 (s, 1H), 8.03 (d, J=1.6 Hz, 1H), 8.40 (t, J=7.2 Hz, 2H), 8.48 (d, J=8.0 Hz, 1H), 8.57-8.60 (m, 2H).

Synthesis of 9-(4-tert-butylpyridin-2-yl)-2'-(1-methyl-1H-benzo[d]imidazol-2-yl)-9H-2,9'-bicarbazole platinum complex PtN8N-tBu

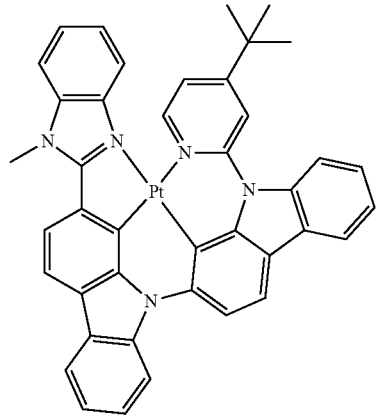

To a dry pressure tube equipped with a magnetic stir bar was added 9-(4-tert-butylpyridin-2-yl)-2'-(1-methyl-1H-benzo[d]imidazol-2-yl)-9H-2,9'-bicarbazole Ligand N8N-tBu (130 mg, 0.218 mmol, 1.0 eq), K₂PtCl₄ (95 mg, 0.229 mmol, 1.05 eq) and ⁿBu₄NBr (7 mg, 0.0218 mmol, 0.1 eq). Then solvent acetic acid (20 mL) was added. The mixture was bubbled with nitrogen for 30 minutes and then the tube was sealed. The mixture was stirred in an oil bath at room temperature for 18 hours, followed at 105-115° C. for three days. Then the mixture was cooled to ambient temperature and water (40 mL) was added slowly. The precipitate was filtered off and washed with water three times. Then the solid was dried in air under reduced pressure. The collected solid was purified through column chromatography on silica gel using dichloromethane/hexane (1:1) as an eluent to obtain the desired product, PtN8N-tBu, as a yellow solid (43 mg in 25% yield). ¹H NMR (DMSO-d₆, 400 MHz): δ 1.40 (s, 9H), 4.39 (s, 3H), 7.32 (d, J=7.6 Hz, 1H), 7.36 (d, J=7.6 Hz, 1H), 7.37-7.48 (m, 4H), 7.52-7.59 (m, 2H), 7.90 (d, J=8.0 Hz, 1H), 7.97 (d, J=8.0 Hz, 1H), 7.99-8.01 (m, 3H), 8.12 (s, 1H), 8.16 (d, J=8.4 Hz, 1H), 8.24 (d, J=8.4 Hz, 2H), 8.28 (d, J=7.6 Hz, 1H), 9.19 (d, J=6.0 Hz, 1H). ¹³C NMR (CDCl₃, 100 MHz): δ 30.25, 35.66, 109.96, 110.14, 113.09, 113.24, 113.73, 114.47, 114.69, 114.83, 115.66, 115.67, 116.54, 117.60, 117.64, 119.94, 120.34, 121.29, 122.18, 122.44, 122.91, 123.33, 124.47, 126.19, 126.43, 128.77, 129.26, 132.49, 136.36, 138.64, 138.95, 139.04, 139.89, 140.74, 144.44, 149.00, 152.87, 163.70.

Figure 6:
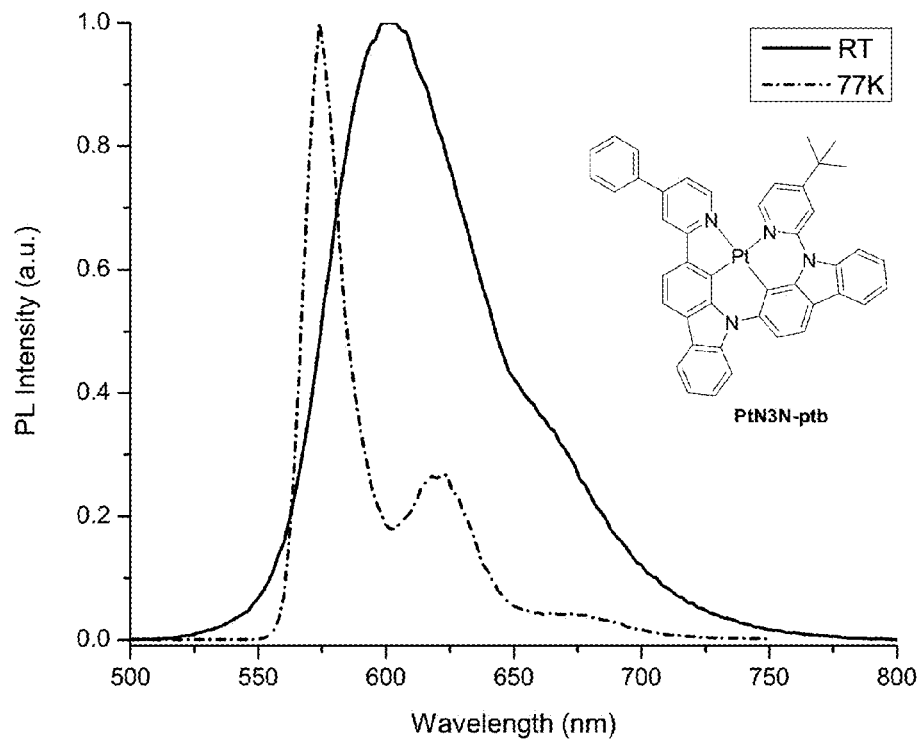
FIG. 6 shows emission spectra of PtN3N-ptb in $CH_2Cl_2$ at room temperature and in 2-methyltetrahydrofuran at 77K.

FIG. 6 shows emission spectra of PtN3N-ptb in $CH_2Cl_2$ at room temperature and in 2-methyltetrahydrofuran at 77K.

Figure 7:
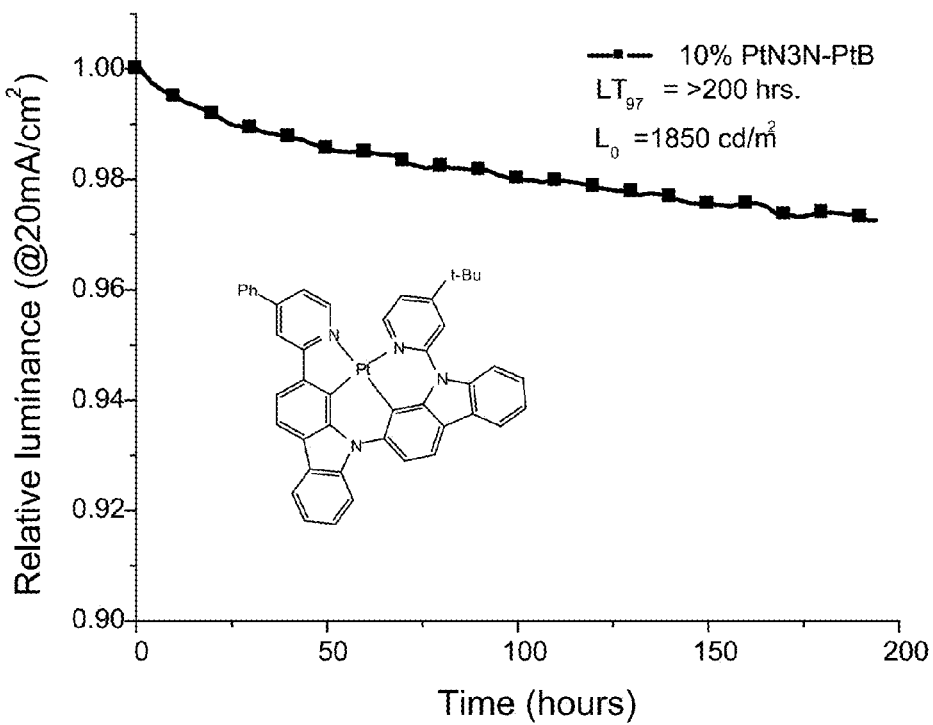
FIG. 7 shows relative luminance versus operational time for a light-emitting device with PtN3N-ptb.

FIG. 7 shows relative luminance at the constant of 20 $mA/cm^2$ versus operational time for a device having a structure of ITO/HATCN(10 nm)/NPD(40 nm)/10% PtN3N-ptb:CBP(25 nm)/BAlq(10 nm)/AlQ$_3$(30 nm)/LiF/Al.

Figure 8:
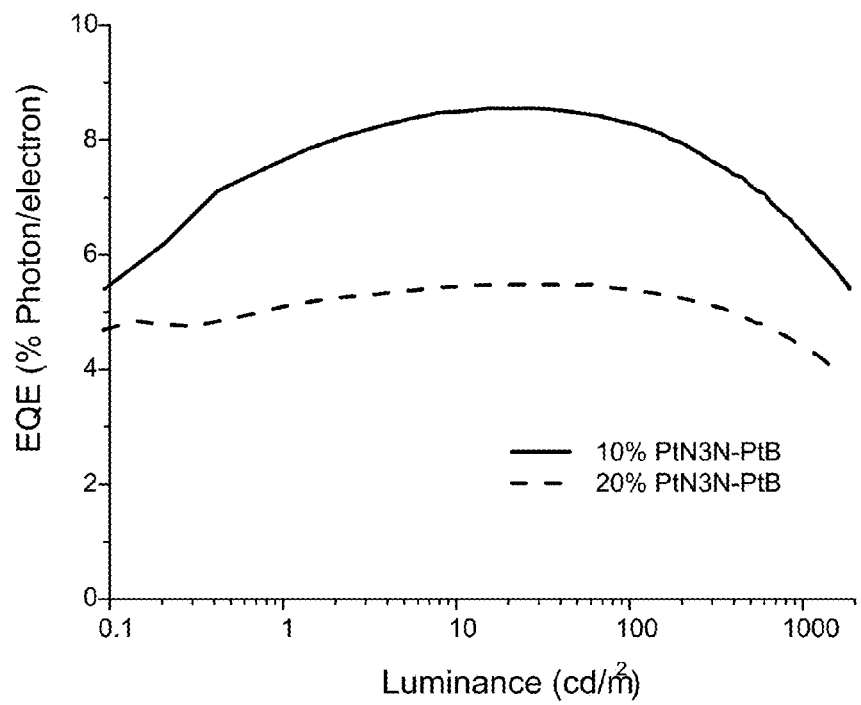
FIG. 8 shows EQE versus luminance for a light-emitting device with PtN3N-ptb.

FIG. 8 shows EQE versus luminance for a device having a structure of ITO/HATCN(10 nm)/NPD(40 nm)/10% PtN3N-ptb:CBP(25 nm)/BAlq(10 nm)/AlQ$_3$(30 nm)/LiF/Al.

Figure 9:
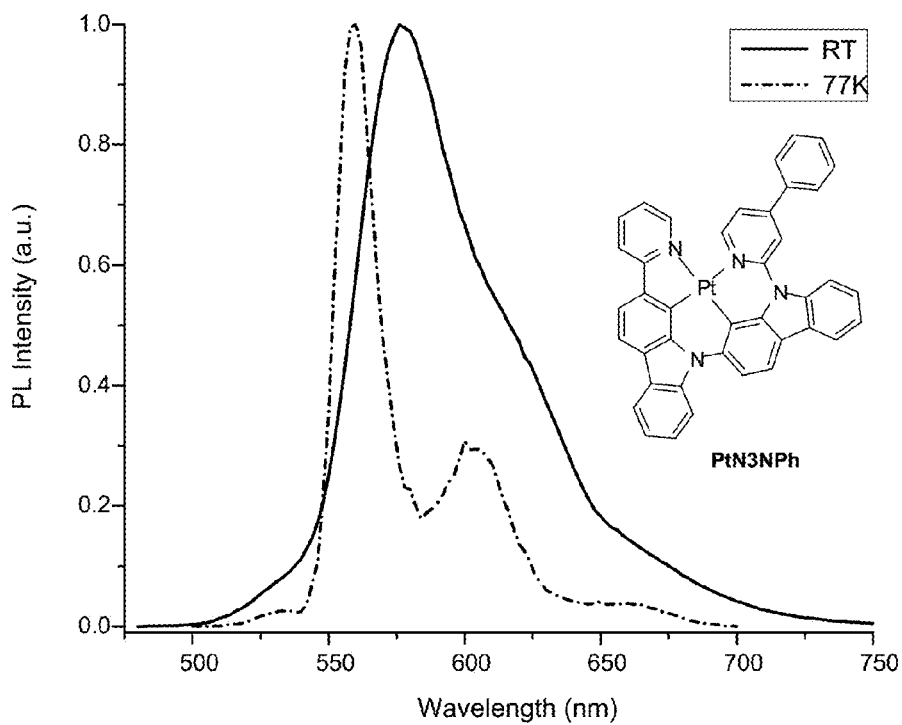
FIG. 9 shows emission spectra of PtN3NPh in $CH_2Cl_2$ at room temperature and in 2-methyltetrahydrofuran at 77K.

FIG. 9 shows emission spectra of PtN3NPh in $CH_2Cl_2$ at room temperature and in 2-methyltetrahydrofuran at 77K.

Figure 10:
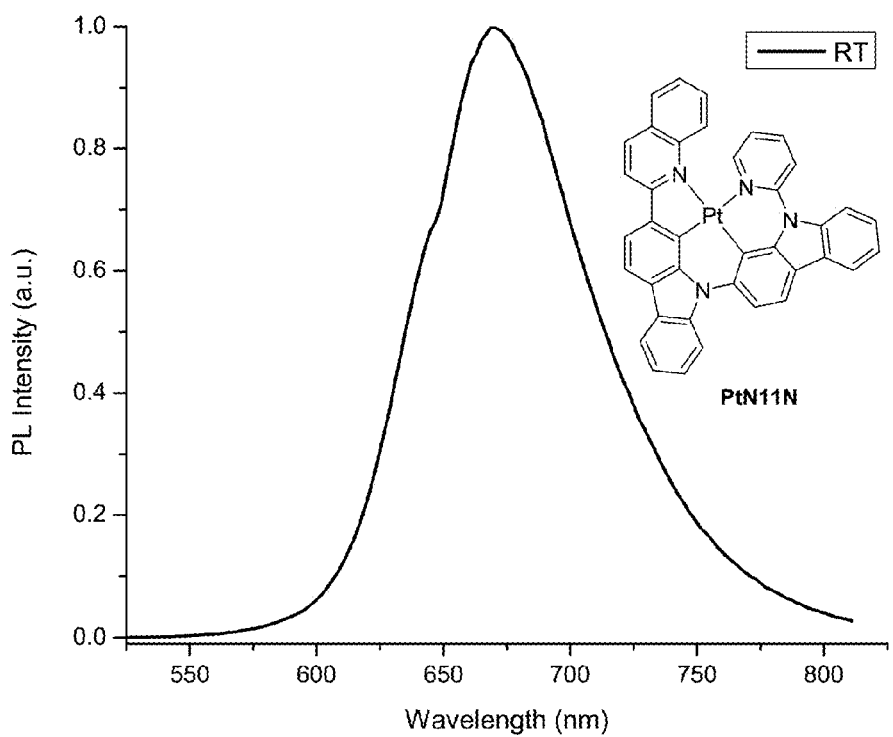
FIG. 10 shows an emission spectrum of PtN11N in $CH_2Cl_2$ at room temperature.

FIG. 10 shows an emission spectrum of PtN11N in $CH_2Cl_2$ at room temperature.

Figure 11:
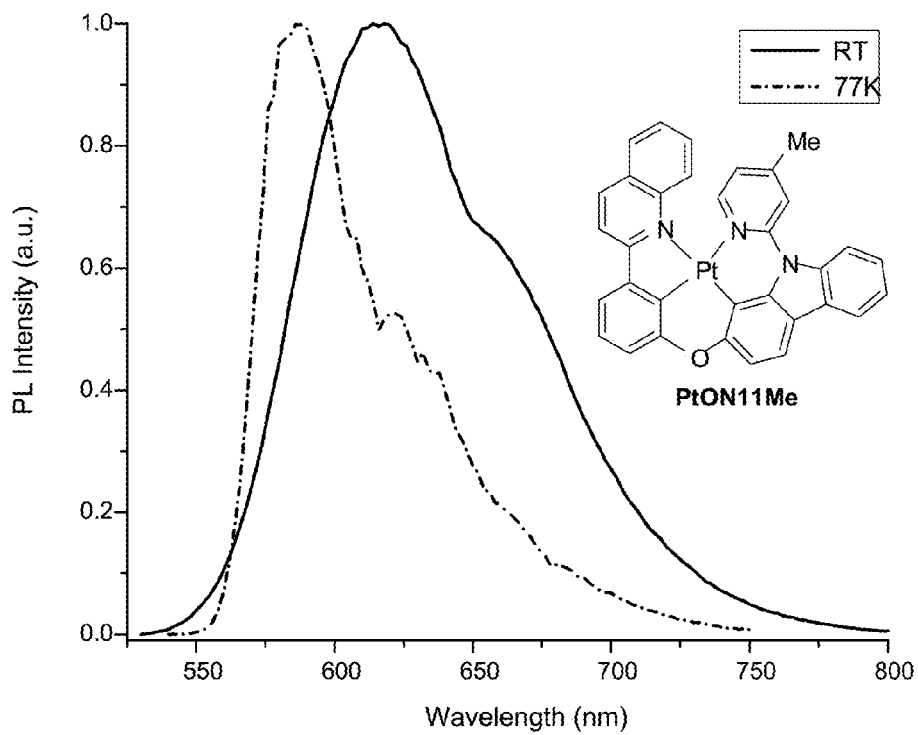
FIG. 11 shows emission spectra of PtON11Me in $CH_2Cl_2$ at room temperature and in 2-methyltetrahydrofuran at 77K.

FIG. 11 shows emission spectra of PtON11Me in $CH_2Cl_2$ at room temperature and in 2-methyltetrahydrofuran at 77K.

Figure 12:
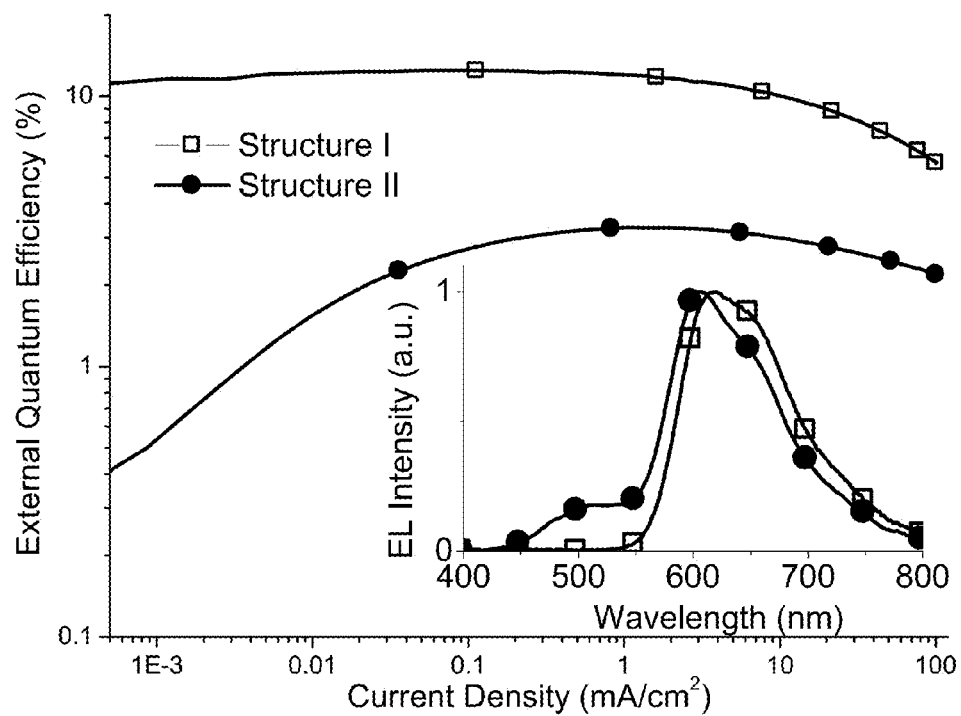
FIG. 12 shows normalized EL spectra and external quantum efficiency-versus current density for PtON11Me in various devices.

FIG. 12 shows normalized EL spectra (inset) and the external quantum efficiency-versus current density for PtON11Me in Structure I (open squares): ITO/HATCN(10 nm)/NPD(40 nm)/TAPC(10 nm)CBP:PtON11Me(2%)/DPPS(10 nm)/BmPyPB(40 nm)/LiF(1 nm)/Al(100 nm) and Structure II (closed circles): ITO/HATCN(10 nm)/NPD(40 nm)/CBP:PtON11Me(2%)/BAlq(10 nm)/Alq(30 nm)/LiF(1 nm)/Al (100 nm).

Figure 13:
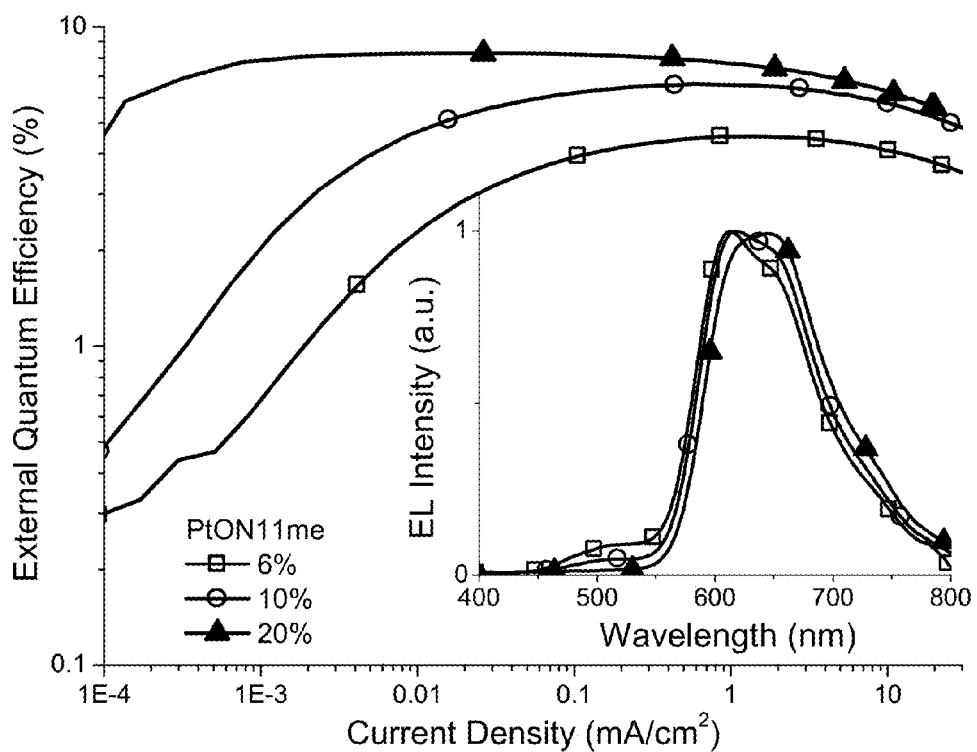
FIG. 13 shows normalized EL spectra and the external quantum efficiency-versus current density for PtON11Me in various devices.

FIG. 13 shows normalized EL spectra (inset) and the external quantum efficiency-versus current density for PtON11Me in Structure II: ITO/HATCN(10 nm)/NPD(40 nm)/CBP: PtON11Me/BAlq(10 nm)/ALQ(30 nm)/LiF(1 nm)/Al(100 nm) for 6% (open squares), 10% (open circles), and 20% (open triangles) PtON11Me concentration in CBP.

Figure 14:
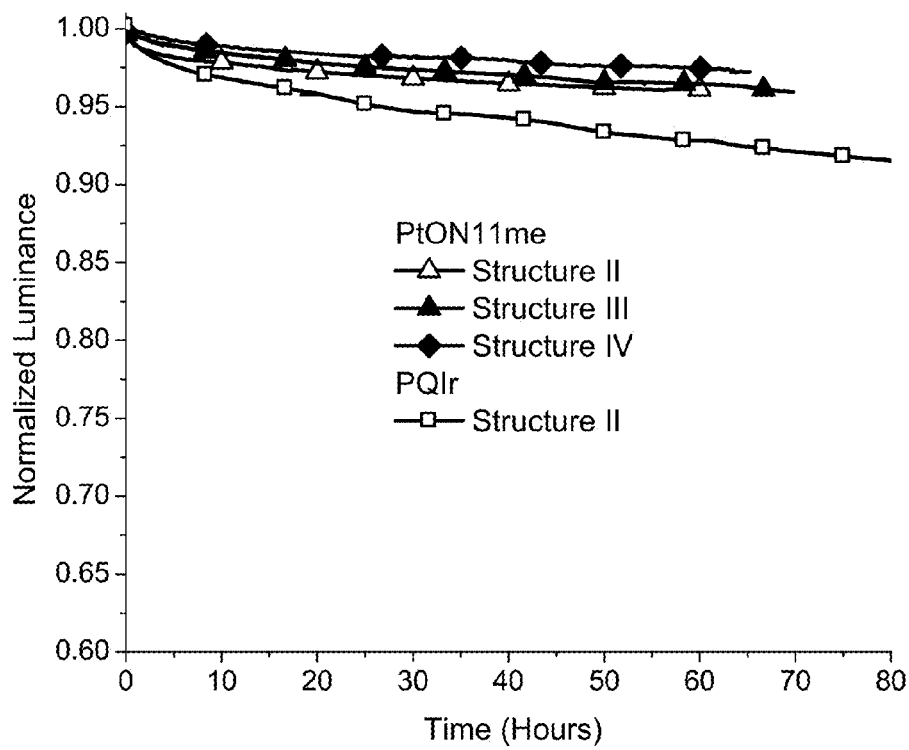
FIG. 14 shows normalized luminance versus time for various devices.

FIG. 14 shows normalized luminance versus time under constant direct current of 20 $mA/cm^2$ for devices of PtON11Me under constant direct current of 20 $mA/cm^2$ for PtON11Me Structure II (open triangles), Structure III (solid triangles), and Structure IV (solid diamonds). The normalized luminance versus time for devices of PQIr in structure II (open squares) is also shown.

Figure 15:
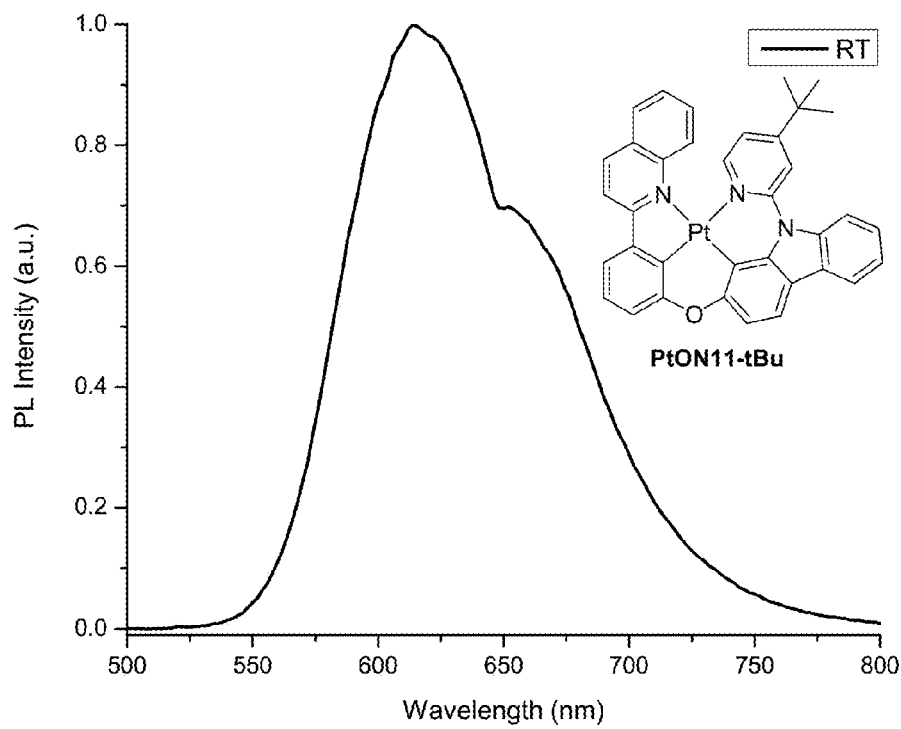
FIG. 15 shows an emission spectrum of PtON11-tBu in $CH_2Cl_2$ at room temperature.

FIG. 15 shows an emission spectrum of PtON11-tBu in $CH_2Cl_2$ at room temperature.

Figure 16:
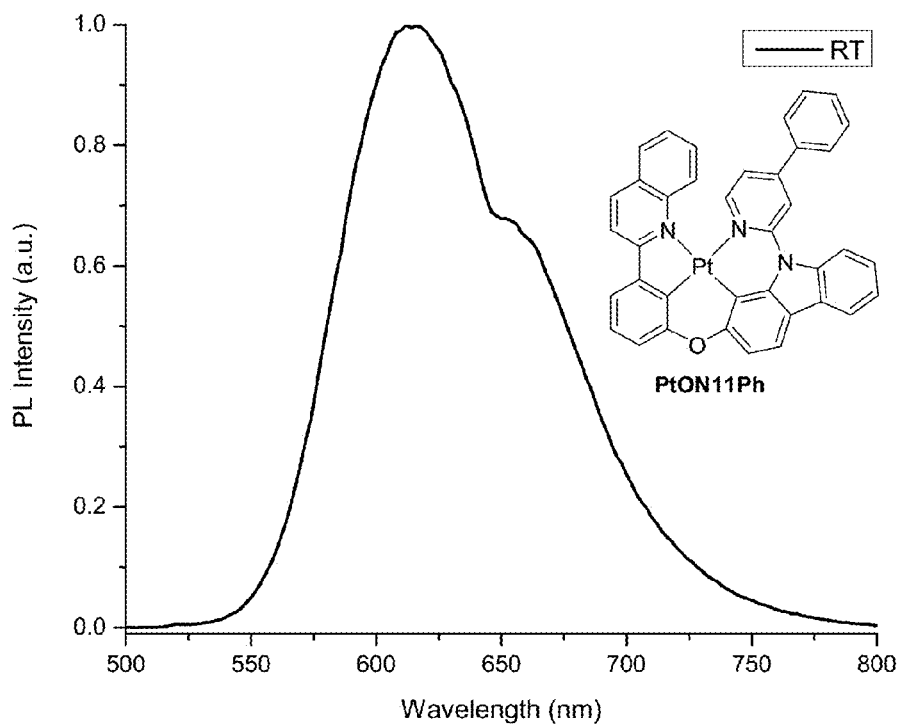
FIG. 16 shows an emission spectrum of PtON11Ph in $CH_2Cl_2$ at room temperature.

FIG. 16 shows an emission spectrum of PtON11Ph in $CH_2Cl_2$ at room temperature.

Figure 17:
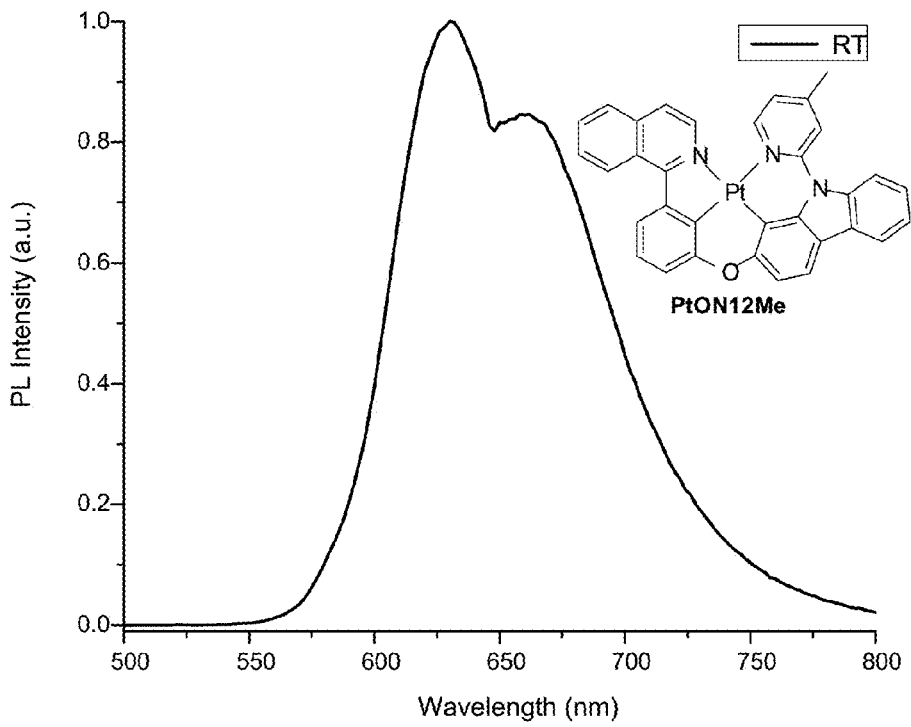
FIG. 17 shows an emission spectrum of PtON12Me in $CH_2Cl_2$ at room temperature.

FIG. 17 shows an emission spectrum of PtON12Me in $CH_2Cl_2$ at room temperature.

Figure 18:
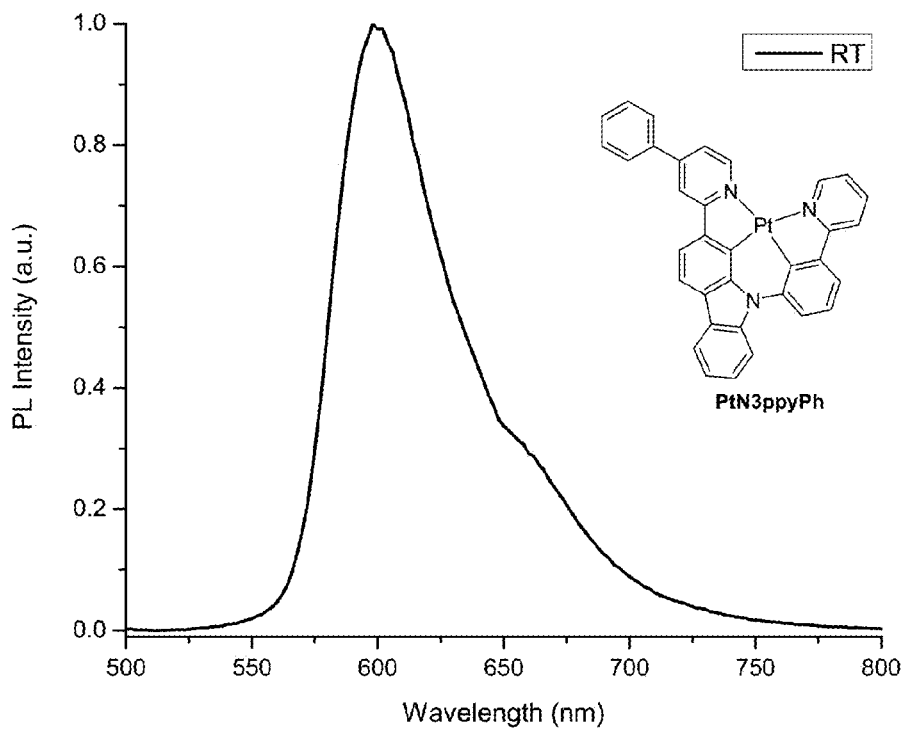
FIG. 18 shows an emission spectrum of PtN3 ppyPh in $CH_2Cl_2$ at room temperature.

FIG. 18 shows an emission spectrum of PtN3ppyPh in $CH_2Cl_2$ at room temperature.

Figure 19:
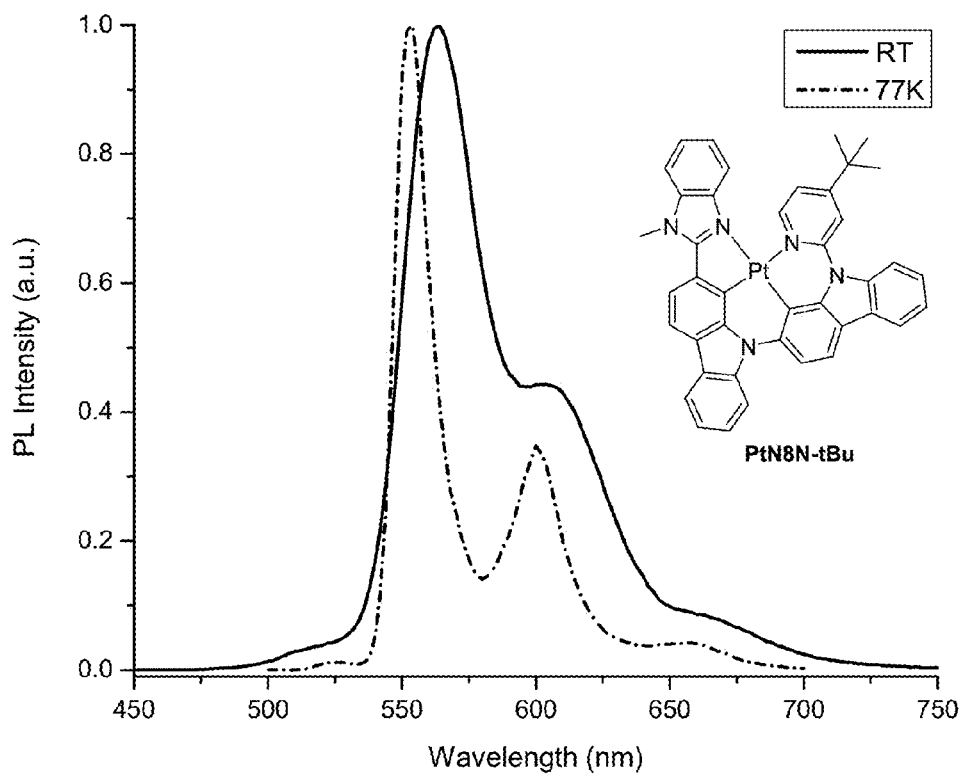
FIG. 19 shows emission spectra of PtN8N-tBu in $CH_2Cl_2$ at room temperature and in 2-methyltetrahydrofuran at 77K.

FIG. 19 shows an emission spectra of PtN8N-tBu in $CH_2Cl_2$ at room temperature and in 2-methyltetrahydrofuran at 77K.

Figure 20:
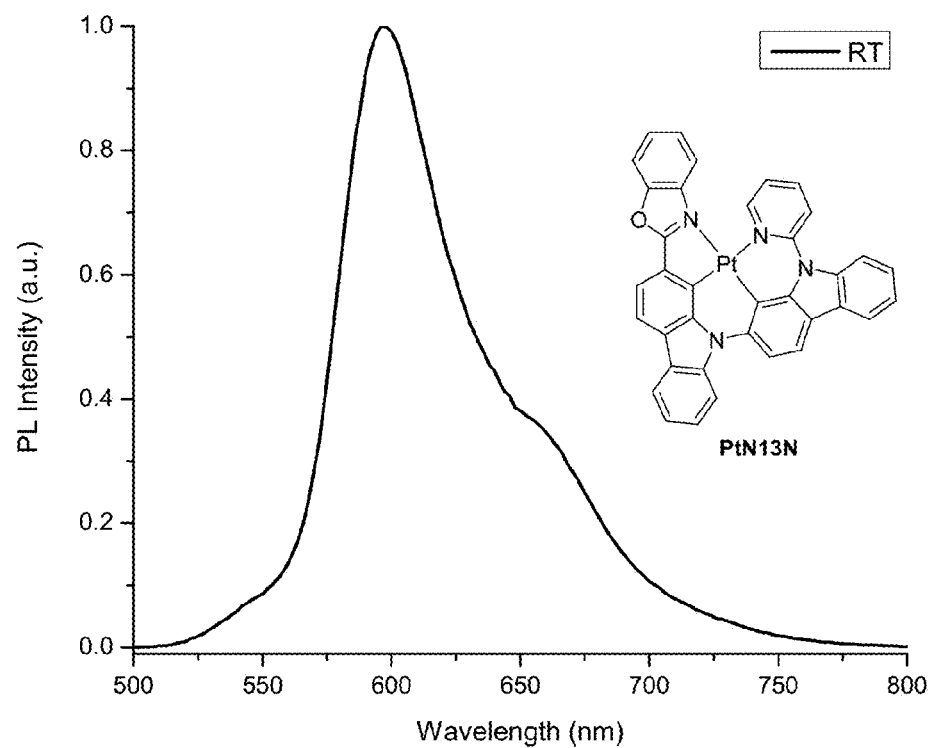
FIG. 20 shows an emission spectrum of PtN13N in $CH_2Cl_2$ at room temperature.

FIG. 20 shows an emission spectrum of PtN13N in $CH_2Cl_2$ at room temperature.

Figure 21:
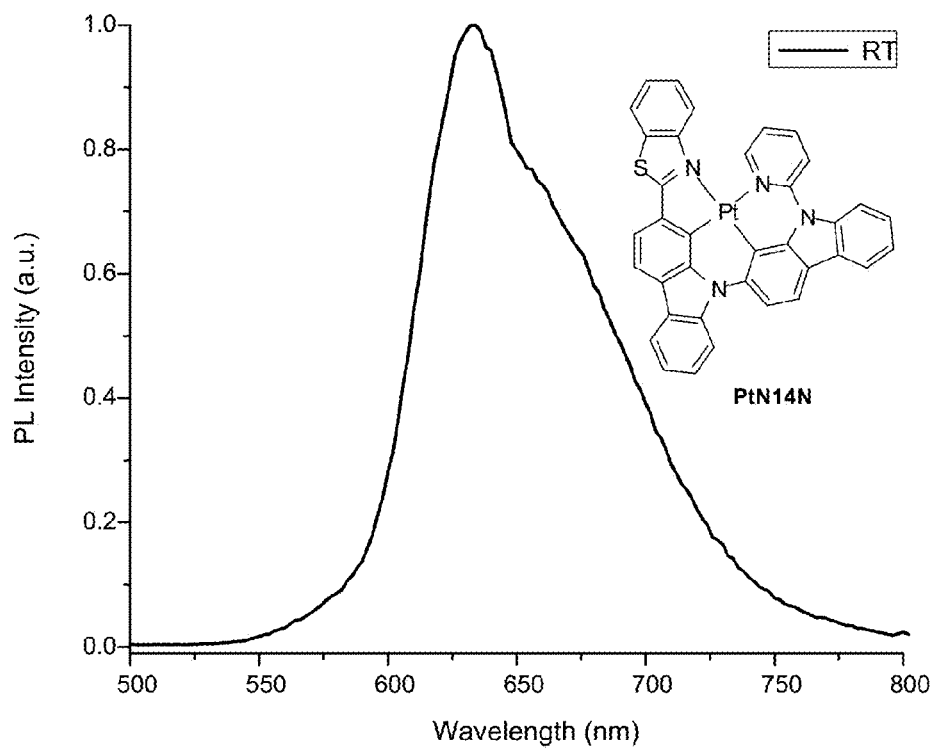
FIG. 21 shows an emission spectrum of PtN14N in $CH_2Cl_2$ at room temperature.

FIG. 21 shows an emission spectrum of PtN14N in $CH_2Cl_2$ at room temperature.

Figure 22:
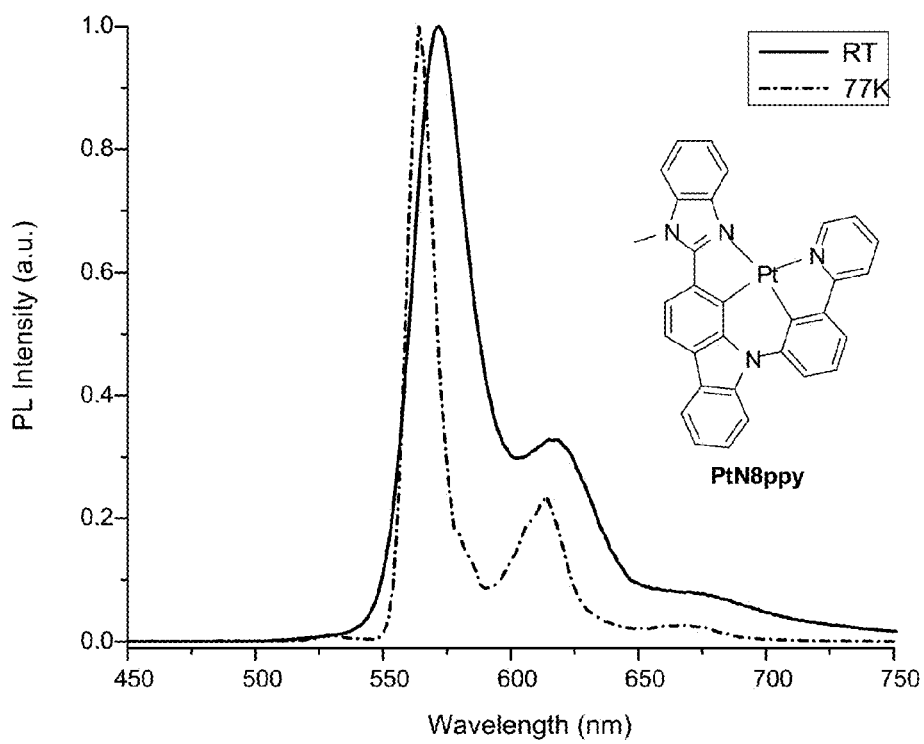
FIG. 22 shows emission spectra of PtN8ppy in $CH_2Cl_2$ at room temperature and in 2-methyltetrahydrofuran at 77K.

FIG. 22 shows emission spectra of PtN8 ppy in $CH_2Cl_2$ at room temperature and in 2-methyltetrahydrofuran at 77K.

Figure 23:
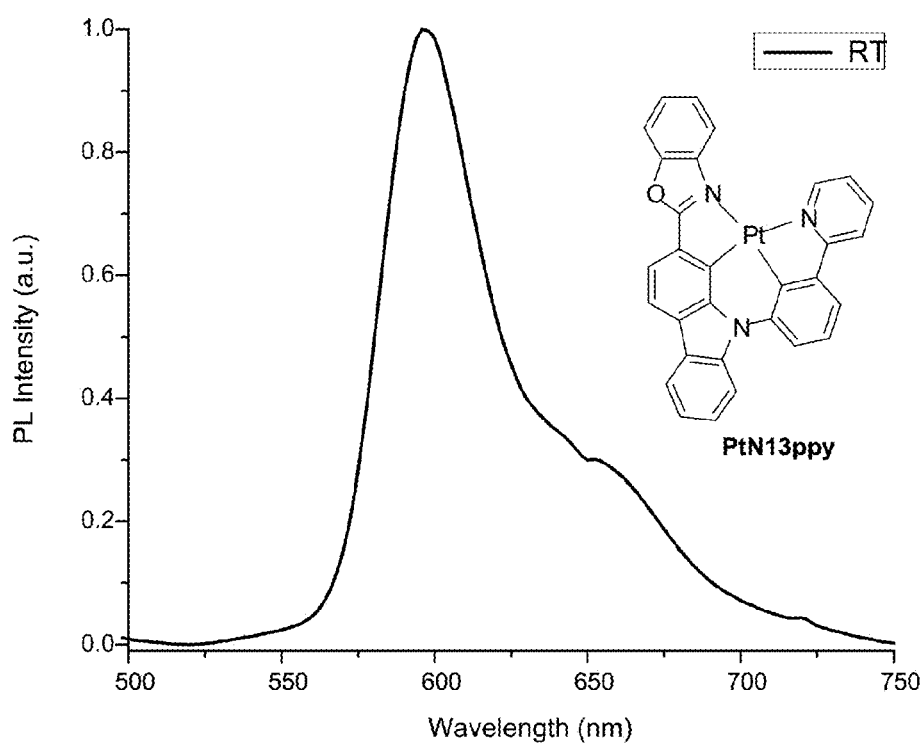
FIG. 23 shows an emission spectrum of PtN13 ppy in $CH_2Cl_2$ at room temperature.

FIG. 23 shows an emission spectrum of PtN13 ppy in $CH_2Cl_2$ at room temperature.

Additional Examples

Figure 24A:
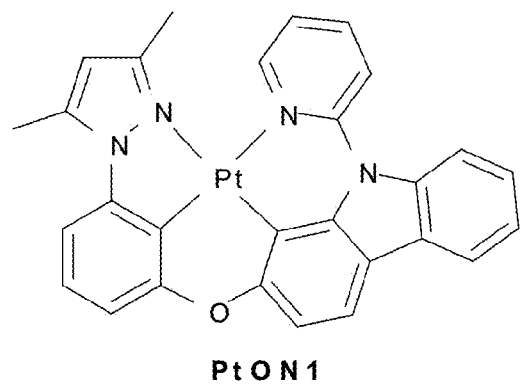
FIGS. 24A and 24B show molecular structures of emitters described herein.

Dipyrazino[2,3-f:2',3'-h]quinoxaline-2,3,6,7,10,11-hexacarbonitrile (HAT-CN) was obtained from Lumtec and N,N'-Bis(naphthalen-1-yl)-N,N'-bis(phenyl)-benzidine (NPD) was obtained from Chemical Alta. Di-[4-(N,N-di-tolyl-amino)-phenyl]cyclohexane (TAPC), 2,6-bis(N-carbazolyl)pyridine (26mCPy), diphenylbis(4-(pyridine-3-yl)phenyl)silane (DPPS), 1,3-bis(3,5-dipyrid-3-yl-phenyl)benzene (BmPyPB), and PtON1 (shown in FIG. 24A) were prepared by methods known in the art. All organic materials were sublimed in a thermal gradient furnace prior to use.

PtN3N-ptb Synthesis

Figure 24B:
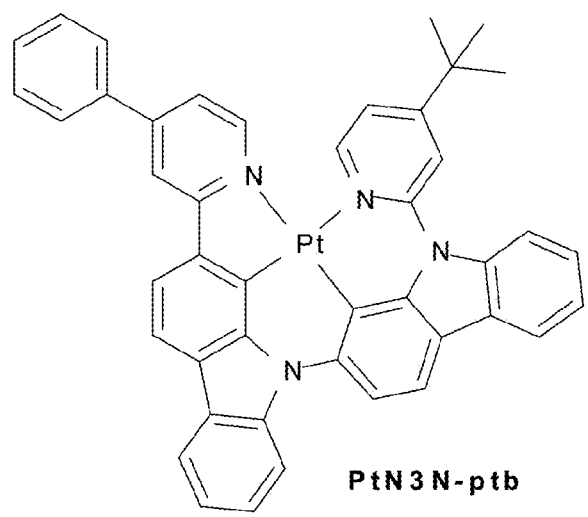

To a dry pressure tube equipped with a magnetic stir bar was added 9-(4-tert-butylpyridin-2-yl)-2'-(4-phenylpyridin-2-yl)-9H-2,9'-bicarbazole (536 mg, 0.87 mmol, 1.0 eq), $K_2PtCl_4$ (378 mg, 0.91 mmol, 1.05 eq) and $^nBu_4NBr$ (28 mg, 0.087 mmol, 0.1 eq). Then solvent acetic acid (52 mL) was added under nitrogen atmosphere. The mixture was bubbled with nitrogen for 30 minutes and then the tube was sealed. The mixture was stirred at room temperature for 20 hours and then at 105-115° C. in an oil bath for another three days, and cooled to ambient temperature. Water (104 mL) was added slowly. After stirring at room temperature for 10 minutes, the precipitate was filtered off and washed with water three times. Then the solid was dried in air under reduced pressure. The collected solid was purified through column chromatography on silica gel using dichloromethane/hexane (2:1) as an eluent to obtain the desired product, PtN3N-ptb, as a red solid (240 mg in 34% yield). The product (335 mg) was further purified by sublimation in a sublimator with four zone controllers at 290° C., 285° C., 190° C., 150° C., $4.1\times10^{-6}$ Torr to obtain red needle crystals (140 mg in 42% yield). $^1H$ NMR (DMSO-$d_6$, 400 MHz): δ 1.27 (s, 9H), 7.19 (t, J=7.6 Hz, 1H), 7.32 (t, J=7.6 Hz, 1H), 7.39-7.54 (m, 6H), 7.69 (dd, J=6.0, 1.6 Hz, 1H), 7.83 (d, J=7.6 Hz, 1H), 7.88 (d, J=8.0 Hz, 1H), 7.93 (d, J=8.0 Hz, 1H), 7.95-8.00 (m, 5H), 8.10-8.14 (m, 3H), 8.37 (d, J=1.2 Hz, 1H), 8.55 (d, J=6.0 Hz, 1H), 8.88 (d, J=6.4 Hz, 1H). $^{13}C$ NMR (DMSO-$d_6$, 100 MHz): δ 29.73, 35.51, 111.17, 112.45, 112.87, 113.79, 114.23, 114.98, 115.24, 116.65, 116.97, 117.96, 118.74, 120.40, 120.44, 120.46, 121.56, 121.70, 122.92, 125.30, 126.06, 126.54, 127.27, 127.73, 128.45, 129.36, 130.19, 136.31, 138.03, 138.12, 138.50, 139.65, 143.17, 144.18, 147.72, 149.32, 149.90, 150.51, 163.62, 165.92. MS (MALDI) for $C_{44}H_{32}N_4Pt$ $[M]^+$: calcd 811.2. found 811.2. The structure of PtN3N-ptb is shown in FIG. 24B.

Device Fabrication and Characterization

Devices were fabricated on glass substrates with previously patterned indium tin oxide (ITO) which formed the anode. Prior to deposition, the substrates were cleaned using a sequence of hand soap scrub then sonication in deionized water, acetone and isopropyl alcohol. Organic and cathode layers were deposited by vacuum thermal evaporation in a system from Trovato Manufacturing, and all depositions were done at a pressure less than $5\times10^{-7}$ Torr. Film thicknesses and deposition rates were monitored using a quartz crystal microbalance. Organic materials were deposited at rates from 0.5 to 1.5 Å/s and LiF was deposited at ~0.2 Å/s. Al cathodes were deposited at 1 to 2 Å/s through a metal shadow mask, without breaking vacuum, to define device areas of 4 $mm^2$ in a crossbar structure. The devices were characterized by current-voltage-luminance measurements and electroluminescence (EL) measurements. Current-voltage-luminance data were collected using a Keithley 2400 sourcemeter, Keithley 6485 picoammeter and Newport 818-UV photodiode. Electroluminescence data were taken using an Ocean Optics HR4000 spectrometer. Electrical characterization was done in a dry nitrogen glovebox before doing the electroluminescence measurements in ambient environment.

Single Emitter Devices

Figure 25A:
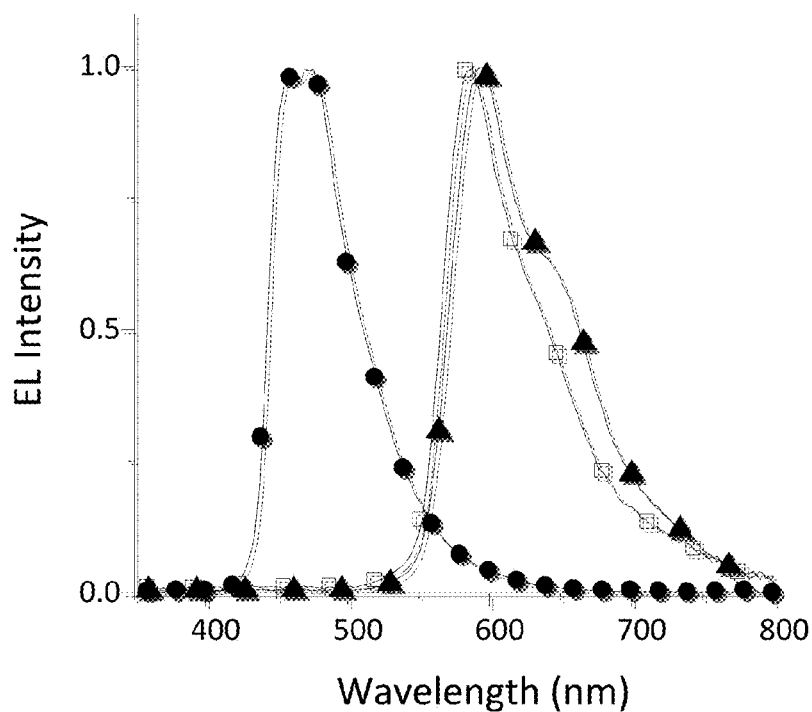
FIG. 25A shows electroluminescent spectra and FIG. 25B shows external quantum efficiency versus current density for various devices.
Figure 25B:
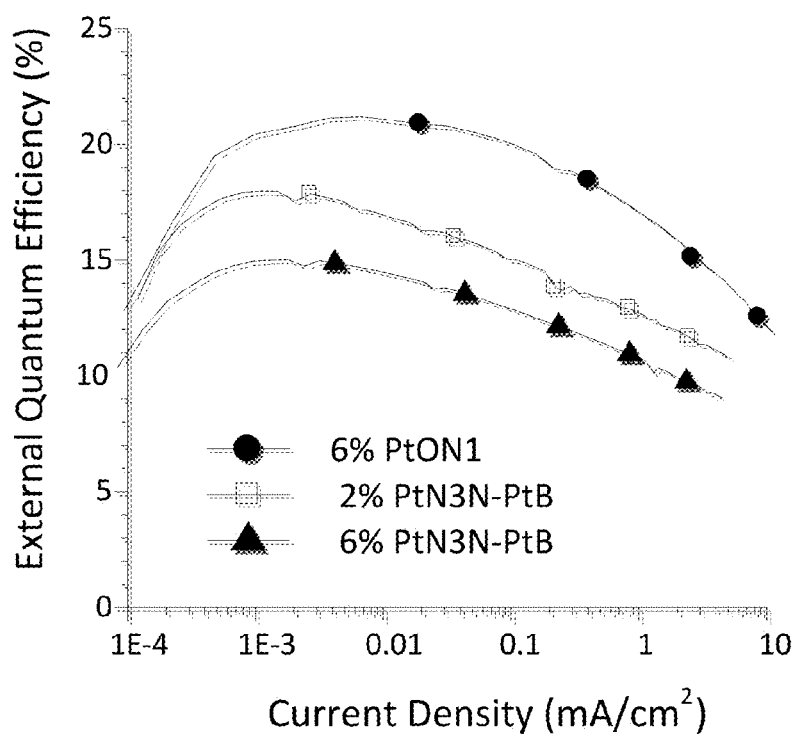

Monochrome devices were fabricated to determine the current-voltage-luminance and external quantum efficiency (EQE) of each emissive layer. The device structure was as follows: ITO/HAT-CN (10 nm)/NPD (40 nm)/TAPC (10 nm)/EML (x % emitter:26mCPy (25 nm)/DPPS (10 nm)/BmPyPB (40 nm)/LiF (1 nm)/Al (100 nm). The blue dopant was PtON1 and the red dopant was PtN3N-ptb. Dopant concentration was 6% PtON1 for the blue in order to optimize the EQE. Red devices, however, were fabricated with dopant concentrations of both 2% PtN3N-ptb and 6% PtN3N-ptb in order to see the effect of dopant concentration on both the EL spectrum and the EQE. Electroluminescent emission (EL) spectra were collected at a current density of 1 mA/cm$^2$. The results are summarized in FIGS. 25A and 25B. The blue device demonstrated strong deep blue emission between 450 nm and 500 nm with CIE (0.15, 0.22). The strong emission as low as 450 nm should yield appropriate breadth of emission to achieve high CRI. Furthermore, the blue device was very efficient with a maximum EQE of 21.2%. The 2% PtN3N-ptb doped device had $\lambda_{max}$ at 588 nm, but with a sharp drop off in emission intensity beyond 600 nm yielding CIE coordinates of (0.57, 0.42). The 6% PtN3N-ptb doped device was slightly red shifted with $\lambda_{max}$ at 594 nm and an elevated shoulder around 650 nm yielding slightly improved CIE coordinates (0.59, 0.40). However, this improved color is accompanied by a significant drop in device performance with peak EQE of 15.0% compared to 18.0% for devices with 2% PtN3N-ptb. The reasons for this drop off in efficiency may be related to charge imbalance and triplet-triplet annihilation processes at the higher dopant concentration. The high efficiencies of both the blue and red emitters and the complimentary nature of their emission spectra make them suitable for the fabrication of two layer white OLEDs employing platinum emitters.

Two-Layer White Devices

There are a large number of strategies for the fabrication of white OLEDs utilizing phosphorescent emitters including: multiple emissive layers, multiple dopants within a single layer, tandem devices, combination of fluorescent and phosphorescent emissive materials, or single doped excimer based white emission. The most common structure typically employs three separate emissive layers, each containing red, green, or blue emissive species since it is easier to achieve the exact specified color by balancing the three emission peaks. However, the fabrication of such a device can prove challenging as modifying the emission spectrum may come with a reduction in efficiency, and optimizing the location of the recombination zone may lead to spectral shift at different driving conditions. Thus, the combination of blue and orange-red emission may be sufficient to optimize a WOLED device for appropriate white color and high efficiency. Furthermore, such a simple structure will elucidate the energy transfer and emission processes within the device to give a clear understanding of the optimal device design.

Figure 26A:
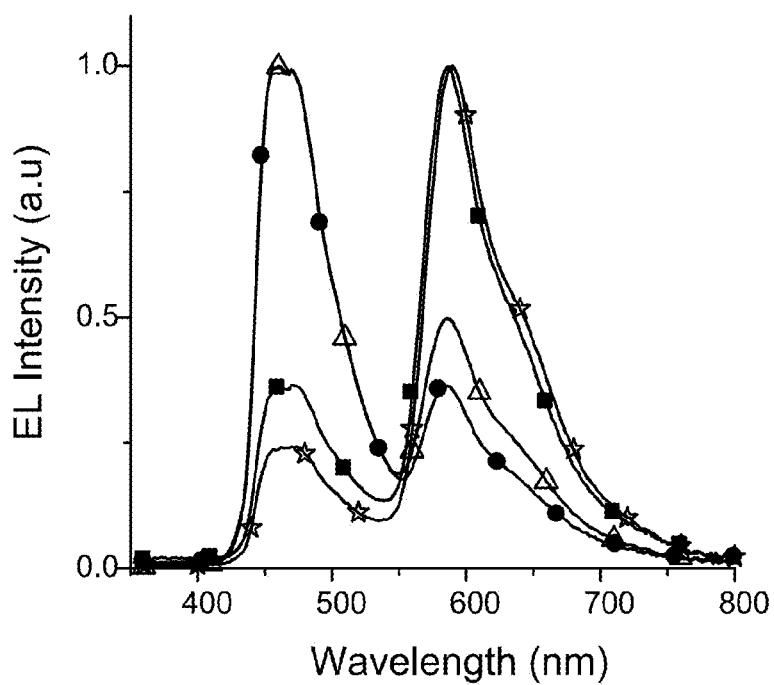
FIG. 26A shows electroluminescent spectra and FIG. 26B shows external quantum efficiency versus current density for various devices.
Figure 26B:
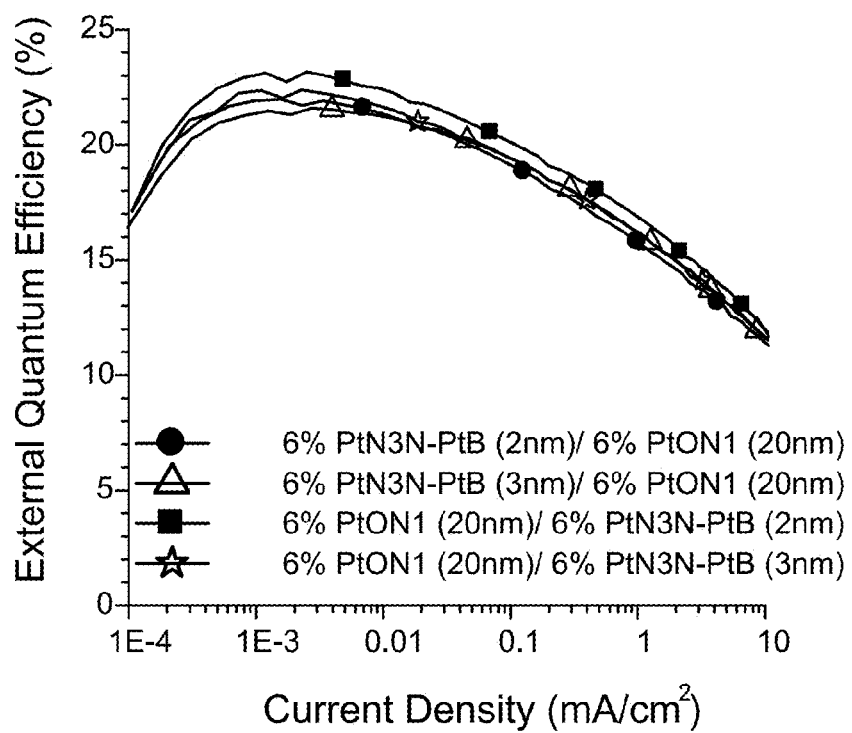

WOLEDs employing two EML layers were using the blue and red emitters in the structure: ITO/HAT-CN (10 nm)/NPD (40 nm)/TAPC (10 nm)/EML1 (6% emitter:26mCPy (x nm)/EML2 (6% emitter:26mCPy (x nm)/DPPS (10 nm)/BmPyPB (40 nm)/LiF (1 nm)/Al (100 nm). A doping concentration of 6% was chosen for the red EML, despite the slightly lower EQE than the 2% red device, since the slight red shift and the more pronounced shoulder should produce WOLEDs with higher color rendering index (CRI). Two structures for the white devices were tested in order to explore the nature of exciton formation and energy transfer within the devices: one with an EML composed of a blue emissive layer followed by a red emissive layer, denoted B/R, and another structure with a red emissive layer followed by a blue emissive layer denoted R/B. The blue EML thickness was fixed at 20 nm in each case, while the red EML thickness was set at either 2 nm or 3 nm. The red layer was kept thin to balance the emission by accounting for favorable energy transfer to the red dopant molecules from other regions of the device. The results are shown in FIGS. 26A and 26B, and a summary of CIE and CRI values as well as efficiency data are presented in Table 1.

TABLE 1

CIE and CRI Values by Device Structure

| | | | 100 cd/m$^2$ | | | 1000 cd/m$^2$ | | |
| --- | --- | --- | --- | --- | --- | --- | --- | --- |
| Structure | CIE | CRI | $\eta_{EQE}$ (%) | $\eta_A$ (cd/A) | $\eta_P$ (lm/W) | $\eta_{EQE}$ (%) | $\eta_A$ (cd/A) | $\eta_P$ (lm/W) |
| 2 nm R/20 nm B | (0.25, 0.25) | — | 16.5 | 29.4 | 18.5 | 12.2 | 22.0 | 11.0 |
| 3 nm R/20 nm B | (0.28, 0.26) | 65 | 18.0 | 31.6 | 19.5 | 13.6 | 24.0 | 11.8 |
| 20 nm B/2 nm R | (0.45, 0.36) | 56 | 18.8 | 39.8 | 25.0 | 14.5 | 30.8 | 15.4 |
| 20 nm B/3 nm R | (0.49, 0.37) | 50 | 18.1 | 36.0 | 21.7 | 13.8 | 27.6 | 13.0 |

The external quantum efficiency data shown in FIG. 26B demonstrates that there is minimal difference between structures with the emissive layer order B/R or R/B with the highest peak quantum efficiency at ~23.1% achieved for the B/R device with an EML 6% PtON1 (20 nm)/6% PtN3N-ptb (2 nm) and the lowest peak EQE of 21.6% for the R/B device with an EML 6% PtN3N-ptb (3 nm)/PtON1 (20 nm). The electroluminescent emission spectra however, were different depending on the order or the thickness, suggesting that the high efficiency may be independent of the emission spectrum. In the R/B structure, the blue emission from the PtON1 layer dominates, while in the B/R structure the red emission from the PtN3N-ptb layer dominates. This tends to suggest that the majority of exciton formation is in the region near the hole blocking layer, DPPS. This can be explained by the strong hole blocking capabilities of DPPS and the strong hole mobility of the hole transport and host materials. Nevertheless, a variety of other energy transfer processes are also present are also present in the device as shown in FIGS. 27A and 27B.

In the R/B device, FIG. 27A, the majority of excitons are formed within the blue emissive layer at the HBL interface, yet some excitons may be formed throughout the EML or could diffuse toward the red emissive layer adjacent to the EBL due to the long triplet diffusion length estimated at up to 100 nm. Excitons near the red emissive layer will undergo rapid radiationless energy transfer to the red dopant molecules due to their lower triplet energies, which in turn will emit the red light. This energy transfer processes has been reported to occur for distances of less than 5 nm, thus the majority of the excitons formed near the HBL interface will not transfer to the PtN3N-ptb emitter since the blue layer is kept sufficiently thick and the blue emission will be dominant. The peak intensity in the red portion of the spectrum increased with increasing red EML thickness due to the increase in number of red dopant species for excitons to form on, indicating that there is likely some degree of direct exciton formation within the red layer. As a result, the CIE coordinates shift from (0.25, 0.25) to (0.28, 0.27) and as the thickness of the red EML is increased from 2 nm to 3 nm and ultimately a CRI of 65 is achieved for the device with a 3 nm 6% PtN3N-ptb/20 nm 6% PtON1 dual emissive layer.

Similarly, in the B/R devices the majority of the excitons form near the HBL interface. As a result the red emission is significantly stronger than that of the blue layer, dispite the relatively thin red emissive layer of only 2 to 3 nm. Also, as discussed previously, excitons within a few nanometers of this layer have a high probability of energy transfer to the red dopant molecules. Yet, due to the thicker PtON1 doped blue layer, excitons formed beyond the Forster radius of the red EML were able to emit from the PtON1 emitters, and thus a small blue peak is still observed. When increasing the thickness of the red EML, there was a decrease in the red emission relative to the blue emission as a result of fewer dopant molecules for emission to occur. Also, the peak emission of 586 nm for the device with 2 nm red EML slightly shifted to 590 nm for the device with 3 nm red EML and also showed a more pronounced shoulder.

Figure 28B:
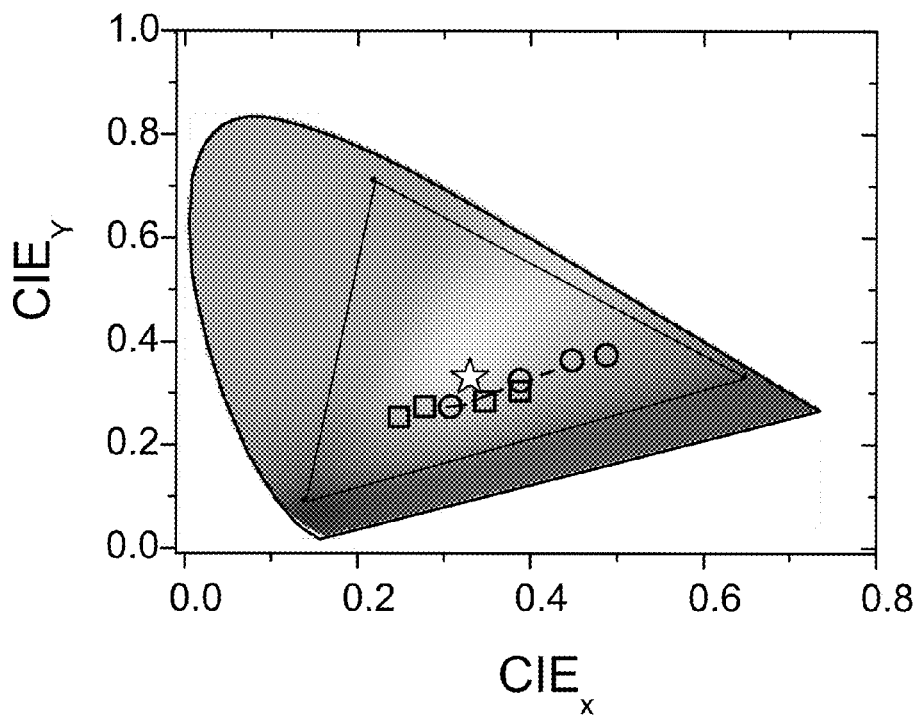
FIG. 28B is a plot of CIE versus red thickness for R/B and B/R.
Figure 28A:
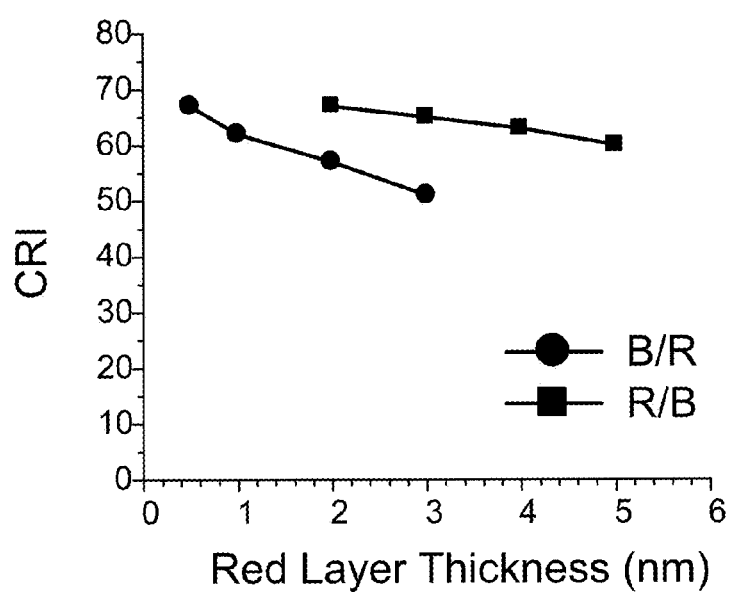
FIG. 28A is a plot of CRI versus red thickness for R/B and B/R.
Figure 29A:
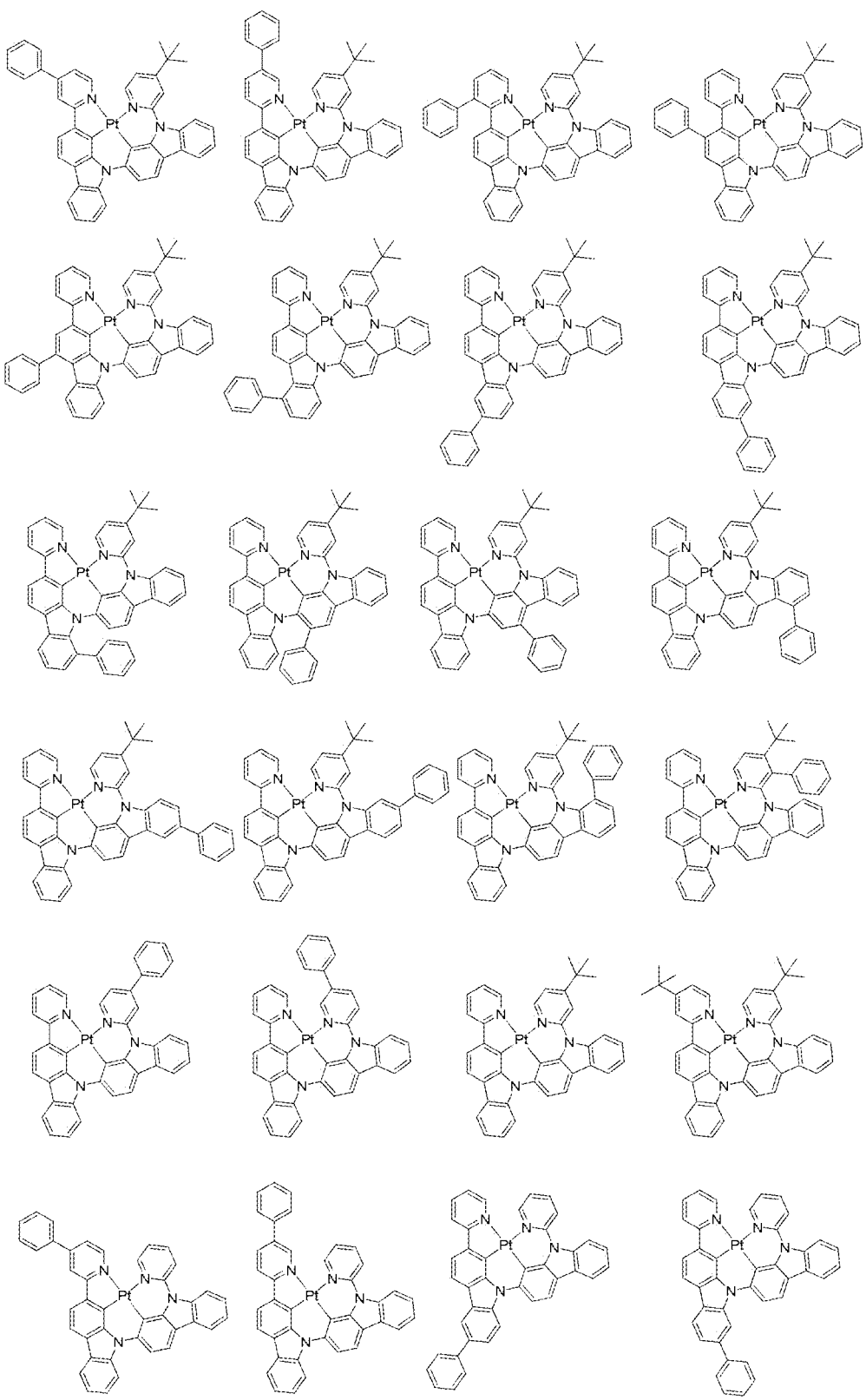
FIGS. 29A-29M show additional examples of emitters prepared as described herein.
Figure 29B:
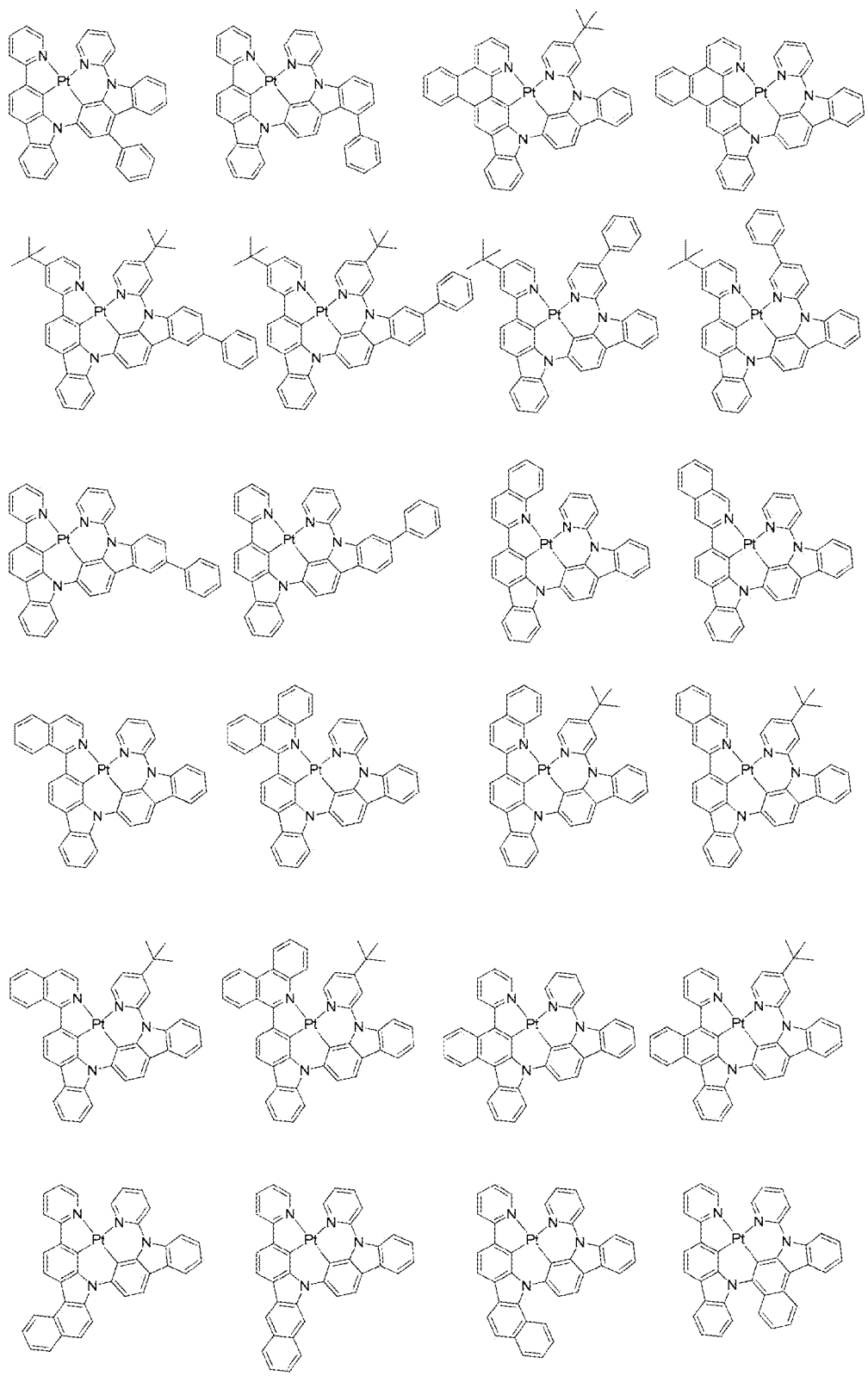
Figure 29C:
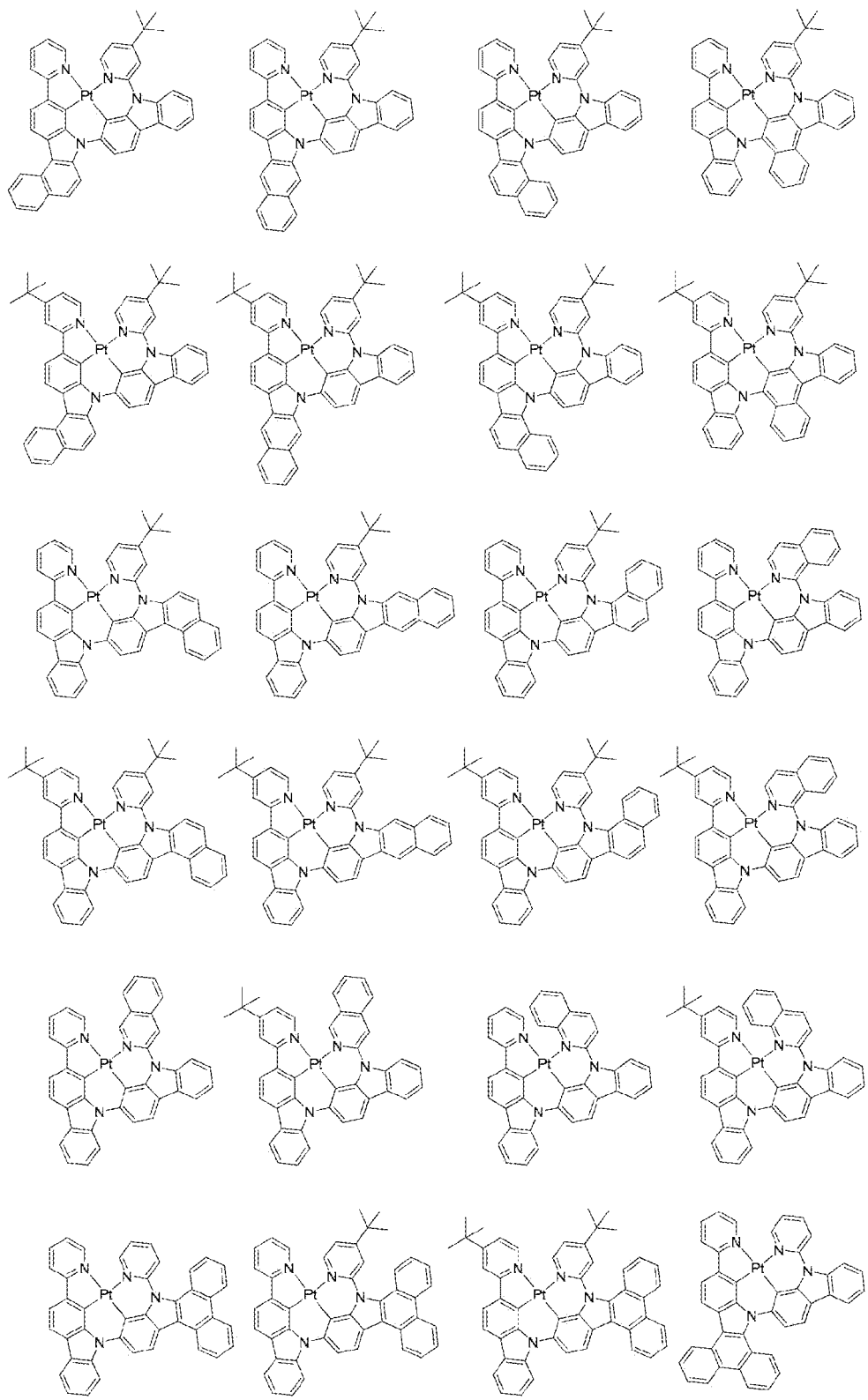
Figure 29D:
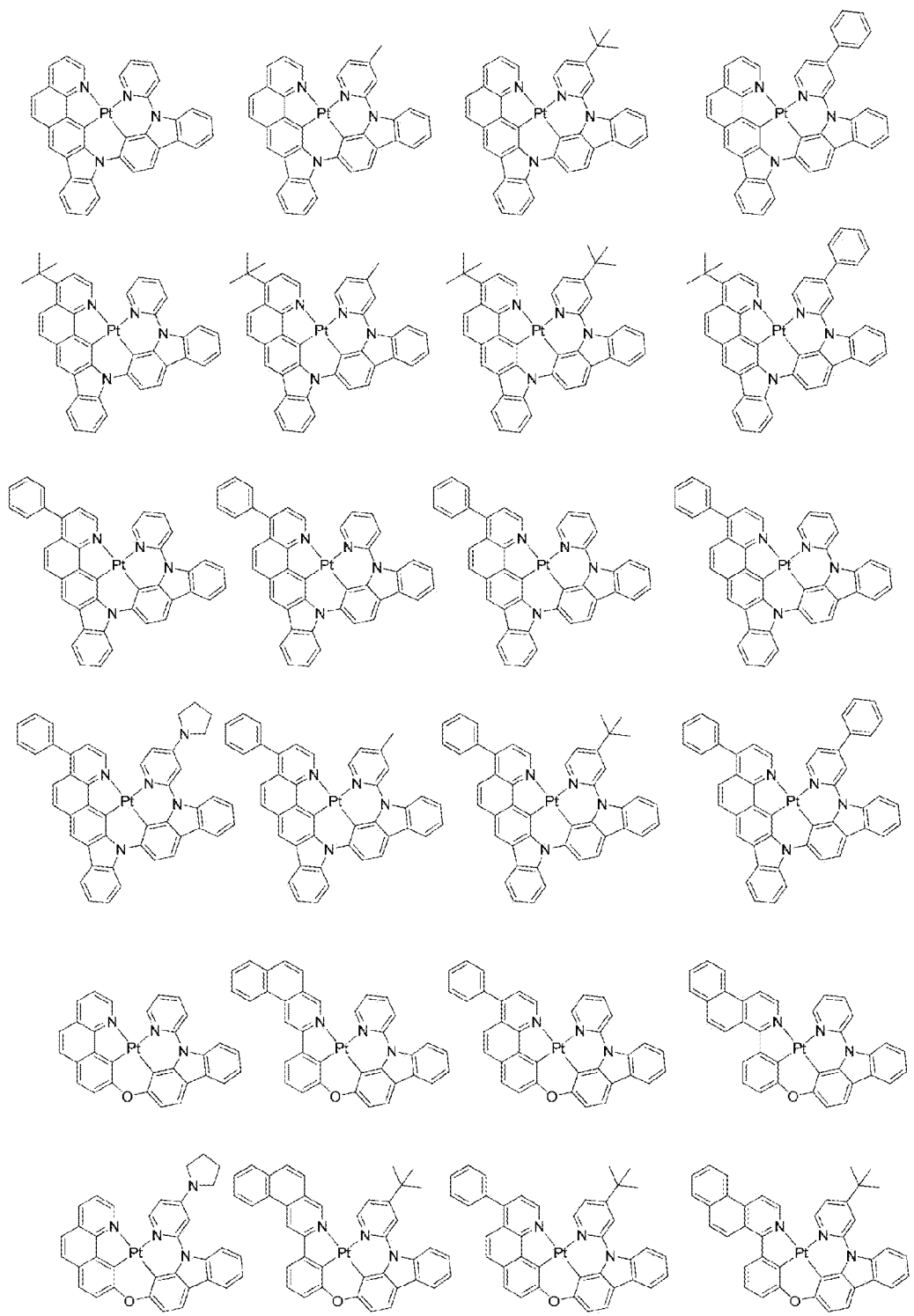
Figure 29E:
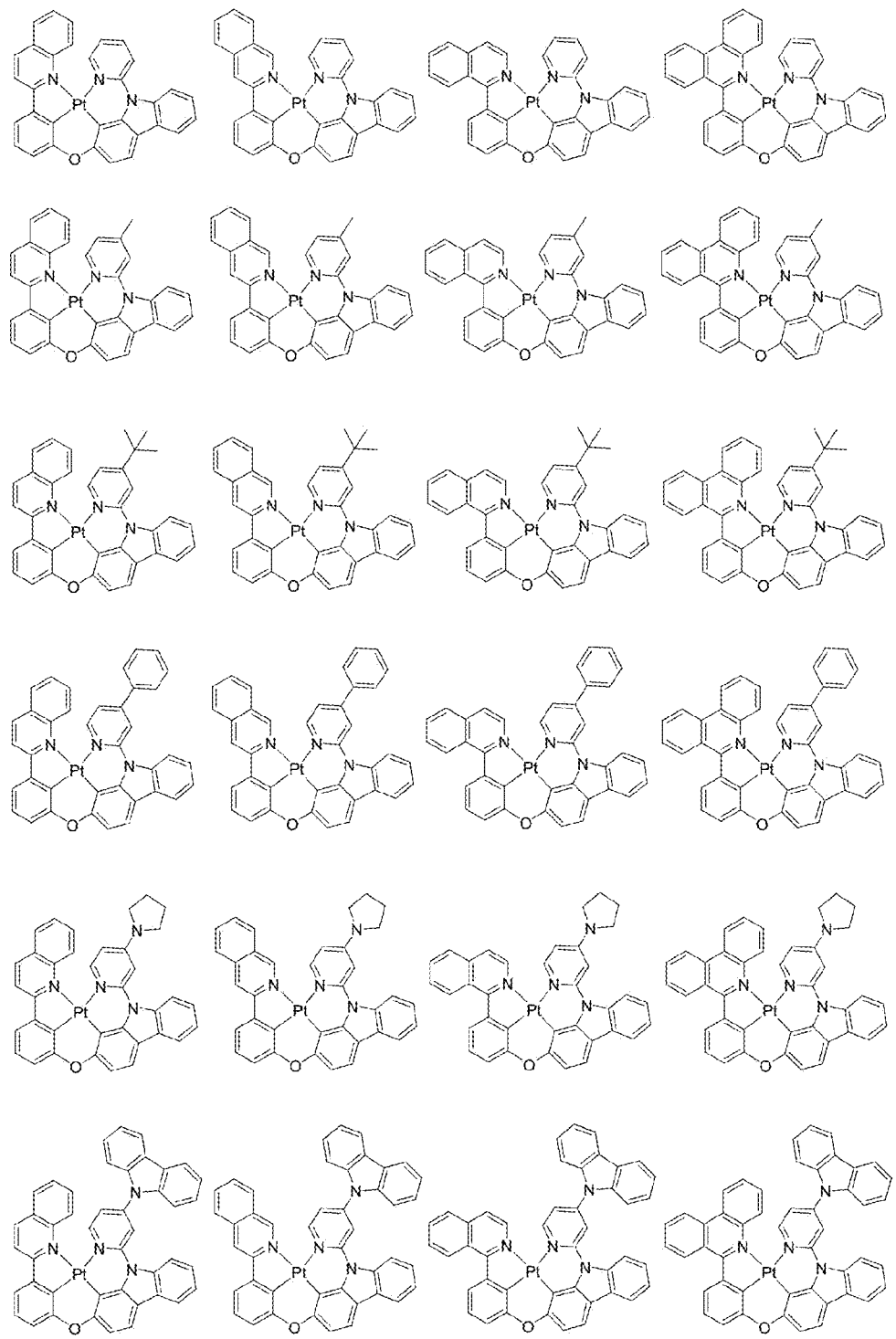
Figure 29F:
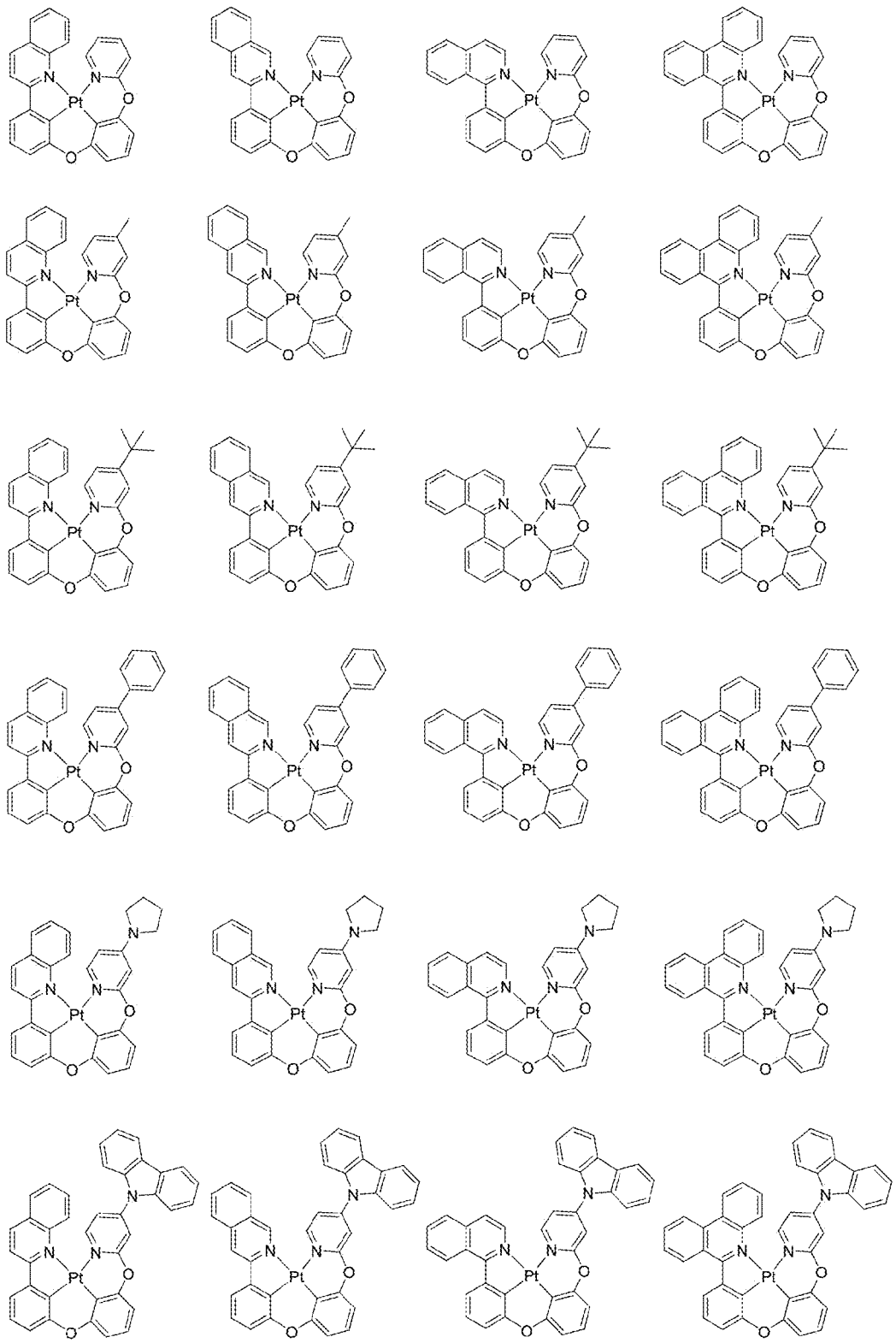
Figure 29G:
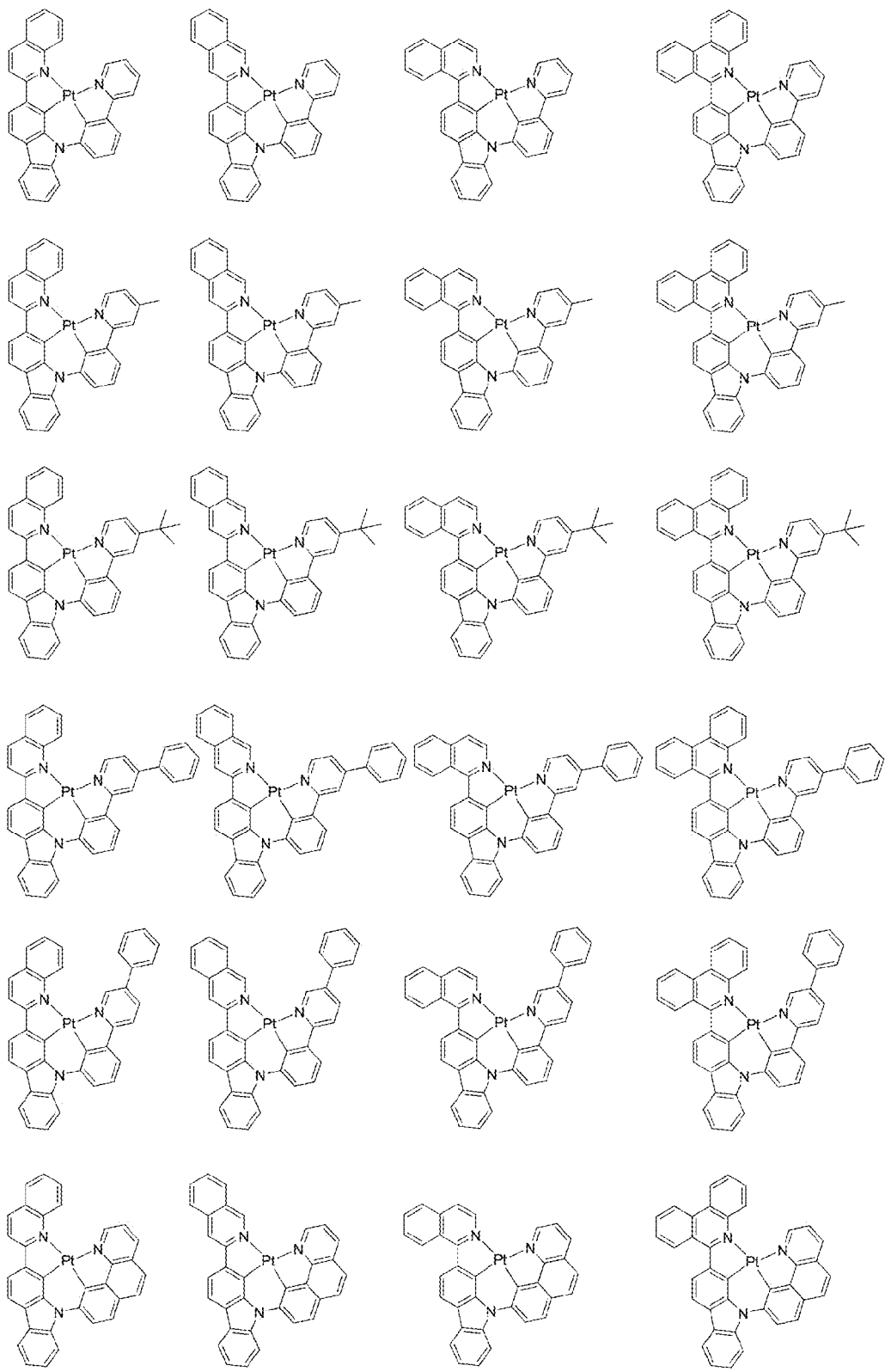
Figure 29H:
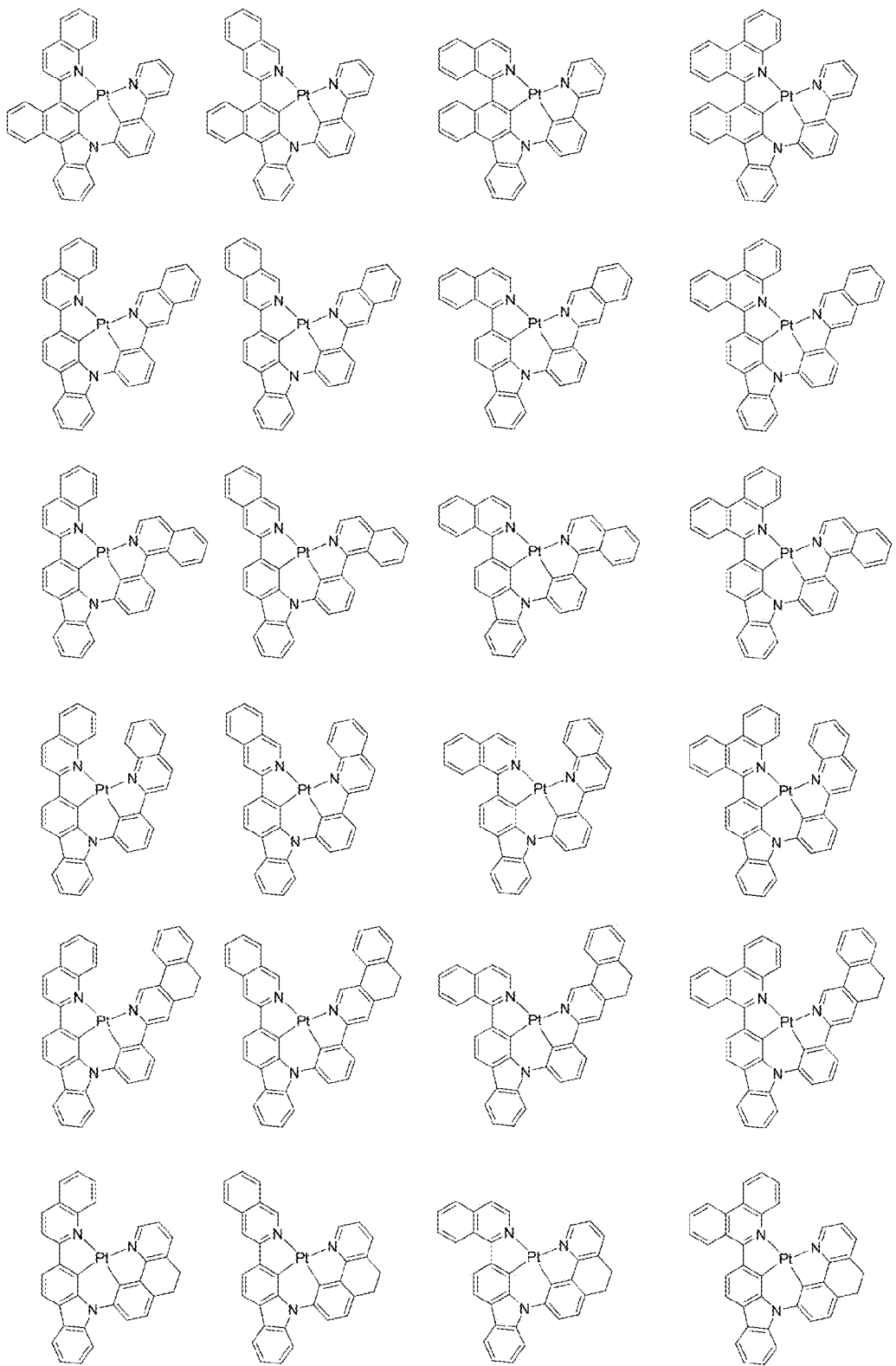
Figure 29I:
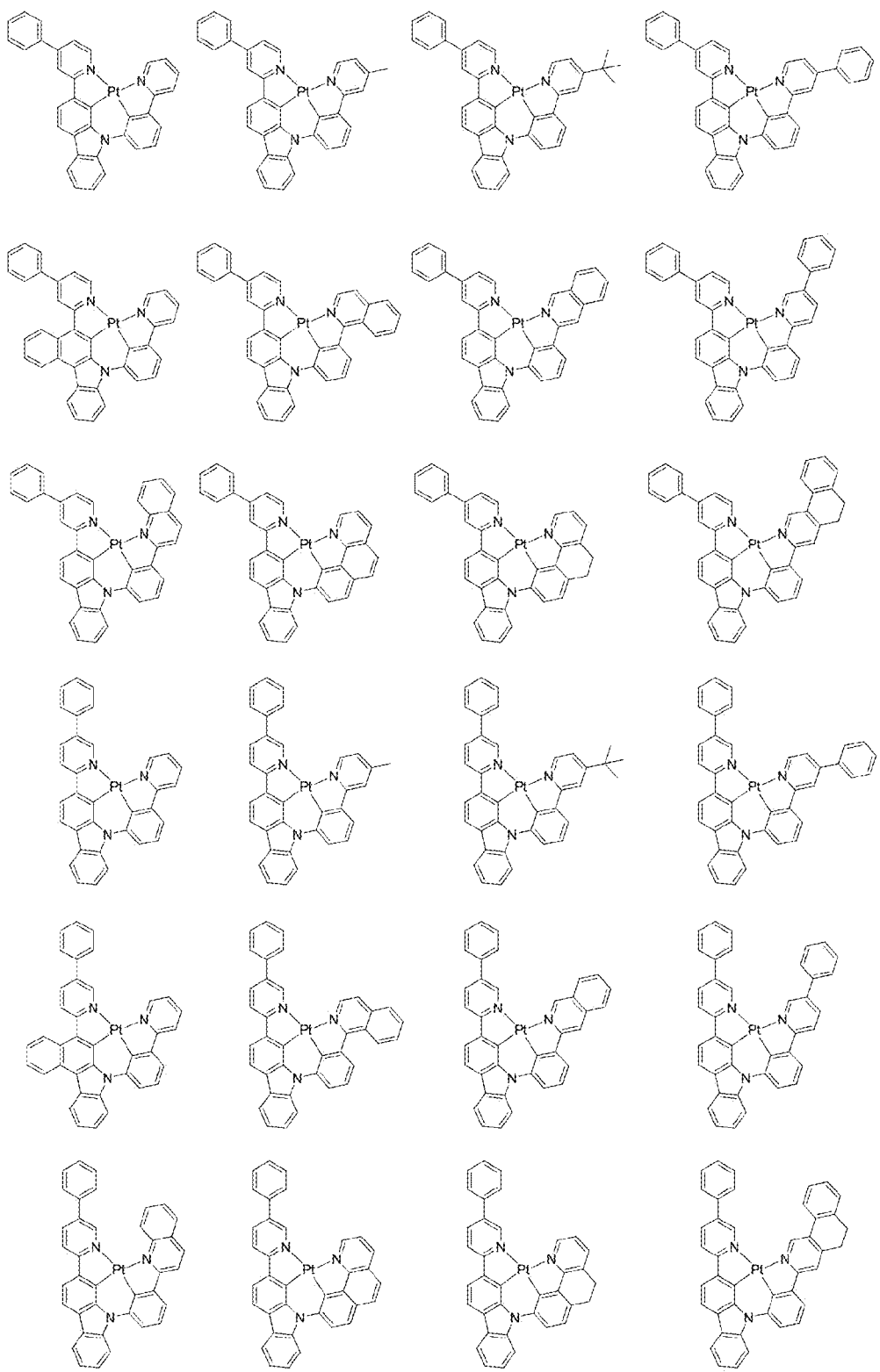
Figure 29J:
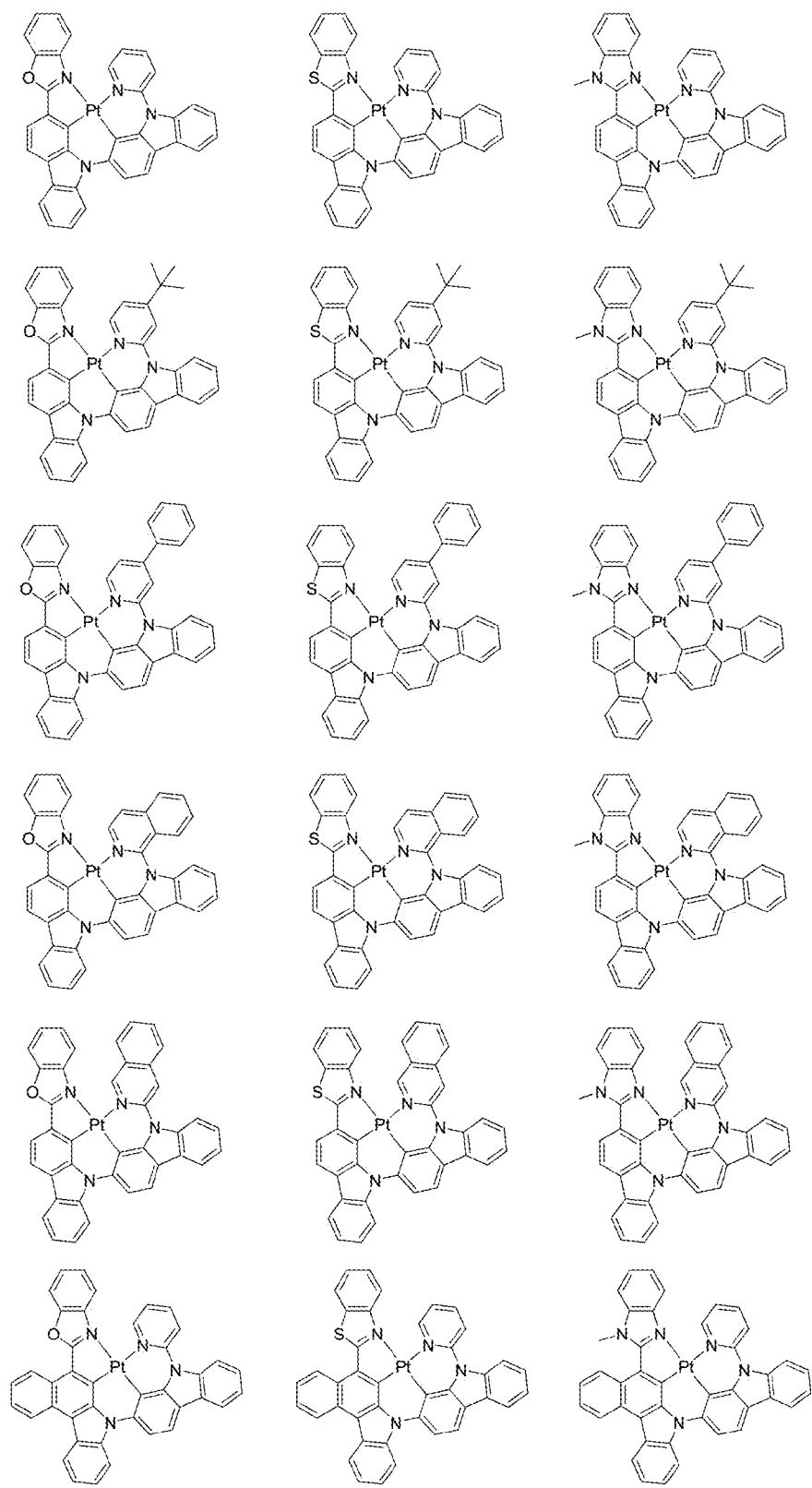
Figure 29K:
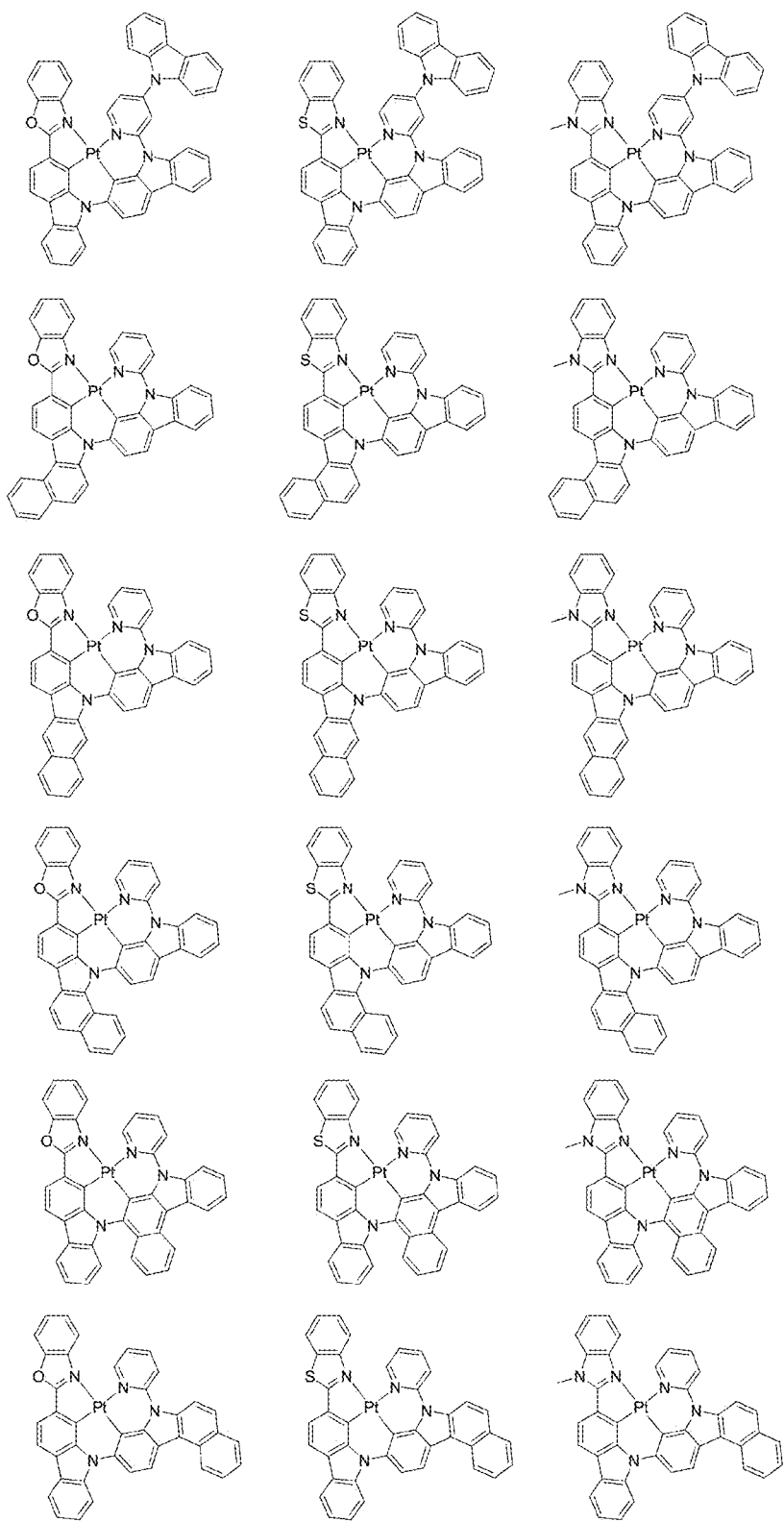
Figure 29L:
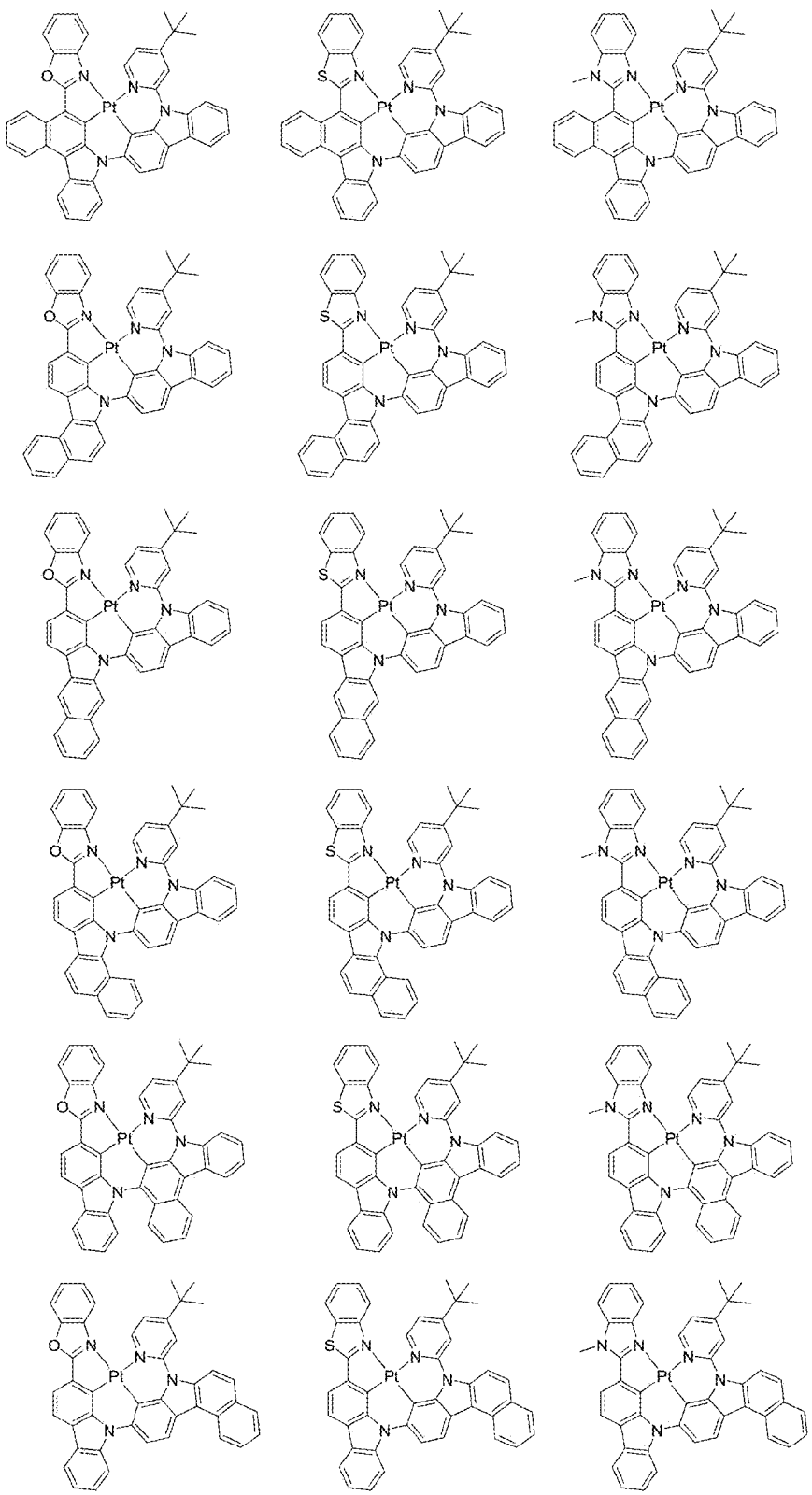
Figure 29M:
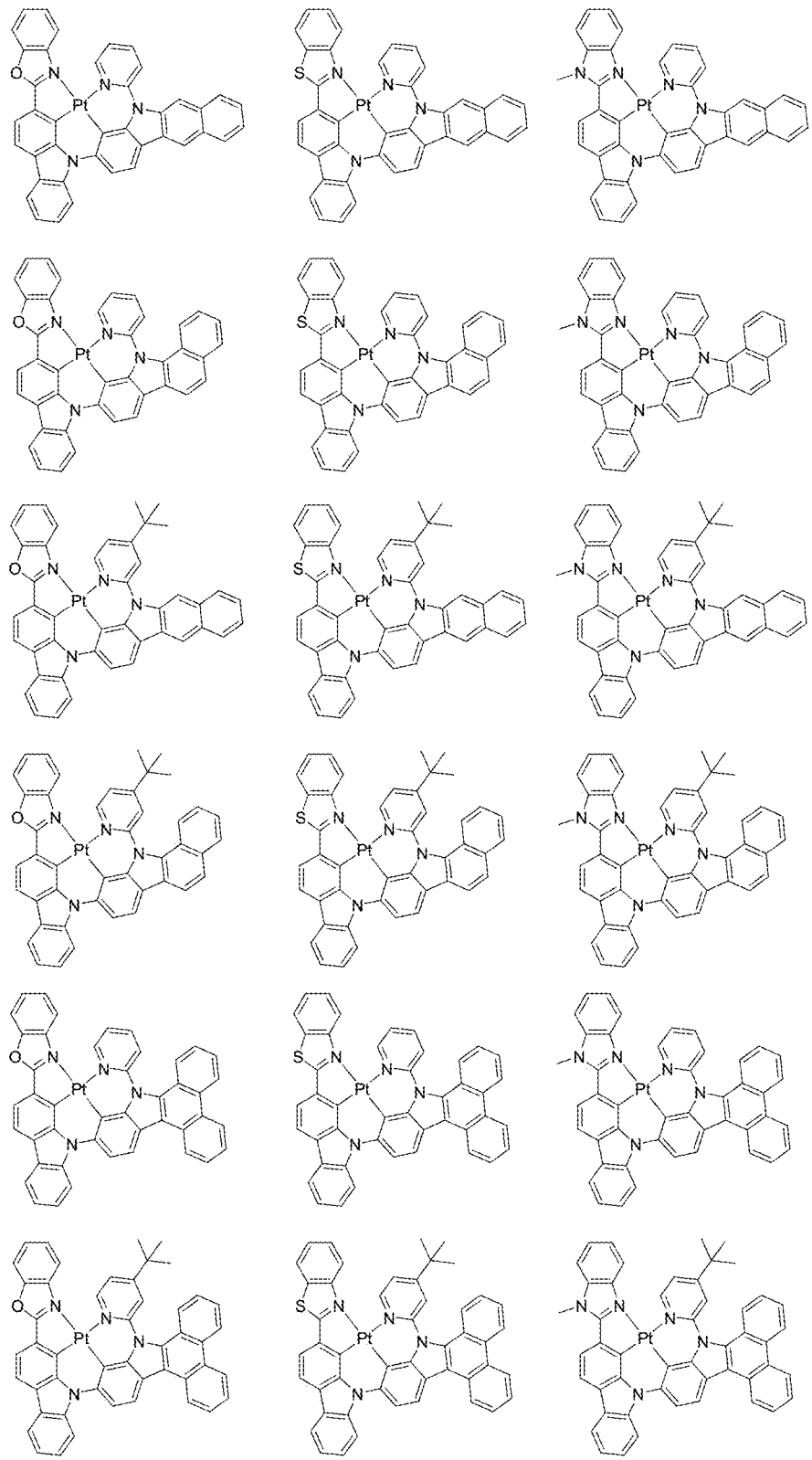

FIG. 28A shows CRI versus red thickness for R/B and B/R. FIG. 28B shows CIE versus red thickness for R/B and B/R. To achieve better color balance between the red and blue emission the red layer thickness was increased in the R/B case and decreased in the B/R case. Ultimately, CIE closest to (0.33, 0.33) considered pure white was achieved for device structures which balanced the red and blue peaks. The emission for both structures have a low CIEy coordinate due to the absence of satisfactory green emission. Furthermore, the CRI decreased with increasing red layer thickness regardless of emission layer order. This was attributed to the fact that as the red peak is increased, the relative amount of green character is reduced due to an emission gap between the PtON1 emission and the PtN3N-ptb. Thus, in order to achieve a white color with high CRI, blue or orange emitters with more green to yellow character may be useful. While the addition of a green emissive layer to the structure may improve emission characteristics, the complexity of the energy transfer processes introduced by an additional layer and the potential tradeoff between efficiency and emission color are factors to be considered.

Thus, a two layer stacked WOLED with EQE over 20% using Pt-based red and blue emitters was demonstrated. Two structures were compared by varying the order of the blue and red emitters in the device. Electroluminescence spectra for devices with the HTL/EBL/R/B/HBL structure had dominant emission in the blue portion of the spectrum, while the converse was true for devices with the emitter layer order reversed. This confirmed that the majority of exciton generation occurs in the layer closest to the hole blocker layer. A maximum CRI of 65 was achieved with 3 nm red/20 nm blue structure. An improved CRI may be obtained by adding a suitable green emitter to the device.

FIGS. 29A-29M show additional examples of emitters synthesized as described herein.

Blue Organic Light-Emitting Diodes

A number of efficient blue OLEDs employing Pt emitters are known. For example, a series of efficient deep-blue-emitting tetradentate Pt complexes such as PtON1 demonstrates peak external quantum efficiencies (EQE) of 25.2% and Commission Internationale de L'Eclairage (CIE) coordinates of (0.15, 0.13). This molecular design also removes the need for fluorine electron-withdrawing groups, as well as the mono-anionic ligands typically needed for the fourth coordination site in pincer complexes, both of which may lead to electrochemical degradation. FIGS. 30A-30D show photoluminescence spectra of PtON1, PtON1-tBu, PtON6-tBu, and PtON7-dtb at room temperature in $CH_2Cl_2$ (solid lines) and 77K in 2-Me-THF (dash-dot lines), along with the molecular structure of each emitter.

Despite this demonstrated success in achieving high efficiencies for Pt complexes, the commonly reported CIE coordinates for claimed "deep-blue" emission fall near (0.15, 0.15) rather than the National Television System Committee (NTSC) coordinates for "pure" blue of (0.14, 0.08). This slight shortcoming actually poses a very substantial challenge since the achievement of a $CIE_y$ value below 0.1 requires that the majority of the emission must fall within the deep-blue region. Consequently, only a few such reports exist, all of which are relatively inefficient. The difficulty in achieving $CIE_s$ value below 0.1 relates to the broad emission or pronounced vibronic progressions characteristics of many phosphorescent metal complexes and consequently, substantial emission in the "green" region. Thus, in order to utilize current phosphorescent emitters for "pure blue" emission, a substantial amount of the emission must be either filtered out or the triplet energy must be increased. The latter strategy renders the emitters incompatible with known stable and efficient host, charge blocking, and transporting materials, illustrating an undesirable trade-off between the deep-blue color and the efficiency or stability. Such is the case for the iridium complex, $Ir(pmb)_3$, which achieved CIE coordinates of (0.17, 0.06) and a peak EQE of only 5.8%.

One strategy to achieve a $CIE_s$ value below 0.1 without significantly shifting the triplet energy is through thermally activated delayed fluorescent materials in which thermal activation from the lower energy triplet excited state to the higher energy singlet state enables a higher energy emission through fluorescence with high quantum yield. Consequently, significant emission between 380-450 nm, with a peak external quantum efficiency of 9.9% has been achieved despite triplet energies below that of common carbazole based hosts. Nevertheless, the efficiency is still much lower than that of many phosphorescent metal complexes, and the resulting broad fluorescent emission contains a sizeable portion of light below 450 nm in the region where the human eye has very low responsivity.

As described herein, an alternative approach to achieve efficient pure blue emission through the development of a series of rigid tetradentate Pt complexes with a narrow spectral bandwidth. These complexes emit with a single dominant emission peak in the deep-blue region with greatly suppressed vibronic sidebands to achieve $CIE_x \approx 0.15$ and $CIE_y < 0.1$. The high spectral purity of these emitters demonstrate little or no wasted emission in the near-UV, where the responsivity of the human eye is low and the triplet energy is high, and there is minimal color contamination from the green region of the visible spectrum. One selected emitter, PtON7-dtb (dtb: di-tert-butyl), achieved a peak EQE of 24.8% and displayed CIE coordinates of (0.148, 0.079) in a device setting.

Figure 30A:
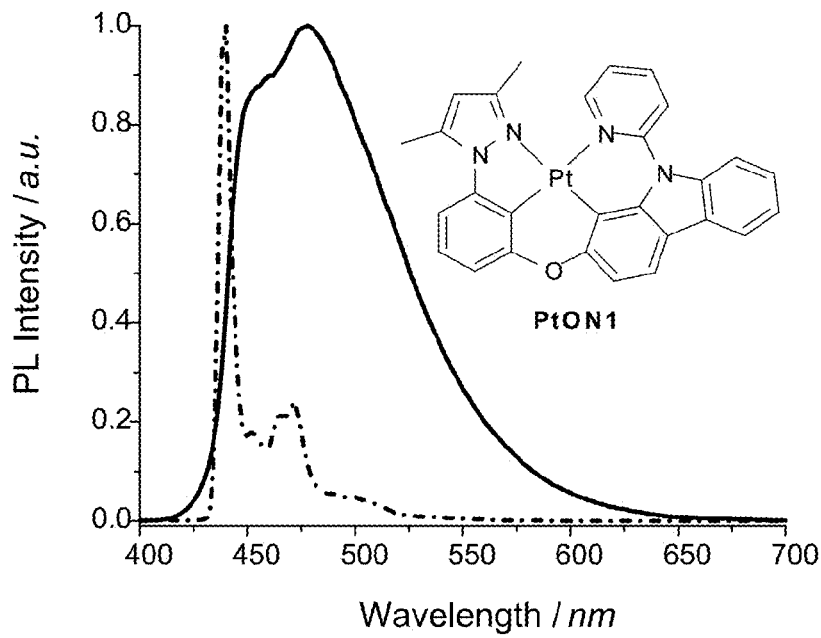
FIGS. 30A-30D show photoluminescence spectra of PtON1, PtON1-tBu, PtON6-tBu, and PtON7-dtb, respectively, at room temperature in $CH_2Cl_2$ and at 77K in 2-MeTHF.
Figure 30B:
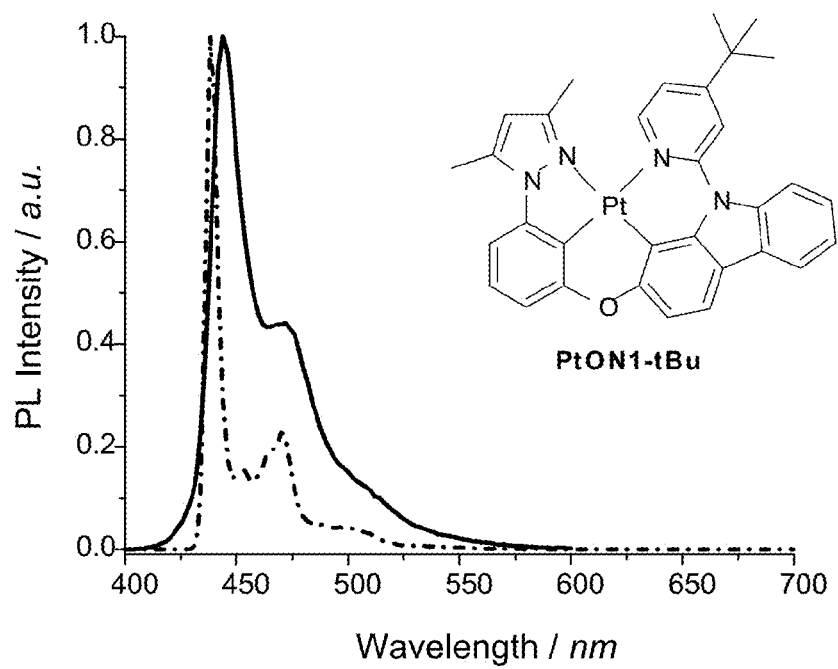

As previously described, deep-blue emission has been achieved using tetradentate cyclometalated Pt complexes that contained phenyl methylimidazole or phenyl pyrazole emissive ligands, such as PtON1. Such a molecular design yields an EQE as high as 25.2% for deep-blue emission. The photoluminescence (PL) spectra of PtON1 at low temperature (77K) in 2-methyltetrahydrofuran (2-methyl-THF) and at room temperature in $CH_2Cl_2$ are shown in FIG. 30A. The low-temperature emission spectrum shows a dominant emission peak at $\lambda_{max}$=440 nm with a small vibronic sideband at 472 nm and a full-width at half-maximum (FWHM) of 6 nm. At room temperature, however, the PtON1 emission spectrum is significantly broadened with a FWHM of 85 nm and a peak emission at 478 nm. This may be attributed to possible dual emission processes originating from both the phenyl pyrazole ligand and the carbazole pyridine ligand, the latter of which is thermally accessible at elevated temperatures. Upon adding an electron-donating group such as tert-butyl (tBu) to the 4-position of the pyridine ring, significant spectral narrowing in the room-temperature emission spectrum is observed for PtON1-tBu (FIG. 30B). The addition of the tert-butyl group does not significantly affect the molecular geometry of PtON1-tBu and its analogs on the basis of single crystal data and density functional theory calculations. The spectral narrowing is attributed to increasing the energy of the $^1$MLCT/$^3$MLCT and $^3$LC states of the carbazole pyridine moiety, resulting in a larger energy separation to minimize the influence of the carbazole pyridine on the room-temperature emission spectrum. Ultimately, a room-temperature photoluminescent emission peak of 444 nm and FWHM of only 20 nm was achieved for PtON1-tBu. Such emission is among the narrowest for any cyclometalated complex and has color purity comparable with or even superior to many quantum-dot LEDs that are widely praised for their high color purity. Furthermore, films of PtON1-tBu doped in poly(methyl methacrylate) (PMMA) demonstrated very high photoluminescent quantum yields of $\phi$=0.88, which are similar to that of PtON1 ($\phi$=0.85).

Figure 30C:
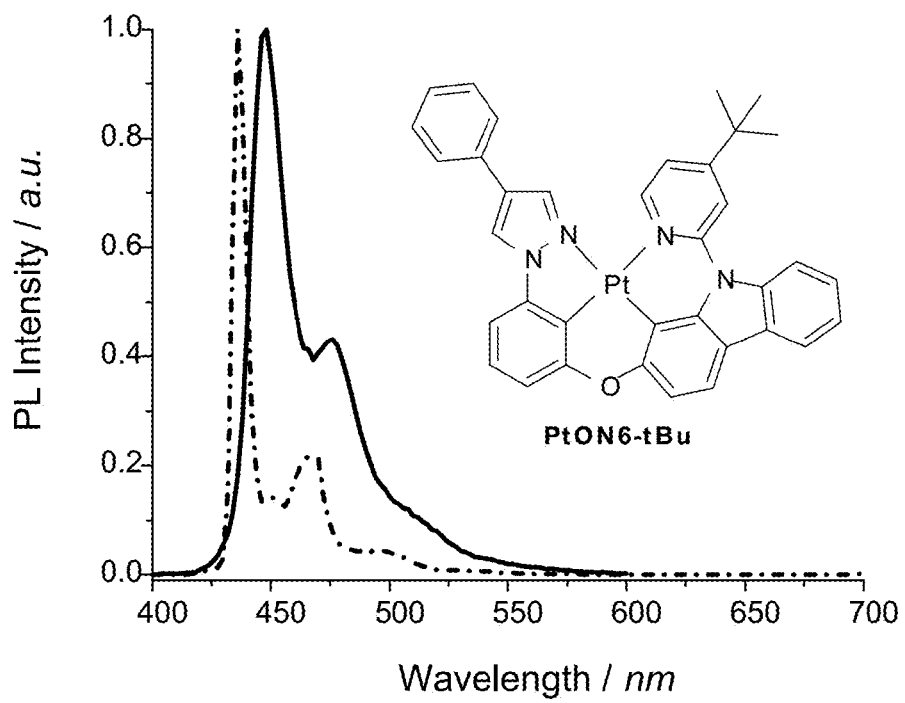
Figure 30D:
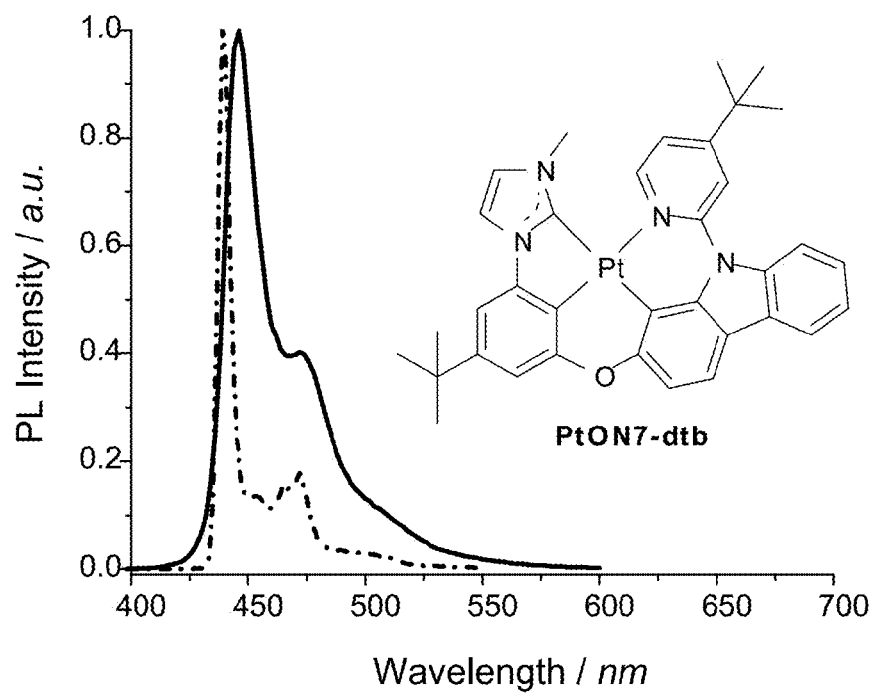

To further illustrate the utility of this molecular design, two other Pt complexes with different emissive ligands, namely PtON6-tBu and PtON7-dtb, were synthesized. Their photoluminescent emission spectra are shown in FIGS. 30C and 30D, respectively. Both of these complexes also demonstrate room-temperature emission spectra with reduced vibronic sidebands yielding deep-blue emission at 448 nm and 446 nm with FWHM values of 20 nm and 19 nm for PtON6-tBu and PtON7-dtb respectively. Furthermore, the photoluminescent quantum yields for all the mentioned complexes are over 0.7 in doped PMMA films. PtON7-tBu was also synthesized and exhibited similar emission spectra, but an additional tert-butyl group was added in order to yield improved thermal stability.

Figure 30E:
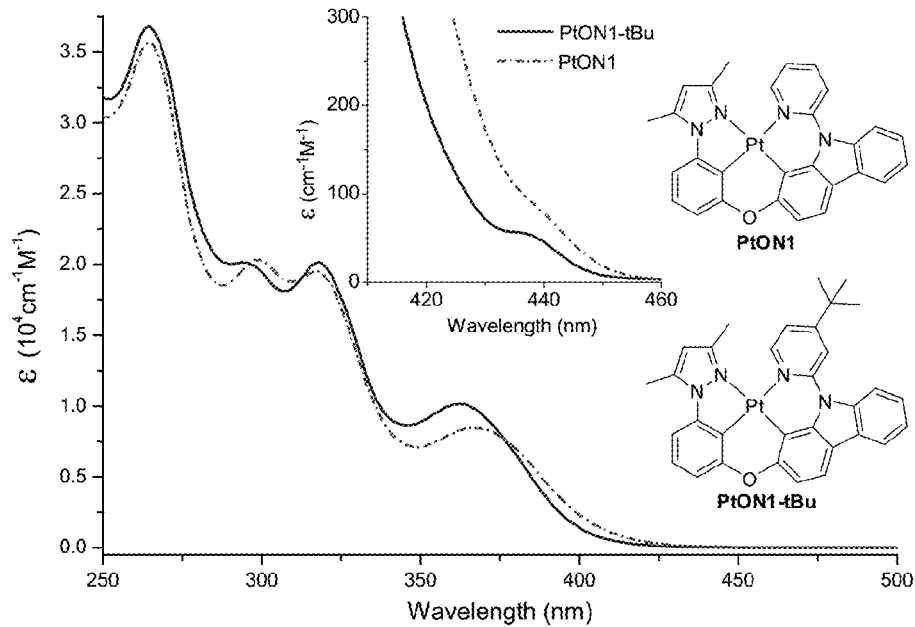
FIG. 30E shows a comparison of room temperature absorption spectra (in $CH_2Cl_2$) of PtON1 and PtON1-tBu.
Figure 30F:
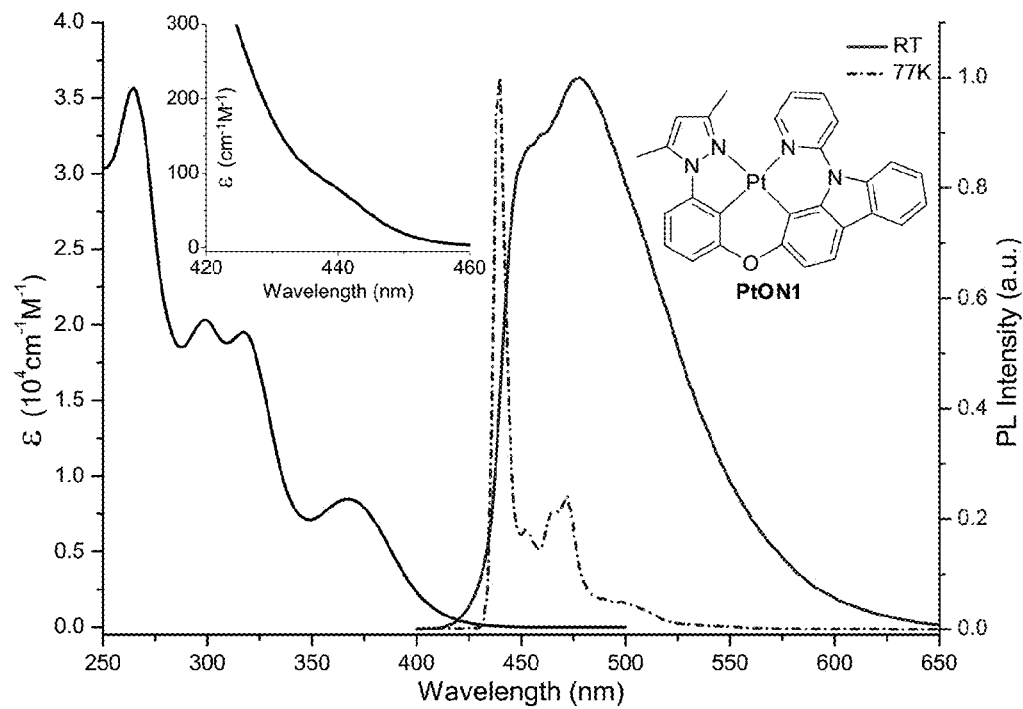
FIG. 30F shows absorption spectra (in $CH_2Cl_2$) and emission spectra (room temperature in $CH_2Cl_2$, 77K in 2-methyl THF) of PtON1.
Figure 30G:
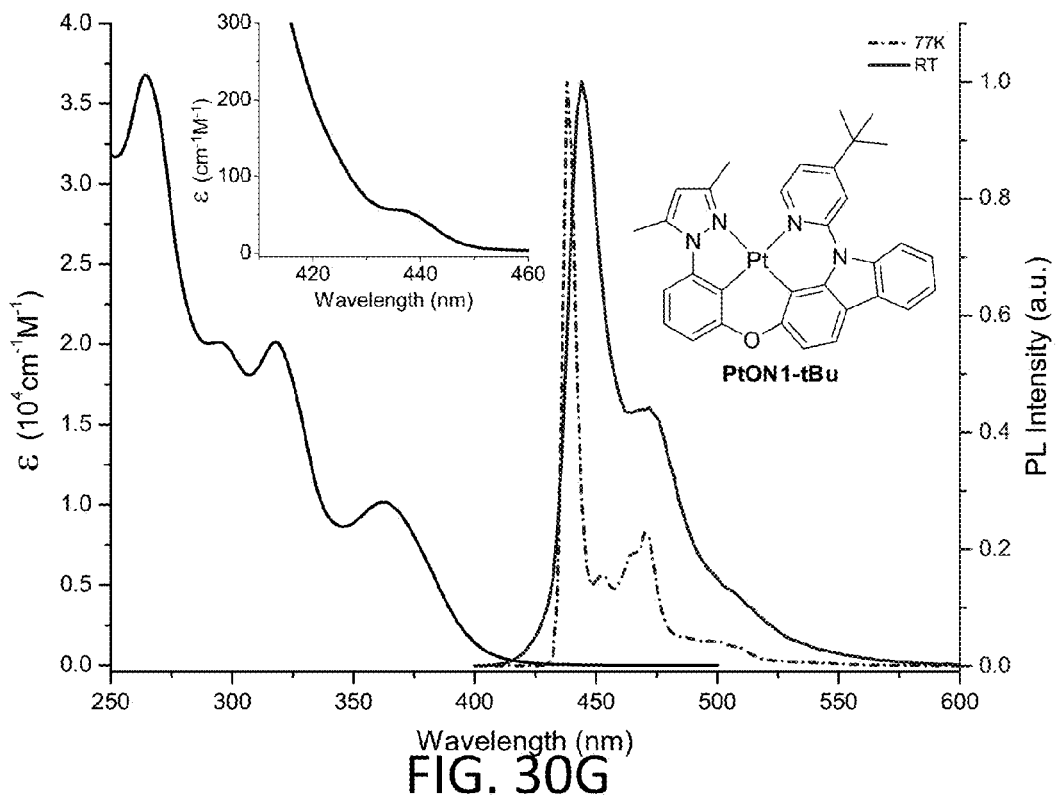
FIG. 30G shows absorption spectra (in $CH_2Cl_2$) and emission spectra (room temperature in $CH_2Cl_2$, 77K in 2-methyl THF) of PtON1-tBu.
Figure 30H:
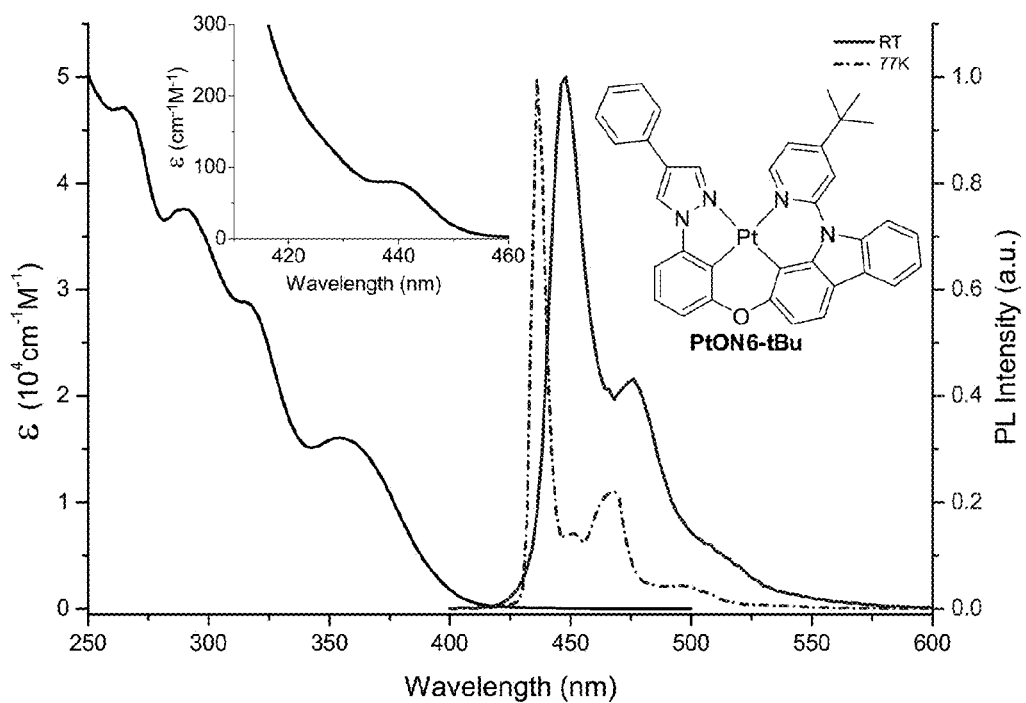
FIG. 30H shows absorption spectra (in $CH_2Cl_2$) and emission spectra (room temperature in $CH_2Cl_2$, 77K in 2-methyl THF) of PtON6-tBu.
Figure 30I:
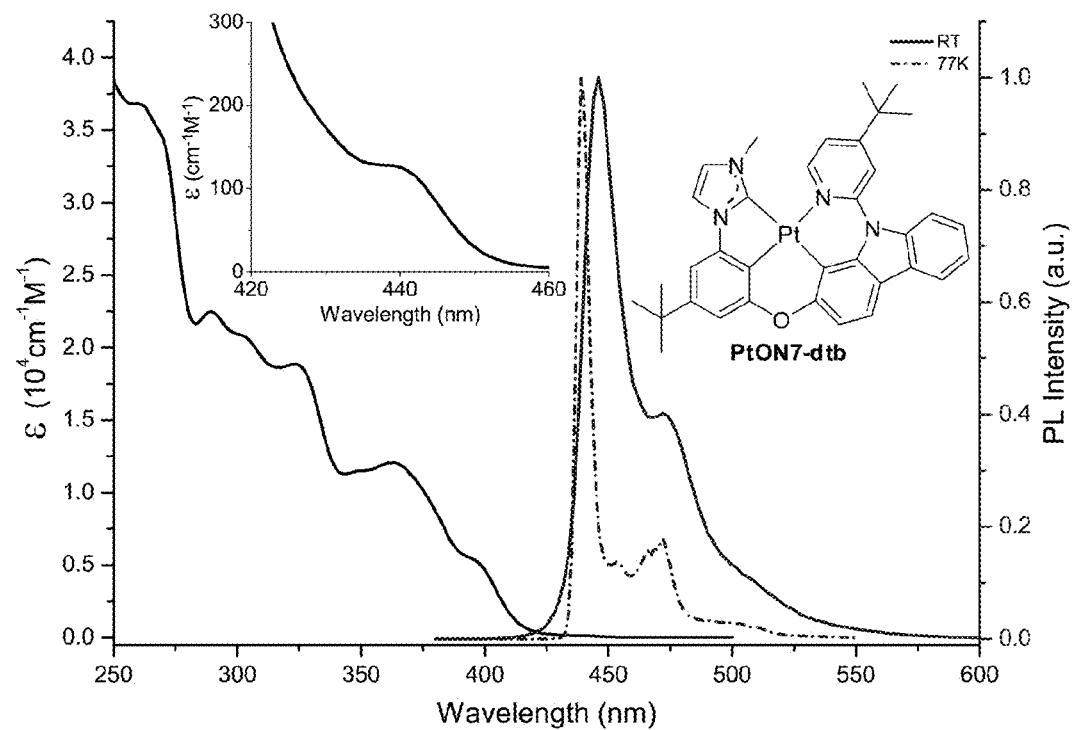
FIG. 30I shows absorption spectra (in $CH_2Cl_2$) and emission spectra (room temperature in $CH_2Cl_2$, 77K in 2-methyl THF) of PtON7-dtb.
Figure 30J:
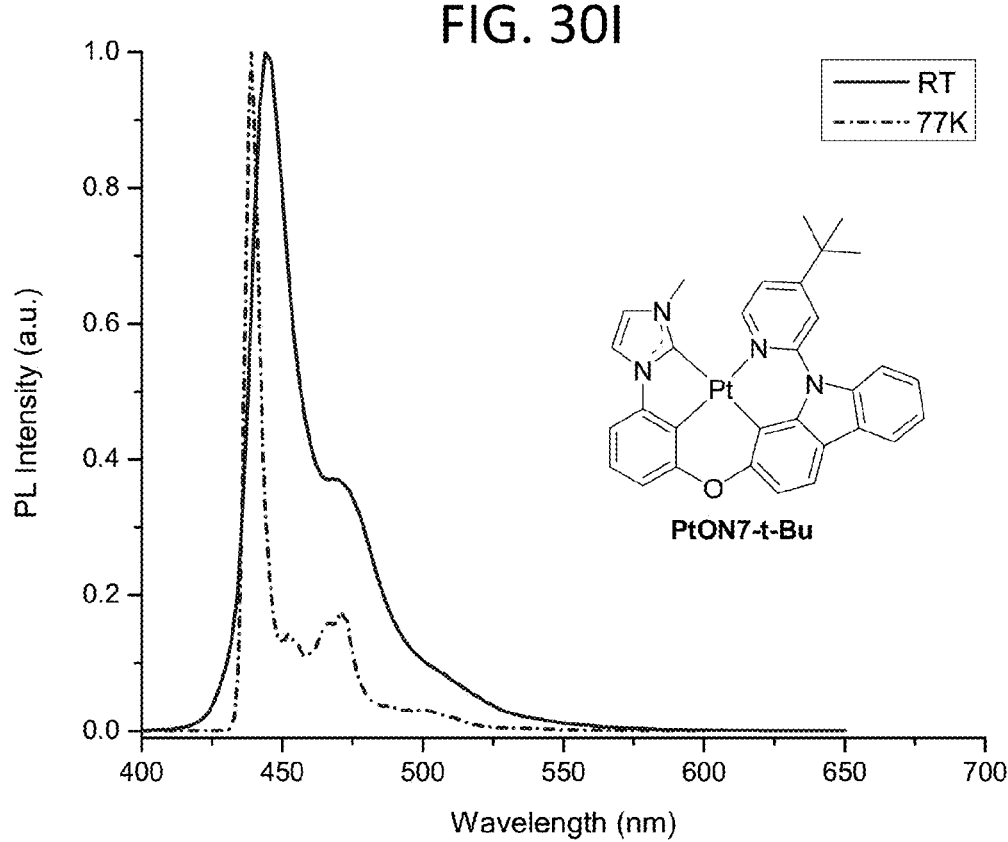
FIG. 30J shows emission spectra of PtON7-tBu at room temperature ($CH_2Cl_2$) and 77K in (2-methyl THF).

FIG. 30E shows a comparison of room temperature absorption spectra (in $CH_2Cl_2$) of PtON1 and PtON1-tBu. The $T_1$ absorption transition and the chemical structures of PtON1 and PtON1-tBu are shown in the inset. FIG. 30F shows absorption spectra (in $CH_2Cl_2$) and emission spectra (room temperature in $CH_2Cl_2$, 77K in 2-methyl THF) of PtON1. The $T_1$ absorption transition and the chemical structure of PtON1 are shown in the inset. FIG. 30G shows absorption spectra (in $CH_2Cl_2$) and emission spectra (room temperature in $CH_2Cl_2$, 77K in 2-methyl THF) of PtON1-tBu. The $T_1$ absorption transition and the chemical structure of PtON1-tBu is shown in the inset. FIG. 30H shows absorption spectra (in $CH_2Cl_2$) and emission spectra (room temperature in $CH_2Cl_2$, 77K in 2-methyl THF) of PtON6-tBu. The $T_1$ absorption transition and the chemical structure of PtON6-tBu are shown in the inset. FIG. 30I shows absorption spectra (in $CH_2Cl_2$) and emission spectra (room temperature in $CH_2Cl_2$, 77K in 2-methyl THF) of PtON7-dtb. The $T_1$ absorption transition and chemical structure of PtON7-dtb are shown in the inset. FIG. 30J shows emission spectra of PtON7-tBu at room temperature ($CH_2Cl_2$) and 77K in (2-methyl THF).

Figure 31A:
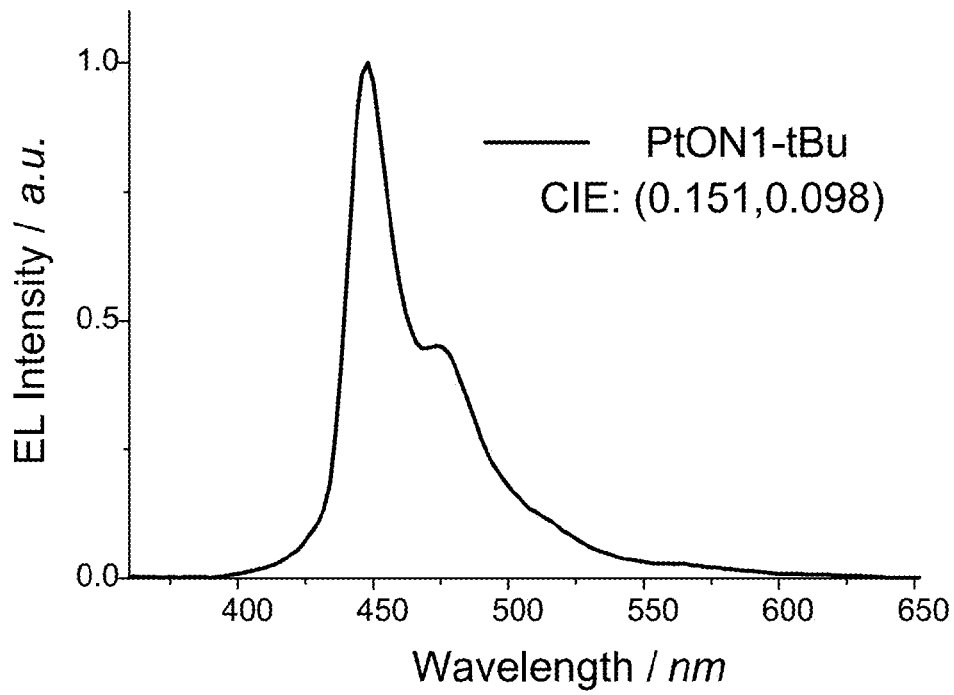
FIGS. 31A-31C show EL spectra of PtON1-tBu, PtON6-tBu, and PtON7-dtb, respectively.
Figure 31B:
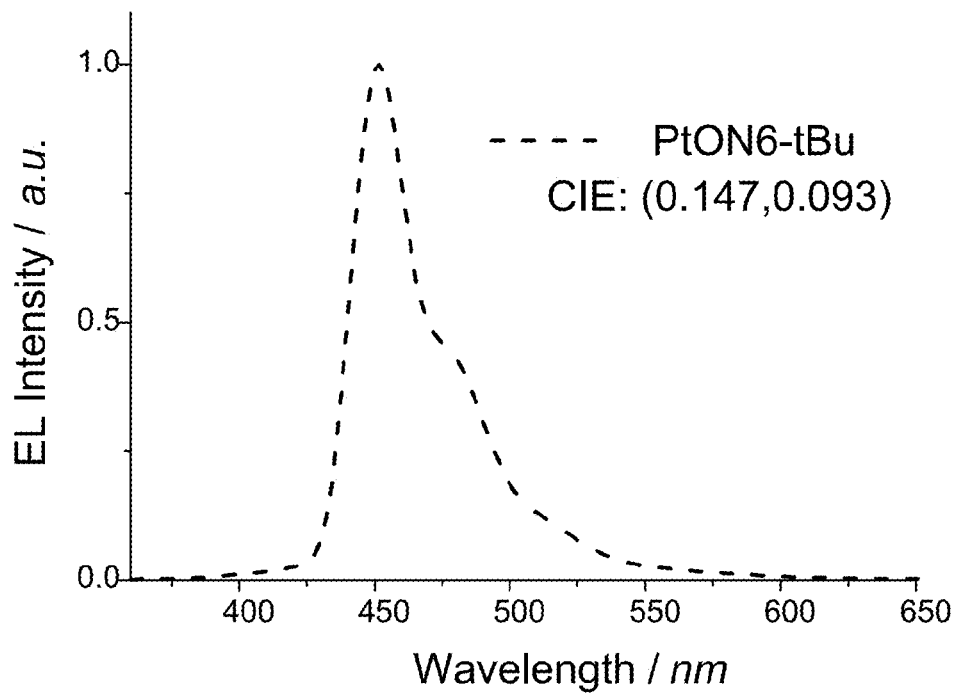
Figure 31C:
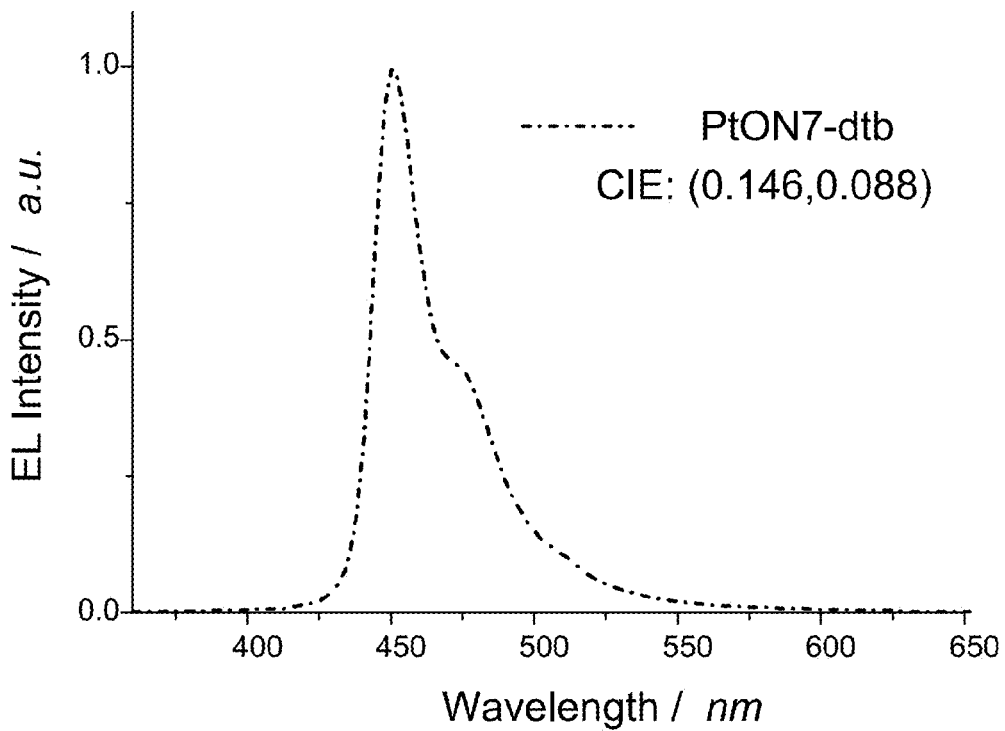
Figure 31D:
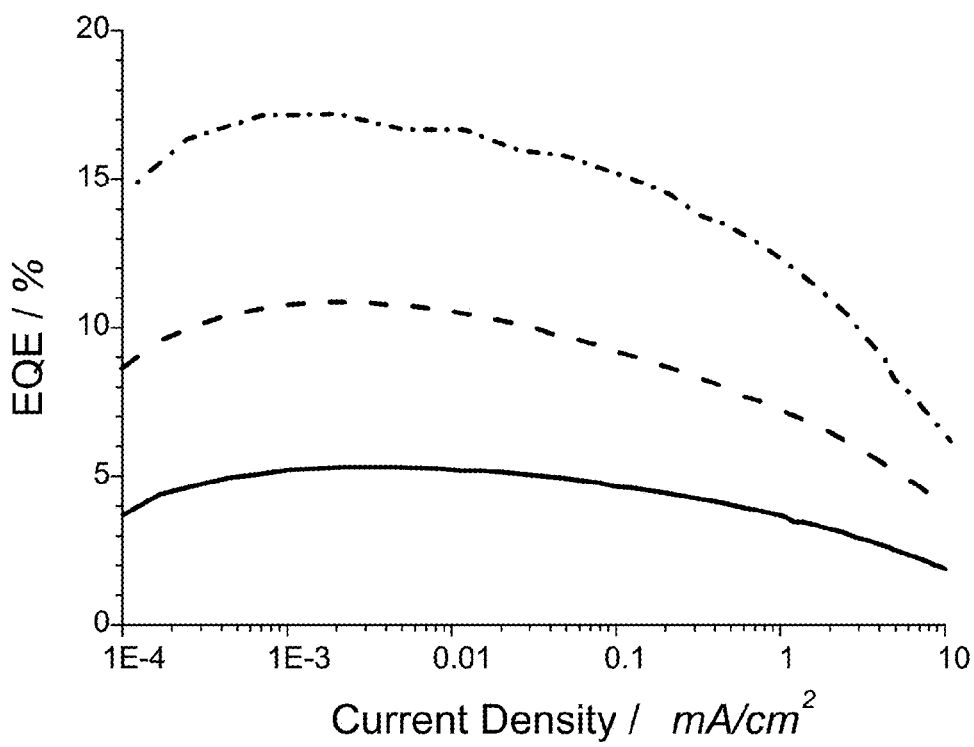
FIG. 31D shows EQE vs current density for devices of each emitter.

Deep-blue OLEDs employing PtON1-tBu, PtON6-tBu, and PtON7-dtb were fabricated with the structure indium tin oxide (ITO)/HATCN (10 nm)/NPD (40 nm)/TAPC (10 nm)/2% dopant: 26mCPy (25 nm)/DPPS (10 nm)/BmPyPB (40 nm)/LiF/Al. The dopant concentration was initially kept low at 2% (w/w) in order to avoid any spectral broadening from aggregation of the Pt complexes. FIGS. 31A-31C show EL Spectra of: PtON1-tBu (solid line), PtON6-tBu (dashed line), and PtON7-dtb (dash-dot line), respectively. FIG. 31D shows EQE vs current density for devices of each emitter in the structure: ITO/HATCN (10 nm)/NPD (40 nm)/TAPC (10 nm)/2% dopant: 26mCPy (25 nm)/DPPS (10 nm)/BmPyPB (40 nm)/LiF/Al. Tabulated spectral and device performance data are given in Table 2.

TABLE 2

Summary of device performance data

| Dopant | Conc. | $\lambda_{max}$ [nm] | FWHM [nm] | $CIE_x$ | $CIE_y$ | $\eta_{EQE}$ (peak) [%] | $\eta_{EQE}$ (100 cd m$^{-2}$) [%] | $\eta_{EQE}$ (500 cd m$^{-2}$) [%] |
|---|---|---|---|---|---|---|---|---|
| PtON1-tBu | 2% | 448 | 24 | 0.151 | 0.098 | 5.3 | 2.7 | — |
| PtON6-tBu | 2% | 452 | 30 | 0.147 | 0.093 | 10.9 | 6.6 | 2.8 |
| PtON7-dtb | 2% | 451 | 23 | 0.146 | 0.088 | 17.2 | 12.4 | 6.7 |
| PtON7-dtb | 6% | 452 | 25 | 0.146 | 0.091 | 19.8 | 14.7 | 9.9 |
| PtON7-dtb | 10% | 452 | 39 | 0.155 | 0.130 | 19.6 | 14.9 | 11.0 |
| PtON7-dtb | 14% | 454 | 47 | 0.161 | 0.169 | 19.0 | 15.5 | 12.2 |
| PtON7-dtb[a] | 6% | 451 | 29 | 0.148 | 0.079 | 24.8 | 22.7 | 16.0 |

1. [a]Using a cohost of TAPC:PO15 (1:1).

All of the complexes show narrow deep-blue emission that is similar to that of the solution PL spectra with emission peaks at 448 nm, 452 nm, and 452 nm, for PtON1-tBu, PtON6-tBu, and PtON7-dtb respectively. Consequently, $CIE_x \approx 0.15$ and $CIE_y < 0.1$ were achieved for all three complexes. The PtON1-tBu emission spectrum, however, shows a possible nonexclusive emission between 400 nm and 425 nm which may be attributed to undesirable energy transfer within the device from the high triplet energy emitter. This is further supported by the low EQE of the 2% PtON1-tBu doped devices peaking at 5.3% and dropping to only 2.7% at 100 cd m$^{-2}$. Devices of PtON6-tBu and PtON7-dtb on the other hand show more exclusive emission in their EL spectra and correspondingly yield better peak EQEs of 10.9% and 17.2% respectively. These results suggest that the slightly higher emission energy of PtON1-tBu ($\lambda_{max}$=448 nm) compared to PtON6-tBu ($\lambda_{max}$=452 nm) and PtON7-dtb ($\lambda_{max}$=451 nm) leads to incompatibility with this efficient device structure, and the present emitters push the limits for triplet energies while remaining compatible with carbazole based hosts such as 26mCPy.

Figure 32A:
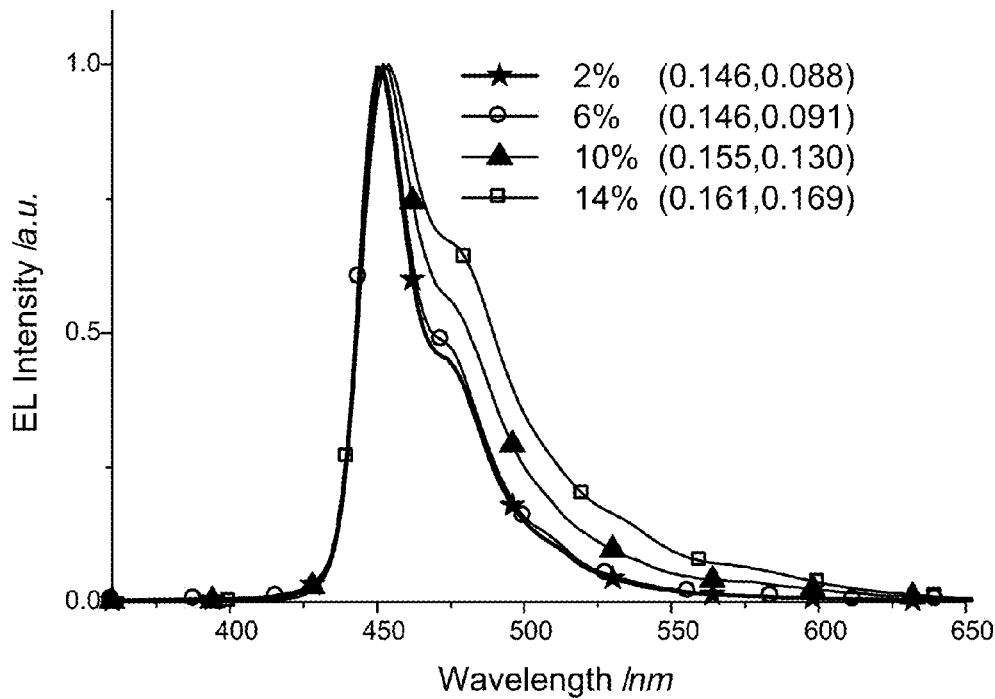
FIGS. 32A and 32B show EL spectra and EQE vs current density, respectively, for PtON7-dtb devices with various dopant concentrations. CIE values are given in the inset of FIG. 32A.
Figure 32B:
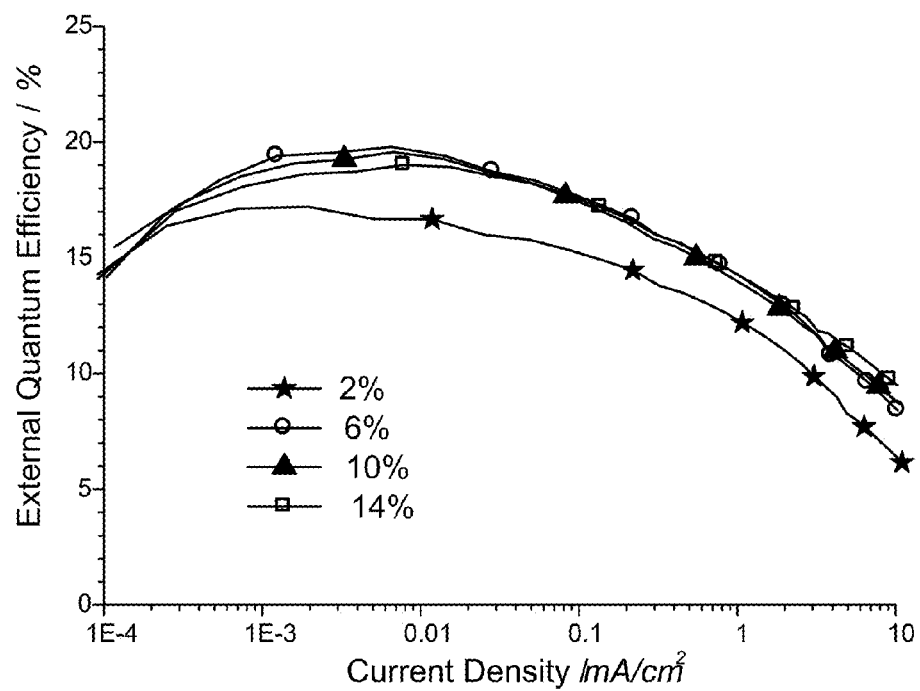

To further improve the efficiency of the devices, the effect of increasing dopant concentration of the efficient PtON7-dtb emitter was studied. Devices were fabricated in the structure: ITO/HATCN (10 nm)/NPD (40 nm)/TAPC (10 nm)/x % PtON7-dtb:26mCPy (25 nm)/DPPS (10 nm)/BmPyPB (40 nm)/LiF/Al for additional dopant concentrations of 6%, 10%, and 14%. FIGS. 32A and 32B show EL spectra and EQE vs current density, respectively, for PtON7-dtb devices with dopant concentrations of 2% (stars), 6% (circles), 10% (triangles), and 14% (squares) in the structure: ITO/HATCN (10 nm)/NPD (40 nm)/TAPC (10 nm)/x % PtON7-dtb: 26mCPy (25 nm)/DPPS (10 nm)/BmPyPB (40 nm)/LiF/Al. CIE values are given in the inset of FIG. 32A. The electroluminescent spectra of PtON7-dtb in FIG. 32A show similar emission spectra for 2% and 6% doping concentrations with CIE coordinates of (0.146, 0.088) and (0.146, 0.091), but further increasing the dopant concentration resulted in significant spectral broadening and CIE coordinates of (0.155, 0.13) and (0.161, 0.169) for 10% and 14% doping concentrations respectively. Efficiency enhancements and reductions in efficiency roll off were achieved for all dopant concentrations between 6 and 14% (FIG. 32B, Table 2) with the highest peak EQE of 19.8% achieved for the 6% PtON7-dtb doped device. It should be noted that the emission does not follow a Lambertian emission profile which may affect the outcoupling efficiencies but more study is needed to elucidate this effect. At 500 cd m$^{-2}$, the EQE increases with doping concentration reaching 12.2% at for the 14% doped device compared to 9.9% and 6.7% for 6% and 2% doped devices. Nevertheless, the superior color purity and high peak efficiencies of the 6% doped device achieves an appropriate balance between high color purity and high efficiency.

To reduce any other potential quenching effects from poor triplet energy alignment with the host or blocking materials and potentially reduce the efficiency roll off at high current densities, the 26mCPy host was replaced with a cohost of TAPC and the high-bandgap electron-transporting material 2,8-bis(diphenylphosphoryl)-dibenzothiophene (PO15). These devices were fabricated in the structure ITO/HATCN (10 nm)/NPD (40 nm)/TAPC (10 nm)/6% PtON7-dtb:47% TAPC:47% PO15 (25 nm)/PO15 (10 nm)/BmPyPB (30 nm)/LiF/Al, where the DPPS hole blocking layer was also replaced by PO15 and the BmPyPB layer thickness was reduced to 30 nm to improve charge balance. As a result of this optimization, the peak EQE improved to 24.8% and remained as high as 22.7% at a practical luminance for display applications of 100 cd m$^{-2}$, which is among the highest efficiencies for deep-blue OLEDs.

Figure 33A:
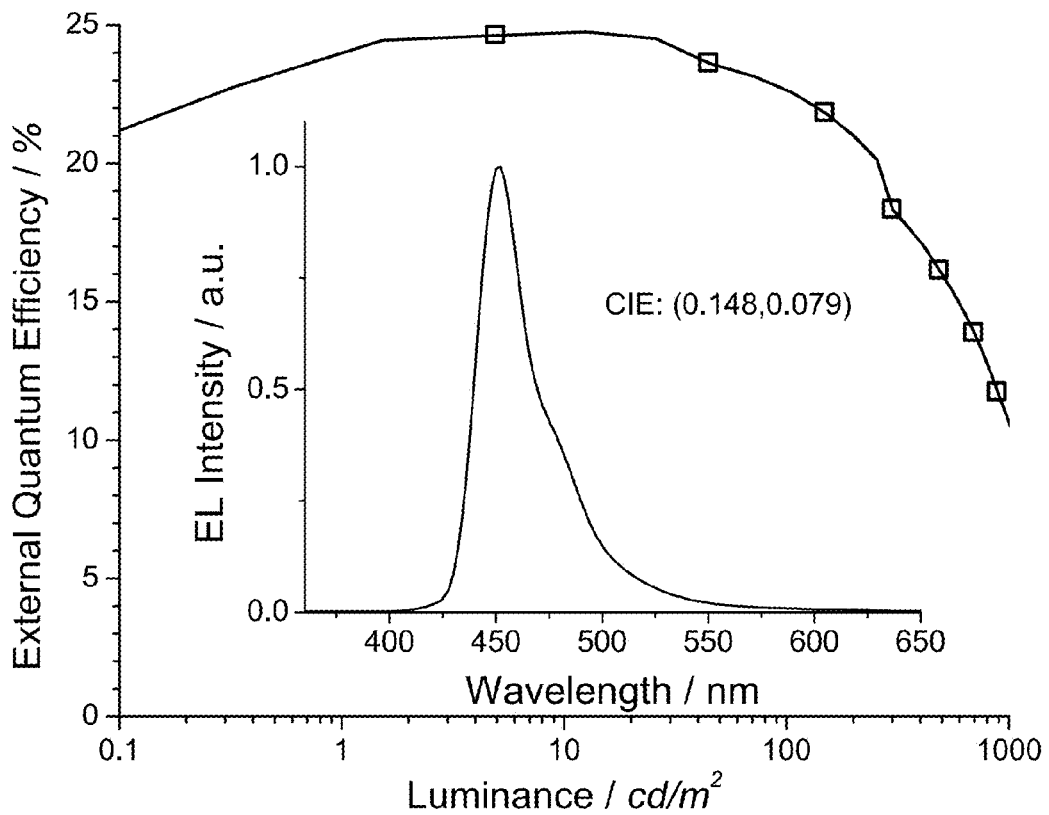
FIG. 33A shows EQE vs luminance for a PtON7-dtb device. The EL spectra and CIE coordinates are shown in the inset.
Figure 33B:
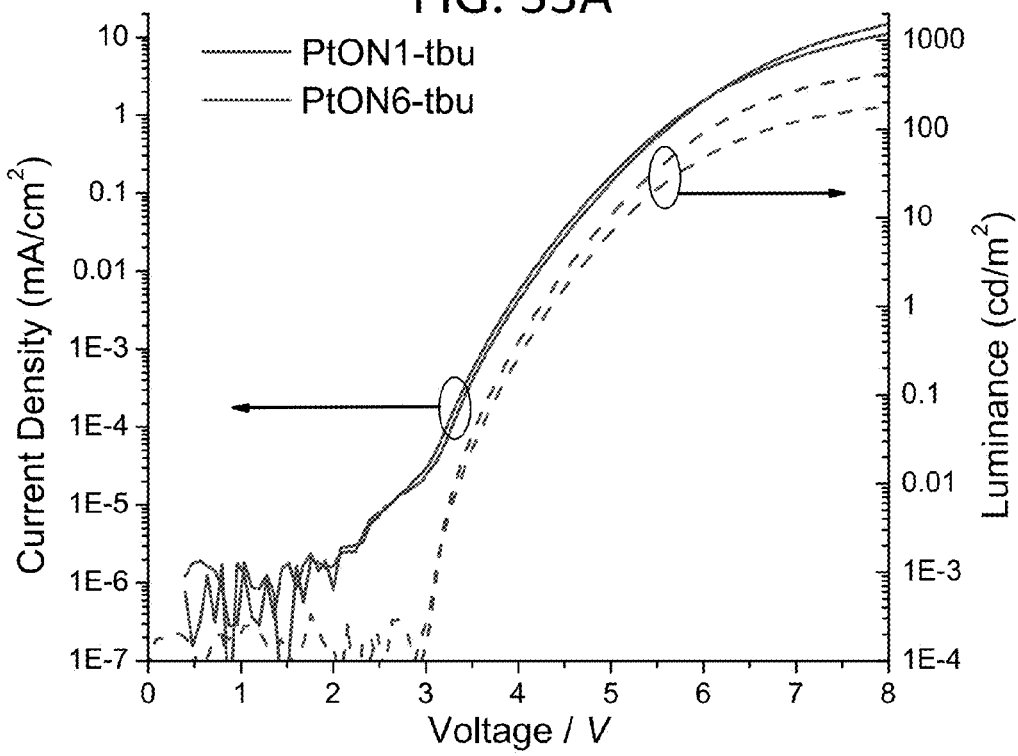
FIG. 33B shows current density and voltage-luminance characteristics for devices of PtON1-tBu and PtON6-tBu.
Figure 33C:
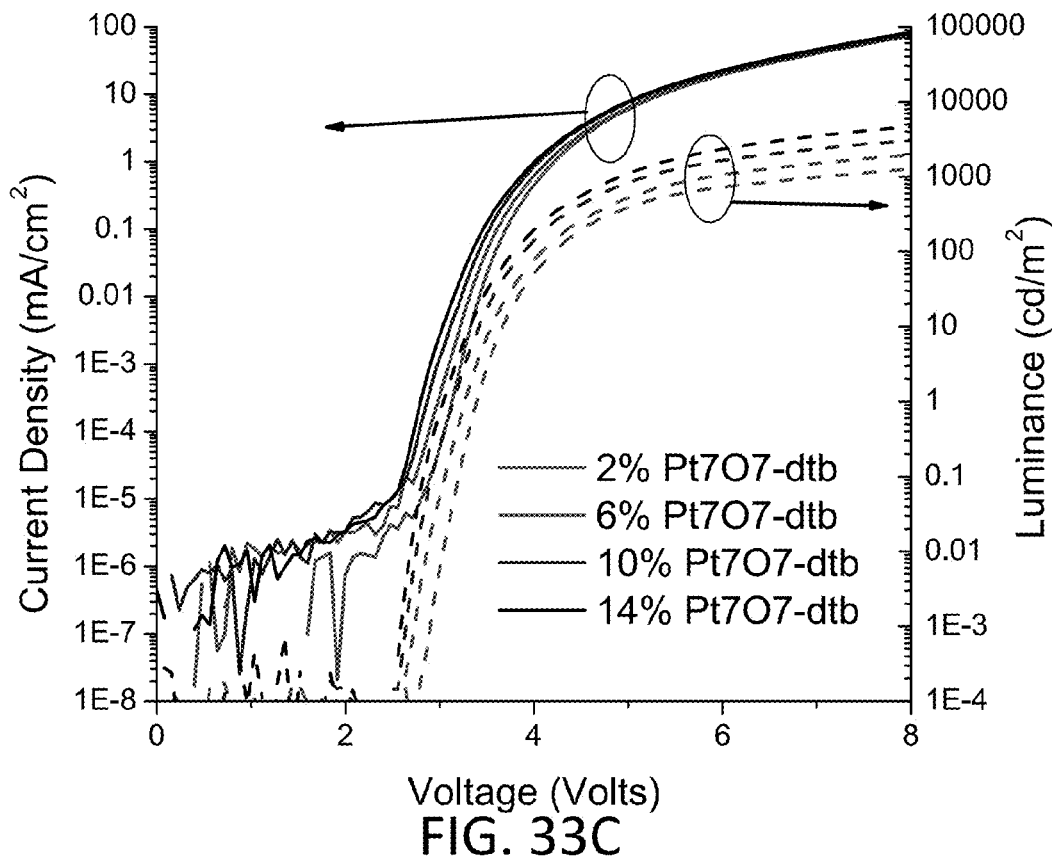
FIG. 33C shows current density-voltage-luminance characteristics for PtON7-dtb devices with various dopant concentrations.
Figure 34A:
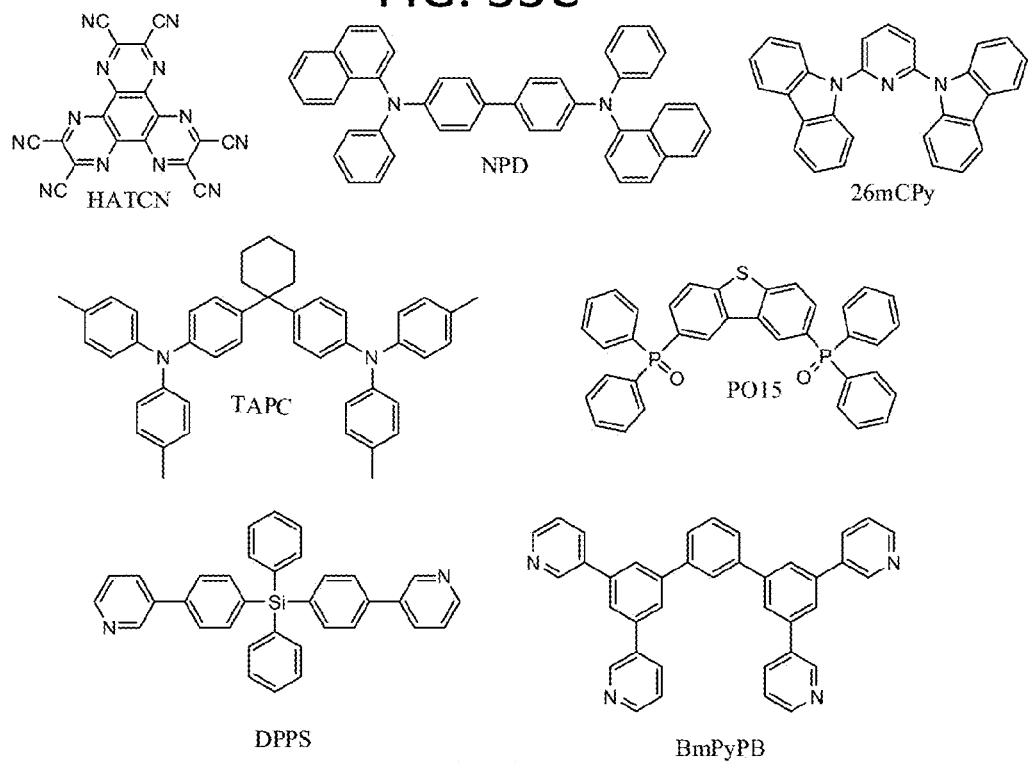
FIG. 34A shows molecular structures of materials used in the OLED devices.
Figure 34B:
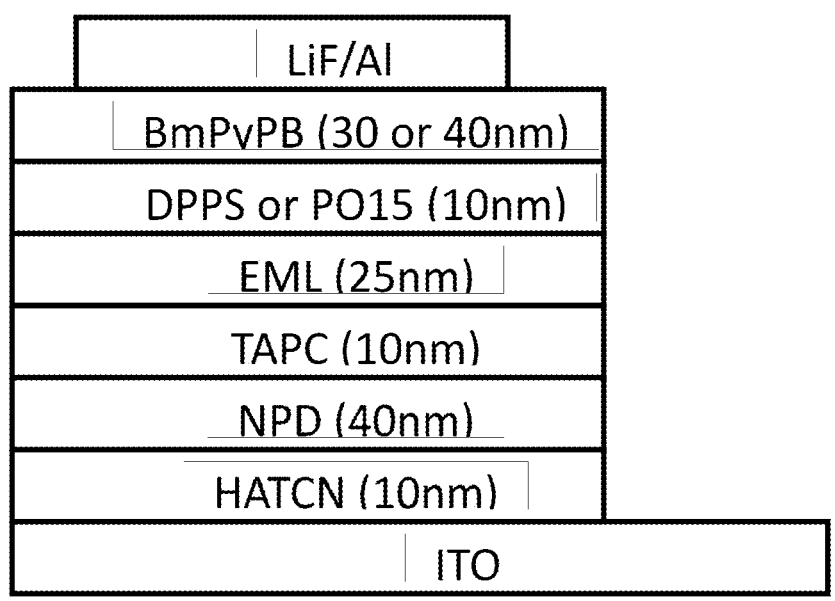
FIG. 34B depicts the device structure.

FIG. 33A shows EQE vs luminance for the PtON7-dtb device in the structure: ITO/HATCN (10 nm)/NPD (40 nm)/TAPC (10 nm)/6% PtON7-dtb: 47% TAPC: 47% PO15 (25 nm)/PO15 (10 nm)/BmPyPB (30 nm)/LiF/Al. The EL Spectra and CIE coordinates are given in the inset. The rapid drop in efficiency at higher luminance may, in part, be related to the rapid degradation of the TAPC or PO15 cohost materials as the luminance peaks then drops with increasing current density beyond 75 mA cm$^{-2}$. The emission color of such a device was also improved in the cohost structure leading to CIE values of (0.148, 0.079) which are remarkably close to the NSTC standards for blue of (0.14, 0.08). FIG. 33B shows current density and voltage-luminance characteristics for devices of PtON1-tBu and PtON6-tBu in a structure of ITO/HATCN(10 nm)/NPD(40 nm)/TAPC(10 nm)/2% Dopant: 26mCPy(25 nm)/DPPS(10 nm)/BmPyPB(40 nm)LiF/Al. FIG. 33C shows current density-voltage-luminance characteristics for PtON7-dtb devices with dopant concentrations of 2%, 6%, 10%, and 14% (in increasing order on the x scale) in the structure: ITO/HATCN(10 nm)/NPD(40 nm)/TAPC(10 nm)/x % PtON7-dtb: 26mCPy(25 nm)/DPPS(10 nm)/BmPyPB(40 nm)/LiF/Al. Molecular structures of materials used in the OLED devices are shown in FIG. 34A, and the device structures for the OLED devices is depicted in FIG. 34B. EML is the emitter doped in either 26mCPy or a cohost (1:1 wt/wt) of TAPC:PO15. Devices were fabricated by vacuum thermal evaporation in the structure of ITO/HATCN (10 nm)/NPD (40 nm)/TAPC (10 nm)/x % dopant: 26mCPy (25 nm)/DPPS (10 nm)/BmPyPB (40 nm)/LiF/Al where HATCN is 1,4,5,8,9,12-hexaazatriphenylene-hexacarbonitrile, NPD is N,N'-diphyenyl-N,N'-bis(1-naphthyl)-1,1'-biphenyl-4,4"-diamine, TAPC is di-[4-(N,N-di-toylyl-amino)-phyenyl]cyclohexane, 26mCPy is 2,6-bis(N-carbazolyl) pyridine, DPPS is diphenyl-bis[4-(pyridin-3-yl)phenyl] silane, and BmPyPB is 1,3-bis[3,5-di(pyridin-3-yl)phenyl] benzene. Devices employing a cohost emissive layer were fabricated in the structure: ITO/HATCN (10 nm)/NPD (40 nm)/TAPC (10 nm)/6% PtON7-dtb: 47% TAPC:47% PO15 (25 nm)/PO15 (10 nm)/BmPyPB (30 nm)/LiF/Al where PO15 is 2,8-bis(diphenylphosphoryl)-dibenzothiophene. All the materials used in the devices were purified via train sublimation in a four-zone thermal-gradient furnace under high vacuum (10$^{-5}$-10$^{-6}$ Torr). Prior to deposition, the pre-patterned ITO-coated glass substrates were cleaned by subsequent sonication in deionized water, acetone, and isopropyl alcohol. Organic layers were deposited at rates of 0.5 to 1.5 Ås$^{-1}$, monitored by quartz-crystal microbalances, in a custom-made vacuum thermal-evaporation chamber built by Travato Man. Inc. The Al cathode was deposited through a shadow mask without breaking vacuum, defining device areas of 0.04 cm$^2$. The current-voltage-luminance characteristics were measured using a Keithley 2400 SourceMeter in conjunction with a Newport 818 Si Photodiode. Electroluminescence spectra were measured with a Horiba-Jobin-Yvon FluoroLog-3 spectrometer.

In summary, a series of efficient "pure" blue emitters with CIE$_s$ values less than 0.1 were developed utilizing rigid tetradentate Pt complexes. These emitters demonstrated dramatically reduced vibronic sidebands compared with their Pt and Ir analogs resulting in FWHM values of ca. 20 nm for peak emission between 440-450 nm. Furthermore, the relationship between the efficiencies in a device setting and the small triplet energy differences between the narrow band emitters suggests that the emission energy of these complexes may be near the limit for being compatible with common carbazole based host materials which tend to be aligned with stable materials for OLEDs with long operational lifetimes. Devices of PtON7-dtb, in particular, demonstrated EQEs of 22.7% at 100 cd m$^{-2}$ peaking at 24.8% and CIE values of (0.148, 0.079) in a cohost structure.

Experimental Procedures

Figure 35:
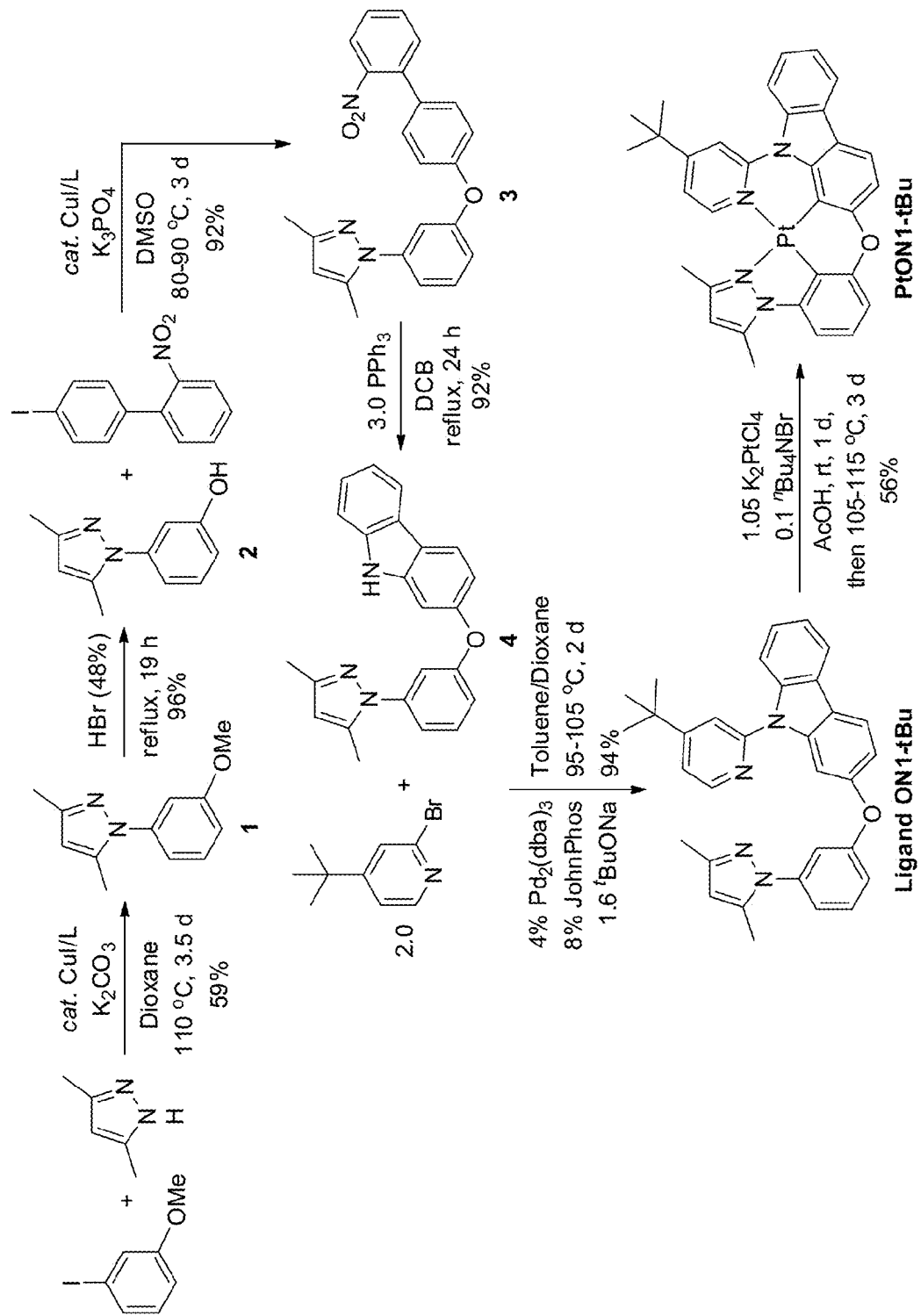
FIG. 35 depicts a method for synthesizing PtON1-tBu

PtON1-tBu was synthesized as shown in FIG. 35.

Synthesis of
1-(3-methoxyphenyl)-3,5-dimethyl-1H-pyrazole 1

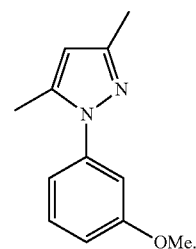

A mixture of 1-iodo-3-methoxybenzene (7.15 mL, 60 mmol, 1.0 eq), 3,5-dimethyl-1H-pyrazole (6.92 g, 72 mmol, 1.2 eq), CuI (0.46 g, 2.4 mmol, 0.04 eq), K$_2$CO$_3$ (17.41 g, 126 mmol, 2.1 eq), trans-1,2-cyclohexanediamine (1.37 g, 12 mmol, 0.2 eq) in dioxane (45 mL) was stirred at a temperature of 110° C. for 3.5 days under a nitrogen atmosphere and then cooled to ambient temperature. The solid was filtered off and washed with ethyl acetate. The filtrate was concentrated under reduced pressure and the residue was purified through column chromatography on silica gel using hexane and ethyl acetate (10:1-3:1) as an eluent to obtain the desired product, 1-(3-methoxyphenyl)-3,5-dimethyl-1H-pyrazole 1, as a brown liquid (7.12 g in 59% yield). $^1$H NMR (DMSO-d$_6$, 400 MHz): δ 2.18 (s, 3H), 2.30 (s, 3H), 3.80 (s, 3H), 6.06 (s, 1H), 6.95 (dd, J=8.0, 2.4 Hz, 1H), 7.02-7.06 (m, 2H), 7.39 (t, J=8.0 Hz, 1H).

Synthesis of 3-(3,5-dimethyl-1H-pyrazol-1-yl)phenol 2

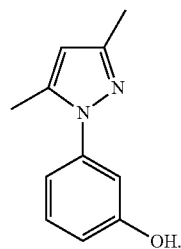

A solution of 1-(3-methoxyphenyl)-3,5-dimethyl-1H-pyrazole 1 (7.10 g, 35.11 mmol) in hydrogen bromide acid (45 mL, 48%) refluxed (110-120° C.) for 19 hours under a nitrogen atmosphere. Then the mixture was cooled to ambient temperature and neutralized with a solution of K$_2$CO$_3$ in water until there was no gas to generate. Then the precipitate was filtered off and washed with water several times. The collected solid was dried in air under reduced pressure to afford the product as a brown solid (6.33 g in 96% yield). $^1$H NMR (DMSO-d$_6$, 400 MHz): δ 2.16 (s, 3H), 2.28 (s, 3H), 6.04 (s, 1H), 6.75-6.77 (m, 1H), 6.86-6.89 (m, 2H), 7.26 (t, J=8.0 Hz, 1H), 9.73 (s, 1H). $^{13}$C NMR (DMSO-d$_6$, 100 MHz): δ 12.29, 13.30, 107.07, 111.10, 113.94, 114.43, 129.71, 138.95, 140.70, 147.57, 157.84.

Synthesis of 3,5-dimethyl-1-(3-(2'-nitrobiphenyl-4-yloxy)phenyl)-1H-pyrazole 3

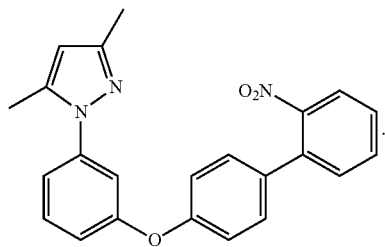 [SMILES: Cc1cc(C)n(-c2cccc(Oc3ccc(-c4ccccc4[N+](=O)[O-])cc3)c2)n1]

A mixture of 3-(3,5-dimethyl-1H-pyrazol-1-yl)phenol 2 (5.00 g, 26.56 mmol, 1.0 eq), 4'-iodo-2-nitrobiphenyl (10.38 g, 31.92 mmol, 1.2 eq), CuI (0.25 g, 1.33 mmol, 0.05 eq), picolinic acid (0.33 g, 2.66 mmol, 0.1 eq) and K$_3$PO$_4$ (11.28 g, 53.12 mmol, 2.0 eq) in DMSO (60 mL) was stirred at a temperature of 80-90° C. for three days under a nitrogen atmosphere, then cooled to ambient temperature. The solid was filtered off and washed with plenty of ethyl acetate (250 mL). The filtrate was washed with water three times and then dried over sodium sulfate and filtered. The filtrate was concentrated under reduced pressure, and the residue was purified through column chromatography on silica gel using hexane/ethyl acetate (10:1-5:1-3:1) as an eluent to obtain the desired product as a sticky liquid (9.38 g in 92% yield). 1HNMR (DMSO-d6, 400 MHz): δ 2.15 (s, 3H), 2.30 (s, 3H), 6.06 (s, 1H), 7.07 (dd, J=8.0, 2.4 Hz, 1H), 7.13-7.16 (m, 3H), 7.30-7.32 (m, 1H), 7.36-7.40 (m, 2H), 7.52 (t, J=8.0, 1H), 7.57 (dd, J=7.6, 1.2 Hz, 1H), 7.59-7.64 (m, 1H), 7.75 (td, J=7.6, 1.2 Hz, 1H), 7.97 (dd, J=8.0, 1.2 Hz, 1H). 13C NMR (DMSO-d6, 100 MHz): δ 12.30, 13.27, 107.63, 114.22, 117.18, 118.91, 118.97, 124.10, 128.81, 129.73, 130.61, 131.84, 132.28, 132.92, 134.33, 139.35, 141.11, 148.20, 148.92, 156.52, 156.67.

Synthesis of 2-(3-(3,5-dimethyl-1H-pyrazol-1-yl)phenoxy)-9H-carbazole 4

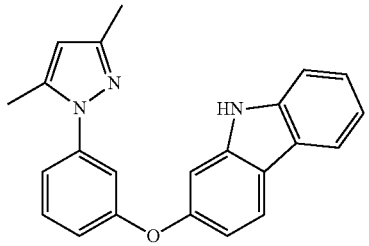

A solution of 3,5-dimethyl-1-(3-(2'-nitrobiphenyl-4-yloxy)phenyl)-1H-pyrazole 3 (2.19 g, 5.68 mmol, 1.0 eq) and PPh3 (4.47 g, 17.04 mmol, 3.0 eq) in 1,2-dichlorobenzene (30 mL) was refluxed (175-185° C.) for 24 hours, then cooled, and the solvent was removed by distillation under high vacuum. The residue was purified through column chromatography on silica gel using hexane/ethyl acetate (10:1-5:1) as an eluent to obtain the desired product as a white solid (1.83 g in 92% yield). 1H NMR (DMSO-d6, 400 MHz): δ 2.11 (s, 3H), 2.28 (s, 3H), 6.02 (s, 1H), 6.92 (dd, J=8.4, 2.0 Hz, 1H), 7.05 (dd, J=8.4, 2.4 Hz, 1H), 7.10 (t, J=2.0 Hz, 1H), 7.13-7.16 (m, 2H), 7.22-7.25 (m, 1H), 7.32-7.36 (m, 1H), 7.46 (d, J=8.0, 1H), 7.47 (t, J=8.4 Hz, 1H), 8.07 (d, J=7.2 Hz, 1H), 8.12 (d, J=8.4 Hz, 1H), 11.25 (s, 1H). 13C NMR (DMSO-d6, 100 MHz): δ 12.30, 13.24, 101.46, 107.52, 110.92, 111.10, 113.37, 116.43, 118.09, 118.87, 119.12, 119.88, 121.50, 122.23, 125.23, 130.36, 139.24, 140.17, 140.68, 140.99, 148.10, 154.44, 158.21.

Synthesis of 9-(4-tert-butylpyridin-2-yl)-2-(3-(3,5-dimethyl-1H-pyrazol-1-yl)phenoxy)-9H-carbazole Ligand ON1-tBu

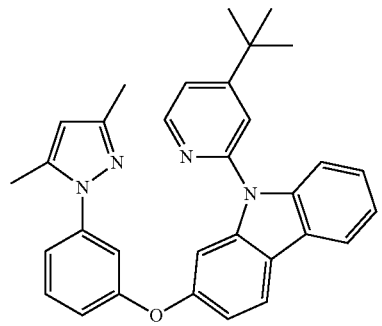

Ligand ON1-tBu

A mixture of 2-(3-(3,5-dimethyl-1H-pyrazol-1-yl)phenoxy)-9H-carbazole 4 (530 mg, 1.5 mmol, 1.0 eq), 2-bromo-4-tert-butylpyridine (642 mg, 3.0 mmol, 2.0 eq), Pd2(dba)3 (55 mg, 0.06 mmol, 0.04 eq), JohnPhos (36 mg, 0.12 mmol, 0.08 eq) and tBuONa (231 mg, 2.4 mmol, 1.6 eq) in toluene (6 m) and dioxane (6 mL) was stirred at a temperature of 95-105° C. for 2 days under a nitrogen atmosphere. Then the mixture was cooled to ambient temperature. The solvent was removed under reduced pressure and the residue was purified through column chromatography on silica gel using hexane/ethyl acetate (10:1-5:1) as an eluent to obtain the desired product as a brown solid (685 mg in 94% yield). 1H NMR (DMSO-d6, 400 MHz): δ1.26 (s, 9H), 2.11 (s, 3H), 2.23 (s, 3H), 6.00 (s, 1H), 7.06-7.08 (m, 1H), 7.10 (dd, J=8.0, 2.4 Hz, 1H), 7.14 (t, J=2.4 Hz, 1H), 7.24-7.26 (m, 1H), 7.31 (t, J=7.2 Hz, 1H), 7.38 (d, J=2.0 Hz, 1H), 7.41-7.48 (m, 3H), 7.61 (d, J=1.6, 1H), 7.74 (d, J=8.4 Hz, 1H), 8.20 (d, J=8.0 Hz, 1H), 8.26 (d, J=8.8 Hz, 1H), 8.55 (d, J=4.8 Hz, 1H). 13C NMR (DMSO-d6, 100 MHz): δ12.21, 13.22, 30.01, 34.81, 101.37, 107.50, 111.11, 113.01, 113.81, 115.78, 116.80, 118.49, 119.27, 119.72, 120.13, 121.11, 121.83, 123.20, 125.90, 130.45, 139.19, 139.43, 139.94, 141.01, 148.07, 149.37, 150.60, 155.32, 157.50, 163.03.

Synthesis of platinum(II) [6-(3,5-dimethyl-1H-pyrazol-1-yl-κN2)-1,2-phenylene-κC1]oxy[9-(4-tert-butyltpyridin-2-yl-κN)-9H-carbazole-1,2-diyl-κC1] (PtON1-tBu)

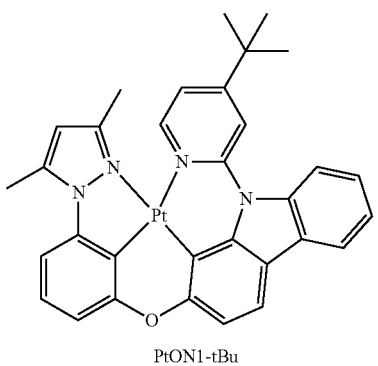

PtON1-tBu

A mixture of 9-(4-tert-butylpyridin-2-yl)-2-(3-(3,5-dimethyl-1H-pyrazol-1-yl)phenoxy)-9H-carbazole Ligand ON1-tBu (635 mg, 1.30 mmol, 1.0 eq), K2PtCl2 (567 mg, 1.37 mmol, 1.05 eq) and nBu4NBr (42 mg, 0.13 mmol, 0.1 eq) in acetic acid (78 mL) was stirred at room temperature for 1 day in a pressure vessel under a nitrogen atmosphere, followed at 105-115° C. for another 3 days, then cooled to ambient temperature. Then water (160 mL) was added to the mixture. The precipitate was filtered off and washed with water three times. The collected solid was dried under reduced pressure and then purified by flash chromatography on silica gel using hexane/dichloromethane (1:1) as an eluent to afford the title compound as a yellow solid (495 mg in 56% yield). The product was further purified by sublimation in a four zone thermal gradient sublimator at 265° C., 260° C., 210° C., 165° C., 3.9×10$^{-6}$ Torr to obtain white crystal in high yield. 1H NMR (CD2Cl2, 400 MHz): δ 1.32 (s, 9H), 2.46 (s, 3H), 2.73 (s, 3H), 6.18 (s, 1H), 6.99-7.03 (m, 2H), 7.20-7.26 (m, 3H), 7.38 (t, J=7.6 Hz, 1H), 7.48 (t, J=8.0 Hz, 1H), 7.79 (d, J=7.6 Hz, 1H), 7.94 (d, J=8.0 Hz, 1H), 8.07 (d, J=8.0 Hz, 1H), 8.09 (d, J=1.2 Hz, 1H), 9.08 (d, J=7.2 Hz, 1H). 1H NMR (DMSO-d6, 400 MHz): δ 1.32 (s, 9H), 2.43 (s, 3H), 2.75 (s, 3H), 6.44 (s, 1H), 6.95 (d, J=8.0 Hz, 1H), 7.17 (d, J=8.4 Hz, 1H), 7.22 (t, J=8.0 Hz, 1H), 7.28 (d, J=7.6 Hz, 1H), 7.34 (dd, J=6.0, 1.6 Hz, 1H), 7.40 (t, J=7.6 Hz, 1H), 7.50 (t, J=7.6 Hz, 1H), 7.86 (d, J=8.4 Hz, 1H), 8.05 (d, J=1.2 Hz, 1H), 8.11 (d, J=8.0 Hz, 1H), 8.16 (d, J=7.6 Hz, 1H), 9.11 (d, J=6.4 Hz, 1H). 13C NMR (CD2Cl2, 100 MHz): δ 14.99, 15.15, 30.24, 35.89, 100.32, 107.22, 110.29, 111.78, 112.79, 113.07, 113.21, 114.78, 115.40, 116.33, 116.36, 120.32, 122.94, 124.45, 124.71, 129.28, 139.07, 142.06, 143.23, 148.44, 149.35, 150.01, 152.80, 153.22, 153.41, 163.97. MS (MALDI) for C32H28N4OPt [M]+: calcd 679.2. found 679.0. Anal. Calcd. For C32H28N4OPt: C, 56.55; H, 4.15; N, 8.24. Found: C, 56.46; H, 4.24; N, 8.17.

Synthesis of PtON6-tBu

Figure 36:
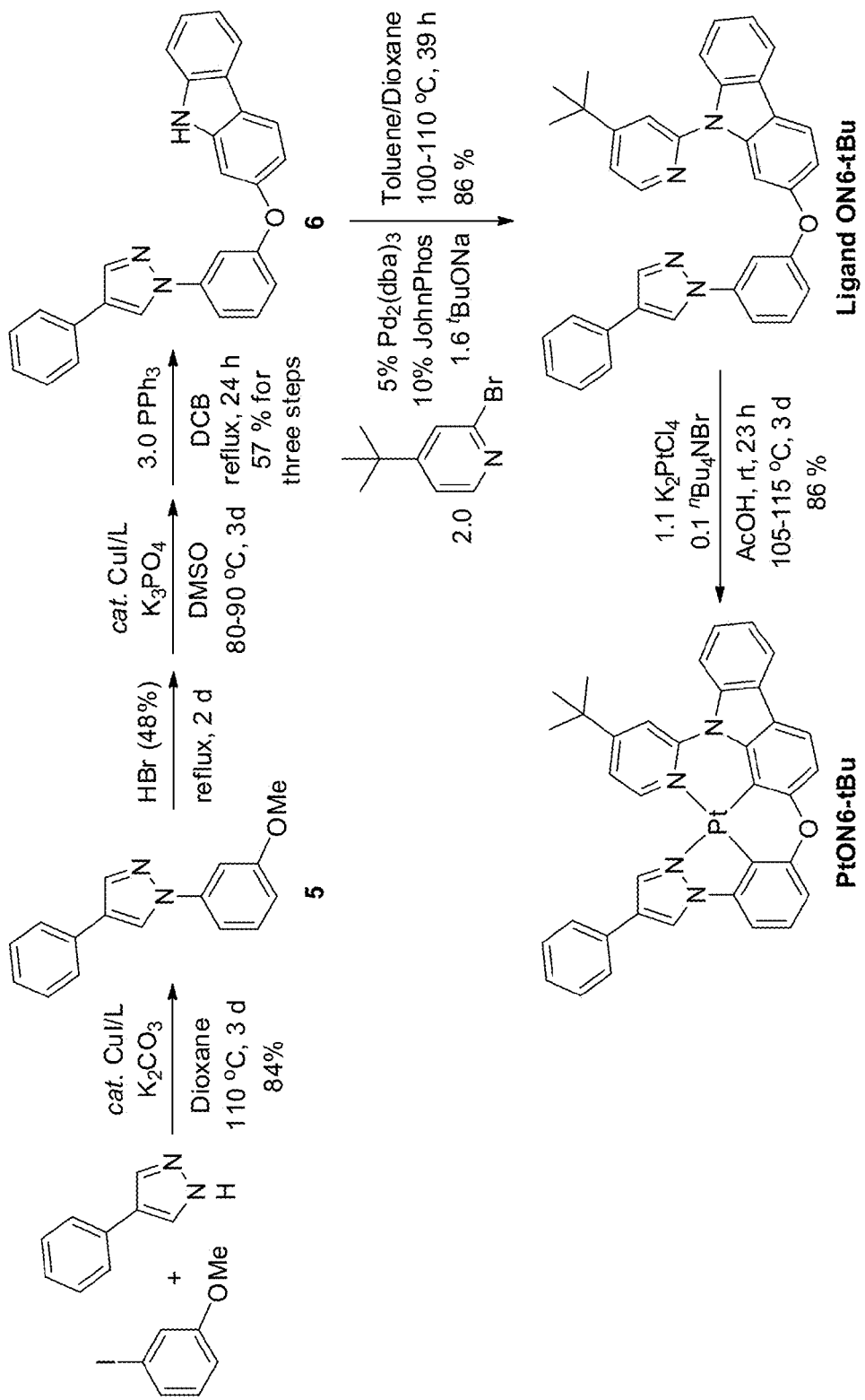
FIG. 36 depicts a method for synthesizing PtON6-tBu.

PtON6-tBu was synthesized as shown in FIG. 36.

Synthesis of 1-(3-methoxyphenyl)-4-phenyl-1H-pyrazole 5

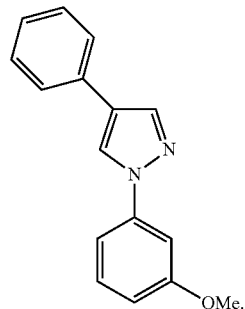 [SMILES: COc1cccc(-n2cc(-c3ccccc3)cn2)c1]

A mixture of 4-phenyl-1H-pyrazole (775 mg, 5.38 mmol, 1.0 eq), 1-iodo-3-methoxybenzene (1510 mg, 768 μL, 6.45 mmol, 1.2 eq), CuI (21 mg, 0.11 mmol, 0.02 eq), K2CO3 (1561 mg, 11.30 mmol, 2.1 eq) and trans-1,2-cyclohexanediamine (123 mg, 1.08 mmol, 0.20 eq) in dioxane (12 mL) was stirred at a temperature of 110° C. for three days, then cooled to ambient temperature. The solvent was removed under reduced pressure and the residue was purified through column chromatography on silica gel using hexane and ethyl acetate (10:1-5:1-3:1) as an eluent to obtain the desired product, 1-(3-methoxyphenyl)-4-phenyl-1H-pyrazole 5, as a colorless liquid (1.13 g in 84% yield). 1H NMR (DMSO-d6, 400 MHz): δ 3.84 (s, 3H), 6.87-6.90 (m, 1H), 7.25 (t, J=7.2 Hz, 1H), 7.38-7.48 (m, 5H), 7.71 (d, J=7.2 Hz, 2H), 8.20 (s, 1H), 9.01 (s, 1H).

Synthesis of 2-(3-(4-phenyl-1H-pyrazol-1-yl)phenoxy)-9H-carbazole 6

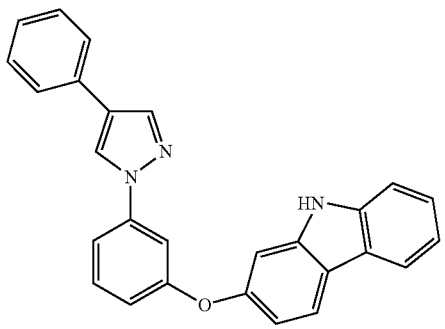

A solution of 1-(3-methoxyphenyl)-4-phenyl-1H-pyrazole 5 (1.10 g, 4.39 mmol) in hydrogen bromide acid (6 mL, 48%) refluxed (110-120° C.) for 2 days under a nitrogen atmosphere, then cooled to ambient temperature and neutralized with a solution of $K_2CO_3$ in water until there was no gas to generate. Then the precipitate was filtered off and washed with water several times. The collected solid was dried in air under reduced pressure to afford the product as a brown solid as a mixture of desired product starting material=100:31 showed by 1H NMR spectrum, which was used directly for the next steps. The brown solid obtained from the last step, 4'-iodo-2-nitrobiphenyl (1209 mg, 3.72 mmol), CuI (30 mg, 0.16 mmol), picolinic acid (38 mg, 0.31 mmol) and $K_3PO_4$ (1316 mg, 6.20 mmol) were added to a dry Schlenk pressure tube equipped with a magnetic stir bar. The tube was evacuated and back-filled with nitrogen. This evacuation and back-fill procedure was repeated twice. Then solvent DMSO (10 mL) was added under a nitrogen atmosphere and the tube was sealed. The mixture was heated to 80-90° C. in an oil bath for 3 days, then cooled to ambient temperature and diluted with water. The mixture was extracted with ethyl acetate three times. The combined organic layer was washed with water three times, dried over sodium sulfate, and filtered. The filtrate was concentrated and the residue was purified through column chromatography on silica gel using hexane and ethyl acetate (10:1-5:1-3:1) as an eluent to obtain the desired product as a sticky liquid 1.13 g, which was used directly for the next step. A solution of the sticky liquid (1100 mg, 2.54 mmol, 1.0 eq) obtained in the last step, PPh3 (1997 mg, 7.61 mmol, 3.0 eq) in 1,2-dichlorobenzene (15 mL) refluxed for 24 hours under a nitrogen atmosphere, then cooled. The solvent was removed by distillation under high vacuum and the residue was purified through column chromatography on silica gel using hexane and ethyl acetate (10:1-5:1-3:1) as an eluent to obtain the desired product, 2-(3-(4-phenyl-1H-pyrazol-1-yl)phenoxy)-9H-carbazole 6 as a white solid 1.00 mg in 57% total yield for the three steps. 1H NMR (DMSO-d6, 400 MHz): δ 6.96 (dd, J=8.4, 2.4 Hz, 1H), 7.01 (dd, J=8.0, 2.4 Hz, 1H), 7.16-7.19 (m, 2H), 7.25 (d, J=7.6 Hz, 1H), 7.35-7.42 (m, 3H), 7.48 (d, J=8.0 Hz, 1H), 7.54 (t, J=8.0 Hz, 1H), 7.63 (t, J=2.4 Hz, 1H), 7.68-7.72 (m, 3H), 8.10 (d, J=8.0 Hz, 1H), 8.16 (d, J=7.2 Hz, 1H), 8.19 (s, 1H), 9.05 (s, 1H), 11.26 (s, 1H).

Synthesis of 9-(4-tert-butylpyridin-2-yl)-2-(3-(4-phenyl-1H-pyrazol-1-yl)phenoxy)-9H-carbazole Ligand ON6-tBu

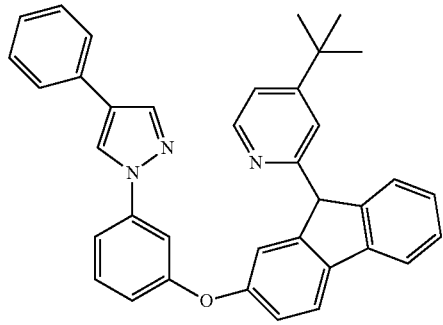

Ligand ON6-tBu 2-(3-(4-Phenyl-1H-pyrazol-1-yl)phenoxy)-9H-carbazole 6 (401 mg, 1.0 mmol, 1.0 eq), $Pd_2(dba)_3$ (46 mg, 0.05 mmol, 0.05 eq), JohnPhos (30 mg, 0.10 mmol, 0.1 eq) and tBuONa (154 mg, 1.6 mmol, 1.6 eq) were added to a dry pressure Schlenk tube equipped with a magnetic stir bar. The tube was evacuated and back-filled with nitrogen, the evacuation and back-fill procedure was repeated twice. Then dry solvent toluene (4 mL), dioxane (4 mL) and 2-bromo-4-tert-butylpyridine (418 mg, 2.0 mmol, 2.0 eq) were added under a nitrogen atmosphere. The tube was sealed and the mixture was stirred at a temperature of 100-110° C. for 39 hours, and cooled to ambient temperature. The solvent was removed under reduced pressure and the residue was purified through column chromatography on silica gel using hexane and ethyl acetate (20:1-15:1-10:1-5:1) as an eluent to obtain the desired product, 9-(4-tert-butylpyridin-2-yl)-2-(3-(4-phenyl-1H-pyrazol-1-yl)phenoxy)-9H-carbazole Ligand ON6-tBu, as a brown solid (460 mg in 86% yield). 1H NMR (DMSO-d6, 400 MHz): δ 1.24 (s, 9H), 7.04 (dd, J=8.0, 2.6 Hz, 1H), 7.16 (dd, J=8.4, 2.4 Hz, 1H), 7.24 (t, J=7.6 Hz, 1H), 7.32-7.47 (m, 6H), 7.53 (t, J=8.4 Hz, 1H), 7.62 (d, J=1.2 Hz, 1H), 7.66 (t, J=2.0 Hz, 1H), 7.69-7.72 (m, 3H), 7.78 (d, J=8.4 Hz, 1H), 8.19 (s, 1H), 8.24 (d, J=7.6 Hz, 1H), 8.31 (d, J=8.8 Hz, 1H), 8.57 (d, J=5.6 Hz, 1H), 9.05 (s, 1H).

Synthesis of platinum(II) [6-(4-phenyl-1H-pyrazol-1-yl-κN2)-1,2-phenylene-κC1]oxy[9-(4-tert-butylpyridin-2-yl-κN)-9H-carbazole-1,2-diyl-κC1] (PtON6-tBu): A mixture of 9-(4-tert-butylpyridin-2-yl)-2-(3-(4-phenyl-1H-pyrazol-1-yl)phenoxy)-9H-carbazole Ligand ON6-tBu (450 mg, 0.84 mmol, 1.0 eq), $K_2PtCl_4$ (383 mg, 0.92 mmol, 1.1 eq) and $nBu_4NBr$ (27 mg, 0.084 mmol, 0.1 eq) in acetic acid (50 mL) was stirred at room temperature for 23 hours in a pressure vessel under a nitrogen atmosphere, followed at 105-115° C. in an oil bath for 3 days, cooled to ambient temperature. Then water (50 mL) was added slowly. After stirring at room temperature for 5 minutes, the precipitate was filtered off and washed with water three times. The collected solid was dried in air under reduced pressure, and then purified through column chromatography on silica gel using dichloromethane as an eluent to obtain the desired product platinum complex, PtON6-tBu, as a yellow solid (525 mg in 86% yield). 510 mg of the product was further purified by sublimation in a four zone thermal gradient sublimator at 260° C., 260° C., 210° C., 170° C., $3.2 \times 10^{-6}$ Torr to obtain yellow needle crystals (280 mg in 55% yield). 1H NMR (DMSO-d6, 400 MHz): δ 1.36 (s, 9H), 6.96 (dd, J=8.0, 0.8 Hz, 1H), 7.19 (d, J=8.4 Hz, 1H), 7.23 (t, J=8.0 Hz, 1H), 7.34 (t, J=7.2 Hz, 1H), 7.39 (t, J=7.6 Hz, 1H), 7.45-7.53 (m, 5H), 7.86-7.90 (m, 3H), 8.06 (d, J=7.6 Hz, 1H), 8.12 (d, J=1.6 Hz, 1H), 8.14-8.16 (m, 1H), 8.63 (s, 1H), 9.21 (d, J=6.4 Hz, 1H), 9.37 (s, 1H). 13C NMR (DMSO-d6, 100 MHz): δ 29.64, 35.46, 98.77, 106.04, 111.18, 112.39, 112.51, 113.26, 114.57, 115.60, 115.72, 118.35, 120.13, 122.88, 123.82, 124.62, 124.73, 125.41, 125.37, 127.33, 127.90, 128.99, 130.80, 136.95, 138.10, 142.01, 146.00, 147.45, 151.96, 152.29, 152.55, 163.03. MS (MALDI) for $C_{36}H_{29}N_4OPt$ $[M^+H]^+$: calcd 728.2. found 728.3. Anal. Calcd. For $C_{36}H_{28}N_4OPt \cdot H_2O$: C, 57.98; H, 4.05; N, 7.51. Found: C, 58.35; H, 3.87; N, 7.55.

Synthesis of PtON7-dtb

Figure 37:
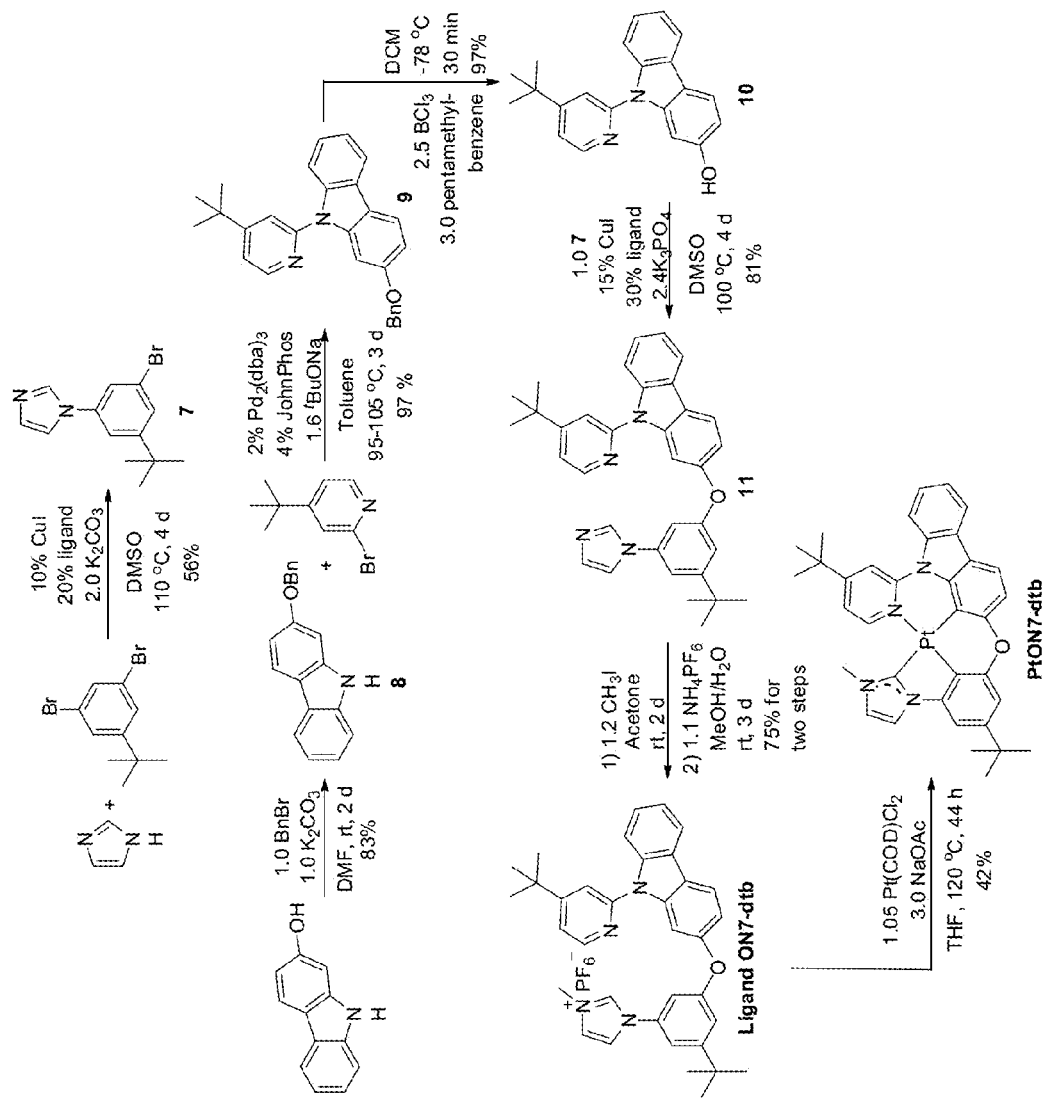
FIG. 37 depicts a method for synthesizing PtON7-dtb.

PtON7-dtb was synthesized as shown in FIG. 37.

Synthesis of 1-(3-bromo-5-tert-butylphenyl)-1H-imidazole 7

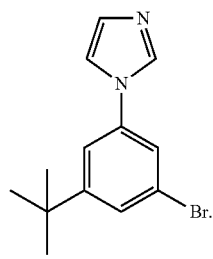 [SMILES: CC(C)(C)c1cc(Br)cc(-n2ccnc2)c1]

A mixture of 1,3-dibromo-5-tert-butylbenzene (2.92 g, 10.0 mmol, 1.0 eq), 1H-imidazole (0.69 g, 10.0 mmol, 1.0 eq), CuI (0.19 g, 1.0 mmol, 0.10 eq), $K_2CO_3$ (2.76 g, 20.0 mmol, 2.0 eq) and 2-(dimethylamino)acetic acid (0.21 g, 2.0 mmol, 0.20 eq) in DMSO (10 mL) was stirred at a temperature of 110° C. for four days under a nitrogen atmosphere, then cooled down to ambient temperature. The mixture was diluted with plenty of ethyl acetate and filtered. The filtrate was washed with water three times, dried over sodium sulfate, then filtered, and the filtrate was concentrated under reduced pressure. The residue was purified through column chromatography on silica gel using hexane and ethyl acetate as an eluent to obtain the desired product, 1-(3-bromo-5-tert-butylphenyl)-1H-imidazole 7, as a brown sticky liquid (1.56 g in 56% yield).

Synthesis of 2-(benzyloxy)-9H-carbazole 8

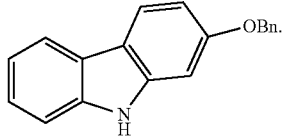 [SMILES: c1ccc(COc2ccc3c(c2)[nH]c2ccccc23)cc1]

A mixture of 9H-carbazol-2-ol (8.57 g, 46.78 mmol, 1.0 eq), BnBr (5.56 mL, 46.78 mmol, 1.0 eq) and $K_2CO_3$ (6.47 g, 46.78 mmol, 2.0 eq) in DMF (70 mL) was stirred at room temperature for two days. Then water (70 mL) was added, the mixture was stirred at room temperature for another 5 minutes. The precipitate was filtered and washed with water three times first, then washed with ethyl acetate once. The collected solid was dried in air under reduced pressure to afford the desired product as a grey solid (10.68 g in 83% yield). 1H NMR (DMSO-d6, 400 MHz): δ 5.21 (s, 2H), 6.86 (dd, J=7.2, 2.0 Hz, 1H), 7.06 (d, J=1.6 Hz, 1H), 7.10-7.13 (m, 1H), 7.28-7.31 (m, 1H), 7.35 (t, J=6.0 Hz, 1H), 7.40-7.44 (m, 3H), 7.52 (d, J=5.6 Hz, 2H), 7.97-8.00 (m, 2H), 11.12 (s, 1H).

Synthesis of 2-(benzyloxy)-9-(4-tert-butylpyridin-2-yl)-9H-carbazole 9

2-(Benzyloxy)-9H-carbazole 9 (6.00 g, 21.95 mmol, 1.0 eq), Pd2(dba)3 (0.40 g, 0.44 mmol, 0.02 eq), JohnPhos (0.26 g, 0.88 mmol, 0.04 eq) and tBuONa (3.38 g, 35.12 mmol, 1.6 eq) were added to a dry pressure Schlenk tube equipped with a magnetic stir bar. The tube was evacuated and back-filled with nitrogen, the evacuation and back-fill procedure was repeated twice. Then dry solvent toluene (70 mL) and 2-bromo-4-tert-butylpyridine (5.64 g, 26.34 mmol, 1.2 eq) were added under a nitrogen atmosphere. The tube was sealed and the mixture was stirred at a temperature of 95-105° C. for three days, and cooled to ambient temperature. The solvent was removed under reduced pressure and the residue was purified through column chromatography on silica gel using hexane and ethyl acetate (10:1-5:1) as an eluent to obtain the desired product, 2-(benzyloxy)-9-(4-tert-butylpyridin-2-yl)-9H-carbazole 9, as a brown solid (8.68 g in 97% yield). 1H NMR (DMSO-d6, 400 MHz): δ 1.38 (s, 9H), 5.17 (s, 2H), 7.03 (dd, J=8.4, 2.0 Hz, 1H), 7.27-7.41 (m, 6H), 7.46-7.48 (m, 2H), 7.51 (dd, J=5.6, 2.0 Hz, 1H), 7.69 (s, 1H), 7.70 (d, J=8.4 Hz, 1H), 8.12-8.14 (m, 2H), 8.64 (d, J=5.2 Hz, 1H).

Synthesis of 9-(4-tert-butylpyridin-2-yl)-9H-carbazol-2-ol 10

A solution of 2-(benzyloxy)-9-(4-tert-butylpyridin-2-yl)-9H-carbazole 9 (3.00 g, 7.38 mmol, 1.0 eq) and pentamethylbenzene (3.33 g, 22.14 mmol, 3.0 eq) in dichloromethane (74 mL) was cooled to −78° C. in a dry ice-acetone bath, then $BCl_3$ (18.45 mL, 18.45 mmol, 1.0 M in dichloromethane) was added dropwise. After that, the mixture was stirred at −78° C. for 30 minutes, then quenched with methanol. The dry ice-acetone bath was removed and the mixture was warmed to room temperature. The pH of the solution was adjusted to about 6-7 using $Et_3N$, then the solution was washed with saturated $NaHCO_3$ solution until there was no gas to generate, dried over sodium sulfate, and filtered. The filtrate was concentrated under reduced pressure and the residue was purified through column chromatography on silica gel using hexane/ethyl acetate (10:1-3:1) first, then dichloromethane/methanol (10:1) as an eluent to obtain the desired product, 9-(4-tert-butylpyridin-2-yl)-9H-carbazol-2-ol 10, as a grey solid (2.27 g in 97% yield). 1H NMR (DMSO-d6, 400 MHz): δ 1.40 (s, 9H), 6.79 (dd, J=8.0, 2.0 Hz, 1H), 7.15 (d, J=2.0 Hz, 1H), 7.25 (t, J=7.2 Hz, 1H), 7.32-7.36 (m, 1H), 7.50 (dd, J=5.6, 1.6 Hz, 1H), 7.65 (d, J=2.0 Hz, 1H), 7.68 (d, J=8.4 Hz, 1H), 8.00 (d, J=8.4 Hz, 1H), 8.07 (d, J=7.6 Hz, 1H), 8.63 (d, J=5.6 Hz, 1H), 9.62 (s, 1H).

Synthesis of 2-(3-tert-butyl-5-(1H-imidazol-1-yl)phenoxy)-9-(4-tert-butylpyridin-2-yl)-9H-carbazole 11

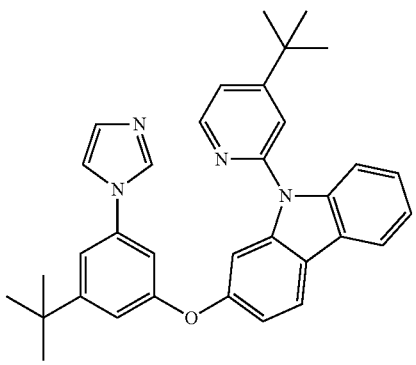

A mixture of 1-(3-bromo-5-tert-butylphenyl)-1H-imidazole 7 (0.98 g, 3.50 mmol, 1.0 eq), 9-(4-tert-butylpyridin-2-yl)-9H-carbazol-2-ol 10 (1.11 g, 3.50 mmol, 1.0 eq), CuI (0.10 g, 0.53 mmol, 0.15 eq), picolinic acid (0.13 g, 1.05 mmol, 0.30 eq) and K_3PO_4 (1.78 g, 8.40 mmol, 2.4 eq) in DMSO (7 mL) was stirred at a temperature of 100° C. for four days under a nitrogen atmosphere, then cooled to ambient temperature. The solid was filtered off and washed with plenty of ethyl acetate. The filtrate was washed with water three times and then dried over sodium sulfate and filtered. The filtrate was concentrated under reduced pressure and the residue was purified through column chromatography on silica gel using hexane/ethyl acetate as an eluent to obtain the desired product as a brown sticky liquid (1.45 g in 81% yield).

Synthesis of 1-(3-tert-butyl-5-(9-(4-tert-butylpyridin-2-yl)-9H-carbazol-2-yloxy)phenyl)-3-methyl-1H-imidazol-3-ium hexafluorophosphate(V) Ligand ON7-dtb

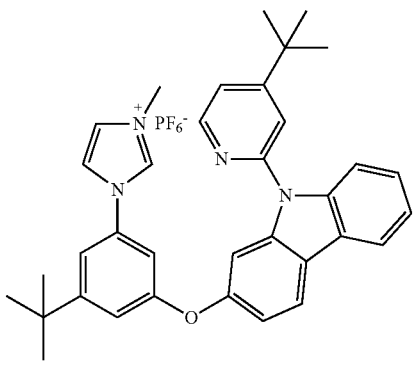

Ligand ON7-dtb

A solution of $CH_3I$ (0.21 mL, 3.38 mmol, 1.2 eq) and 2-(3-tert-butyl-5-(1H-imidazol-1-yl)phenoxy)-9-(4-tert-butylpyridin-2-yl)-9H-carbazole 11 (1.45 g, 2.82 mmol, 1.0 eq) in acetone (10 mL) was stirred in a sealed vessel at room temperature for two days. Then the solvent was removed under reduced pressure and the residue was purified through column chromatography on silica gel using hexane/ethyl acetate (1:1) first, then only ethyl acetate, then dichloromethane/methanol (10:1) as an eluent to obtain the desired product as a brown solid (1.57 g) which was used directly for the next step. The brown solid (1.57 g, 2.39 mmol, 1.0 eq) was added to a mixture of $MeOH/H_2O$ (12 mL/8 mL). The mixture was stirred for 30 min until the solid was entirely dissolved. Then $NH_4PF_6$ (0.43 g, 2.63 mmol, 1.1 eq) was added to the solution. The mixture was stirred at room temperature for three days, diluted with deionized water. The precipitate was collected through filtration, washed with water and $Et_2O$. Then the solid was dried in air to give the desired product, Ligand ON7-dtb, as a brown powder (1.42 g in 71% total yield) for the two steps.

Synthesis of platinum(II) [6-(1,3-dihydro-3-methyl-2H-imidazol-2-ylidene-κC2)-4-tert-butyl-1,2-phenylene-κC1]oxy[9-(4-tert-butyltpyridin-2-yl-κN)-9H-carbazole-1,2-diyl-κC1] (PtON7-dtb)

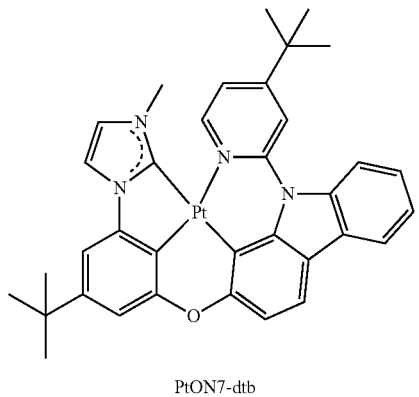

PtON7-dtb

A mixture of 1-(3-tert-butyl-5-(9-(4-tert-butylpyridin-2-yl)-9H-carbazol-2-yloxy)phenyl)-3-methyl-1H-imidazol-3-ium hexafluorophosphate(V) Ligand ON7-dtb (960 mg, 1.42 mmol, 1.0 eq), Pt(COD)Cl_2 (558 mg, 1.49 mmol, 1.05 eq; COD=cyclooctadiene) and NaOAc (349 mg, 4.26 mmol, 3.0 eq) in THF (43 mL) was stirred in a pressure vessel at a temperature of 120° C. for 44 hours under a nitrogen atmosphere, cooled to ambient temperature. The solvent was removed under reduced pressure and the residue was purified through column chromatography on silica gel using dichloromethane as an eluent to obtain the desired product platinum complex, PtON7-dtb, as a yellow solid (431 mg in 42% yield). 600 mg of the product was further purified by sublimation in a four zone thermal gradient sublimator at 280° C., 275° C., 190° C., 150° C., 3.0×10$^{-6}$ Torr to obtain a yellow solid (503 mg in 83% yield). 1H NMR (DMSO-d6, 400 MHz): δ 1.28 (s, 9H), 1.35 (s, 9H), 3.83 (s, 3H), 6.84 (s, 1H), 7.18 (d, J=8.0 Hz, 1H), 7.23 (dd, J=6.4, 1.2 Hz, 1H), 7.27 (s, 1H), 7.35 (t, J=7.6 Hz, 1H), 7.42 (s, 1H), 7.44 (t, J=7.2 Hz, 1H), 7.81 (d, J=8.4 Hz, 1H), 8.02 (d, J=8.0 Hz, 1H), 8.03 (s, 1H), 8.10 (d, J=6.8 Hz, 1H), 8.11 (s, 1H), 9.37 (d, J=6.4 Hz, 1H). 13C NMR (DMSO-d6, 100 MHz): δ 29.65, 31.36, 34.52, 35.39, 36.85, 103.90, 107.00, 109.56, 112.13, 112.55, 114.43, 114.90, 115.81, 115.89, 116.43, 117.11, 120.02, 122.61, 124.34, 128.04, 138.23, 143.19, 147.83, 148.36, 148.98, 151.38, 153.70, 155.67, 163.40, 182.07. MS (MALDI) for $C_{35}H_{34}N_4OPt$ [M]$^+$: calcd 721.2. found 721.0. Anal. Calcd. For $C_{35}H_{34}N_4OPt$: C, 58.24; H, 4.75; N, 7.76. Found: C, 58.20; H, 4.82; N, 7.80.

Red Phosphorescent Emitters

A stable and efficient red Pt(II) complex, platinum(II)-9-(4-tert-butylpyridin-2-yl)-2'-(4-phenylpyridin-2-yl)-9H-2,9'-bicarbazole (PtN3N-ptb) is disclosed. This complex is incorporated in a device setting employing functional materials. Devices employing PtN3N-ptb display an estimated operational lifetime, $LT_{97}$, of 638 hours at an initial luminance of 1000 $cd/m^2$ with low turn-on voltage and a peak EQE of 10.8%. A maximum forward viewing EQE of 21.5% was achieved for PtN3N-ptb devices by adopting different host material system. Thus, long operational lifetimes and high efficiencies are achieved.

Figure 38:
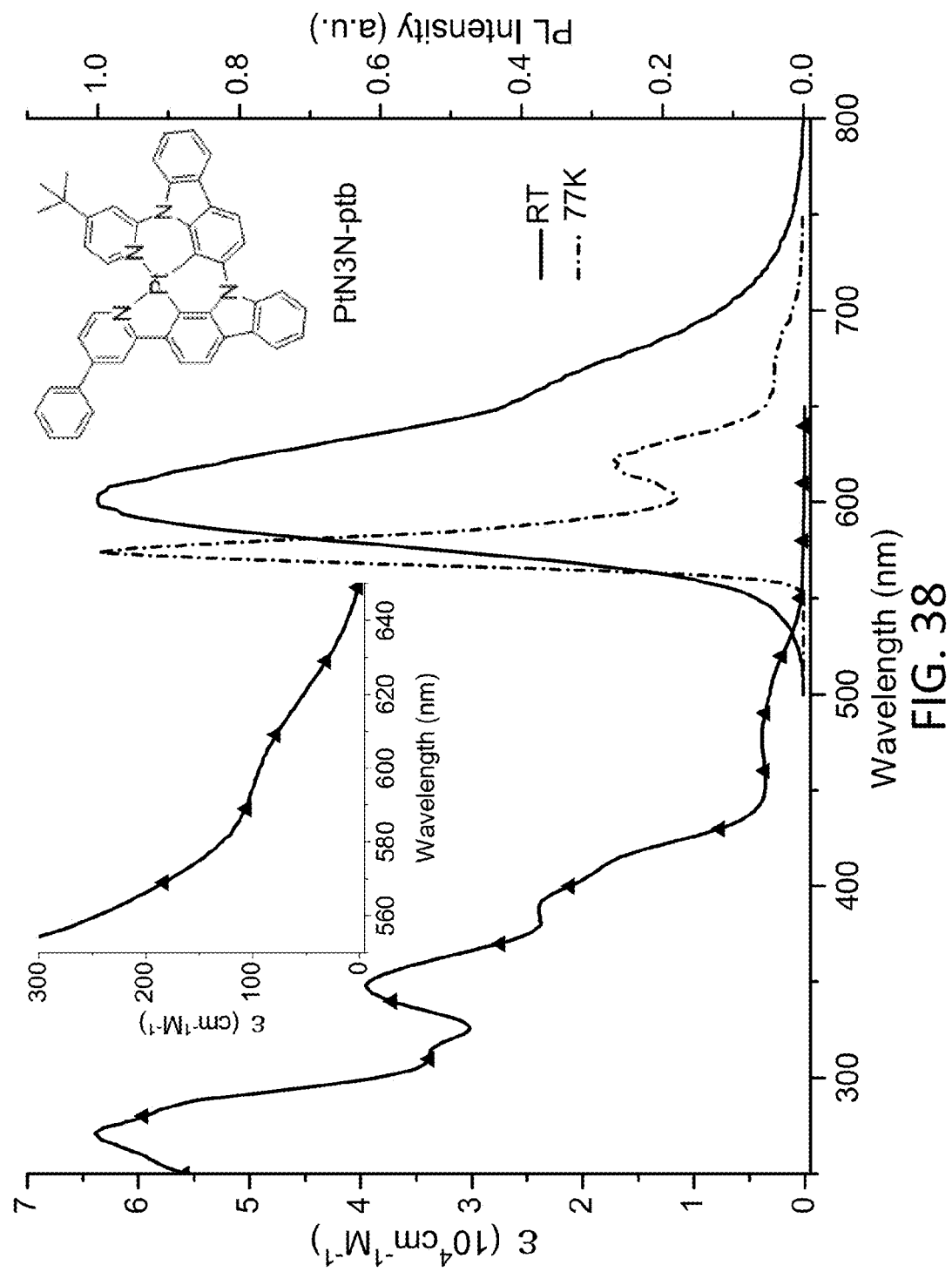
FIG. 38 shows an absorption spectrum of PtN3N-ptb measured in $CH_2Cl_2$ at room temperature and emission spectra of PtN3N-ptb measured in $CH_2Cl_2$ at room temperature and in 2-methyl-THF at 77K.

PtN3N-ptb acts as an efficient red phosphorescent emitter for white OLEDs with EQEs greater than 20%, indicating that PtN3N-ptb can be useful for displays and solid-state lighting applications. The chemical structure of PtN3N-ptb, illustrated in the inset of FIG. 38, employs a tetradentate cyclometalating ligand included a 4-phenylpyridyl-carbazole as a lumophore bonded to 4-tert-butylpyridyl-carbazole. The room temperature absorption and emission spectra of PtN3N-ptb in $CH_2Cl_2$ and low temperature (77K) emission spectrum in 2-methyl-THF are also shown in FIG. 38. Three characteristic types of well-resolved absorption bands are observed. The high energy, very strong absorption bands (250-400 nm, $\epsilon=2.4$-$6.4\times10^4$ $cm^{-1}M^{-1}$) are attributed to allowed $^1(\pi\text{-}\pi^*)$ transitions localized on the cyclometalating ligand. The strong bands located at longer wavelength (450-550 nm, $\epsilon=3890$ $cm^{-1}M^{-1}$) can be assigned to metal-to-ligand-charge-transfer (MLCT) transitions. The weaker, lowest energy broad absorption bands between (560-650 nm, $\epsilon=120$ $cm^{-1}M^{-1}$) can be identified as the triplet transition ($T_1$) on the basis of the small energy shift between absorption and emission at room temperature. Compared to other tetradentate Pt complexes, the triplet absorption of PtN3N-ptb is broad and has a higher extinction coefficient, which has a good overlap with its own triplet emission at room temperature. PtN3N-ptb shows a structured emission spectrum at low temperature with a dominant emission peak at 574 nm and a small vibronic sideband at 622 nm. However, the room temperature emission spectrum exhibits a 28 nm shift to 602 nm and has less vibronic features with significantly broadening relative to the 77K emission spectrum. This can be attributed to more $^1MLCT/^3MLCT$ characters in its lowest excited state.

To evaluate the operational stability and electroluminescent (EL) properties of PtN3N-ptb, the device was fabricated and tested using a stable device structure, Structure 1: ITO/HATCN(10 nm)/NPD(40 nm)/10% PtN3N-ptb:CBP(25 nm)/Balq(10 nm)/Alq$_3$(40 nm)/LiF(1 nm)/Al(100 nm), where HATCN is 1,4,5,8,9,12-hexaazatriphenylene-hexacarbonitrile, NPD is N,N'-diphyenyl-N,N'-bis(1-naphthyl)-1,1'-biphenyl-4,4''-diamine, CBP is 4,4'-bis(N-carbazolyl) biphenyl, BAlq is bis(-methyl-8-quinolinolato) (biphenyl-4-olato) aluminum and Alq is tris-(8-hydroxyquinoline) aluminum. The EL spectrum, current density-voltage (J-V) characteristics, forward viewing external quantum efficiency-luminance curve and relative luminance-operational lifetime curve of the devices are shown in FIGS. 39A-39D. The relative luminance versus operational lifetime characteristic (FIG. 39D) was assessed under accelerated condition at a constant driving current of 20 $mA/cm^2$. Structure 1 showed a non-exclusive electroluminescent (EL) spectrum with a dominant peak at 606 nm, which was broader than the PL spectrum of PtN3N-ptb in the solution of $CH_2Cl_2$ at room temperature. This broadening is attributed to the strong self-absorption of PtN3N-ptb. The blue luminescence is attributed to the emission of the hole transporting material 4,4'-bis[N-(1-naphthyl)-N-phenylaminobiphenyl (NPD), indicating that some degree of electron or exciton transfer from CBP to NPD occurs. Structure 1 demonstrated a maximum forward viewing EQE of 8.2% and EQE of 7.8% at a luminance of 100 $cd/m^2$. Remarkably, Structure 1 also demonstrated a very good operational lifetime, $LT_{97}=329$ hrs, with the initial luminance ($L_0$) of 1330 $cd/cm^2$, which can be translated to a $LT_{97}$ at 1000 $cd/cm^2$ of 534 hrs using the formula $LT(L_1)=LT(L_0)(L_0/L_1)^{1.7}$. The operational lifetime of Structure 1 demonstrated that PtN3N-ptb can be employed as a stable phosphorescent dopant for OLED applications.

Figure 39A:
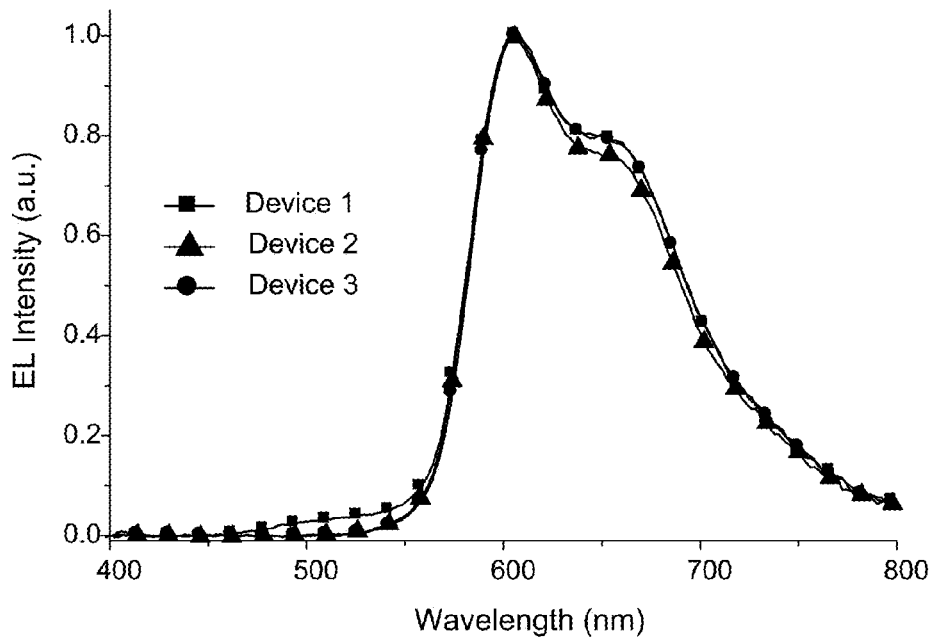
FIGS. 39A-39D show EL spectra, current density-voltage characteristics, EQE versus luminance, and relative luminance versus operation lifetime at constant current of 20 $mA/cm^2$, respectively, for various devices.
Figure 39B:
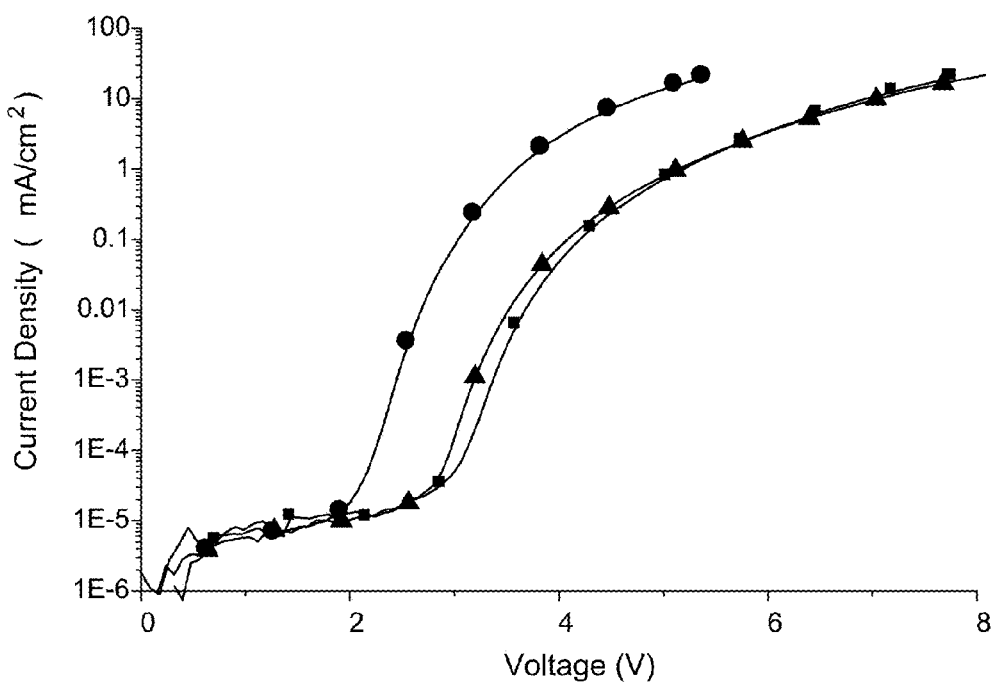
Figure 39C:
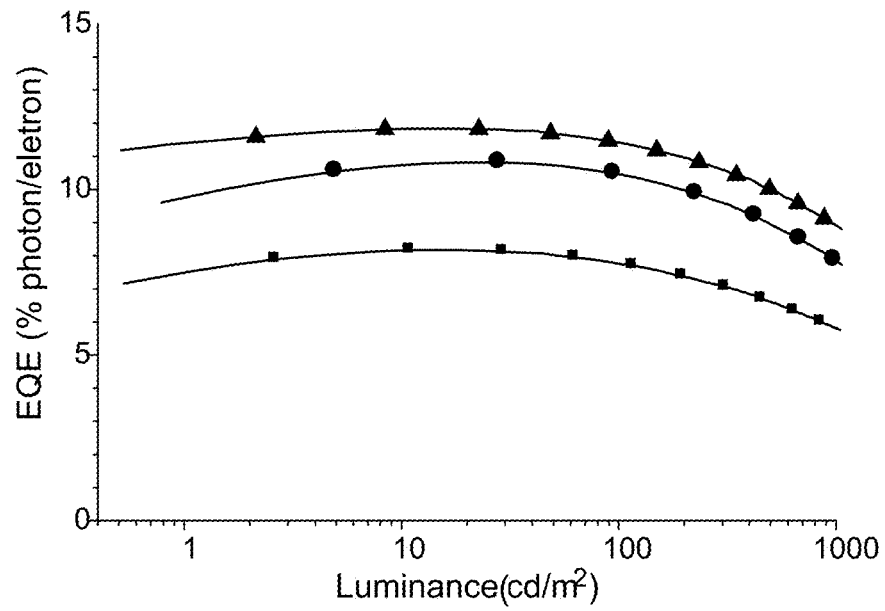
Figure 39D:
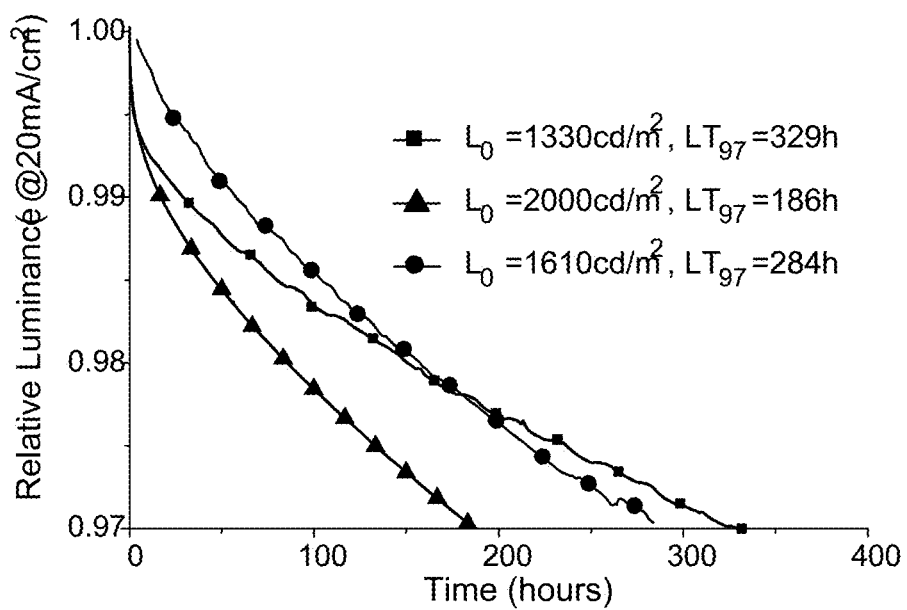

To reduce or eliminate the residual NPD emission and improve the device efficiency, a 10 nm TrisPCz layer was added as an electron and exciton blocking layer (EBL) for Structure 2: ITO/HATCN(10 nm)/NPD(40 nm)/TrisPCz (10 nm)/10% PtN3N-ptb:CBP(25 nm)/Balq(10 nm)/Alq$_3$(40 nm)/LiF(1 nm)/Al(100 nm), where TrisPCz was 9,9',9''-triphenyl-9H,9'H,9''H-3,3':6'3''-tercarbazole. Since TrisPCz has a higher lowest unoccupied molecular orbital (LUMO) level (-5.6 eV) than that of host material CBP (-5.9 eV), as well as a higher triplet energy (2.7 eV compared to 2.6 eV), it is able to confine electrons and excitons inside the EML effectively and resulted in exclusive EL spectrum originating from PtN3N-ptb. Thus device efficiency was improved to a peak EQE of 11.8%, EQE of 11.4% at a luminance of 100 $cd/m^2$ was achieved (FIG. 39C). The enhanced performance may be also attributed to a more balanced ratio of electrons and holes in the EML, resulting in a wider and more efficient combination zone to reduce the hole accumulation at the interface between the EML and EBL, which promotes device operational stability. Structure 2 exhibited an operational lifetime, $LT_{97}$, of 186 hours at an initial luminance of 1875 $cd/cm^2$, corresponding to an improved lifetime at 1000 $cd/cm^2$ of 542 hours (Table 3). These results indicate that TrisPCz acts as a stable electron blocking material to improve device efficiency and operational stability.

TABLE 3

Summary of device performance data.

| Structure[a] | Emitting layer | | EQE (%) | | | CIE (x, y) | $L_0$ ($cd/m^2$) | $LT_{97}$ (h) at $L_0$ | $LT_{97}$ (h) 1000 $cd/m^2$ |
|---|---|---|---|---|---|---|---|---|---|
| | Host | Dopant Conc. | Peak | 100 $cd/m^2$ | 1000 $cd/m^2$ | | | | |
| 1 | CBP | 10% | 8.2 | 7.8 | 5.8 | (0.61, 0.38) | 1330 | 329 | 534 |
| 2 | CBP | 10% | 11.8 | 11.4 | 8.9 | (0.63, 0.37) | 1875 | 186 | 542 |
| 3 | CBP | 10% | 10.8 | 10.4 | 7.8 | (0.63, 0.37) | 1610 | 284 | 638 |

TABLE 3-continued

Summary of device performance data.

| Structure[a] | Emitting layer | | EQE (%) | | | CIE (x, y) | $L_0$ (cd/m$^2$) | $LT_{97}$ (h) at $L_0$ | $LT_{97}$ (h) 1000 cd/m$^2$ |
|---|---|---|---|---|---|---|---|---|---|
| | Host | Dopant Conc. | Peak | 100 cd/m$^2$ | 1000 cd/m$^2$ | | | | |
| 3 | TrisPCz | 10% | 12.1 | 11.9 | 9.8 | (0.63, 0.37) | 1980 | 128 | 408 |
| 3 | Bebq$_2$ | 10% | 16.3 | 14.4 | 10.4 | (0.61, 0.39) | 2394 | 37 | 163 |
| 3 | Bebq$_2$ | 6% | 18.0 | 15.3 | 10.5 | (0.60, 0.40) | 2656 | 14 | 68 |
| 3 | Bebq$_2$ | 2% | 21.5 | 19.2 | 13.5 | (0.58, 0.42) | 3743 | 2.7 | 25 |

[a]Structure 1: ITO/HATCN/NPD/EML/Balq/Alq$_3$/LiF/Al; Structure 2: ITO/HATCN/NPD/TrisPCz/EML/Balq/Alq$_3$/LiF/Al; Structure 3: ITO/HATCN/NPD/TrisPCz/EML/Balq/BPyTP/LiF/Al.

Besides efficiency and operational lifetime, turn-on voltage is also an important device performance parameter in the application of displays and lighting. Low driving voltage results in low power consumption and also has a positive effect on the enhancement of the device operational stability. In Structure 3, ITO/HATCN(10 nm)/NPD(40 nm)/TrisPCz (10 nm)/10% PtN3N-ptb:CBP(25 nm)/BAlq(10 nm)/BPyTP (40 nm)/LiF(1 nm)/Al(100 nm), BpyTP (2,7-Di(2,2'-bipyridin-5-yl)triphenylene) was incorporated into the device as an electron transport material. Structure 3 exhibited a lower driving voltage compared to previous devices with Alq$_3$ as an ETL. To reach a current density of 1 mA/cm$^2$, the driving voltages were 5.2 V for both of Structure 1 and 2, however, just 3.6 V for Structure 3 (FIG. 39B). This enhancement was largely attributable to the higher electron mobility of BPyTP than that of Alq$_3$, because BPyTP adopts a fairly parallel orientation on the substrate, while Alq$_3$ packs randomly. Additionally, it should be noted that Structure 3 demonstrated an operational lifetime, LT$_{97}$, of 284 hours at an initial luminance of 1610 cd/cm$^2$, which was estimated to be a LT$_{97}$ of 638 hours at 1000 cd/m$^2$. Structure 3 displayed a small drop in maximum forward viewing EQE to 10.8%, but remained at 10.4% at a luminance of 100 cd/m$^2$ (FIG. 39A). This indicates that BPyTP is suitable as a stable electron transport material with lower driving voltages.

To further improve the device efficiency, host materials were also optimized. The CBP host was replaced by either TrisPCz or BeBq in Structure 3: ITO/HATCN(10 nm)/NPD (40 nm)/TrisPCz (10 nm)/10% PtN3N-ptb:Host (25 nm)/BAlq(10 nm)/BPyTP(40 nm)/LiF(1 nm)/Al(100 nm). The EQE-luminance curves and relative luminance-operational lifetime curves of the devices were presented in FIGS. 40A and 40B. FIG. 40C shows the device architecture and the chemical structures of the organic materials used in the devices.

Figure 40A:
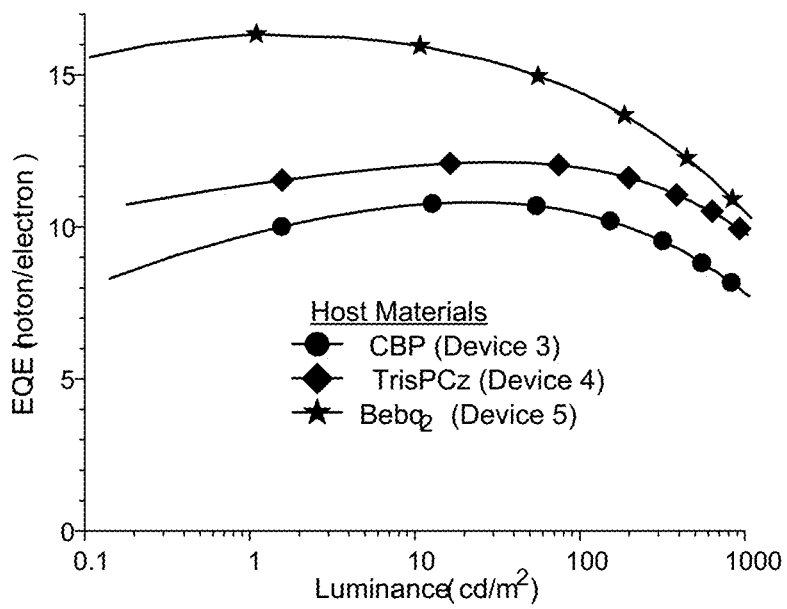
FIGS. 40A and 40B show EQE versus luminance and relative luminance versus operation lifetime at constant current of 20 $mA/cm^2$, respectively, for PtN3N-ptb devices with various host materials.
Figure 40B:
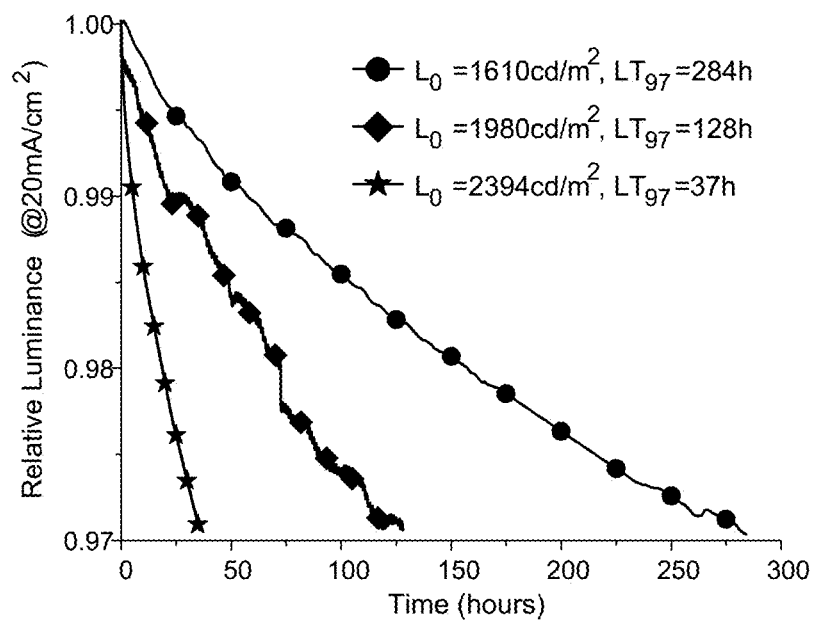
Figure 40C:
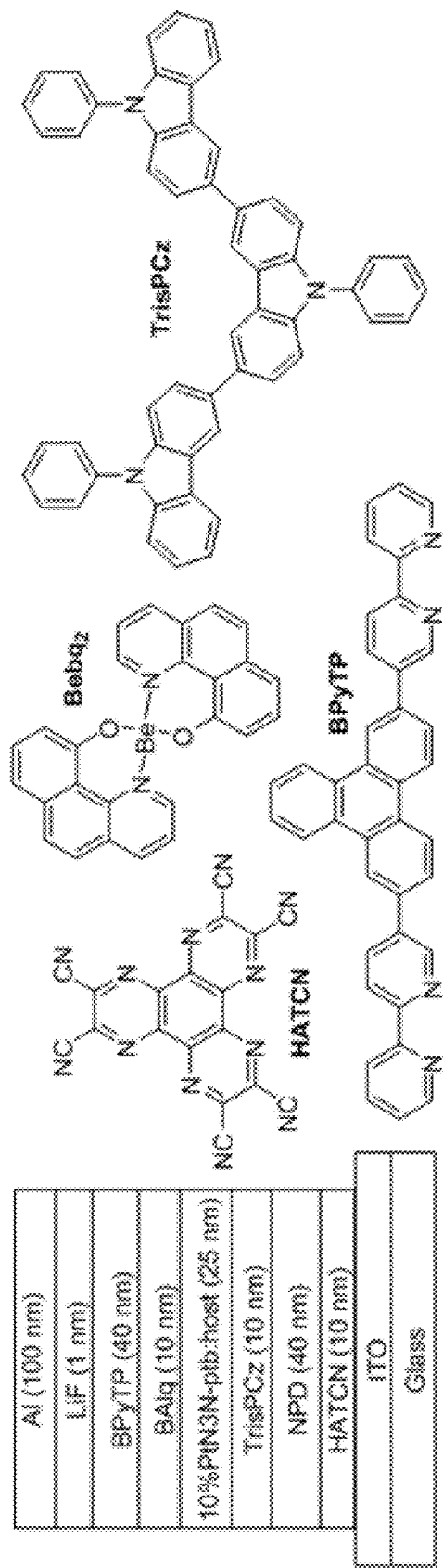
FIG. 40C depicts the device architecture and chemical structures of organic materials used in various devices.

The device employing a TrisPCz host displayed enhanced peak EQE compared to the CBP devices of 12.1% with low roll off to 11.9% and 9.8% at 100 and 1000 cd/m$^2$ respectively (FIG. 40A). Additionally, the operational lifetime, LT$_{97}$, of 128 hours at an initial luminance of 1890 cd/cm$^2$, which corresponds to 408 hours at 1000 cd/cm$^2$, was still comparable to that of the CBP device. The device employing the Bebq$_2$ host material achieved even higher peak EQE value of 16.3% for 10% dopant concentration. The enhanced device efficiencies could be attributed to the improved charge balance in the emitting layer, resulting in a wider and more efficient recombination zone, since Bebq$_2$ was ambipolar and had a high electron mobility (2×10$^{-5}$ cm$^2$/Vs at an electric field of 6.4×10$^5$ V/cm). However, this enhancement came at the expense of device operational lifetime which dropped to 163 hrs at 1000 cd/m$^2$. It is suspected that this reduction in lifetime is related to the irreversible oxidation and reduction processes of the Bebq$_2$ host material.

Figure 41A:
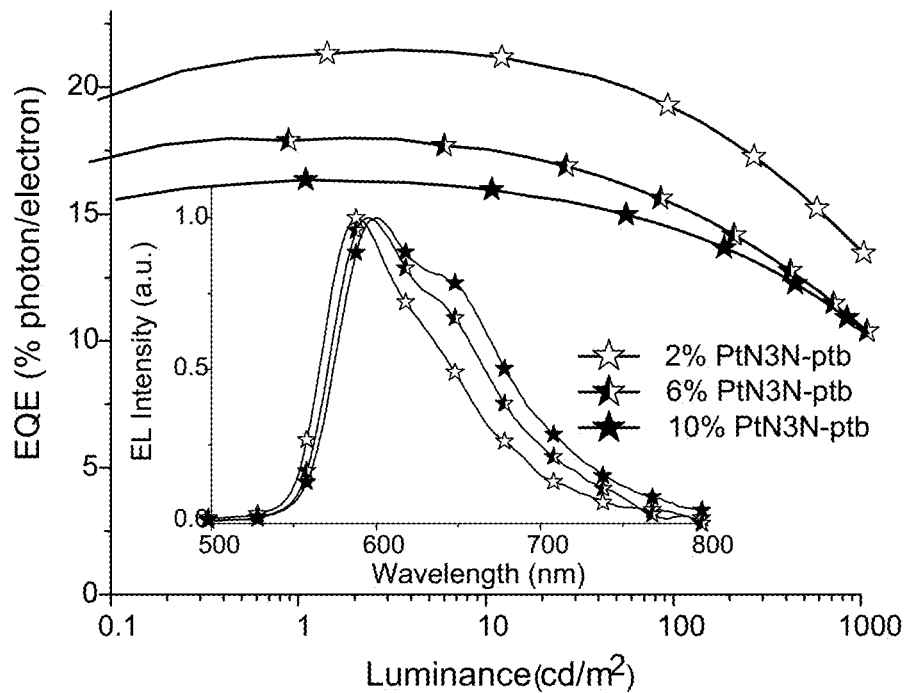
FIGS. 41A and 41B show EQE versus luminance with EL spectra (inset) and relative luminance versus operation lifetime at constant current of 20 $mA/cm^2$, respectively, for devices with different concentrations of PtN3N-ptb doped in $Bebq_2$.
Figure 41B:
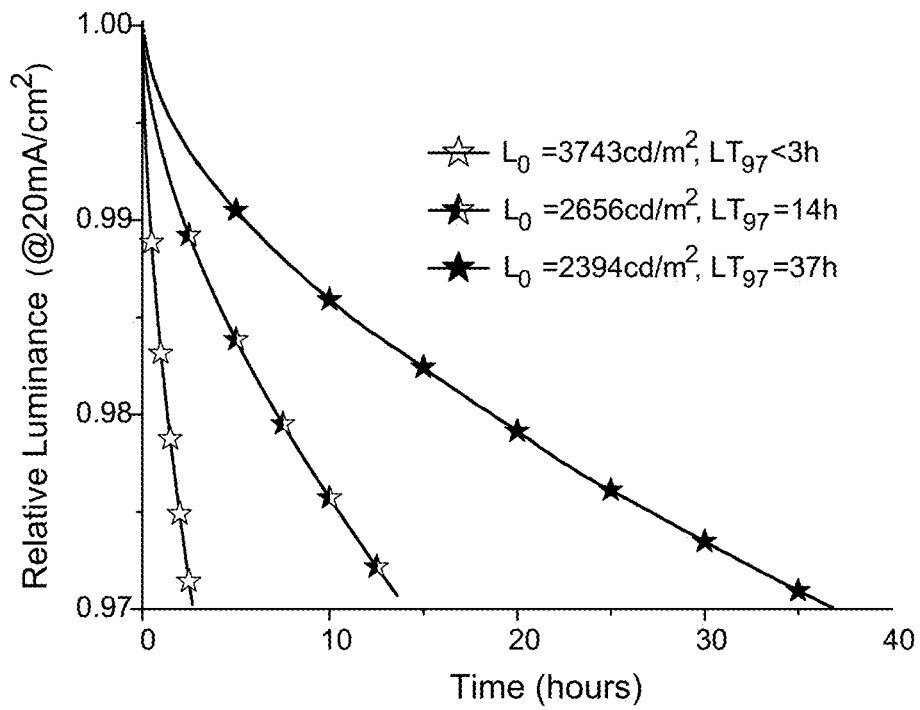

In order to probe the effects of decreasing the dopant concentration on both the efficiency and the lifetime, the dopant concentration was decreased to 6% and 2% in a Bebq$_2$ host for Structure 3: ITO/HATCN(10 nm)/NPD(40 nm)/TrisPCz (10 nm)/x % PtN3N-ptb:Bebq$_2$ (25 nm)/BAlq(10 nm)/BPyTP(40 nm)/LiF(1 nm)/Al(100 nm) (x=10, 6 or 2). As seen in FIG. 41A, the EQE increases with decreasing dopant concentration. For the 2% PtN3N-ptb-doped device a peak EQE of 21.5% was achieved, falling to 19.2% and 13.5% at 100 and 1000 cd/m$^2$ respectively. The higher roll off in this case is similar to the performance observed in many lightly doped devices due to poor charge balance and the higher concentration of excitons on a smaller number of dopant molecules. For low dopant concentrations, the EL spectra is much narrower than that of the 10% doped devices. This is attributed to the strong self-absorption of PtN3N-ptb for the 10% doped devices, which may also explain the lower efficiencies for the higher concentrations. The operational lifetimes dropped significantly with decreasing dopant concentration (FIG. 41B). They exhibited 163 hrs, 68 hrs and 25 hrs for 10%, 6% and 2%-doped devices at 1000 cd/m$^2$ respectively (Table 3). While lower than those for the CBP host device, these operational lifetimes are still excellent for lifetimes to 97% initial luminance, and are expected to be in the range of many hundreds to thousands of hours if tested to LT$_{80}$ or lower. The reason for the decrease in lifetime with decreasing dopant concentration could be due to charges and excitons residing mostly on the suspected unstable Bebq$_2$ material. A summary of the device characteristics and the operational lifetime values for the EL devices described herein are listed in Table 3.

A series of stable and efficient red phosphorescent OLEDs was fabricated employing phenyl-pyridyl-carbazole based tetradentate cyclometalated Pt(II) complex, PtN3N-ptb, as emitting dopant and utilizing a commercially available host, transporting, and blocking materials. By implementing PtN3N-ptb in the electrochemically stable device architectures, long operational lifetimes were achieved with estimated LT$_{97}$ of over 600 hrs at luminance of 1000 cd/m$^2$, which are superior to that of its platinum analog, TLEC-025 which achieved 720 hrs to only 80% initial luminance while still employing proprietary materials. A significantly improved maximum forward viewing EQE of 21.5% was achieved for device 5 at a low dopant concentration employing Bebq$_2$ as host material. Additionally, it was clarified that BPyTP can act as a stable electron transport material and lower turn-on voltage significantly because of its high electron mobility. Accordingly, Pt(II) complexes can act as stable and efficient dopants with long operational lifetimes, which can be enhanced with selected host and transporting materials. Thus, molecular and device architecture design in the development of stable Pt(II) based phosphorescent emitters for commercial solid-state lighting and display applications have been demonstrated.

EXPERIMENTAL PROCEDURES

Devices were fabricated by vacuum thermal evaporation in the following structures: ITO/HATCN(10 nm)/NPD(40 nm)/EML/Balq(10 nm)/Alq₃(40 nm)/LiF(1 nm)/Al(100 nm) (Structure 1), ITO/HATCN(10 nm)/NPD(40 nm)/TrisPCz(10 nm)/EML/Balq(10 nm)/Alq₃(40 nm)/LiF(1 nm)/Al(100 nm) (Structure 2), ITO/HATCN(10 nm)/NPD(40 nm)/TrisPCz(10 nm)/EML/BAlq(10 nm)/BPyTP(40 nm)/LiF(1 nm)/Al(100 nm) (Structure 3), Where the EML consisted of a host (either CBP, TrisPCZ, or Bebq₂) and PtN3N-ptb doped to 2%, 6%, or 10%, where HATCN is 1,4,5,8,9,12-hexaazatriphenylene-hexacarbonitrile, NPD is N,N'-diphyenyl-N,N'-bis(1-naphthyl)-1,1'-biphenyl-4,4"-diamine, Bebq₂ is bis(benzo[h]quinolin-10-olato-κN,κO)beryllium(II), TrisPCz is 9,9',9"-triphenyl-9H,9'H,9"H-3,3':6'3"-tercarbazole, BpyTP is 2,7-di(2,2'-bipyridin-5-yl)triphenylene. Prior to deposition, the pre-patterned ITO coated glass substrates were cleaned by subsequent sonication in deionized water, acetone, and isopropanol. Organic layers were deposited at rates of 0.5 to 1.5 Å/s, monitored by quartz crystal microbalances, in a custom-made vacuum thermal evaporation chamber built by Travato Man. Inc. The Al cathode was deposited through a shadow mask without breaking vacuum, defining device areas of 0.04 cm². The current-voltage-luminance characteristics were measured using a Keithley 2400 SourceMeter in conjunction with a Newport 818 Si Photodiode. Electroluminescent spectra were measured with an Ocean Optics USB2000 spectrometer.

A number of embodiments have been described. Nevertheless, it will be understood that various modifications may be made without departing from the spirit and scope of the disclosure. Accordingly, other embodiments are within the scope of the following claims.

What is claimed is:

1. A compound represented by one of the following chemical structures:

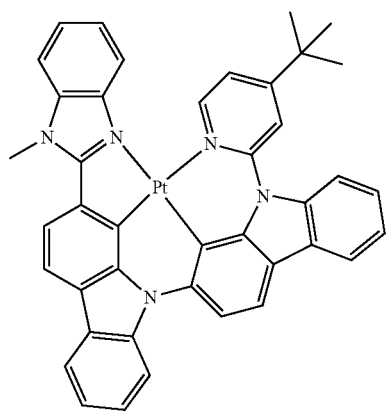

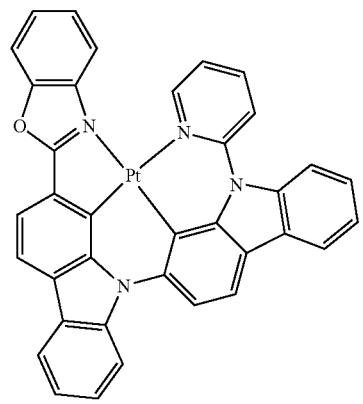

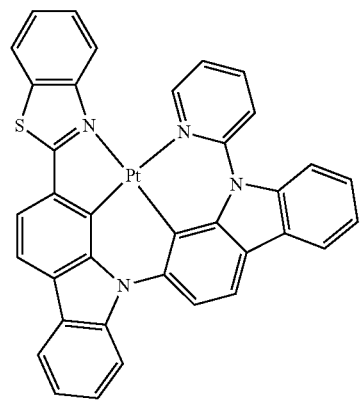

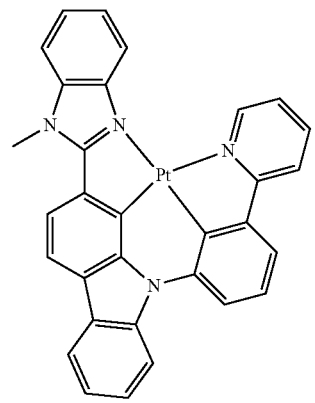

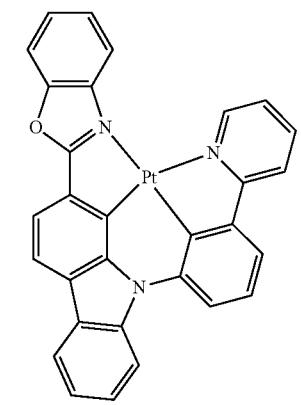

-continued

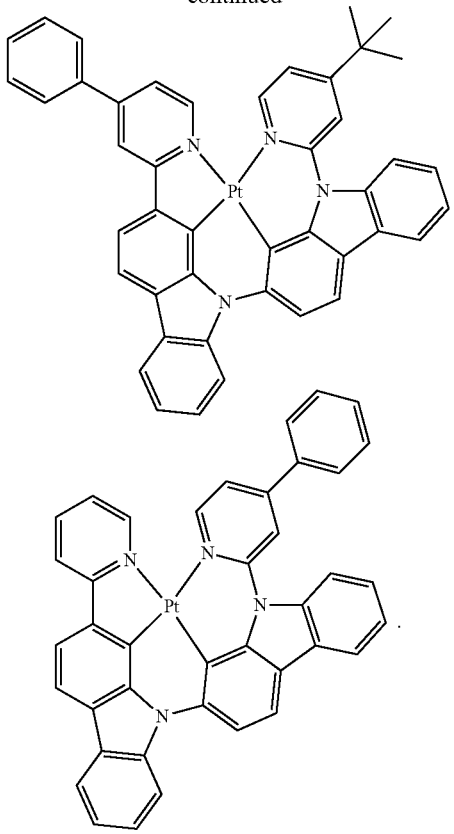

2. A light-emitting device comprising the compound of claim 1 as an emitter.

3. An OLED device comprising the compound of claim 1 as an emitter.

4. A luminescent display device comprising the compound of claim 1.

5. A compound represented by one of the following chemical structures:

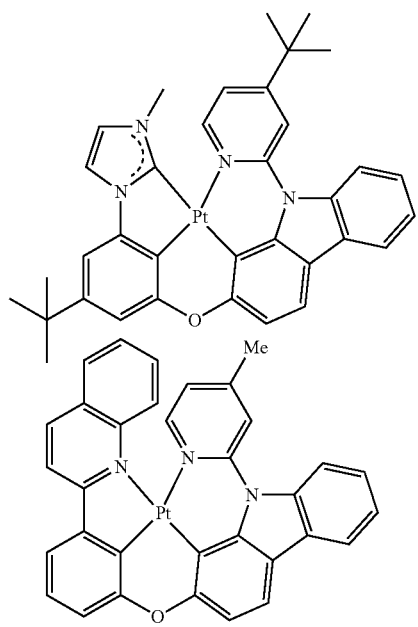

-continued

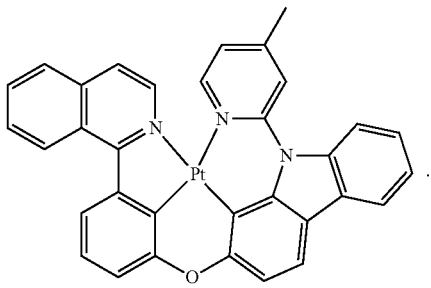

6. A light-emitting device comprising the compound of claim 5 as an emitter.

7. An OLED device comprising the compound of claim 5 as an emitter.

8. A luminescent display device comprising the compound of claim 5.

9. A compound represented by one of the following chemical structures:

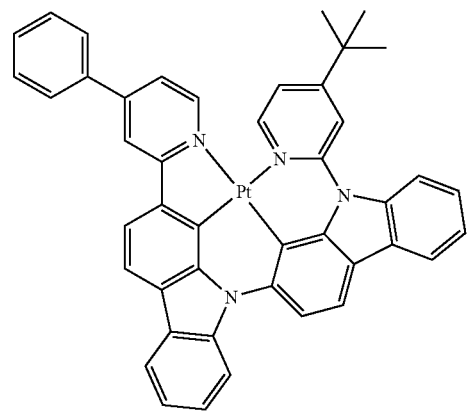

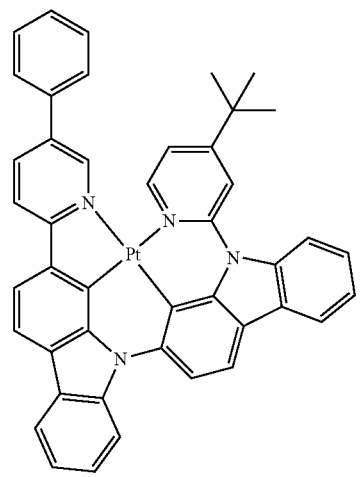

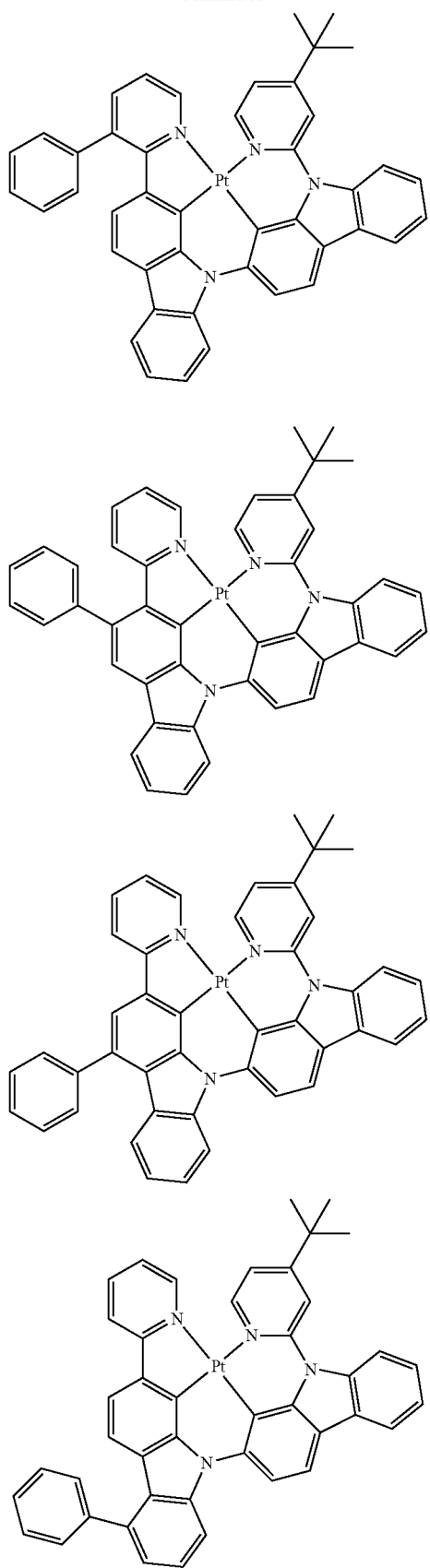
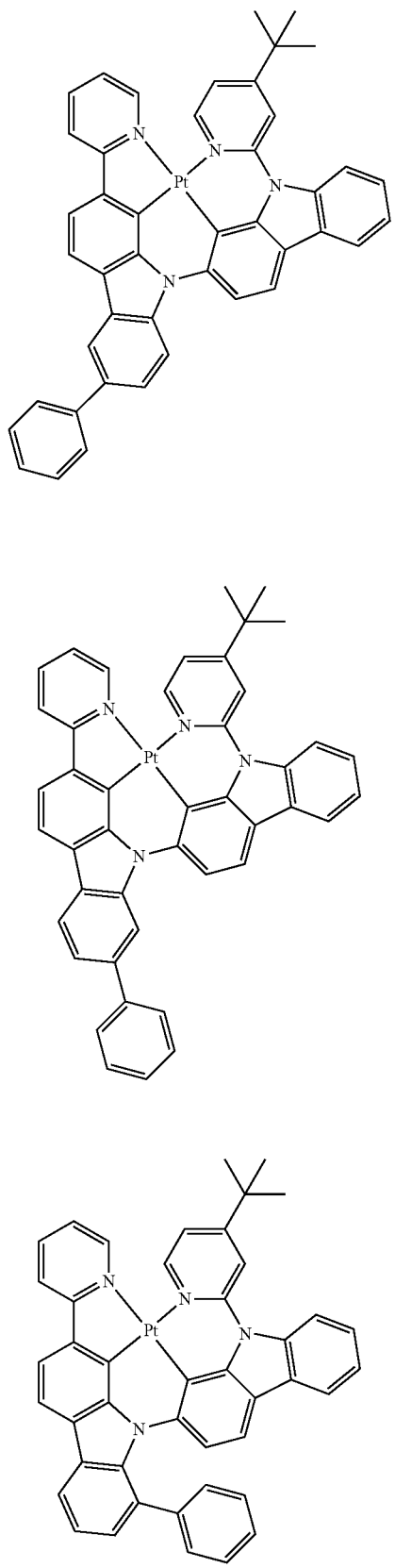

51
-continued
52
-continued
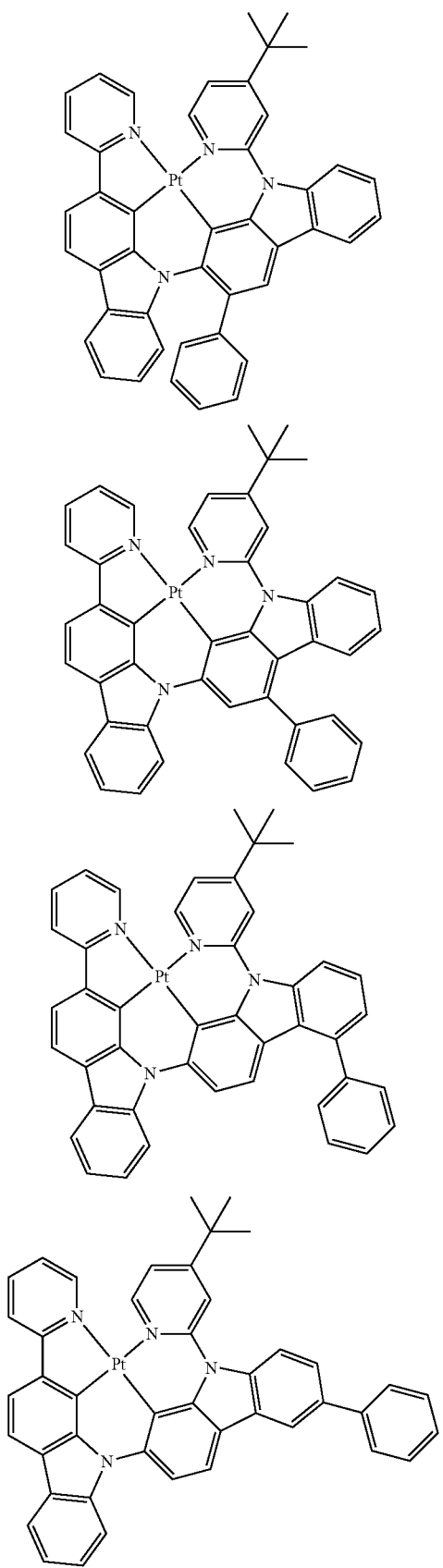
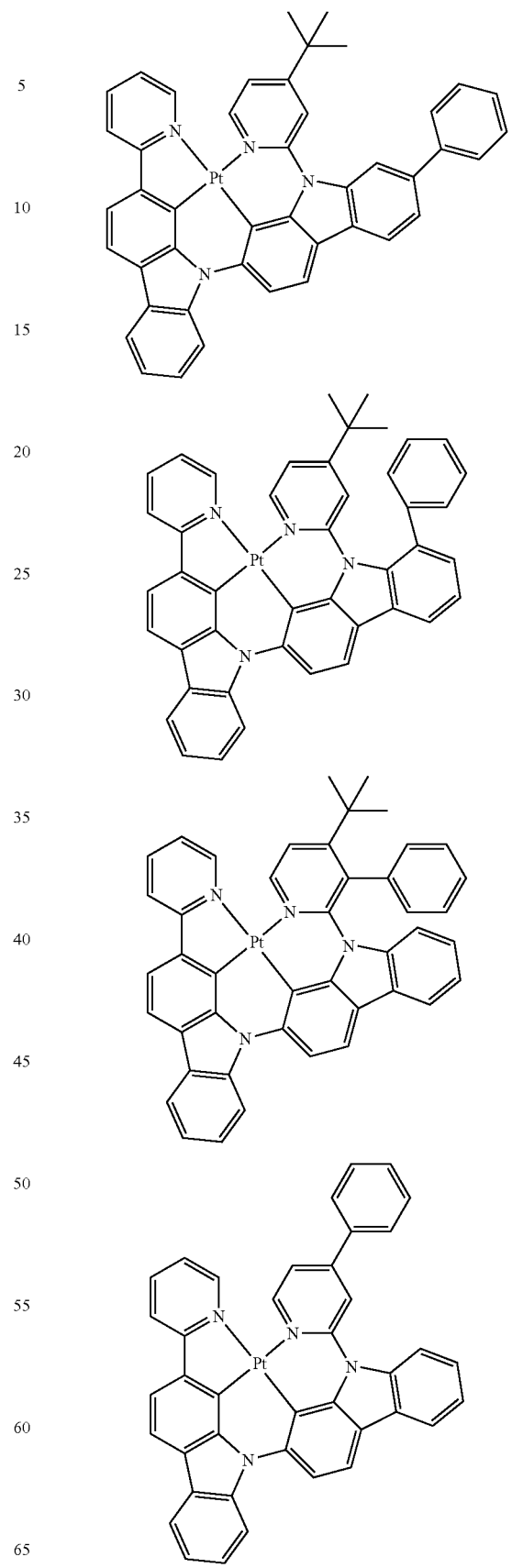

53
-continued
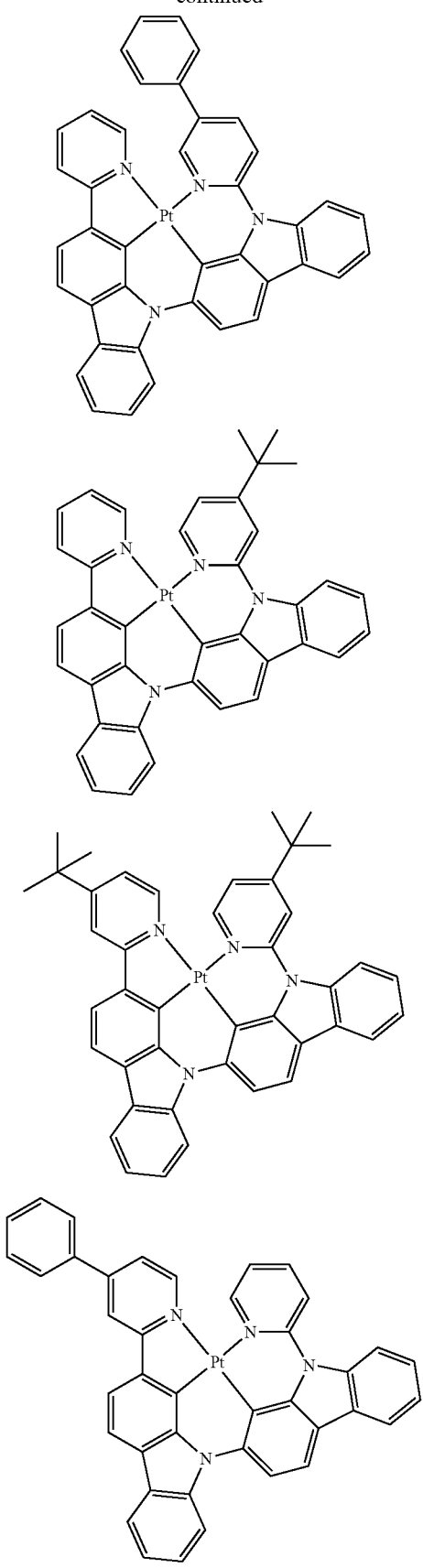
54
-continued
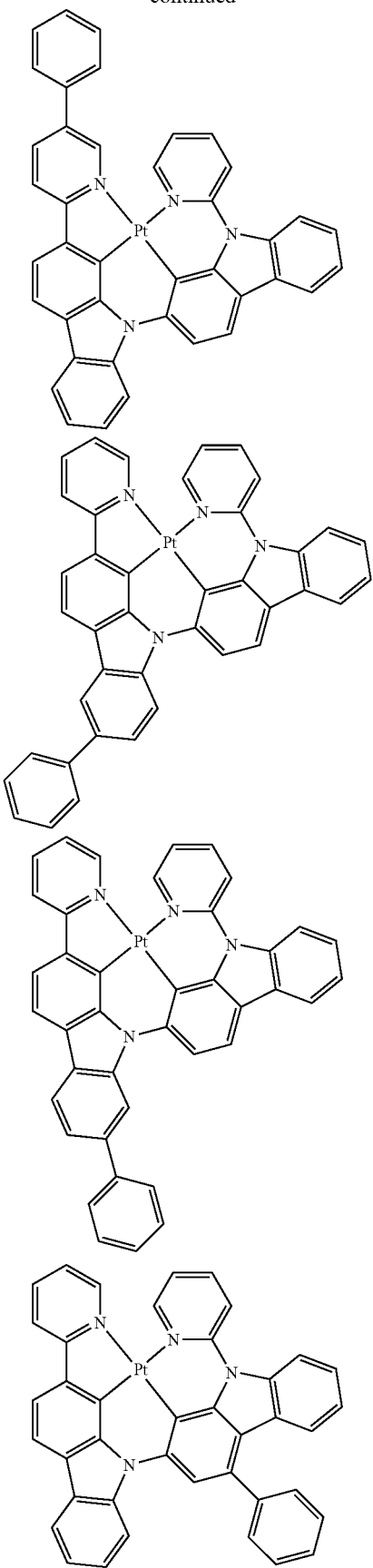

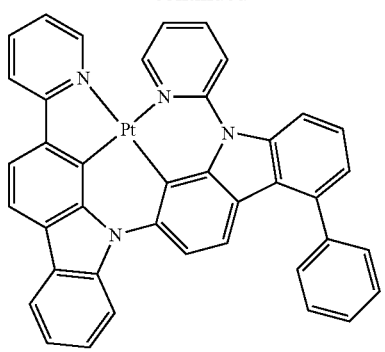
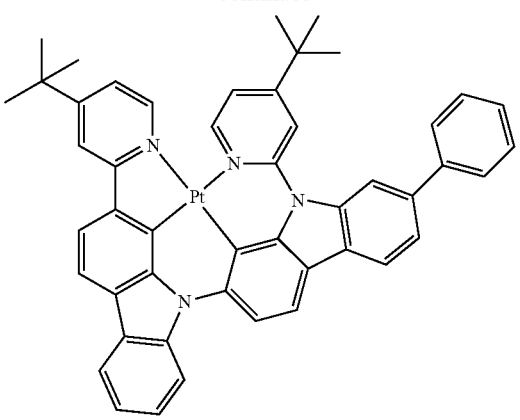
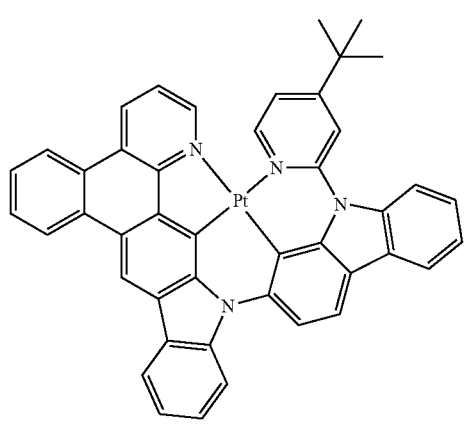
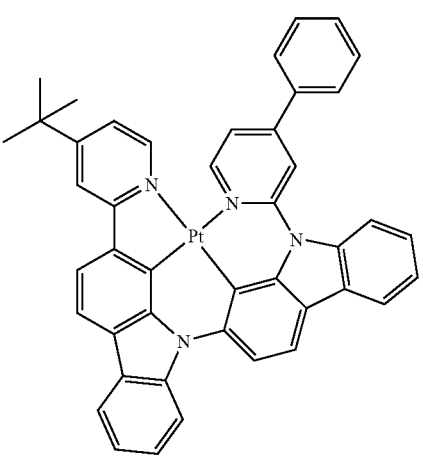
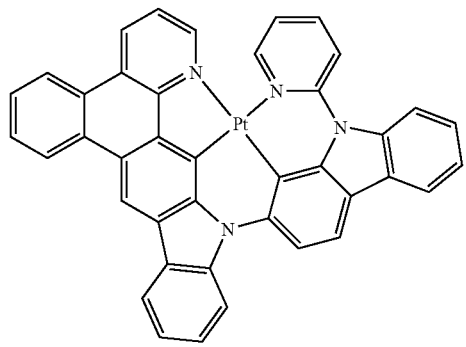
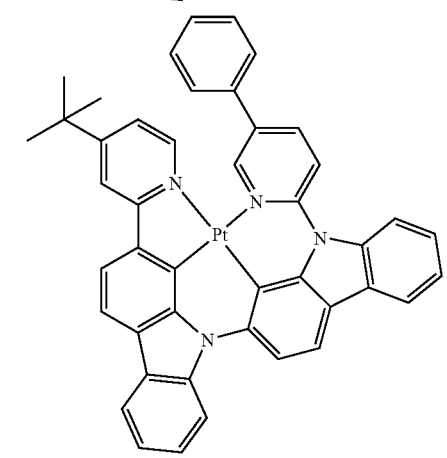
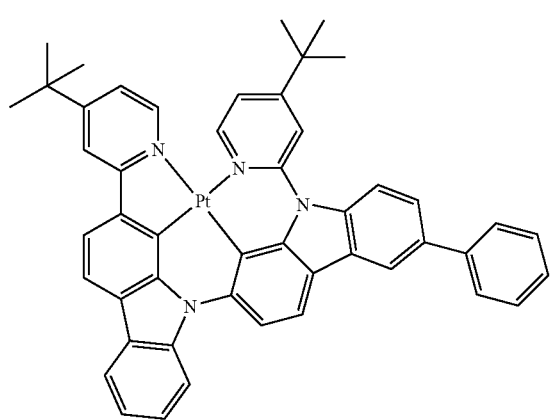
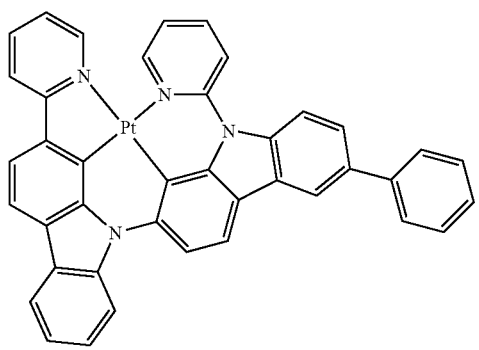

57
-continued
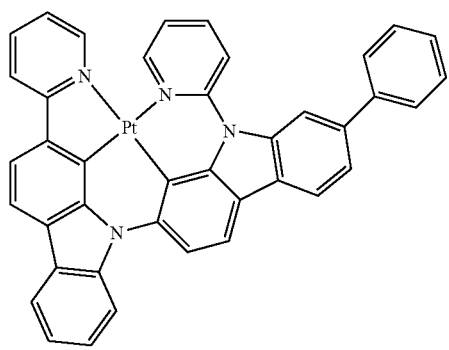
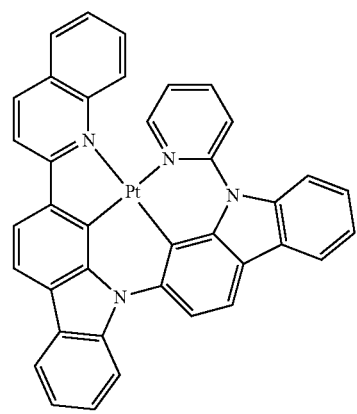
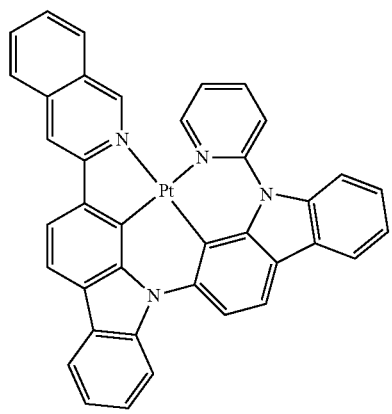
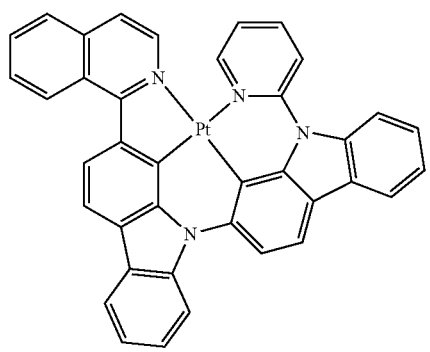
58
-continued
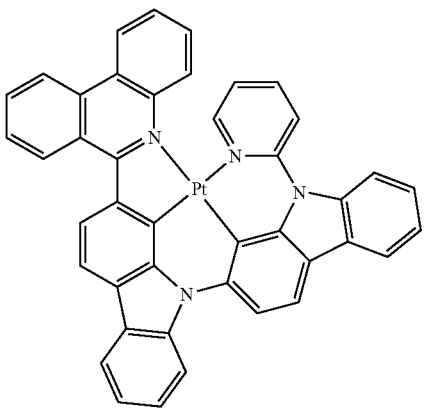
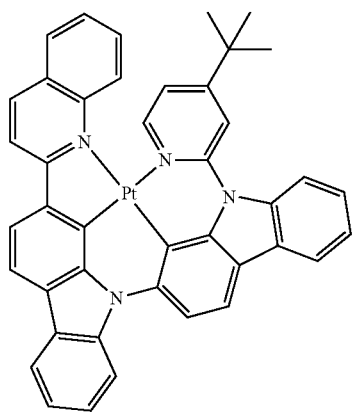
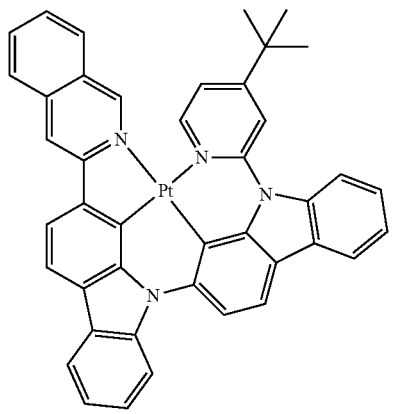
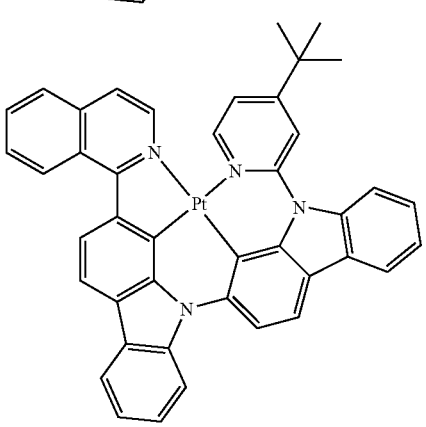

| 59 -continued | 60 -continued |
|---|---|
| 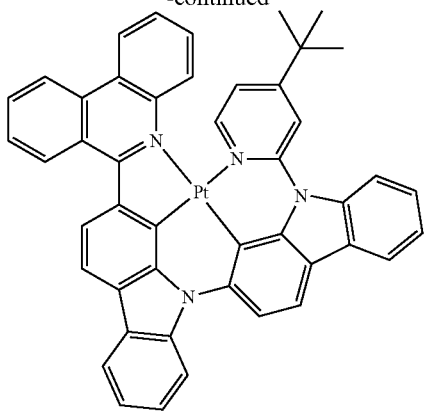 | 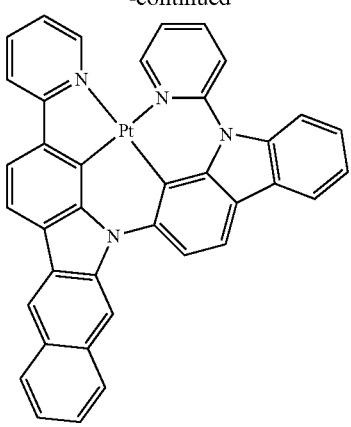 |
| 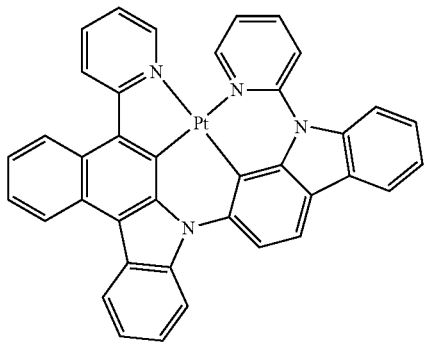 | 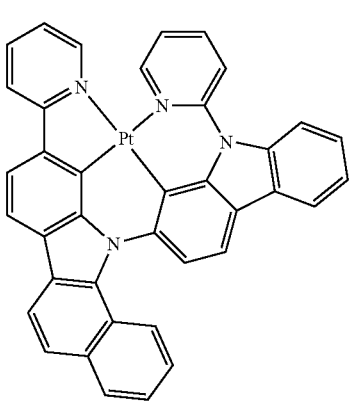 |
| 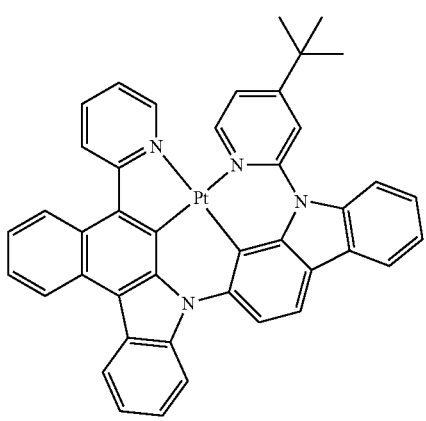 | 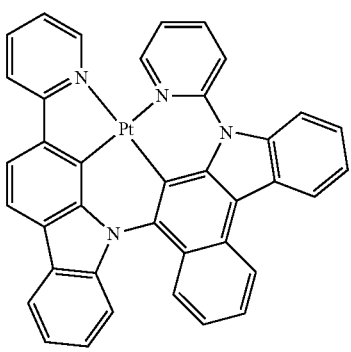 |
| 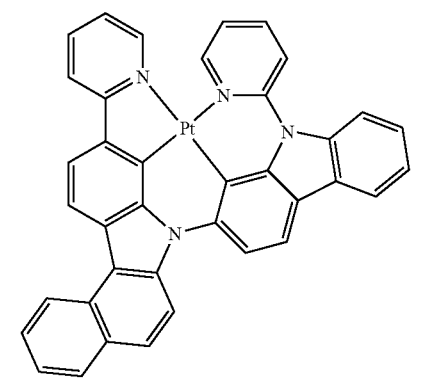 | 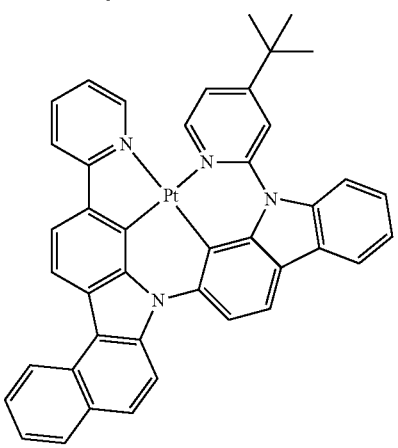 |

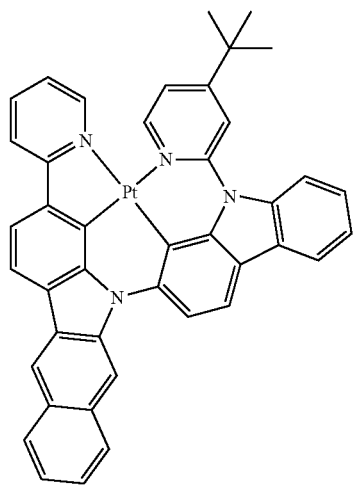
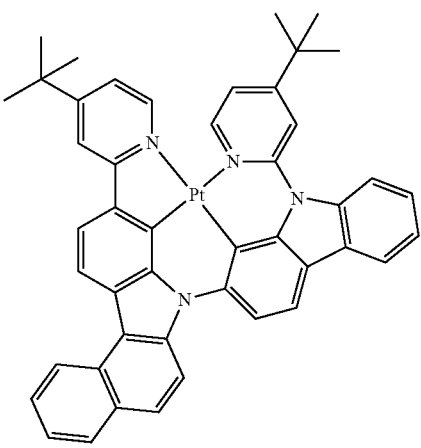
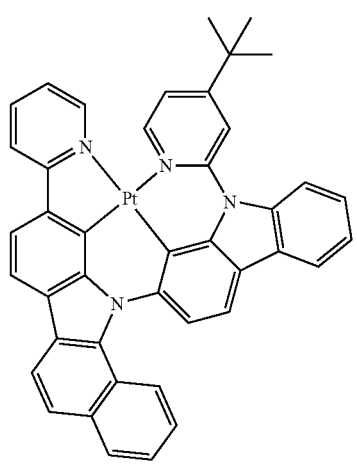
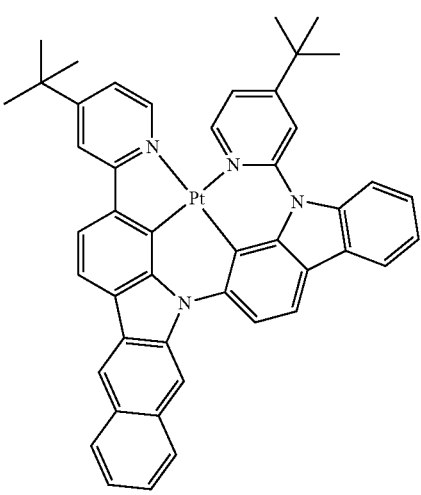
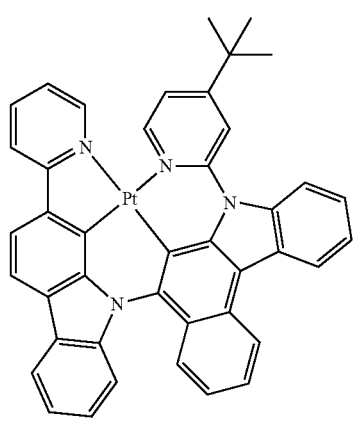
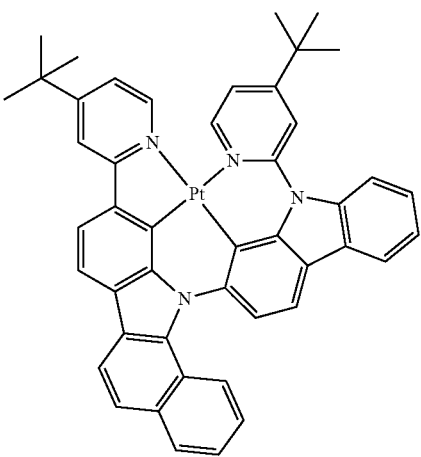

63
-continued
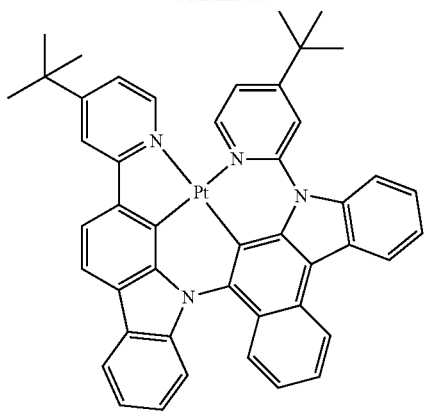
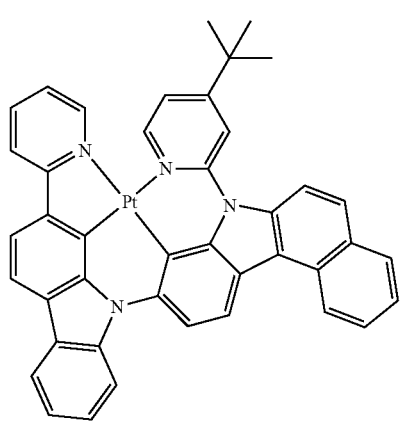
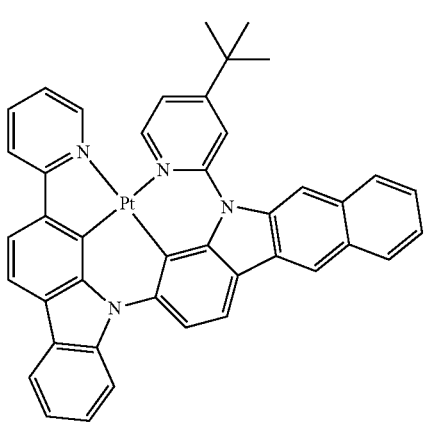
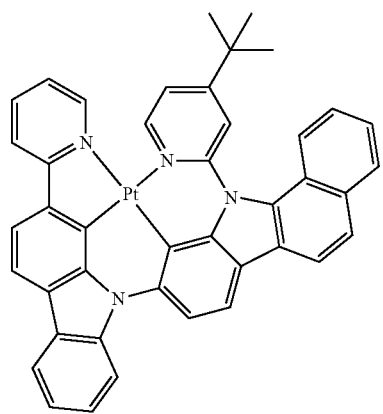
64
-continued
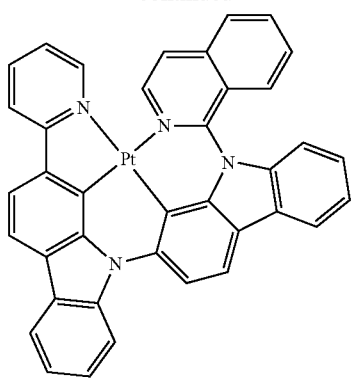
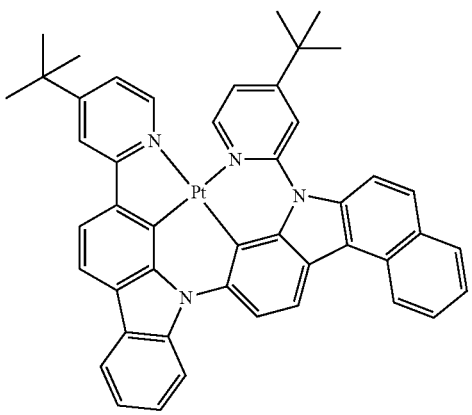
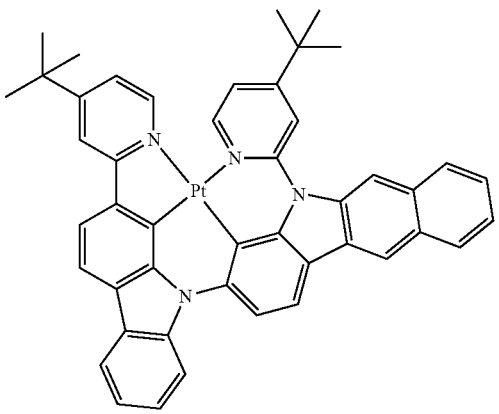
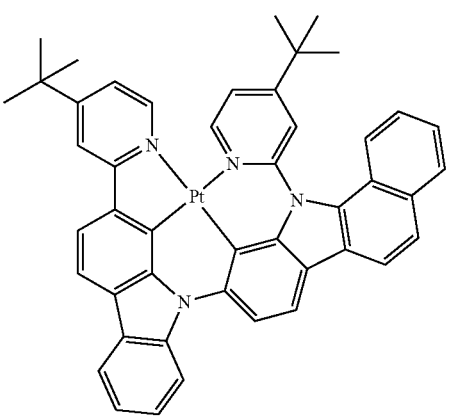

-continued
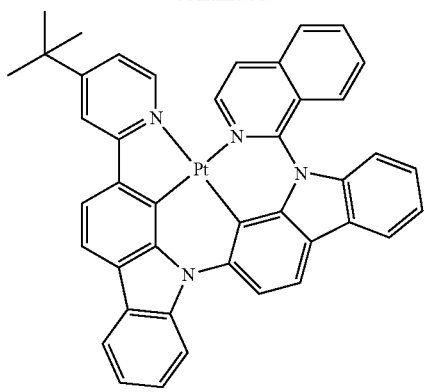
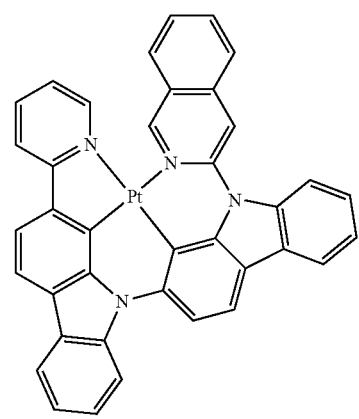
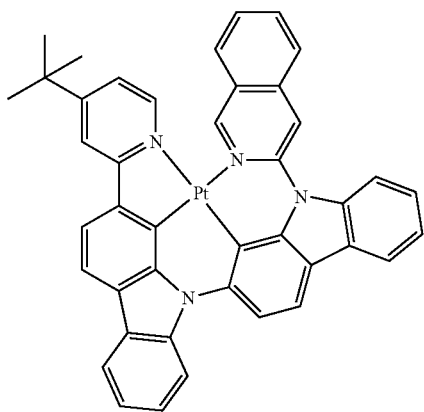
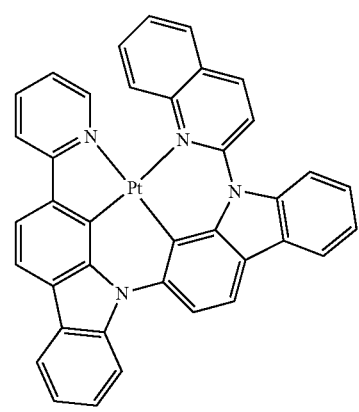
-continued
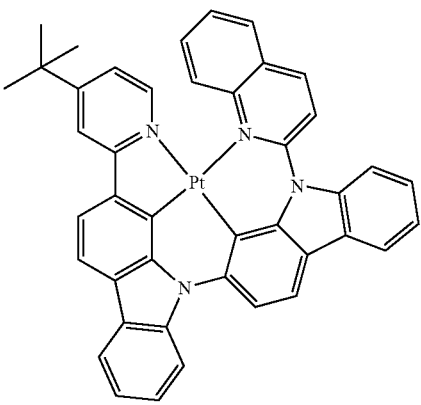
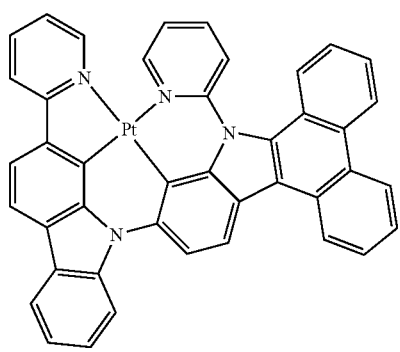
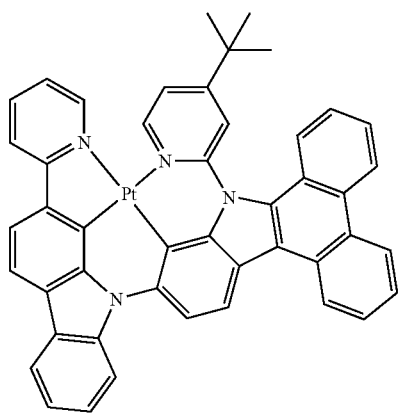
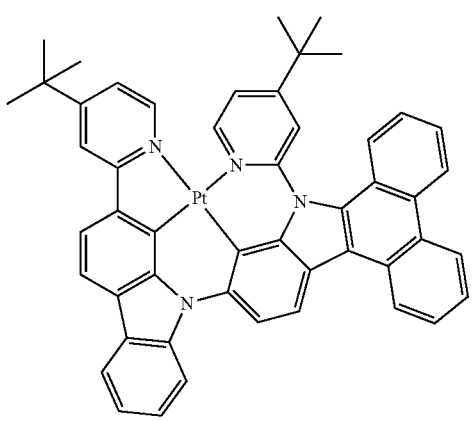

67
-continued
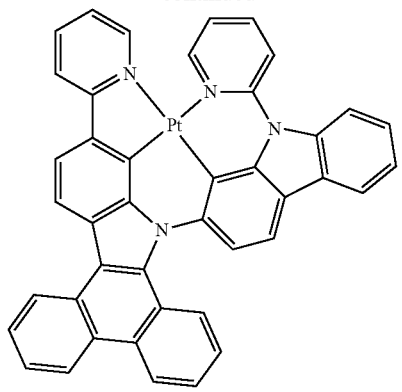
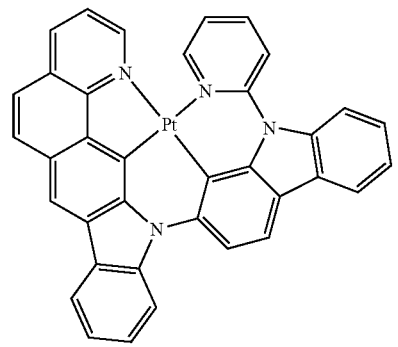
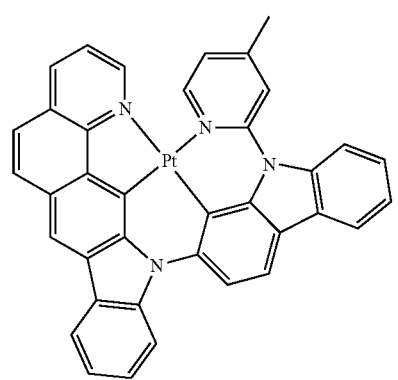
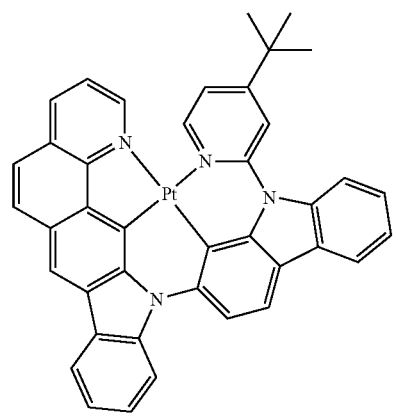
68
-continued
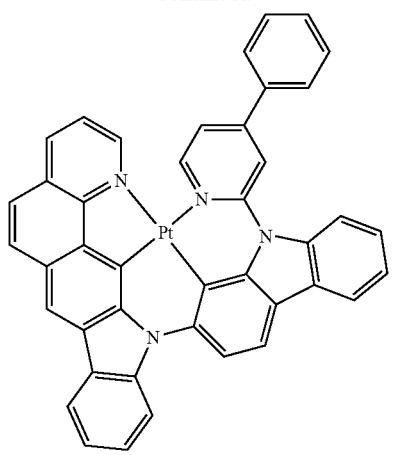
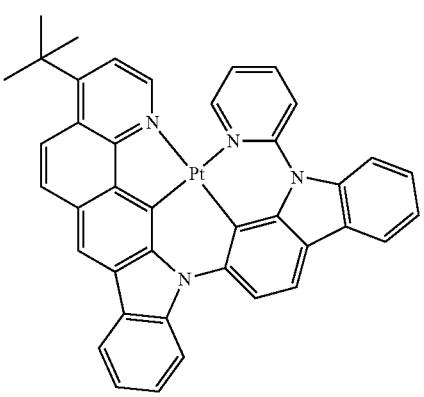
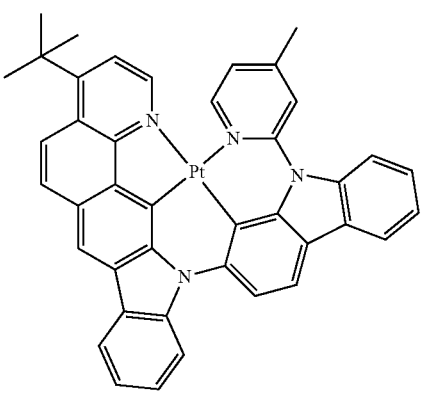
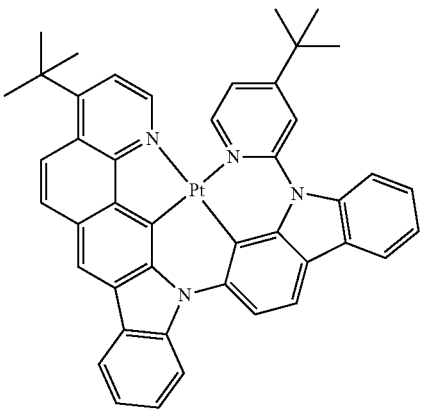

-continued
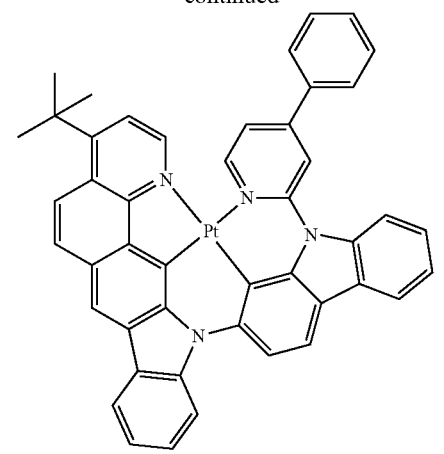
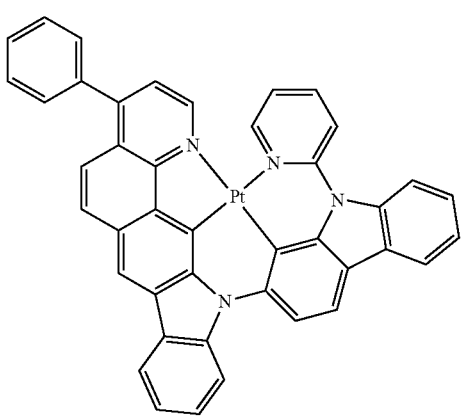
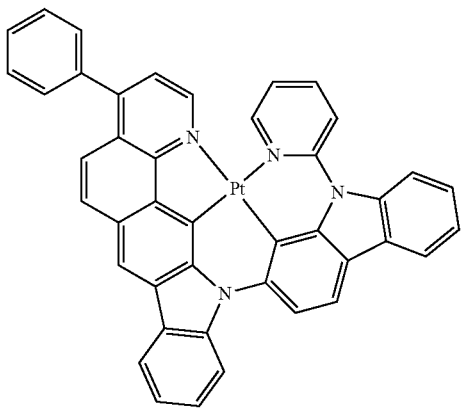
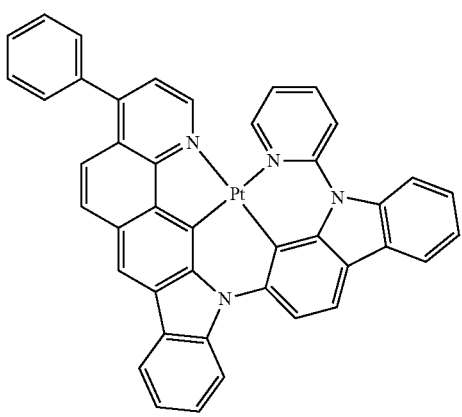
-continued
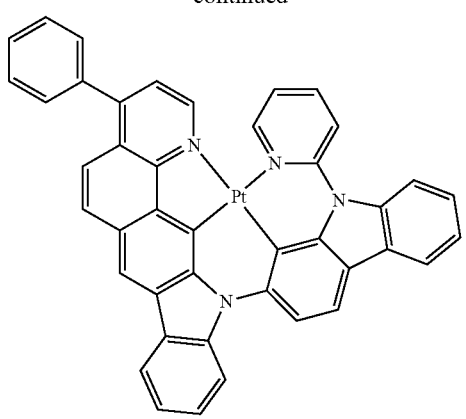
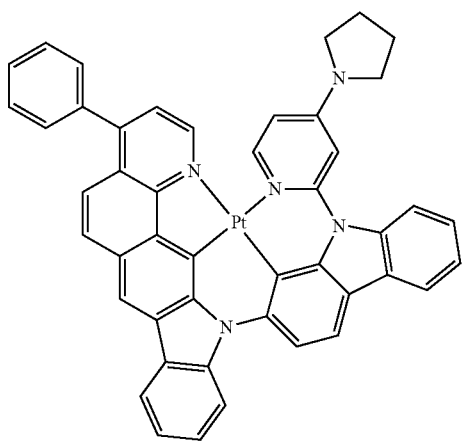
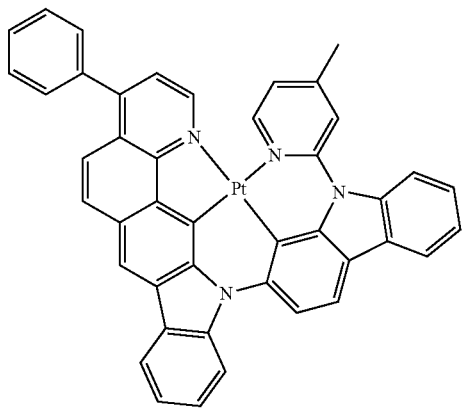
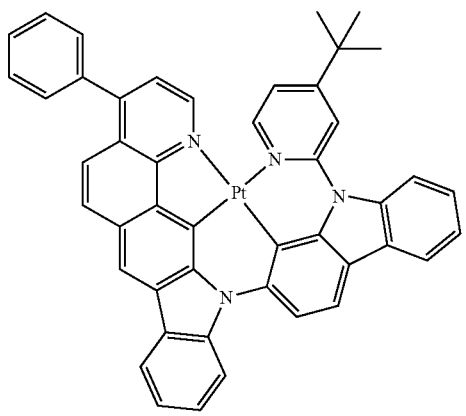

71
-continued
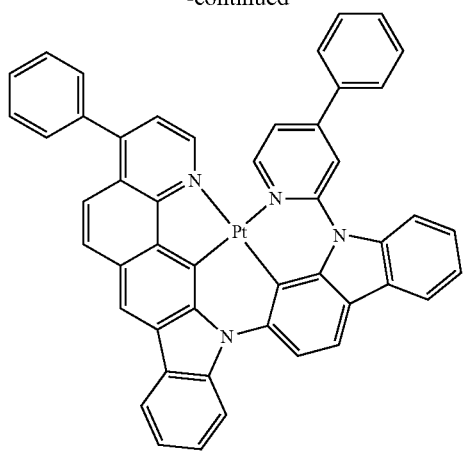
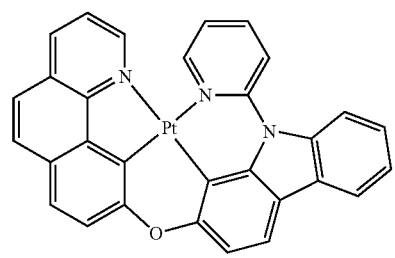
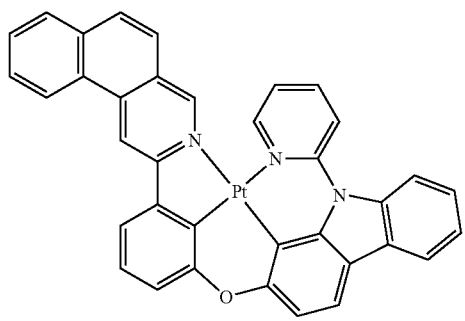
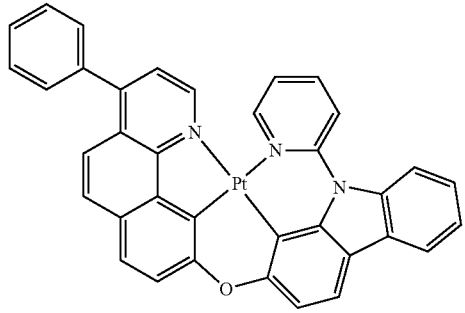
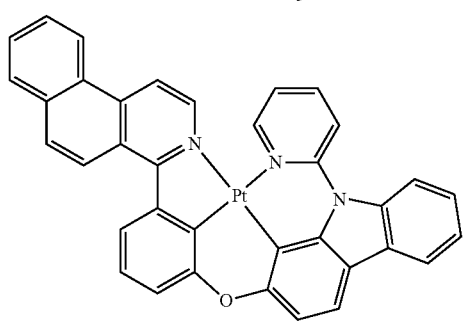
72
-continued
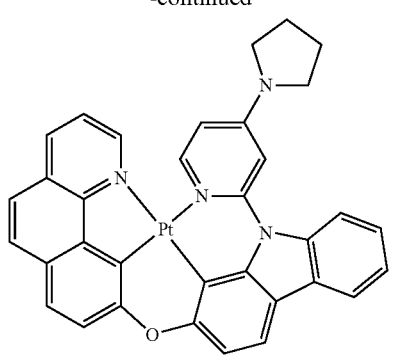
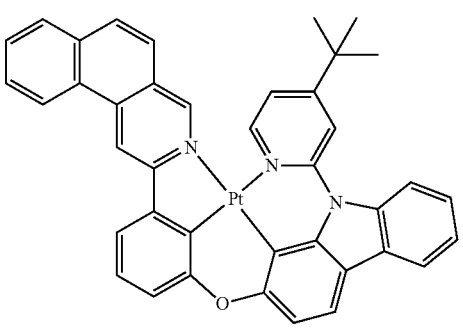
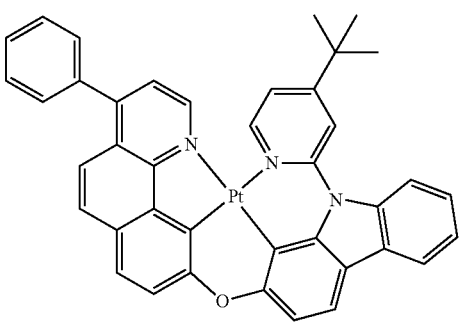
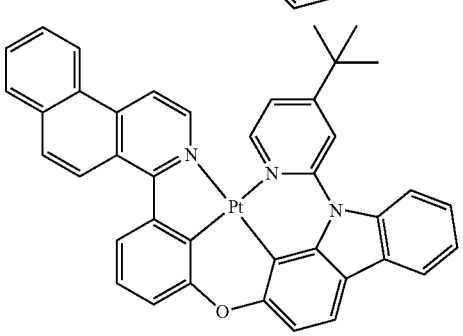
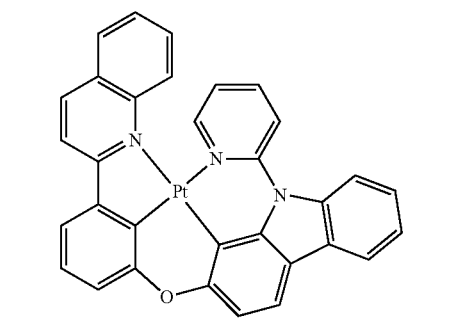

73
-continued
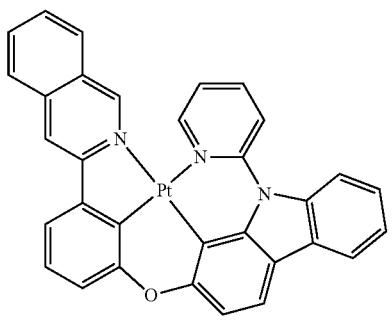
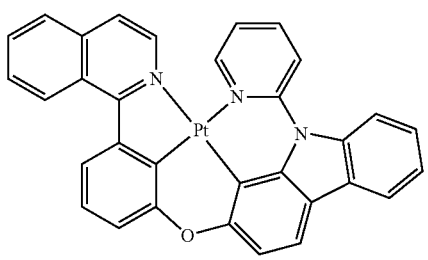
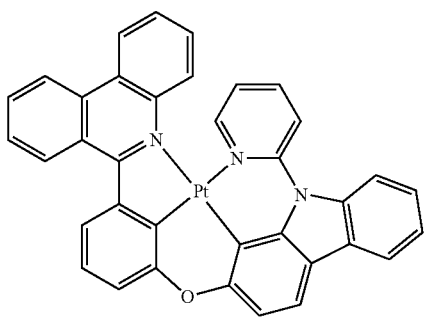
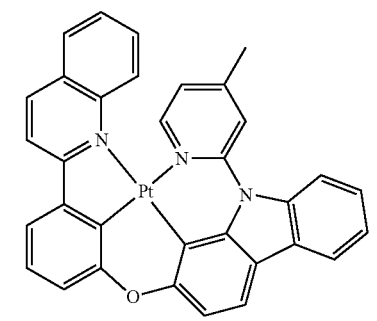
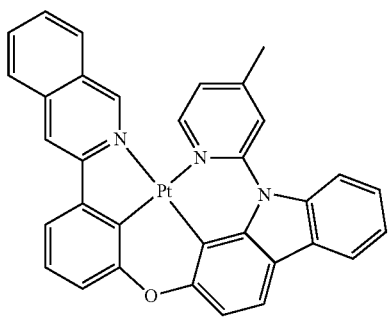
74
-continued
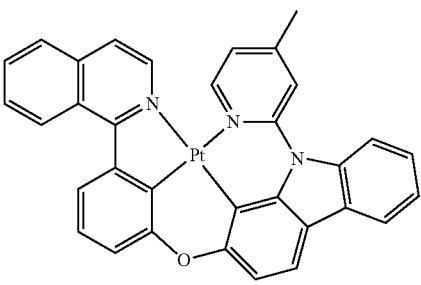
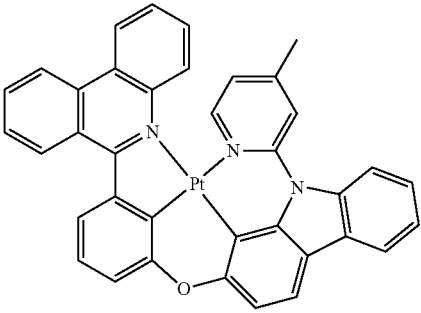
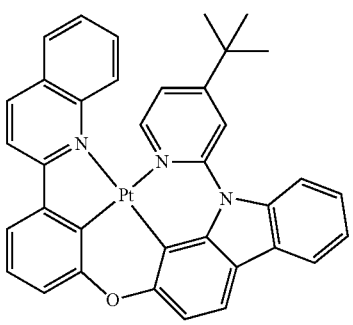
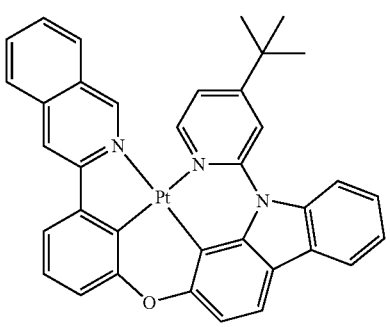
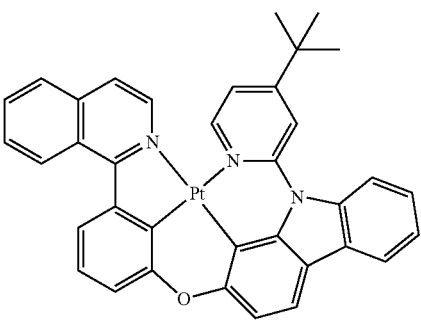

75
-continued
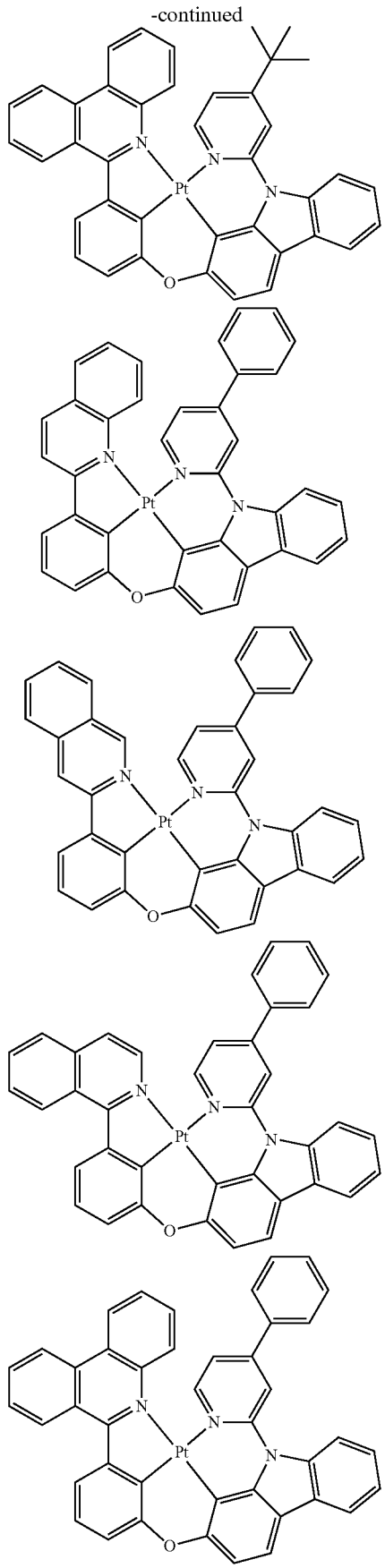
76
-continued
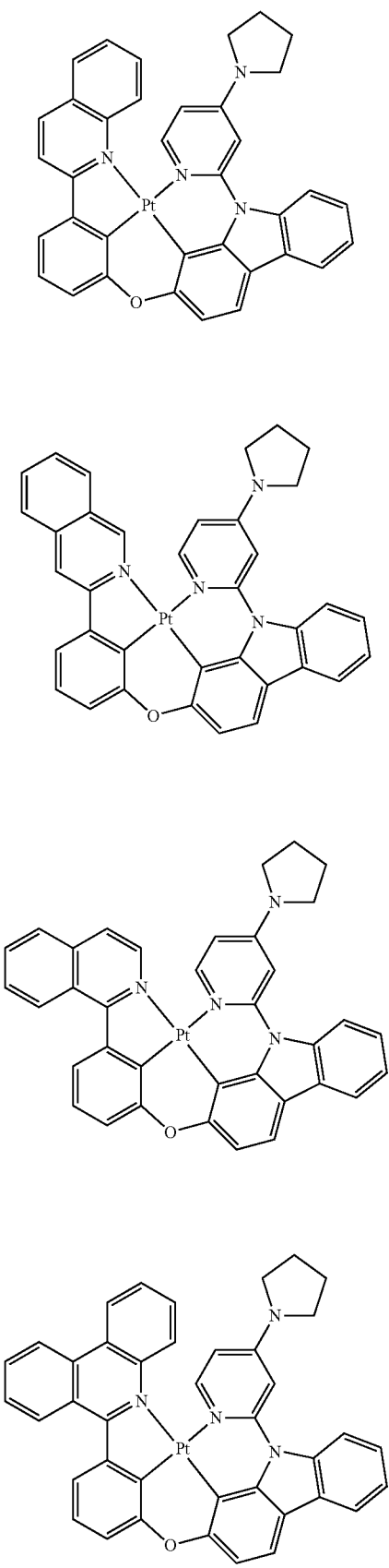

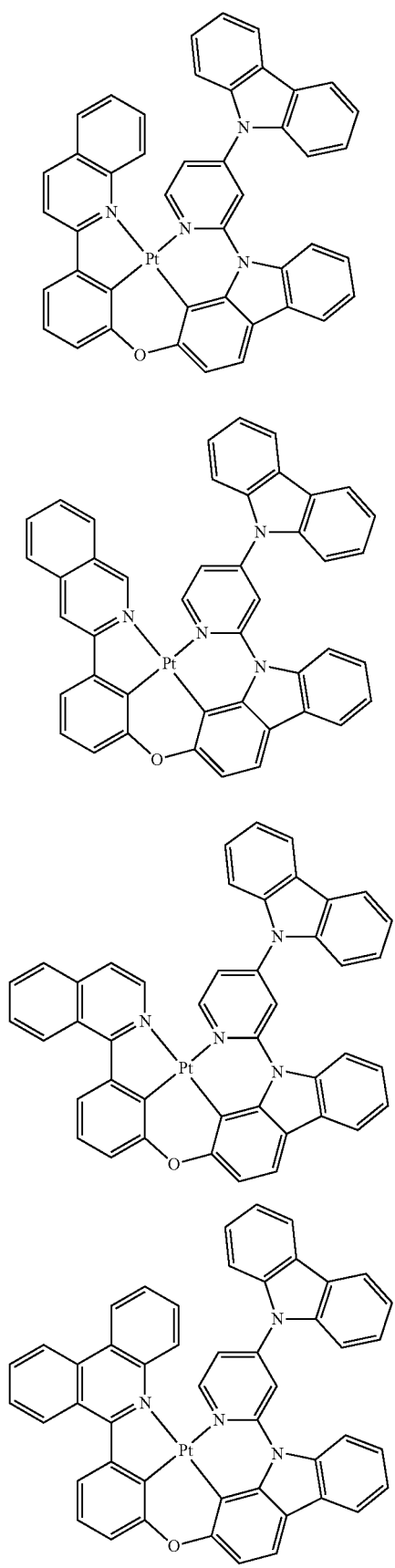
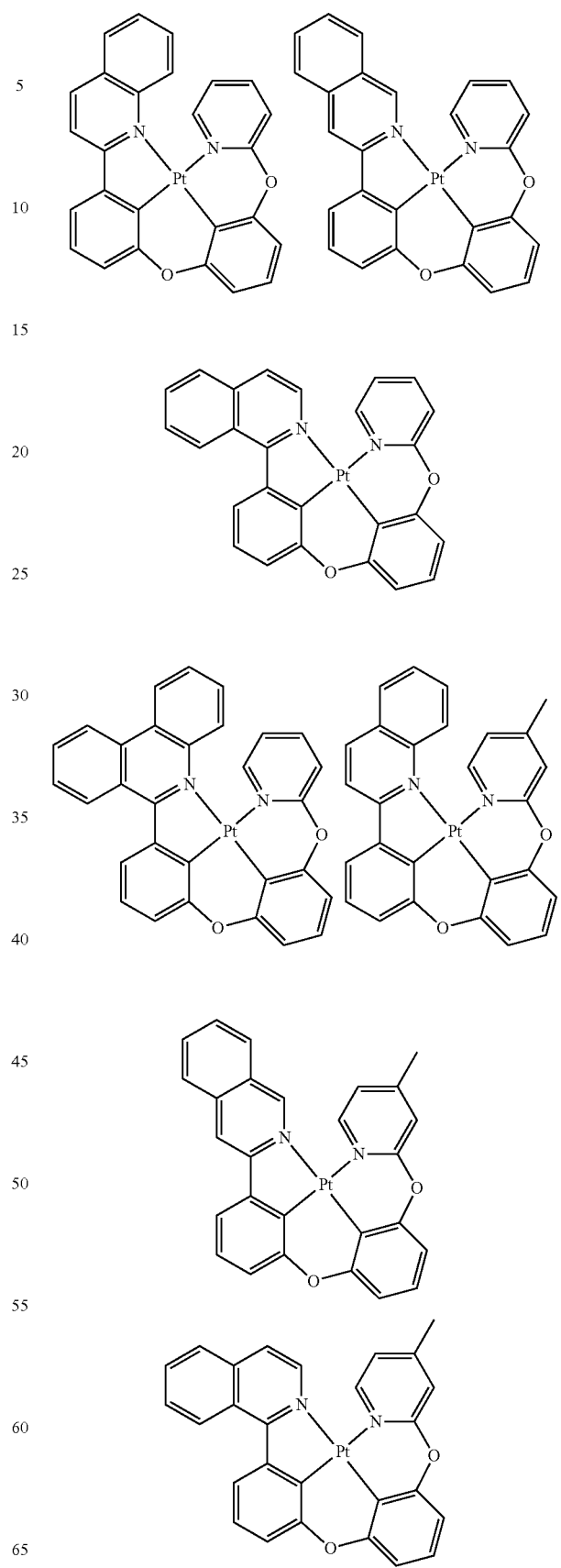

-continued
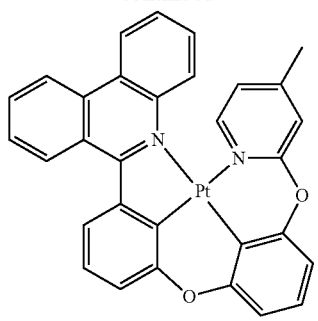
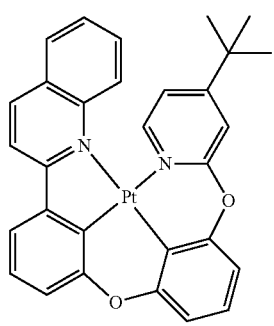
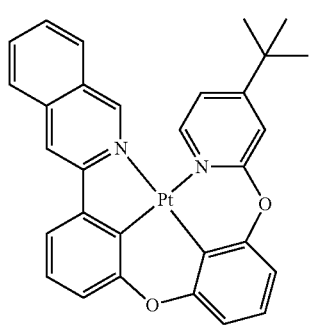
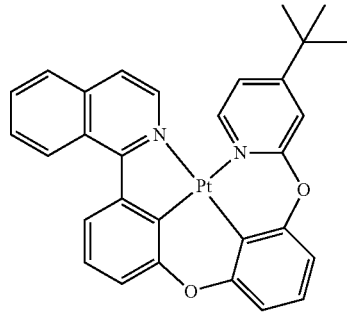
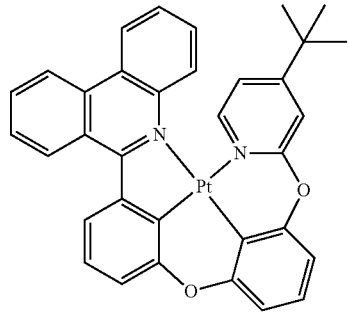
-continued
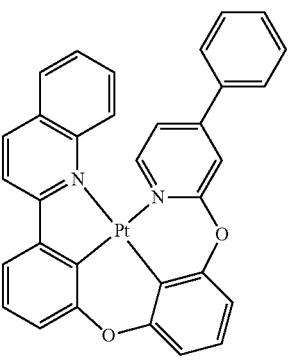
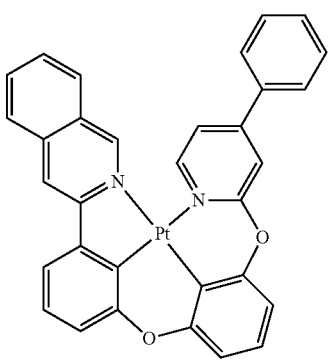
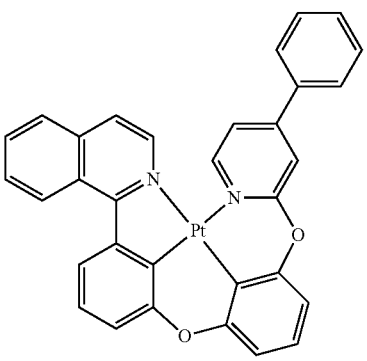
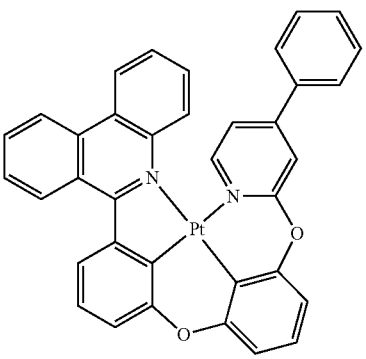

81
-continued
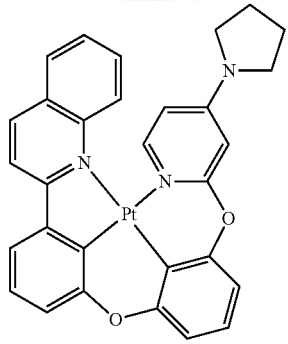
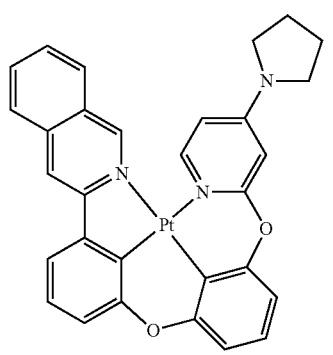
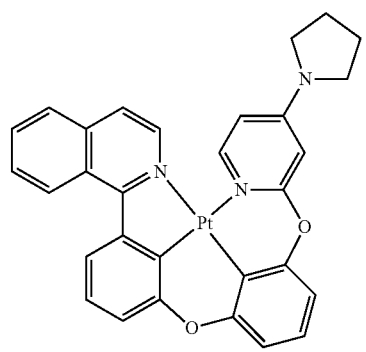
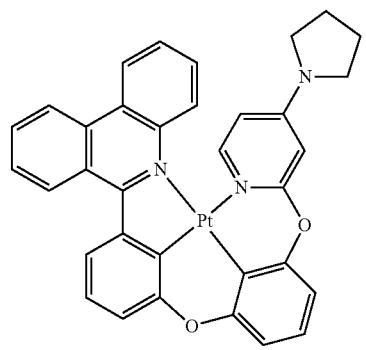
82
-continued
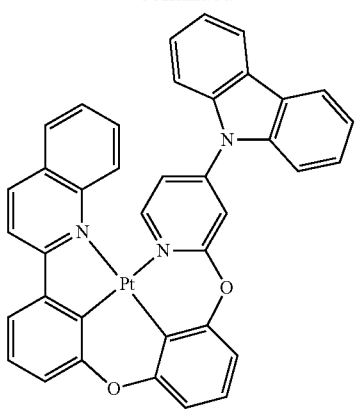
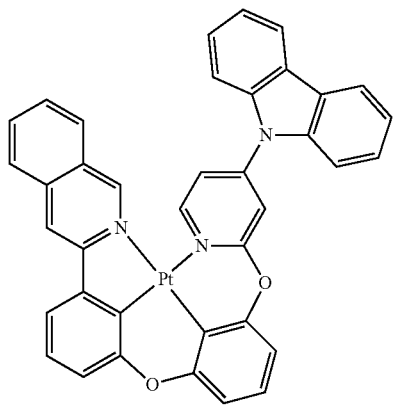
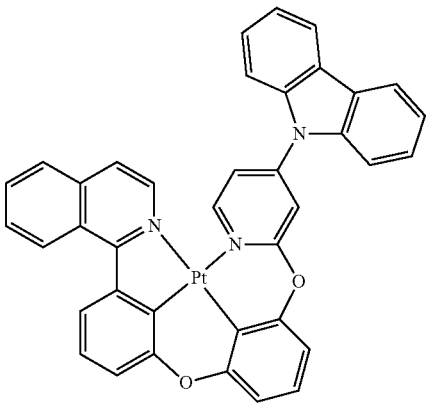
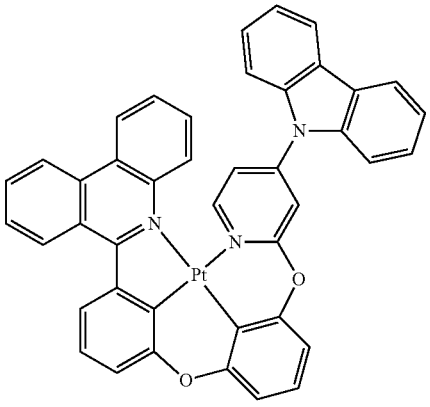

83
-continued
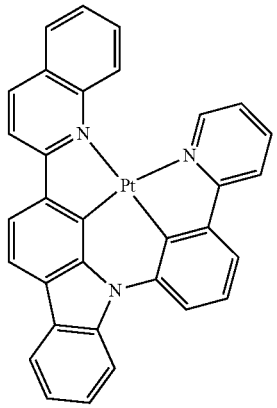
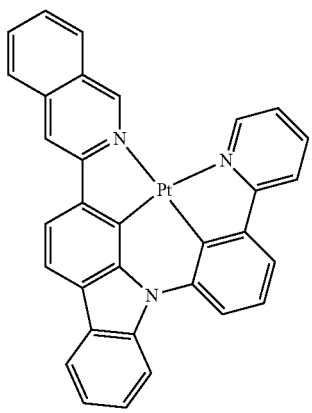
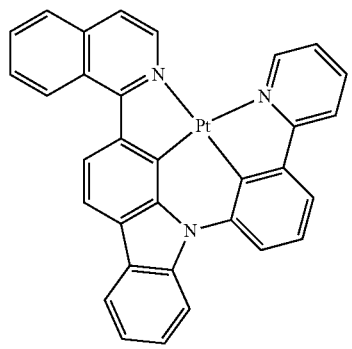
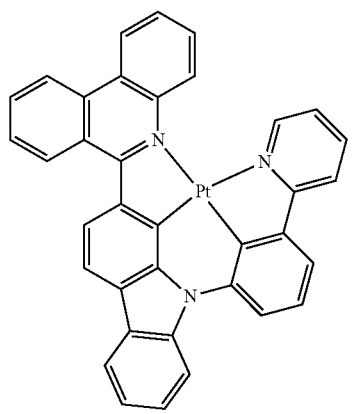
84
-continued
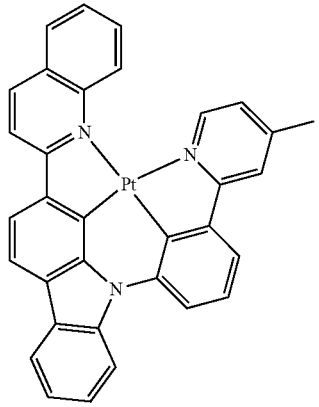
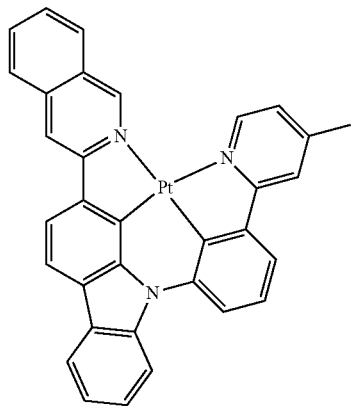
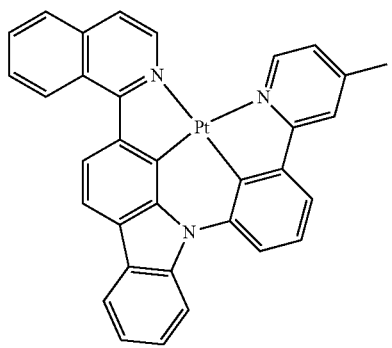
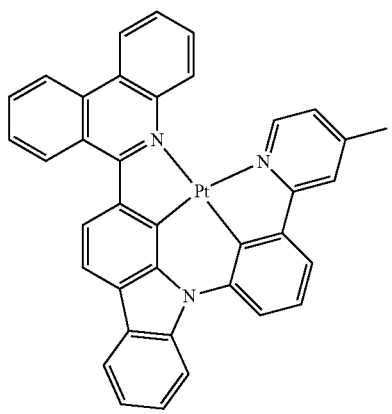

85
-continued
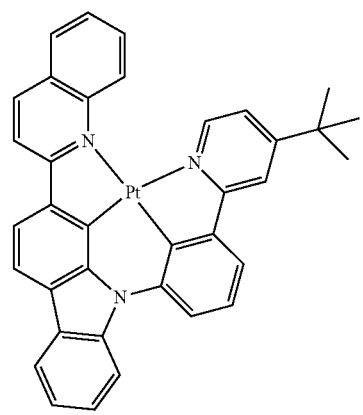
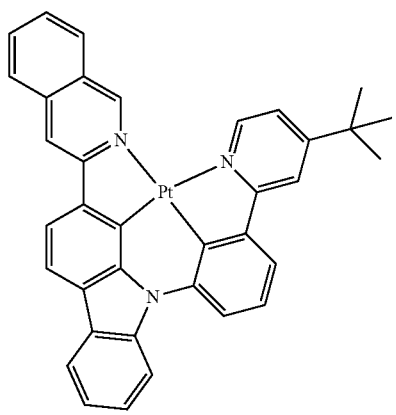
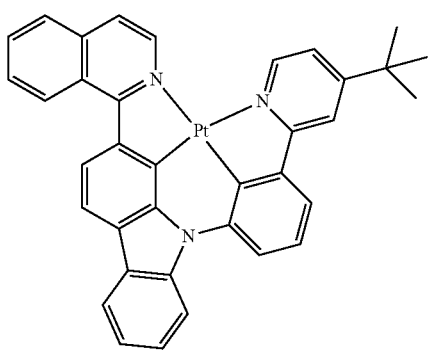
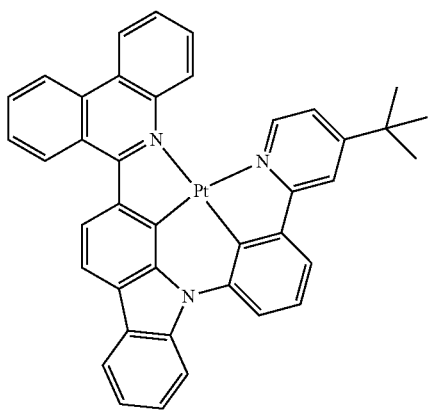
86
-continued
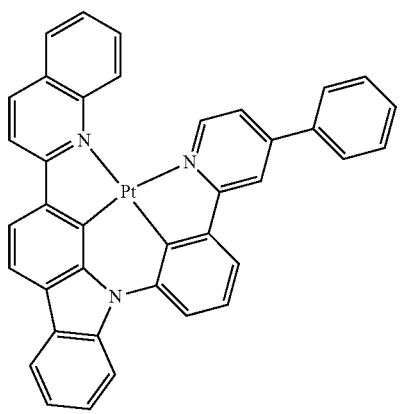
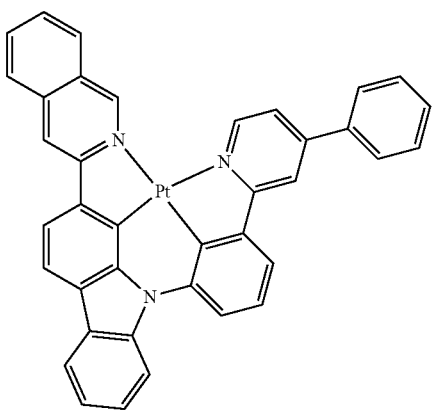
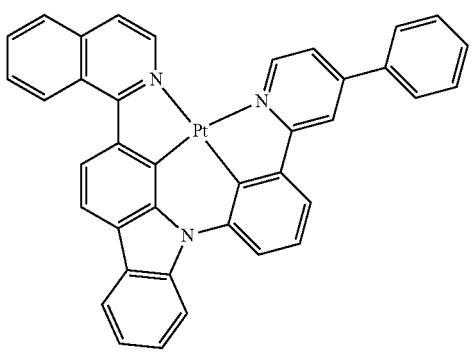
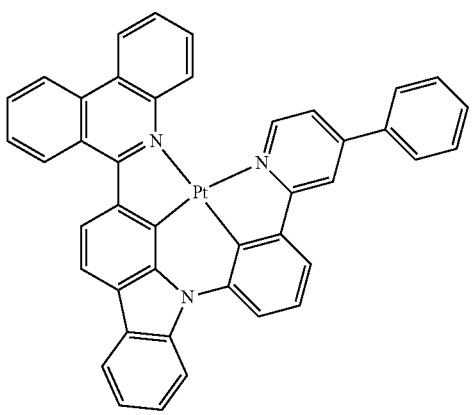

87
-continued
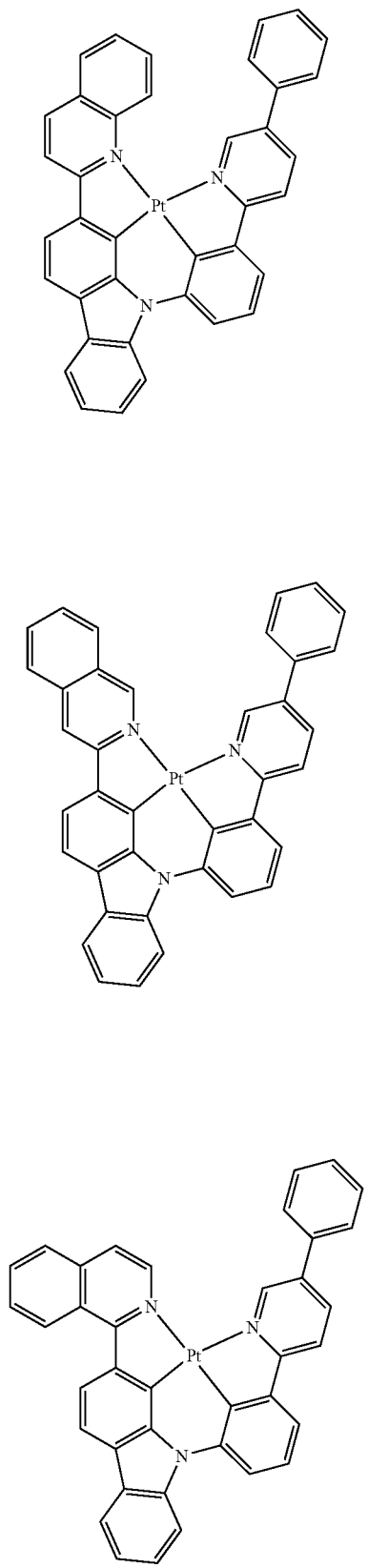
88
-continued
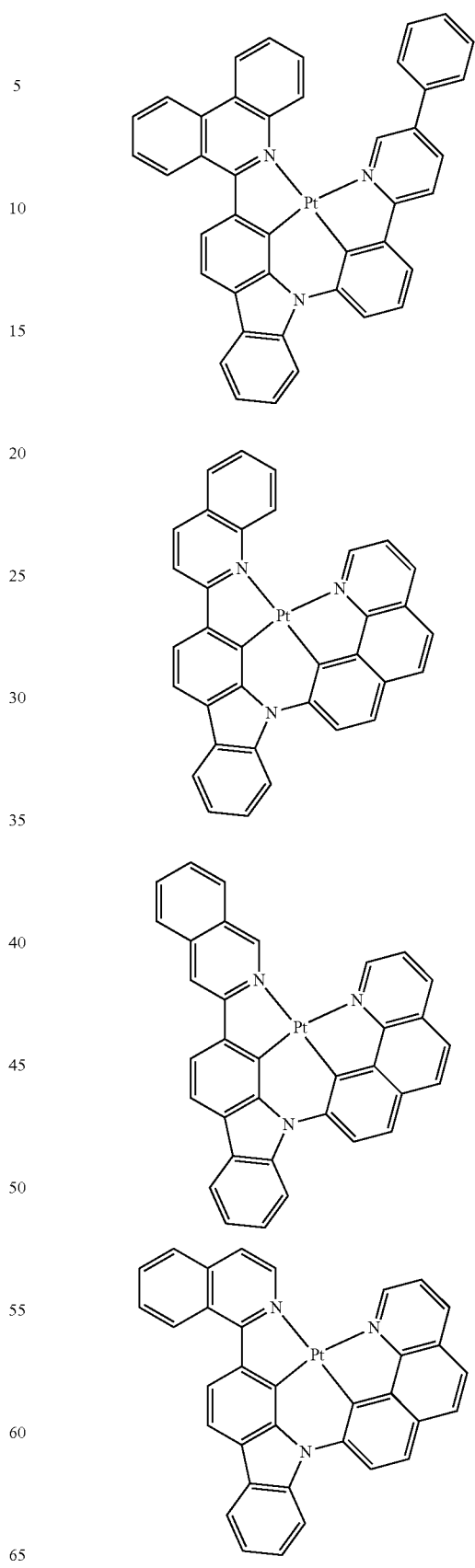

-continued
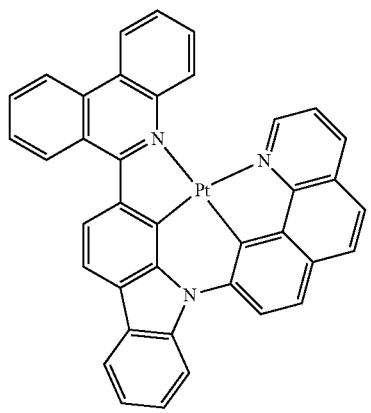
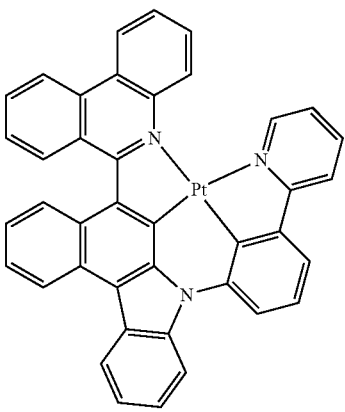
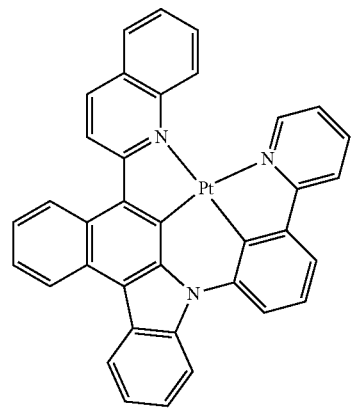
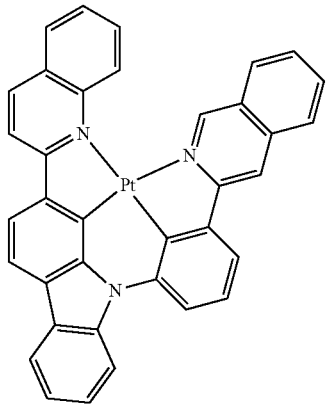
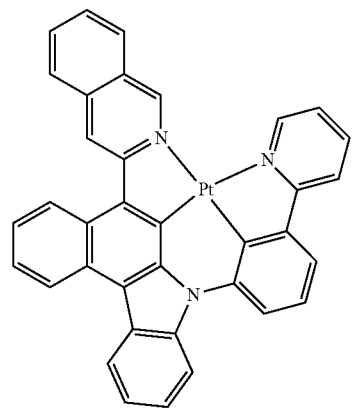
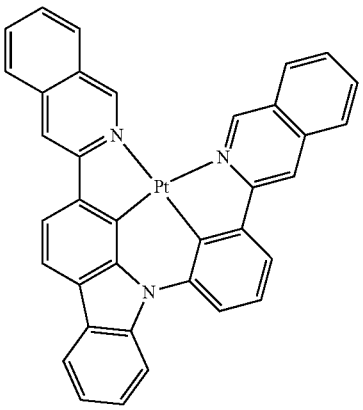
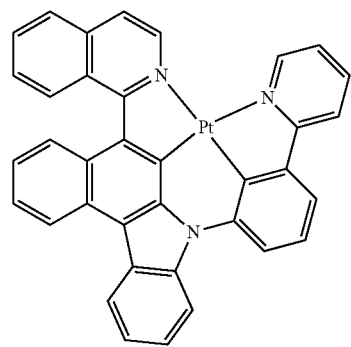
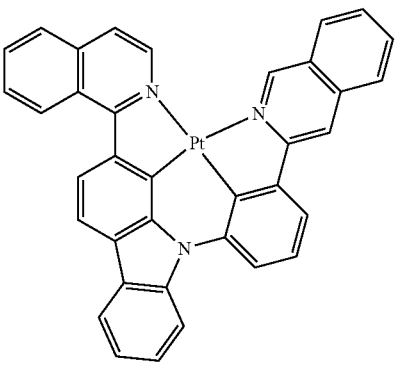

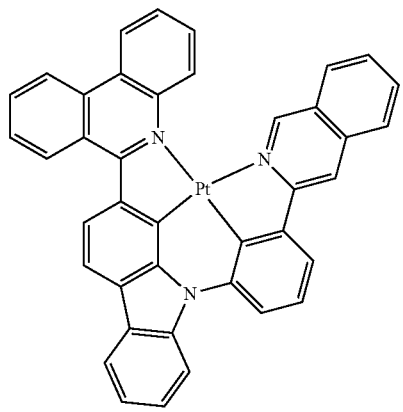
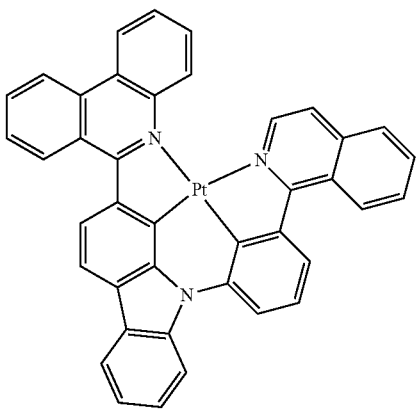
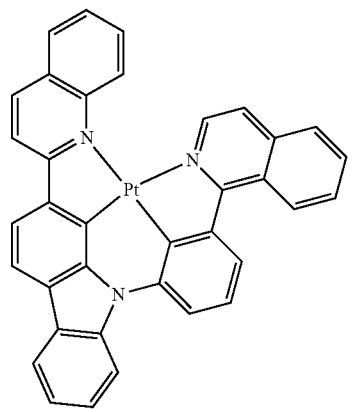
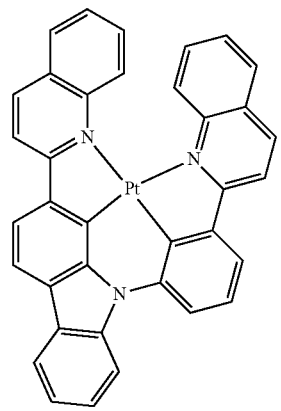
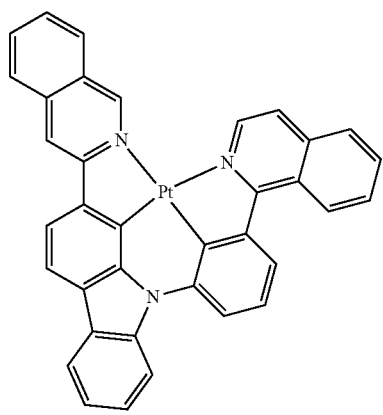
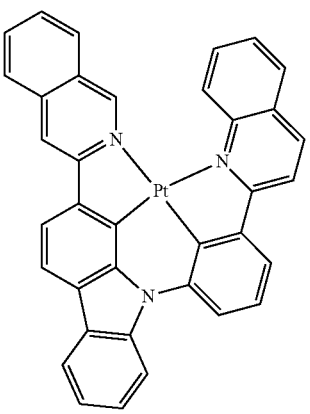
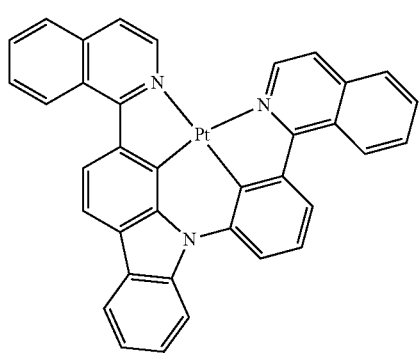
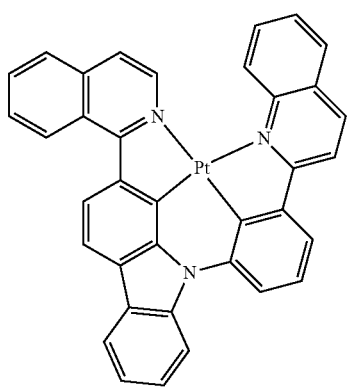

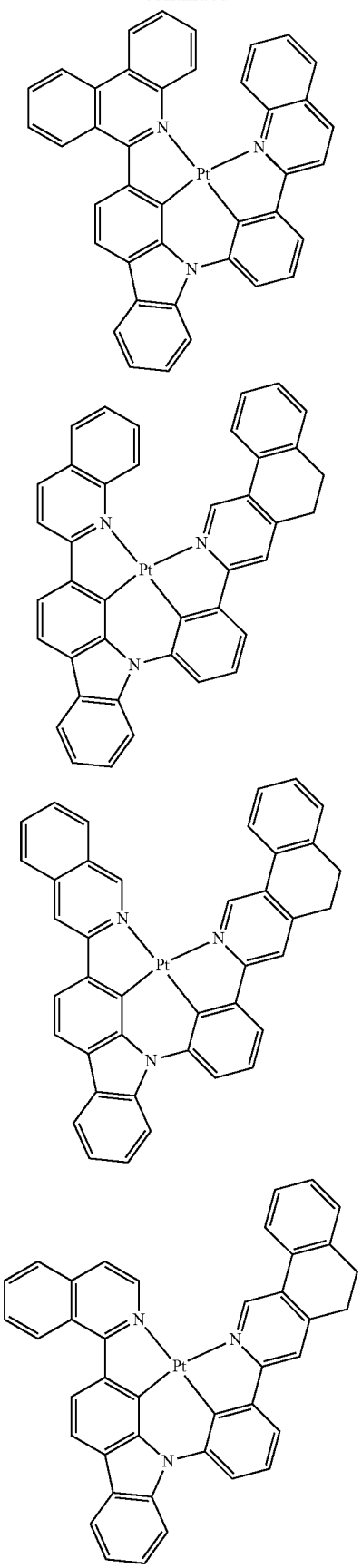

| 95 -continued | 96 -continued |
|---|---|
| 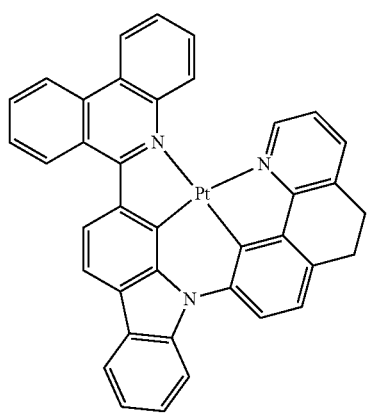 | 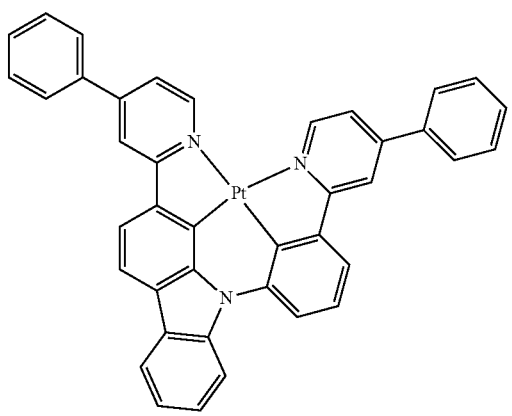 |
| 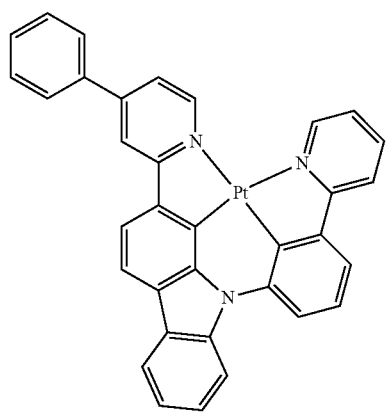 | 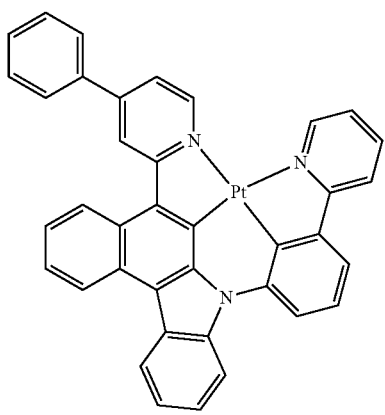 |
| 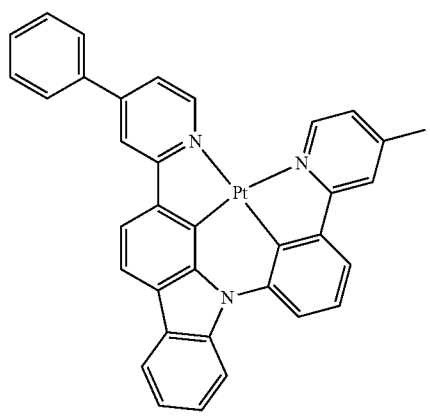 | 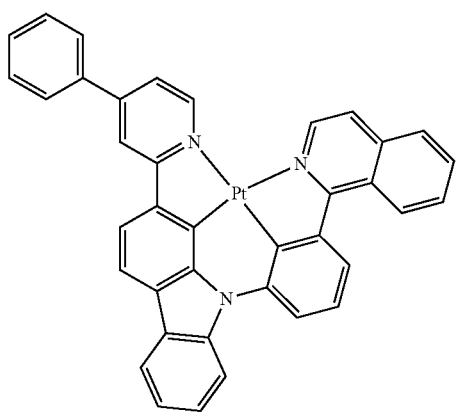 |
| 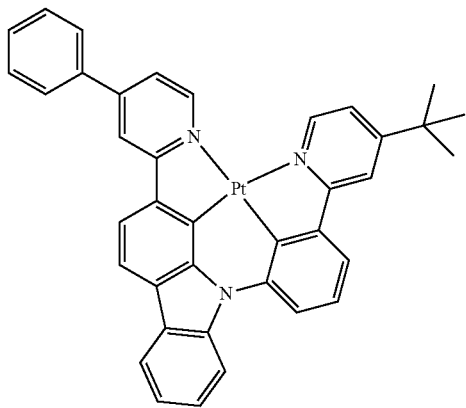 | 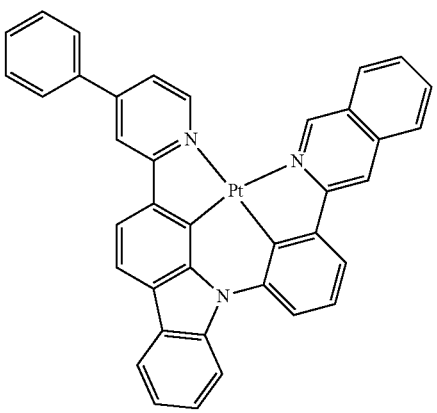 |

97
-continued
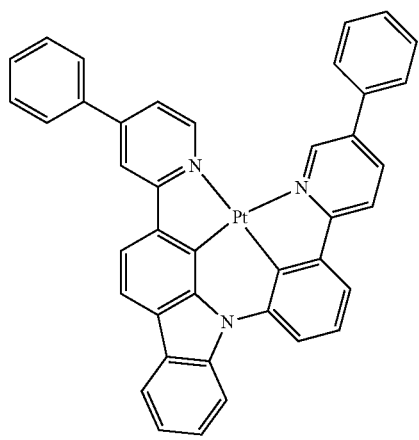
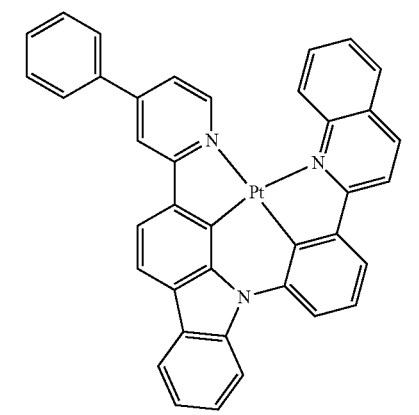
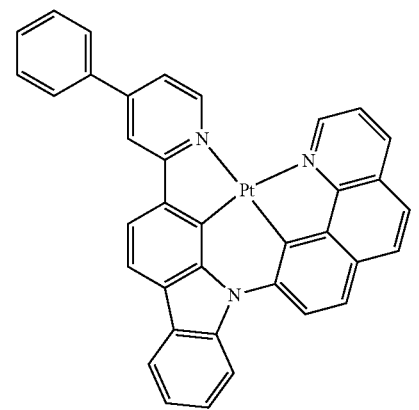
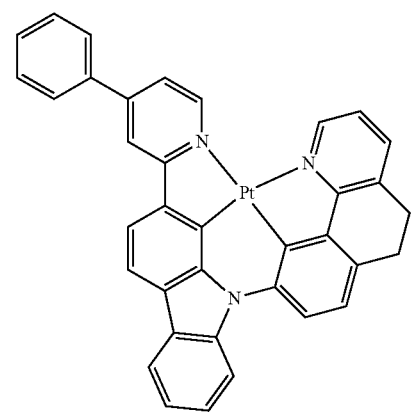
98
-continued
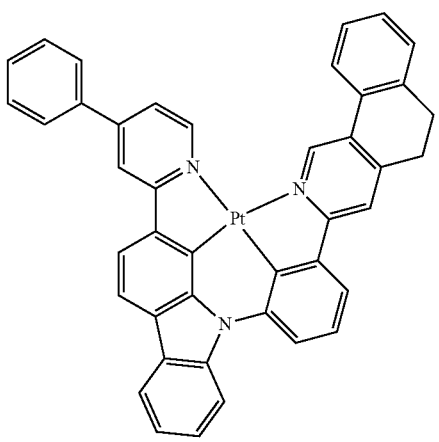
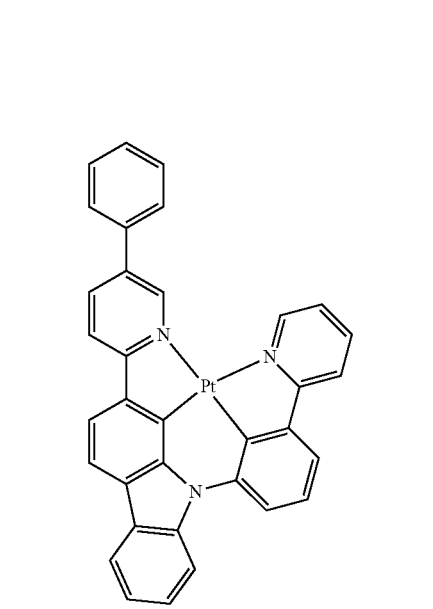
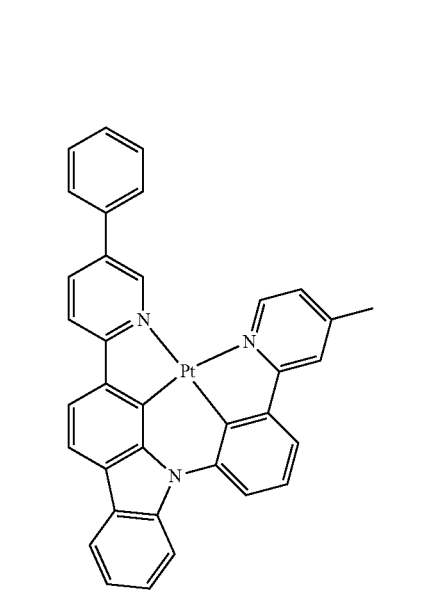

99
-continued
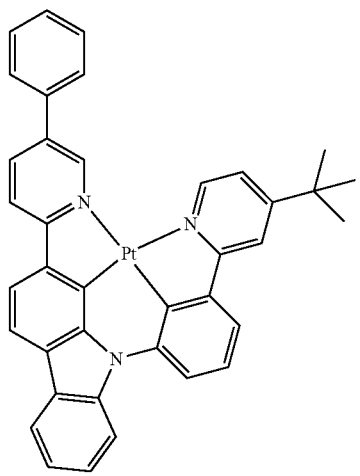
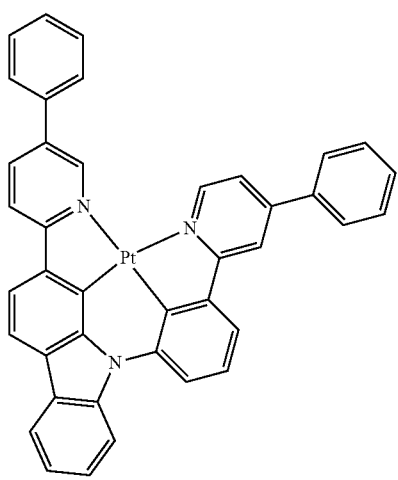
100
-continued
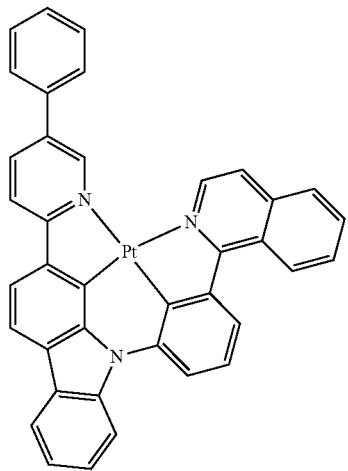
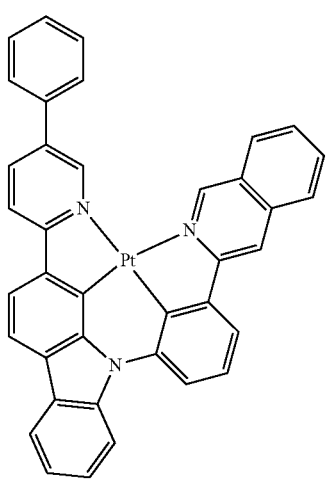
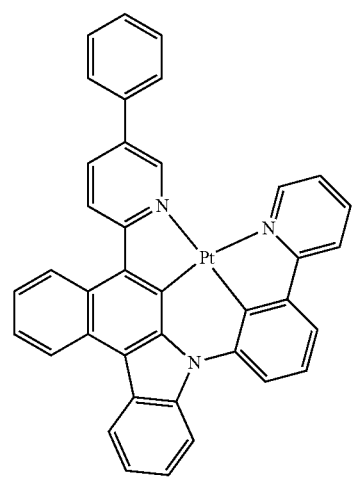

101
-continued
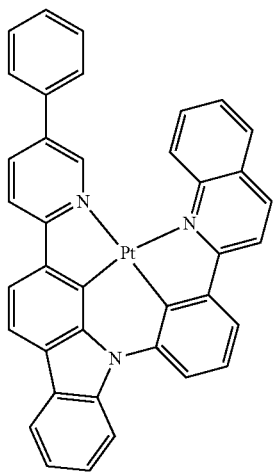
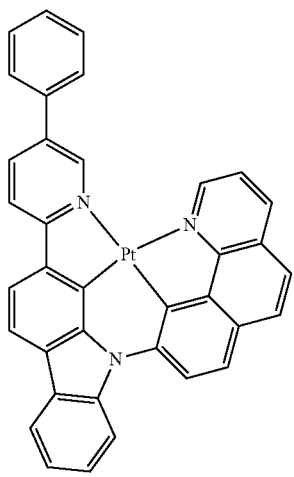
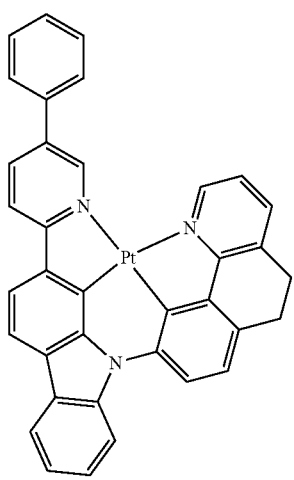
102
-continued
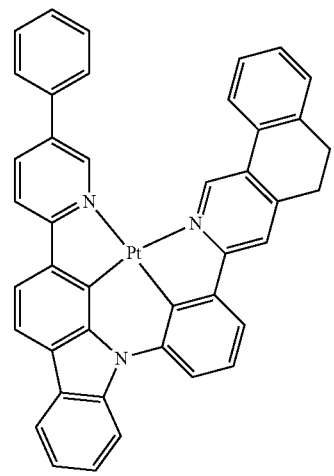
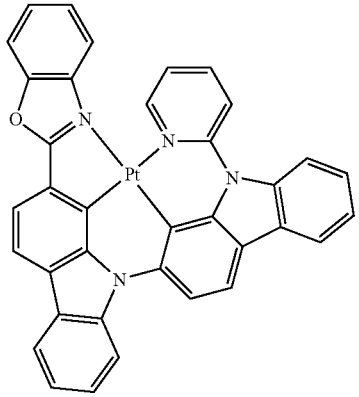
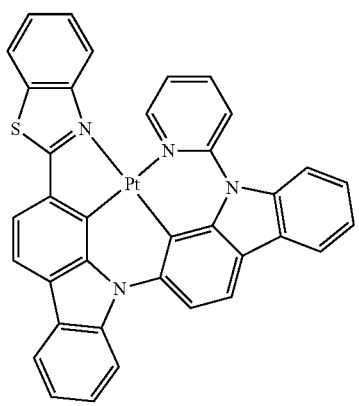
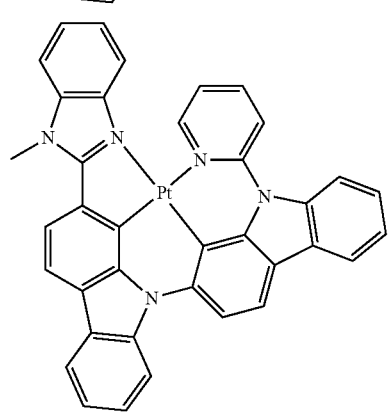

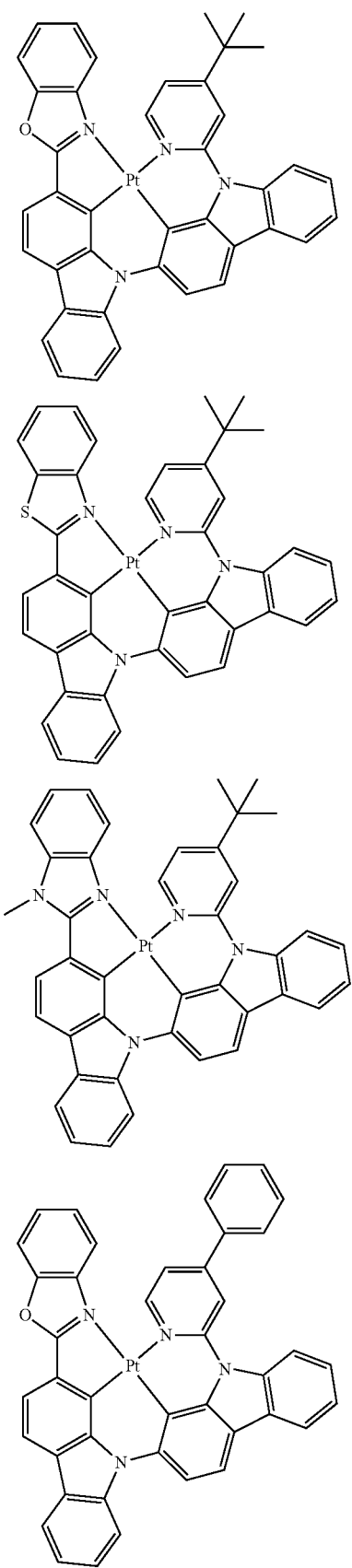
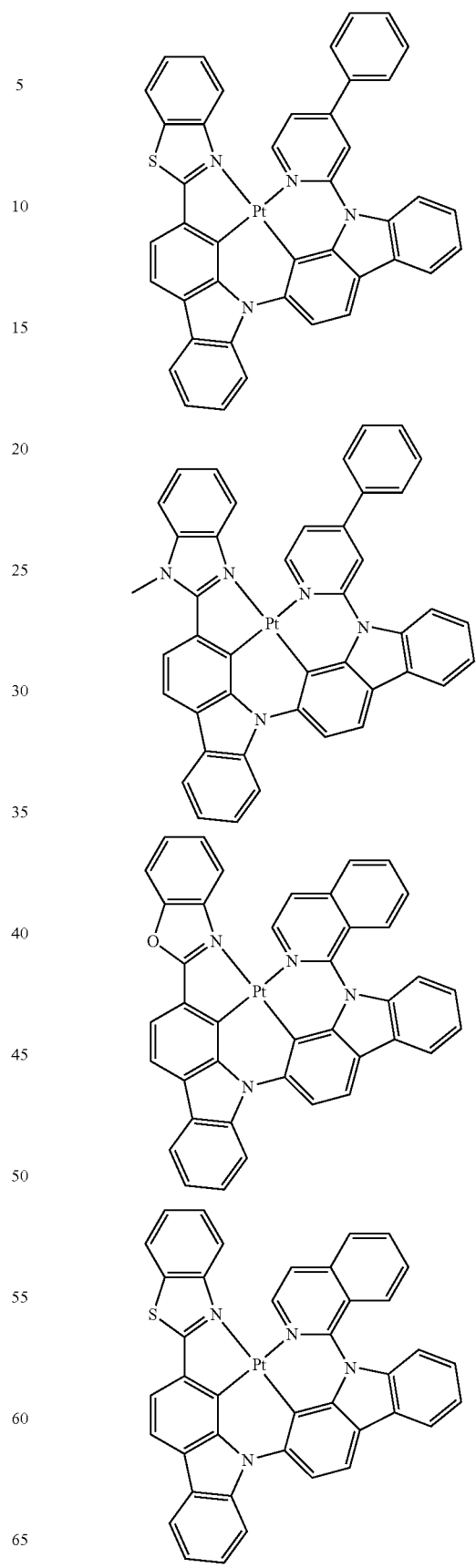

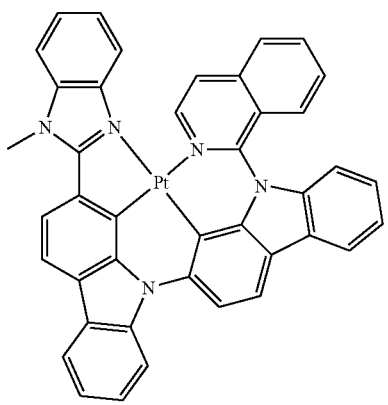
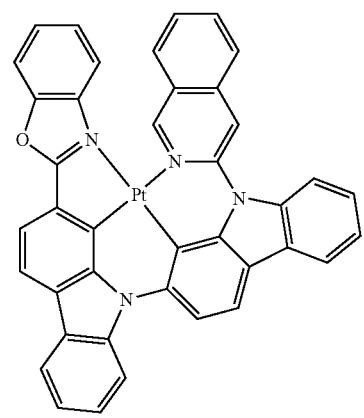
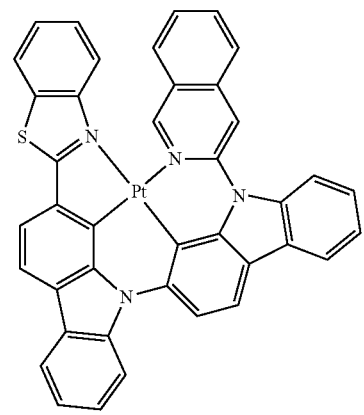
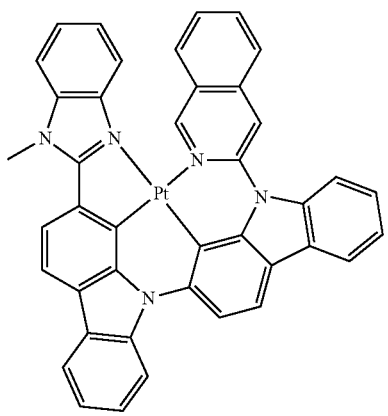
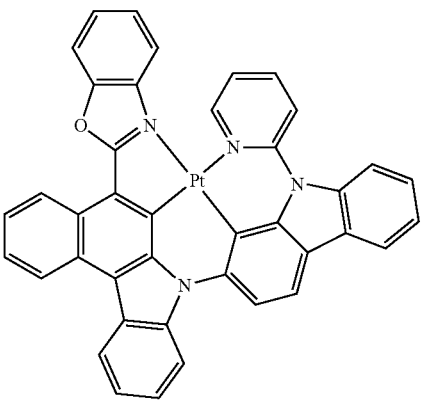
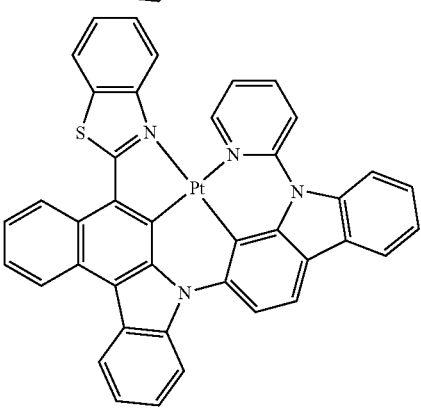
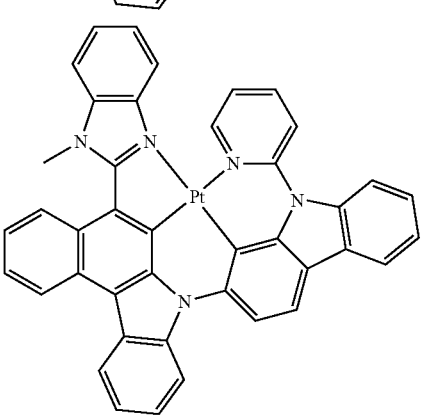
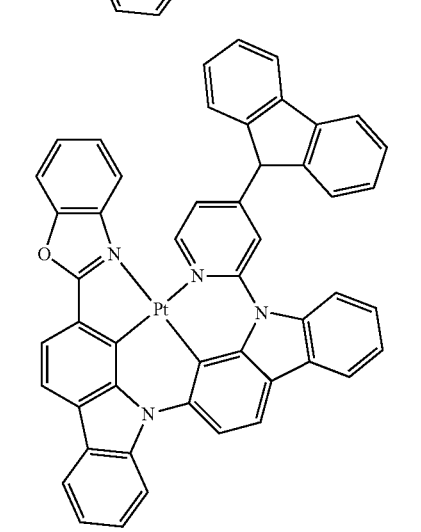

107
-continued
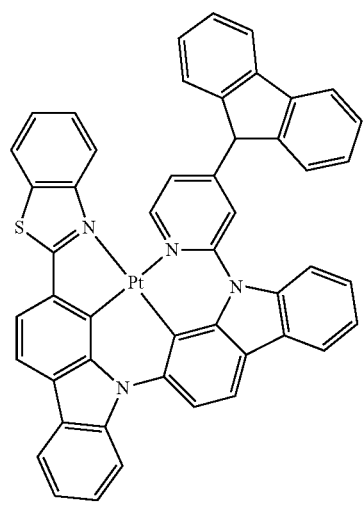
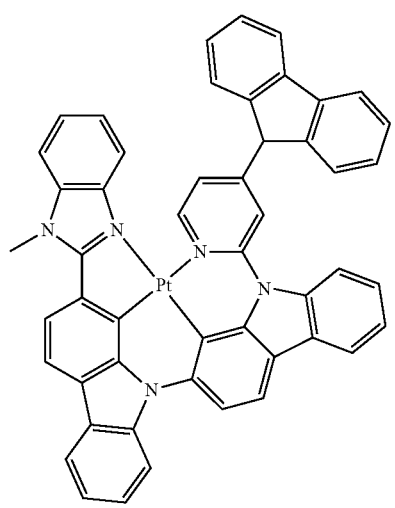
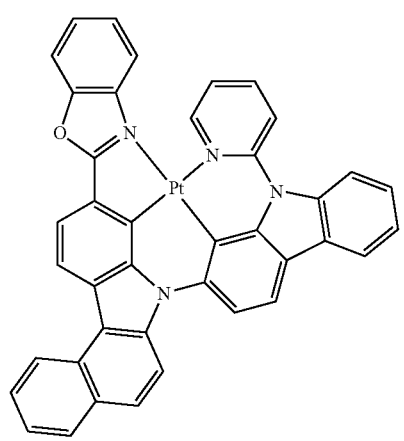
108
-continued
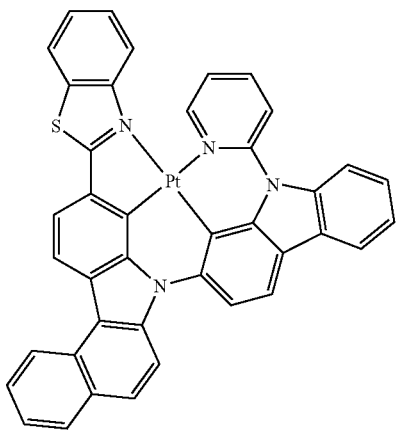
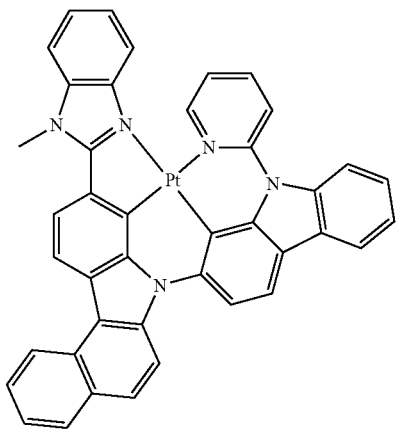
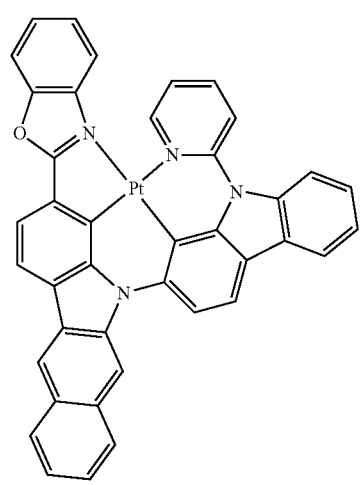

109
-continued
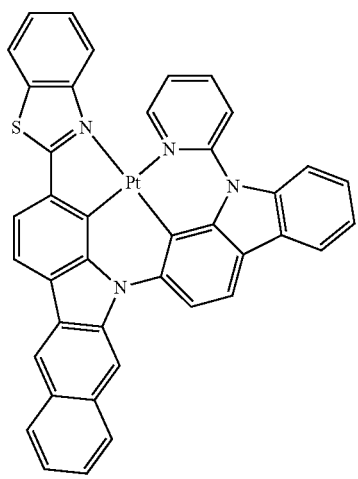
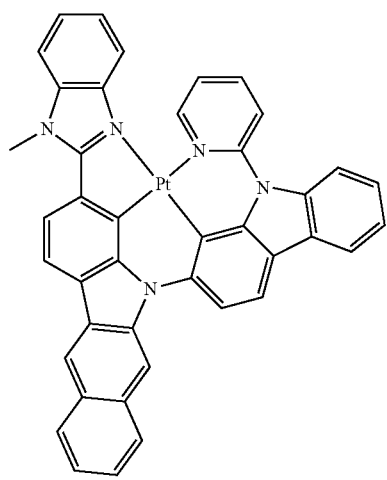
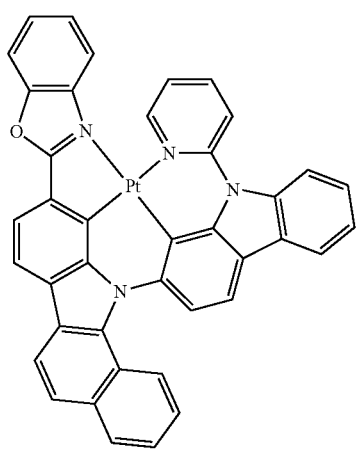
110
-continued
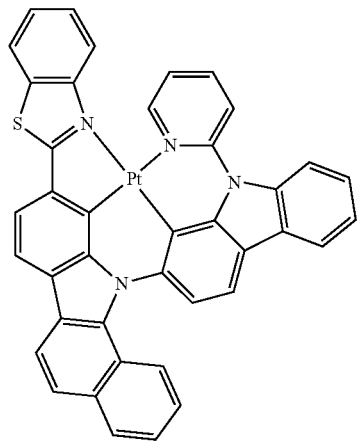
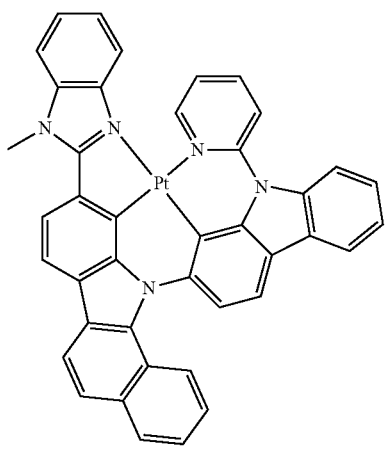
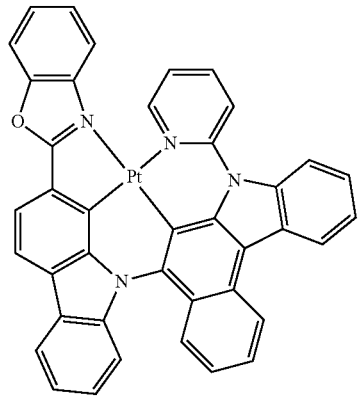
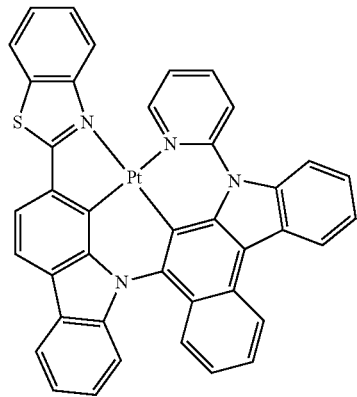

111
-continued
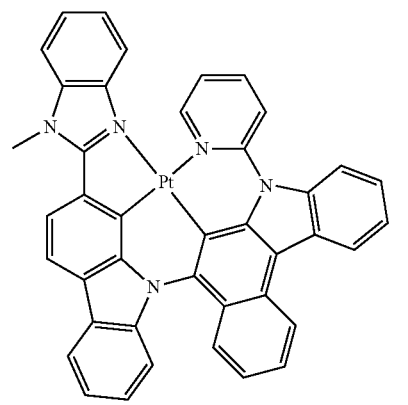
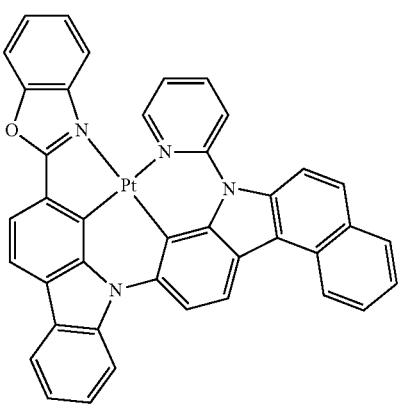
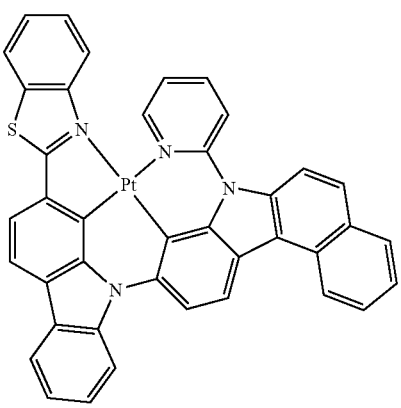
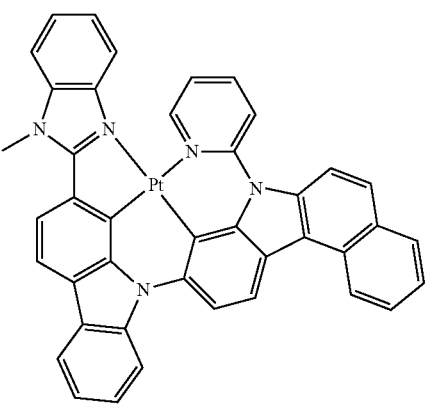
112
-continued
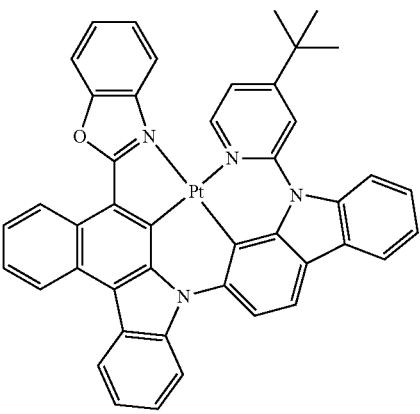
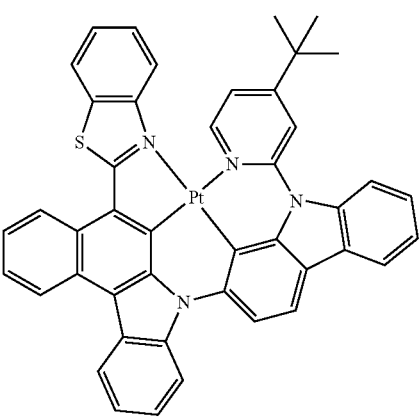
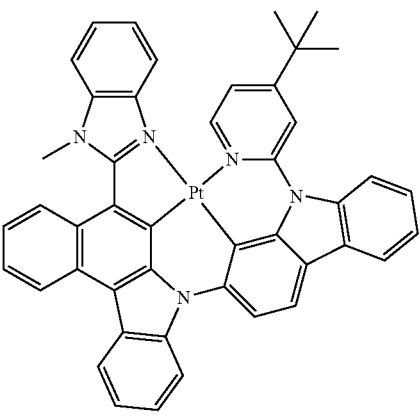
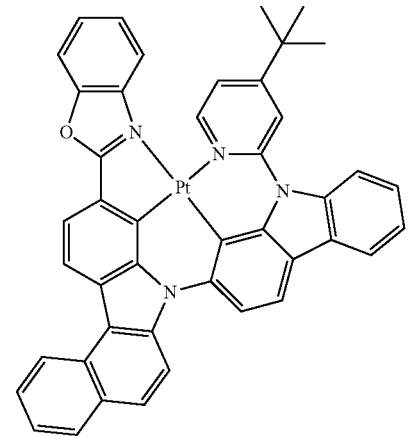

113
-continued
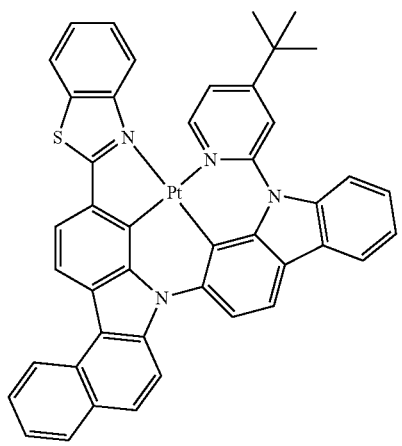
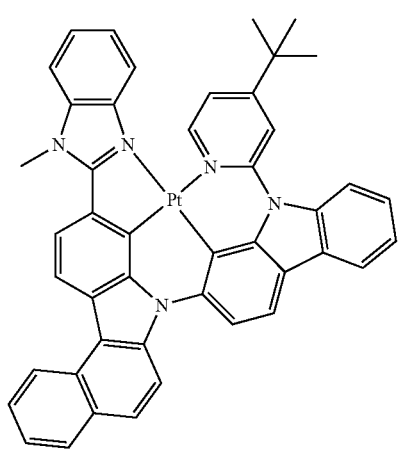
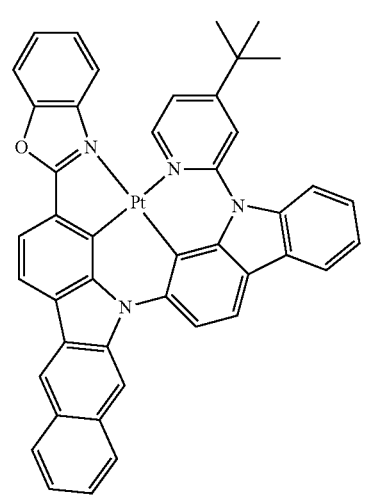
114
-continued
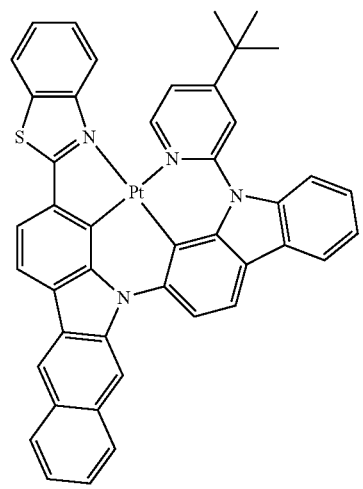
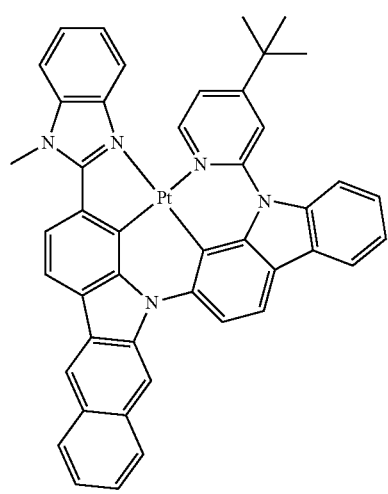
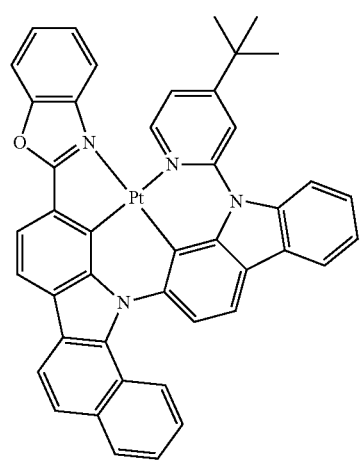

115
-continued
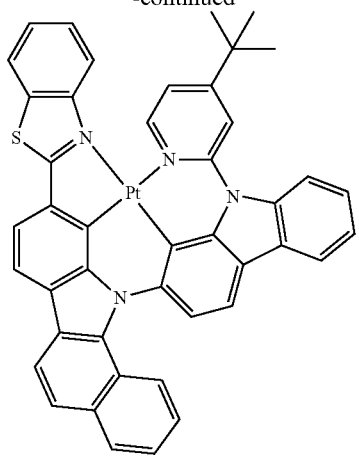
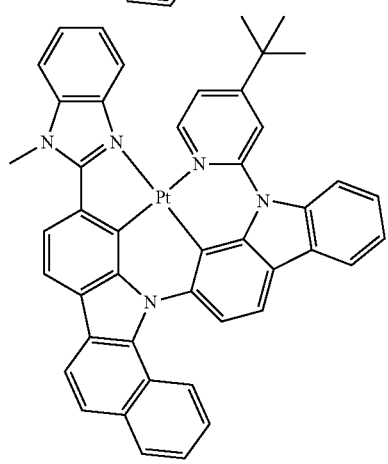
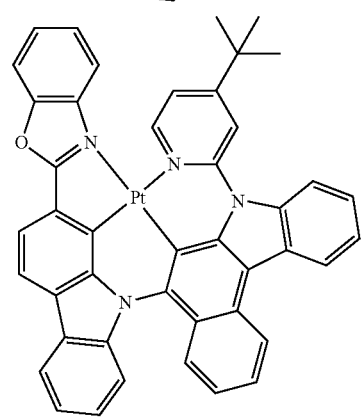
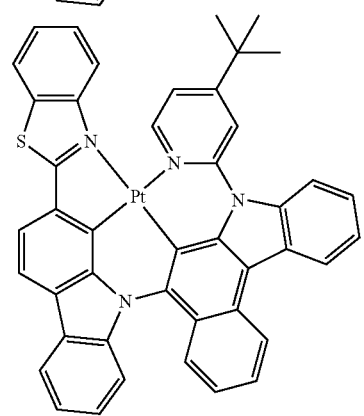
116
-continued
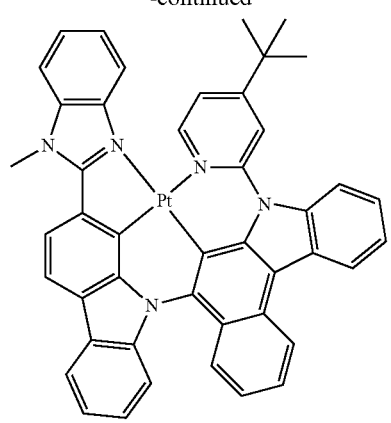
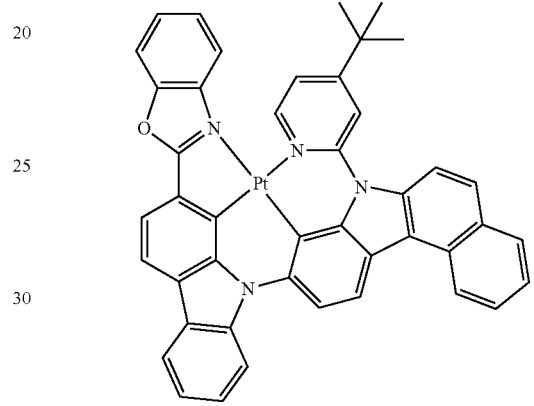
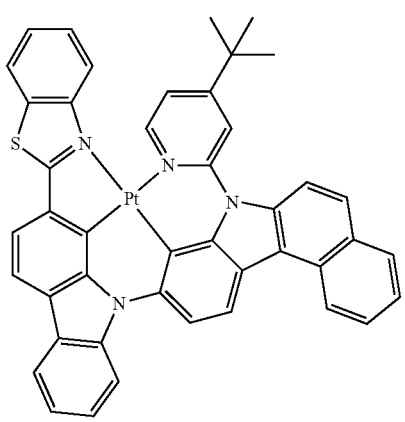
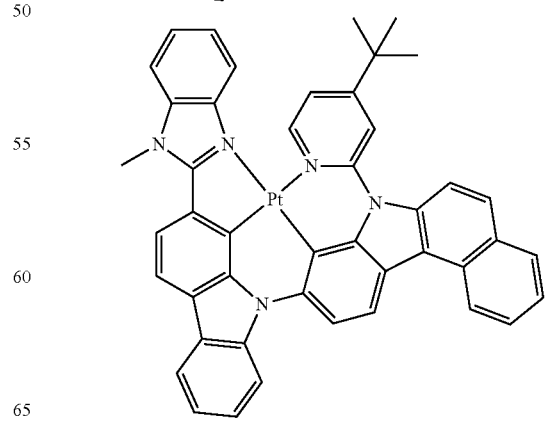

117
-continued
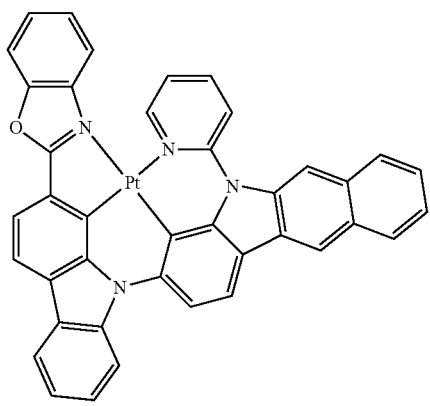
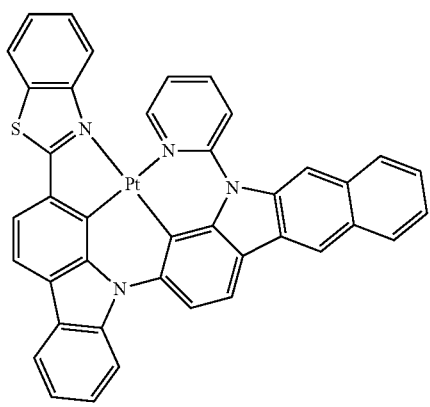
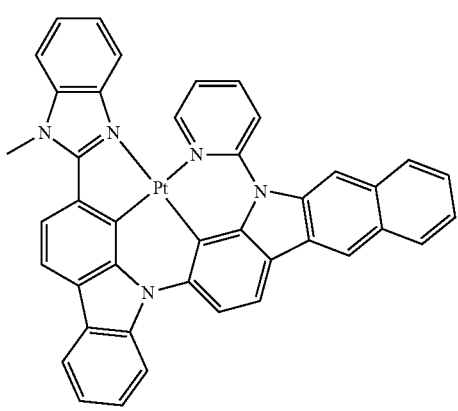
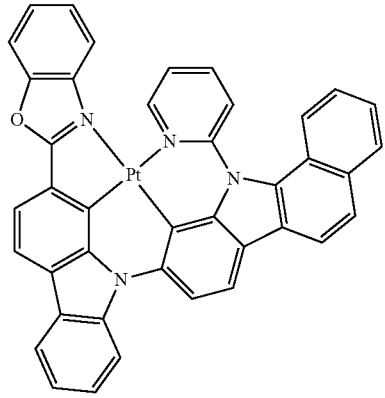
118
-continued
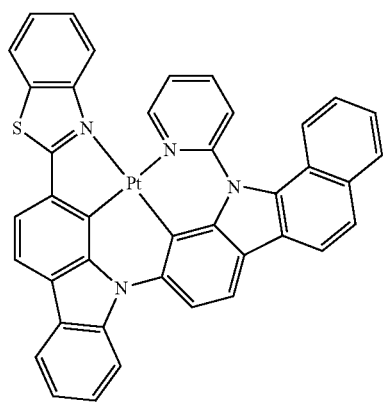
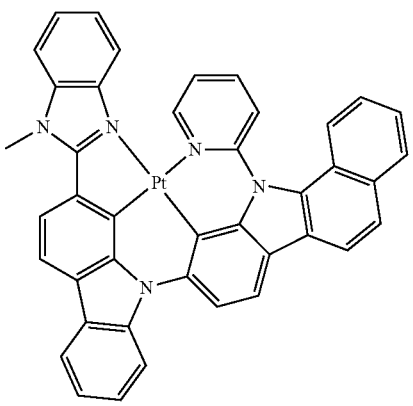
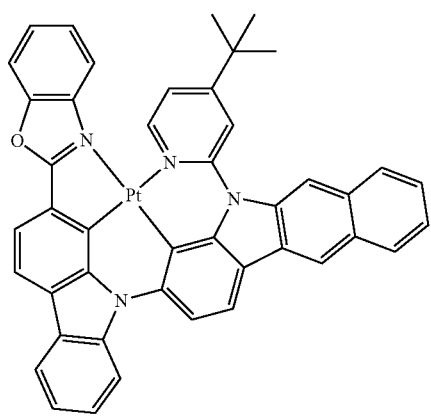
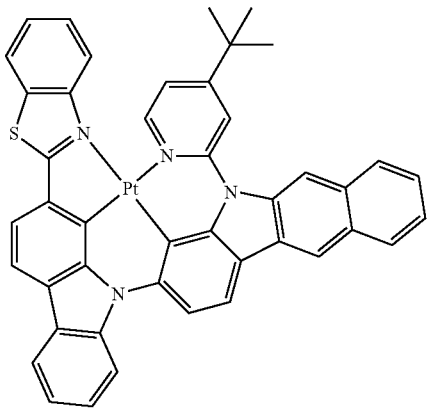

119
-continued
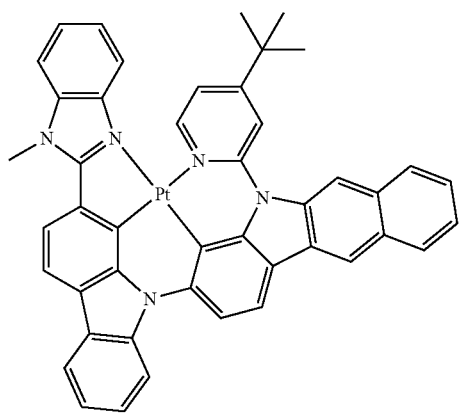
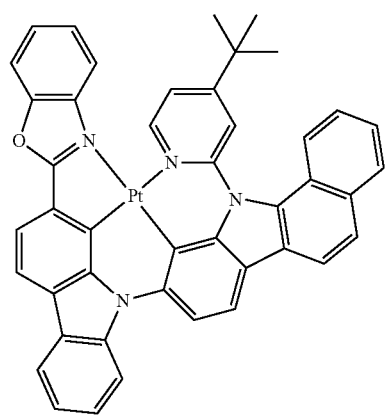
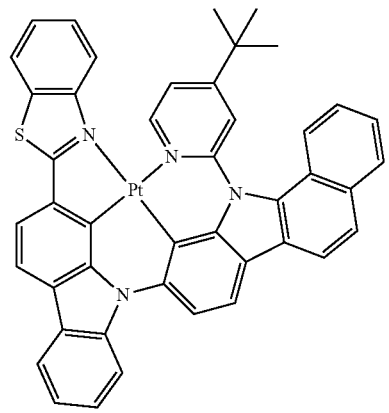
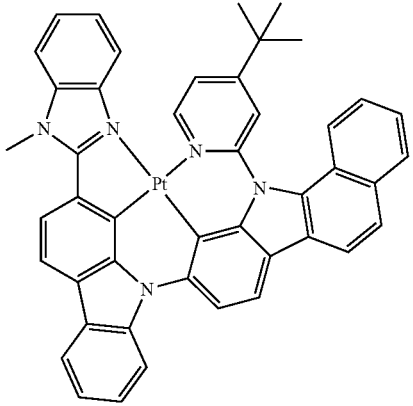
120
-continued
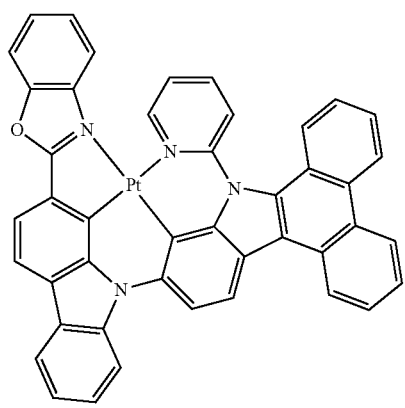
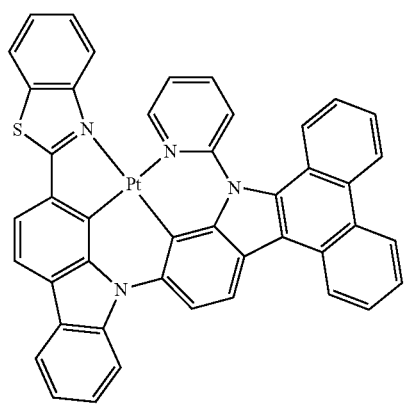
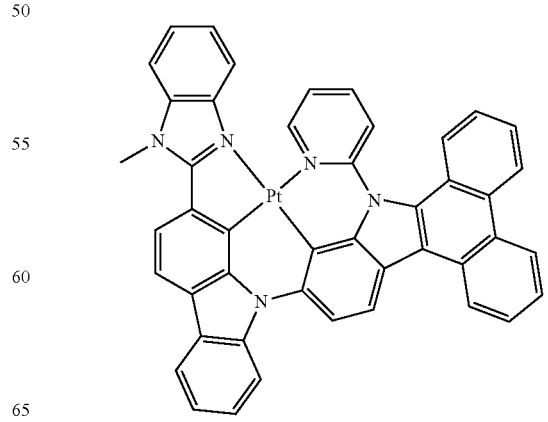

121
-continued
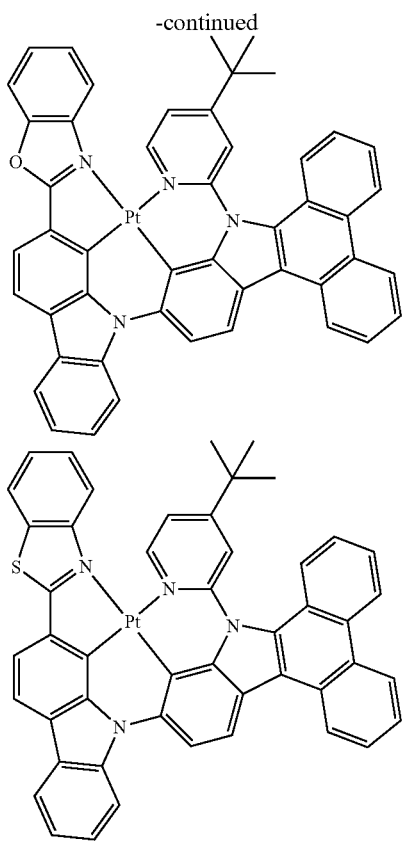
122
-continued
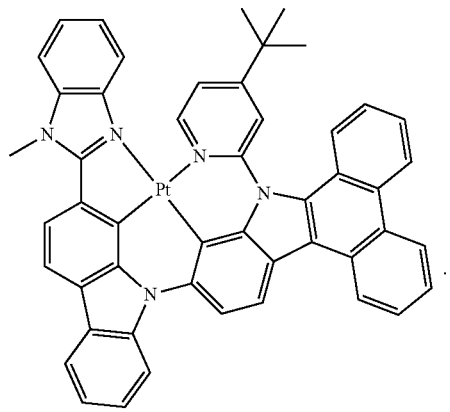
10. A light-emitting device comprising the compound of claim 9 as an emitter.
11. An OLED device comprising the compound of claim 9 as an emitter.
12. A luminescent display device comprising the compound of claim 9.
* * * * *